(12) United States Patent  
Cartledge et al.

(10) Patent No.: US 9,782,584 B2  
(45) Date of Patent: Oct. 10, 2017

(54) TRANSCUTANEOUS ELECTROSTIMULATOR AND METHODS FOR ELECTRIC STIMULATION

(71) Applicant: Nervana, LLC, Boca Raton, FL (US)

(72) Inventors: Richard Cartledge, Boca Raton, FL (US); Daniel Cartledge, Boca Raton, FL (US); Ami Brannon, Lake Worth, FL (US); Kermit Falk, Orlando, FL (US); Gregory L. Mayback, Cooper City, FL (US)

(73) Assignee: Nervana, LLC, Deerfield Beach, FL (US)

( * ) Notice: Subject to any disclaimer, the term of this patent is extended or adjusted under 35 U.S.C. 154(b) by 0 days.

(21) Appl. No.: 14/738,156

(22) Filed: Jun. 12, 2015

(65) Prior Publication Data

US 2015/0360030 A1 Dec. 17, 2015

Related U.S. Application Data

(60) Provisional application No. 62/011,985, filed on Jun. 13, 2014, provisional application No. 62/121,759, filed on Feb. 27, 2015.

(51) Int. Cl.
  *A61N 1/00* (2006.01)
  *A61N 1/36* (2006.01)
  (Continued)

(52) U.S. Cl.
  CPC ....... *A61N 1/36014* (2013.01); *A61N 1/0456* (2013.01); *A61N 1/0472* (2013.01);
  (Continued)

(58) Field of Classification Search
  CPC .......................... A61N 1/36014; A61N 1/0456
  (Continued)

(56) References Cited

U.S. PATENT DOCUMENTS

| 3,490,458 | A | 1/1970 | Allison |
| 4,503,863 | A | 3/1985 | Katims |

(Continued)

FOREIGN PATENT DOCUMENTS

| WO | 9905519 A1 | 5/1990 |
| WO | 0135896 A1 | 5/2001 |
| WO | 2006073484 A2 | 7/2006 |
| WO | 2010032114 | 3/2010 |
| WO | 2011030214 A1 | 3/2011 |
| WO | 2012127306 A3 | 9/2012 |
| WO | 2015024945 | 2/2015 |

OTHER PUBLICATIONS

EnteroMedics, "EnteroMedics Announces the FDA Has Rescheduled the Advisory Committee Meeting Date to Jun. 17, 2014 for Review of Maestro(R) Rechargeable System," Mar. 10, 2014.

(Continued)

*Primary Examiner* — Nadia A Mahmood  
(74) *Attorney, Agent, or Firm* — Mayback & Hoffman, P.A.; Gregory L. Mayback

(57) ABSTRACT

A transcutaneous electrostimulation device includes an electrostimulation generator providing at an output a nerve electro stimulation signal, an electronic signal conduit conductively connected to the output of the generator, and an electrode coupler shaped to form fit an ear canal of a human ear and having at least one electrostimulation electrode. The electrode is conductively connected to the electronic signal conduit to receive the nerve electrostimulation signal and is positioned at the electrode coupler to contact tissue within an ear canal and apply the nerve electrostimulation signal to the tissue transcutaneously. An audio source outputs audio signals. The electrode coupler has a speaker receiving the audio signals for output into the ear canal when the electrode coupler is worn. The generator sends the nerve electrostimulation signal to the electrode coupler while the audio signals are output. The generator modulates the nerve electrostimulation signal based upon the audio signals.

20 Claims, 63 Drawing Sheets

(51) Int. Cl.
　　　*H04R 1/10*　　　(2006.01)
　　　*A61H 39/00*　　(2006.01)
　　　*A61N 1/04*　　　(2006.01)
　　　*A61N 1/05*　　　(2006.01)

(52) U.S. Cl.
　　　CPC ........ *A61N 1/36032* (2013.01); *A61H 39/002* (2013.01); *A61H 2205/027* (2013.01); *A61N 1/0476* (2013.01); *A61N 1/0526* (2013.01); *H04R 1/1008* (2013.01); *H04R 1/1016* (2013.01)

(58) Field of Classification Search
　　　USPC .............................................. 607/60, 136, 9
　　　See application file for complete search history.

(56) References Cited

U.S. PATENT DOCUMENTS

| | | | |
|---|---|---|---|
| 4,865,048 A | 9/1989 | Eckerson |
| 4,875,484 A | 10/1989 | Anzai |
| 4,966,164 A | 10/1990 | Colsen |
| 5,097,821 A | 3/1992 | Eakin |
| 5,163,444 A | 11/1992 | Braverman |
| 5,205,285 A | 4/1993 | Baker, Jr. |
| 5,231,988 A | 8/1993 | Wernicke et al. |
| 5,263,480 A | 11/1993 | Wernicke |
| 5,269,303 A | 12/1993 | Wernicke |
| 5,299,569 A | 4/1994 | Wernicke |
| 5,304,112 A | 4/1994 | Mrklas et al. |
| 5,324,287 A | 6/1994 | Szeles |
| 5,330,515 A | 7/1994 | Rutecki |
| 5,514,175 A | 5/1996 | Kim et al. |
| 5,540,730 A | 7/1996 | Terry, Jr. et al. |
| 5,540,734 A | 7/1996 | Zabara |
| 5,707,400 A | 1/1998 | Terry, Jr. |
| 5,712,917 A | 1/1998 | Offutt |
| 6,104,956 A | 8/2000 | Naritoku |
| 6,449,507 B1 | 9/2002 | Hill et al. |
| 6,556,868 B2 | 4/2003 | Naritoku |
| 6,564,102 B1 | 5/2003 | Boveja |
| 6,587,719 B1 | 7/2003 | Barrett |
| 6,587,727 B2 | 7/2003 | Osorlo |
| 6,609,025 B2 | 8/2003 | Barrett |
| 6,610,713 B2 | 8/2003 | Tracey |
| 6,622,038 B2 | 9/2003 | Barrett |
| 6,622,047 B2 | 9/2003 | Barrett |
| 6,671,556 B2 | 12/2003 | Osorio |
| 6,684,105 B2 | 1/2004 | Cohen |
| 6,721,603 B2 | 4/2004 | Zabara |
| 6,760,626 B1 | 7/2004 | Boveja |
| 6,920,357 B2 | 7/2005 | Osorio |
| 6,961,618 B2 | 11/2005 | Osorio |
| 7,076,307 B2 | 7/2006 | Boveja |
| 7,142,910 B2 | 11/2006 | Puskas |
| 7,203,548 B2 | 4/2007 | Whitehurst |
| 7,263,405 B2 | 8/2007 | Boveja |
| 7,292,890 B2 | 11/2007 | Whitehurst |
| 7,310,552 B2 | 12/2007 | Puskas |
| 7,310,557 B2 | 12/2007 | Maschino |
| 7,336,993 B1 | 2/2008 | Szeles |
| 7,340,299 B2 | 3/2008 | Puskas |
| 7,403,820 B2 | 7/2008 | DiLorenzo |
| 7,532,935 B2 | 5/2009 | Maschino |
| 7,555,344 B2 | 6/2009 | Maschino |
| 7,596,414 B2 | 9/2009 | Whitehurst |
| 7,613,511 B2 | 11/2009 | Wu |
| 7,620,455 B2 | 11/2009 | Maschino |
| 7,630,757 B2 | 12/2009 | Dorfmeister |
| 7,636,602 B2 | 12/2009 | Fassio |
| 7,657,310 B2 | 2/2010 | Buras |
| 7,660,637 B2 | 2/2010 | Szeles |
| 7,706,875 B2 | 4/2010 | Buras |
| 7,725,188 B2 | 5/2010 | Errico |
| 7,769,461 B2 | 8/2010 | Whitehurst |
| 7,778,703 B2 | 8/2010 | Gross |
| 7,781,486 B2 | 8/2010 | Szeles |
| 7,783,362 B2 | 8/2010 | Whitehurst |
| 7,797,042 B2 | 9/2010 | Dietrich |
| 7,801,603 B2 | 9/2010 | Westlund |
| 7,819,883 B2 | 10/2010 | Westlund |
| 7,840,278 B1 | 11/2010 | Puskas |
| 7,840,280 B2 | 11/2010 | Parnis |
| 7,846,084 B2 | 12/2010 | McNew |
| 7,860,570 B2 | 12/2010 | Whitehurst |
| 7,869,879 B2 | 1/2011 | Errico |
| 7,869,880 B2 | 1/2011 | Errico et al. |
| 7,869,884 B2 | 1/2011 | Scott |
| 7,899,539 B2 | 3/2011 | Whitehurst |
| 7,904,175 B2 | 3/2011 | Scott |
| 7,914,468 B2 | 3/2011 | Shalon |
| 7,917,230 B2 | 3/2011 | Bly |
| 7,962,214 B2 | 6/2011 | Byerman |
| 7,996,088 B2 | 8/2011 | Marrosu |
| 8,010,198 B2 | 8/2011 | Libbus |
| 8,027,724 B2 | 9/2011 | Wei |
| 8,150,508 B2 | 4/2012 | Craig |
| 8,150,524 B2 | 4/2012 | Maschino |
| 8,160,701 B2 | 4/2012 | Zhao |
| 8,175,699 B2 | 5/2012 | Szeles |
| 8,219,188 B2 | 7/2012 | Craig |
| 8,219,202 B2 | 7/2012 | Giftakis et al. |
| 8,280,505 B2 | 10/2012 | Craig |
| 8,290,584 B2 | 10/2012 | Westlund |
| 8,380,315 B2 | 2/2013 | Degiorgio |
| 8,386,045 B2 | 2/2013 | Zhao |
| 8,401,634 B2 | 3/2013 | Whitehurst |
| 8,401,640 B2 | 3/2013 | Zhao |
| 8,406,877 B2 | 3/2013 | Smith |
| 8,412,326 B2 | 4/2013 | Arcot-Krishnamurthy |
| 8,412,334 B2 | 4/2013 | Whitehurst |
| 8,412,338 B2 | 4/2013 | Faltys |
| 8,417,344 B2 | 4/2013 | Colborn |
| 8,423,134 B2 | 4/2013 | Buschman |
| 8,423,157 B2 | 4/2013 | Moffitt |
| 8,428,734 B2 | 4/2013 | Rigaux |
| 8,457,734 B2 | 6/2013 | Libbus |
| 8,504,161 B1 | 8/2013 | Kornet et al. |
| 8,506,469 B2 * | 8/2013 | Dietrich ............. A61N 1/36017 600/9 |
| 8,509,919 B2 | 8/2013 | Yoo |
| 8,543,202 B2 | 9/2013 | Goetz et al. |
| 8,548,604 B2 | 10/2013 | Whitehurst |
| 8,562,536 B2 | 10/2013 | Osorio et al. |
| 8,571,654 B2 | 10/2013 | Libbus |
| 8,577,458 B1 | 11/2013 | Libbus et al. |
| 8,594,805 B2 | 11/2013 | Ordonez |
| 8,600,505 B2 | 12/2013 | Libbus |
| 8,612,002 B2 | 12/2013 | Faltys |
| 8,620,450 B2 | 12/2013 | Tockman |
| 8,630,707 B2 | 1/2014 | Zhao |
| 8,630,709 B2 | 1/2014 | Libbus |
| 8,660,647 B2 | 2/2014 | Parnis |
| 8,660,666 B2 | 2/2014 | Craig |
| 8,676,330 B2 | 3/2014 | Simon |
| 8,700,150 B2 | 4/2014 | Libbus |
| 8,700,163 B2 | 4/2014 | Terry, Jr. |
| 8,702,584 B2 | 4/2014 | Rigaux et al. |
| 8,712,547 B2 | 4/2014 | Whitehurst |
| 8,718,779 B2 | 5/2014 | Whitehurst |
| 8,725,259 B2 | 5/2014 | Kornet |
| 8,750,987 B2 | 6/2014 | Pu |
| 8,755,892 B2 | 6/2014 | Amurthur |
| 8,761,417 B2 | 6/2014 | Oser |
| 8,762,065 B2 | 6/2014 | DiLorenzo |
| 8,768,469 B2 | 7/2014 | Tweden |
| 8,768,471 B2 | 7/2014 | Colborn |
| 8,781,582 B2 | 7/2014 | Ziegler |
| 8,781,583 B2 | 7/2014 | Cornelussen |
| 8,781,597 B2 | 7/2014 | DiLorenzo |
| 8,788,034 B2 | 7/2014 | Levine |
| 8,805,512 B1 | 8/2014 | Greiner et al. |
| 8,805,513 B2 | 8/2014 | Libbus |
| 8,818,524 B2 | 8/2014 | Ordonez |
| 8,838,230 B2 | 9/2014 | Chan |

(56) References Cited

U.S. PATENT DOCUMENTS

| | | |
|---|---|---|
| 8,843,210 B2 | 9/2014 | Simon |
| 8,848,964 B2 | 9/2014 | Erdel |
| 8,849,409 B2 | 9/2014 | Colborn |
| 8,855,767 B2 | 10/2014 | Faltys |
| 8,855,775 B2 | 10/2014 | Leyde |
| 8,868,177 B2 | 10/2014 | Simon |
| 8,874,205 B2 | 10/2014 | Simon |
| 8,874,218 B2 | 10/2014 | Terry, Jr. |
| 8,885,861 B2 | 11/2014 | Beck |
| 8,903,509 B2 | 12/2014 | Tockman |
| 8,914,120 B2 | 12/2014 | Lee |
| 8,914,123 B2 | 12/2014 | Rigaux |
| 8,918,178 B2 | 12/2014 | Simon |
| 8,918,191 B2 | 12/2014 | Libbus |
| 8,923,990 B2 | 12/2014 | Libbus |
| 8,929,990 B2 | 1/2015 | Moffitt |
| 8,942,816 B2 | 1/2015 | Greiner et al. |
| 8,942,824 B2 | 1/2015 | Yoo |
| 8,948,873 B2 | 2/2015 | Simon |
| 8,954,143 B2 | 2/2015 | Thenuware et al. |
| 8,959,687 B2 | 2/2015 | Bond |
| 8,965,511 B2 | 2/2015 | Greiner et al. |
| 8,965,518 B2 | 2/2015 | Ellrich |
| 8,965,522 B2 | 2/2015 | Libbus |
| 8,989,857 B2 | 3/2015 | Heck |
| 8,996,116 B2 | 3/2015 | Faltys |
| 9,002,448 B2 | 4/2015 | Libbus |
| 9,011,355 B2 | 4/2015 | Ehrenreich |
| 9,031,669 B2 | 5/2015 | Zhang |
| 9,037,247 B2 | 5/2015 | Simon |
| 9,042,981 B2 | 5/2015 | Yoo |
| 9,042,988 B2 | 5/2015 | DiLorenzo |
| 9,050,472 B2 | 6/2015 | Arcot-Krishnamurthy |
| 9,061,136 B2 | 6/2015 | Zhao |
| 9,066,845 B2 | 6/2015 | Peterson et al. |
| 9,078,801 B2 | 7/2015 | Greiner et al. |
| 9,079,030 B2 | 7/2015 | Holloway |
| 9,089,267 B2 | 7/2015 | Ordonez |
| 9,089,691 B2 | 7/2015 | Libbus |
| 9,089,716 B2 | 7/2015 | Peterson et al. |
| 9,089,719 B2 | 7/2015 | Simon |
| 9,108,041 B2 | 8/2015 | Craig |
| 9,126,050 B2 | 9/2015 | Simon |
| 9,162,064 B2 | 10/2015 | Faltys |
| 9,173,811 B2 | 11/2015 | Greiner et al. |
| 9,174,041 B2 | 11/2015 | Faltys |
| 9,198,828 B2 | 12/2015 | Greiner et al. |
| 9,205,258 B2 | 12/2015 | Simon |
| 9,211,410 B2 | 12/2015 | Levine |
| 9,211,413 B2 | 12/2015 | Ziegler |
| 9,216,290 B2 | 12/2015 | Terry, Jr. |
| 9,233,243 B2 | 1/2016 | Moon |
| 9,242,085 B2 | 1/2016 | Hershey |
| 2001/0003799 A1 | 6/2001 | Boveja |
| 2003/0045909 A1 | 3/2003 | Gross et al. |
| 2003/0045914 A1 | 3/2003 | Cohen et al. |
| 2005/0049655 A1 | 3/2005 | Boveja et al. |
| 2005/0069161 A1 | 3/2005 | Kaltenbach et al. |
| 2005/0154425 A1 | 7/2005 | Boveja |
| 2005/0154426 A1 | 7/2005 | Boveja |
| 2005/0165458 A1 | 7/2005 | Boveja |
| 2005/0165460 A1* | 7/2005 | Erfan ............... A61N 1/326 607/57 |
| 2006/0064037 A1 | 3/2006 | Shalon |
| 2006/0122675 A1 | 6/2006 | Libbus et al. |
| 2006/0293721 A1 | 12/2006 | Tarver |
| 2007/0027504 A1 | 2/2007 | Barrett |
| 2007/0213786 A1 | 9/2007 | Sackellares |
| 2007/0250145 A1 | 10/2007 | Kraus |
| 2008/0021517 A1 | 1/2008 | Dietrich |
| 2008/0033229 A1 | 2/2008 | Park |
| 2008/0051852 A1 | 2/2008 | Dietrich |
| 2008/0125620 A1 | 5/2008 | McNew |
| 2009/0018462 A1 | 1/2009 | Bell |
| 2009/0082831 A1 | 3/2009 | Paul et al. |
| 2010/0057154 A1 | 3/2010 | Dietrich |
| 2011/0046432 A1 | 2/2011 | Simon et al. |
| 2011/0054569 A1 | 3/2011 | Zitnik et al. |
| 2011/0166546 A1 | 7/2011 | Jaax |
| 2011/0166624 A1 | 7/2011 | Dietrich |
| 2011/0178569 A1 | 7/2011 | Parnis |
| 2011/0208257 A1 | 8/2011 | Labuschagne |
| 2011/0257701 A1 | 10/2011 | Strother et al. |
| 2011/0307029 A1 | 12/2011 | Hargrove |
| 2012/0149973 A1 | 6/2012 | Holloway |
| 2012/0221087 A1 | 8/2012 | Parnis |
| 2012/0226333 A1 | 9/2012 | Szeles |
| 2012/0290035 A1 | 11/2012 | Levine et al. |
| 2012/0316622 A1 | 12/2012 | Whitehurst |
| 2013/0072996 A1* | 3/2013 | Kilgard ............... A61N 1/37235 607/3 |
| 2013/0131746 A1 | 5/2013 | Simon et al. |
| 2013/0150923 A1 | 6/2013 | Schnetz et al. |
| 2013/0184792 A1 | 7/2013 | Simon |
| 2013/0237948 A1 | 9/2013 | Donders et al. |
| 2013/0238050 A1 | 9/2013 | Simon et al. |
| 2013/0245464 A1 | 9/2013 | Colborn |
| 2013/0245486 A1 | 9/2013 | Simon |
| 2013/0303828 A1 | 11/2013 | Hargrove |
| 2013/0310909 A1 | 11/2013 | Simon |
| 2013/0317573 A1 | 11/2013 | Zhu |
| 2013/0317580 A1 | 11/2013 | Simon |
| 2014/0039578 A1 | 2/2014 | Whitehurst |
| 2014/0046406 A1 | 2/2014 | Ellrich et al. |
| 2014/0058189 A1 | 2/2014 | Stubbeman |
| 2014/0126752 A1 | 5/2014 | Beck et al. |
| 2014/0135886 A1 | 5/2014 | Cook et al. |
| 2014/0142654 A1 | 5/2014 | Simon |
| 2014/0148872 A1 | 5/2014 | Goldwasser et al. |
| 2014/0200634 A1 | 7/2014 | Libbus |
| 2014/0206945 A1 | 7/2014 | Liao |
| 2014/0207203 A1 | 7/2014 | Ternes |
| 2014/0213961 A1 | 7/2014 | Whitehurst |
| 2014/0214113 A1 | 7/2014 | Greiner et al. |
| 2014/0214119 A1 | 7/2014 | Greiner et al. |
| 2014/0214125 A1 | 7/2014 | Greiner et al. |
| 2014/0214126 A1 | 7/2014 | Greiner et al. |
| 2014/0236040 A1 | 8/2014 | Moon |
| 2014/0236261 A1 | 8/2014 | Ternes |
| 2014/0243932 A1 | 8/2014 | Libbus |
| 2014/0257438 A1 | 9/2014 | Simon |
| 2014/0324118 A1 | 10/2014 | Simon |
| 2015/0005839 A1 | 1/2015 | Sabesan |
| 2015/0012055 A1 | 1/2015 | Greiner et al. |
| 2015/0012056 A1 | 1/2015 | Greiner et al. |
| 2015/0025421 A1 | 1/2015 | Wagner |
| 2015/0142082 A1 | 5/2015 | Simon |
| 2015/0202433 A1 | 7/2015 | Franke |
| 2015/0216762 A1 | 8/2015 | Oohashi |
| 2015/0265830 A1 | 9/2015 | Simon |
| 2015/0265836 A1 | 9/2015 | Simon |
| 2015/0306392 A1 | 10/2015 | Sabesan |
| 2015/0321006 A1 | 11/2015 | Greiner et al. |
| 2015/0321007 A1 | 11/2015 | Greiner et al. |
| 2015/0321014 A1 | 11/2015 | Peterson et al. |
| 2015/0360030 A1 | 12/2015 | Cartledge |
| 2016/0001096 A1 | 1/2016 | Mishelevich |
| 2016/0008220 A1 | 1/2016 | Greiner et al. |
| 2016/0008221 A1 | 1/2016 | Greiner et al. |
| 2016/0008222 A1 | 1/2016 | Greiner et al. |
| 2016/0008620 A1 | 1/2016 | Stubbeman |

OTHER PUBLICATIONS

Tomé et al., "Protein, amino acids, vagus nerve signaling, and the brain," Am J Clin Nutr 2009; 90(suppl), 838S-843S.

Jones et al., "Transitional Care Interventions to Prevent Readmissions for People With Heart Failure," Comparative Effectiveness Review No. 133. (Prepared by the Research Triangle Institute—University of North Carolina Evidence-based Practice Center under Contract No. 290-2012-00008-I), AHRQ Publication No. 14-EHC021-EF, Rockville, MD: Agency for Healthcare Research and Quality, May 2014.

(56) References Cited

OTHER PUBLICATIONS

Miner et al., "Feasibility of Percutaneous Vagus Nerve Stimulation for the Treatment of Acute Asthma Exacerbations," Academic Emergency Medicine 2012,19: 421-429, 2012.
Rush et al., "Vagus Nerve Stimulation (VNS) for Treatment-Resistant Depressions: A Multicenter Study," Biol Psychiatry 2000, 47: 276-286.
Greif et al., "Transcutaneous Electrical Stimulation of an Auricular Acupuncture Point Decreases Anesthetic Requirement," Anesthesiology 2002; 96: 306-12.
He et al., "Auricular Acupuncture and Vagal Regulation," Evidence-Based Complementary and Alternative Medicine vol. 2012, Article ID 786839.
Ikramuddin et al., "Effect of Reversible Intermittent Intra-abdominal Vagal Nerve Blockade on Morbid Obesity: The ReCharge Randomized Clinical Trial," JAMA. 2014;312(9):915-922.
Wang et al., "Deqi Sensations of Transcutaneous Electrical Nerve Stimulation on Auricular Points," Evidence-Based Complementary and Alternative Medicine vol. 2013, Article ID 371543.
Mandel et al., "Vasoconstriction by Electrical Stimulation: New Approach to Control of Non-Compressible Hemorrhage," Scientific Reports, 3, 2111 (2013).
Vanoli et al., "Vagal Stimulation and Prevention of Sudden Death in Conscious Dogs With a Healed Myocardial Infarction," Circulation Research vol. 68, No. 5 May 1991, 1471.
DiMarco, "Selective Vagal Stimulation for Rate Control in Atrial Fibrillation," Circulation, 2002;106:1746-1747.
Ando et al., "Efferent Vagal Nerve Stimulation Protects Heart Against Ischemia-Induced Arrhythmias by Preserving Connexin43 Protein," Circulation. 2005;112:164-170 (Jul. 12, 2005).
Hauptman et al., "Rationale and study design of the INcrease of Vagal TonE in Heart Failure study: INOVATE-HF," Am Heart J 2012;163:954-962.e1 (Jun. 2012).
Butler et al., "Hospital Strategies to Reduce Heart Failure Readmissions: Where Is the Evidence?," JACC vol. 60, No. 7, 2012, 615-617 (Aug. 14, 2012).
Széles et al., "Peripheral blood perfusion controlled by auricular vagus nerve stimulation," ktu International Conference "Biomedical Engineering," vol. 17, No. 1 (2013), 73-77.
Smith, "Cranial Electrotherapy Stimulation: Its First Fifty Years, Plus Three—A Monograph," Tate Publishing (2008).
Schmitt et al., "Cranial Electrotherapy Stimulation as a Treatment for Anxiety in Chemically Dependent Persons," Alcoholism: Clinical and Experimental Research, vol. 10, No. 2, Mar./Apr. 1986.
Rosenthal, "Electrosleep: A Double-Blind Clinical Study," Biological Psychiatry, vol. 4, No. 2, 1972, p. 179.
Bystritsky et al., "A Pilot Study of Cranial Electrotherapy Stimulation for Generalized Anxiety Disorder," J. Clin. Psyciatry 69:3 Mar. 2008, p. 412-417.
Gilula et al., "Cranial Electrotherapy Stimulation Review: A Safer Alternative to Psychopharmaceuticals in the Treatment of Depression," Journal of Neurotherapy, vol. 9(2) 2005, p. 7.
Winick, "Cranial electrotherapy stimulation (CES): A Safe and Effective Low Cost Means of Anxiety Control in a Dental Practice," General Dentistry, Jan.-Feb. 1999, p. 50.
Overcash, "Cranial Electrotherapy Stimulation in Patients Suffering from Acute Anxiety Disorders," American Journal of Electromedicine, 16(1): 49-51, 1999.
De Felice, "Cranial Electrotherapy Stimulation (CES) in the Treatment of Anxiety and Other Stress-Related Disorders: A Review of Controlled Clinical Trials," Stress Medicine, vol. 13: 31-42 (1997).
Gunther et al., "Cranial Electrotherapy Stimulation for the Treatment of Depression," Journal of Psychosocial Nursing, vol. 48, No. 11, 2010, p. 37.
Greenman et al., "A double-blind randomized placebo controlled study of cranial electrotherapy stimulation for the treatment of depression in bipolar II disorder," Beth Israel Mt. Sinai Medical Center, New York, NY, The Family Center for Bipolar (May 9, 2014).

Ryan et al., "Effects of Transcerebral Electrotherapy (Electrosleep) on State Anxiety According to Suggestibility Levels," Biological Psychiatry, vol. 11, No. 2, 1976, p. 233.
Philip et al., "Efficiency of Transcranial Electrostimulation on Anxiety and Insomnia Symptoms During a Washout Period in Depressed Patients: A Double-Blind Study," Biological Psychiatry, Mar. 1, 1991; 29(5) p. 451-456.
Von Richthofen et al., "Electrosleep Therapy: A Controlled Study of Its Effects in Anxiety Neurosis," Can. J. Psychiatry vol. 25, No. 3, p. 213.
Krupitsky et al., "The Administration of Transcranial Electric Treatment for Affective Disturbances Therapy in Alcoholic Patients," Drug and Alcohol Dependence, 27 (1991), 1-6.
Shealy et al., "Cerebrospinal Fluid and Plasma Neurochemicals: Response to Cranial Electrical Stimulation," J. Neurol Orthop Med Surg (1998) 18:94-97.
Shealy et al., "Depression: A Diagnostic, Neurochemical Profile & Therapy with Cranial Electrical Stimulation (CES)," Journal of Neurological & Orthopaedic Medicine & Surgery, vol. 10, Issue 4, Dec. 1989.
Liss et al., "Modulated Electric Energy Stimulators," Report presented at the American Academy of Pain Management Conference, Las Vegas, NV, Sep. 1999.
Liss et al., "Physiological and Therapeutic Effects of High Frequency Electrical Pulses," Integrative Physiological and Behavioral Science, Apr.-Jun. 1996, vol. 31, No. 2, 88-94.
Habib et al., "Alternating Low Frequency Stimulation of Medial Septal and Commissural Fibers Induces NMDA-Dependent, Long-Lasting Potentiation of Hippocampal Synapses in Urethane-Anesthetized Rats," Hippocampus 19:299-307 (2009).
Ferdjallah et al., "Potential and Current Density Distributions of Cranial Electrotherapy Stimulation (CES) in a Four-Concentric-Spheres Model," IEEE Transactions on Biomedical Engineering, vol. 43, No. 9, Sep. 1996.
Lande et al., "Efficacy of cranial electric stimulation for the treatment of insomnia: A randomized pilot study," Complementary Therapies in Medicine (2013) 21, 8-13.
Hearst et al., "Electrosleep Therapy: A Double-Blind Trial," Arch Gen Psychiatry, vol. 30, Apr. 1974.
Rosenthal et al., "Electrosleep—A Clinical Trial," Amer. J. Psychiat. 127:4, Oct. 1970, p. 175.
Kentucky Sleep Society, "Quarterly Newsletter," Kentucky Sleep Society, Quarterly Newsletter, Sep. 2011.
Weiss, "The Treatment of Insomnia Through the Use of Electrosleep: An EEG Study," The Journal of Nervous and Mental Disease, vol. 157, No. 2, p. 108.
Gabis et al., "Pain Reduction Using Transcranial Electrostimulation: A Double-Blind 'Active Placebo' Controlled Trial," J Rehabil Med 2009; 41: 256-261.
Lichtbroun et al., "The Treatment of Fibromyalgia with Cranial Electrotherapy Stimulation," Journal of Clinical Rheumatology, vol. 7, No. 2, Apr. 2001, p. 72.
Gabis et al., "Immediate Influence of Transcranial Electrostimulation on Pain and β-Endorphin Blood Levels: An Active Placebo-Controlled Study," Am J Phys Med Rehabil 2003; 82: 81-85.
Tan et al., "Efficacy of cranial electrotherapy stimulation for neuropathic pain following spinal cord injury: a multi-site randomized controlled trial with a secondary 6-month open-label phase," The Journal of Spinal Cord Medicine (2011) vol. 34, No. 3, p. 285.
Kirsch et al., "The Use of Cranial Electrotherapy Stimulation in the Management of Chronic Pain: A Review," NeuroRehabilitation 14 (2000) 85-94.
Davis et al., "Serotonin and central nervous system fatigue: nutritional considerations," Am J Clin Nutr 2000, 72(suppl): 573S-8S.
Sackeim et al., "Vagus Nerve Stimulation (VNS™) for Treatment-Resistant Depression: Efficacy, Side Effects, and Predictors of Outcome," Neuropsychopharmacology 2001, vol. 25, No. 5.
George et al., "Noninvasive techniques for probing neurocircuitry and treating illness: vagus nerve stimulation (VNS), transcranial magnetic stimulation (TMS) and transcranial direct current stimulation (tDCS)," Neuropsychopharmacology Reviews (2010) 35, 301-316.

(56) References Cited

OTHER PUBLICATIONS

Rong et al., "Transcutaneous vagus nerve stimulation for the treatment of depression: a study protocol for a double blinded randomized clinical trial," BMC Complementary and Alternative Medicine 2012, 12: 255.
International Search Report & Written Opinion of PCT/US15/35715 dated Sep. 16, 2015.
Clancy, et al., "Non-invasive Vagus Nerve Stimulation in Healthy Humans Reduces Sympathetic Nerve Activity", Brain Stimulation Journal, Nov.-Dec. 2014, pp. 871-877, vol. 7, Issue 6.
Roger Dobson, "The ear tickler that helps you lose weight: electrical pulses interfere with appetite signals between the stomach and brain", https://www.dailymail.co.uk, Feb. 10, 2016, England.
Centre Hospitalier Universitaire De Saint-Étienne, France, "Preoperative Treatment With Noninvasive: Intra-auricular Vagus Nerve Stimulation Pending Bariatric Surgery (OBESITE)" (Full Text View & Tabular View), https://www.clinicaltrials.gov, Jan. 5, 2016.
Biegler GMBH, "Electrical stimulation, P-STIM", www.biegler.com/pstim.en.html, Aug. 17, 2015.
Kraus et al., "BOLD fMRI deactivation of limbic and temporal brain structures and mood enhancing effect by transcutaneous vagus nerve stimulation," J Neural Transm (2007) 114: 1485-1493.
Frangos et al., "Activation of Human Vagus Nerve Afferent Projections via Electrical Stimulation of External Ear: fMRI Evidence," Annual Meeting of the Society for Neuroscience, Neuroscience 2012, Oct. 2012, pp. 891.09/MM17.
Gandolla et al., "Functional Electrical Stimulation: FMRI Study of Mechanism of Action in Healthy Subjects," NeuroEngineering and Medical Robotics Laboratory, Politecnico di Milano, 2012.
Saiote et al., "Combining functional magnetic resonance imaging with transcranial electrical stimulation," Frontiers in Human Neuroscience, Aug. 5, 2013, vol. 7, Article 435.
Liu et al., "BOLD fMRI activation induced by vagus nerve stimulation in seizure patients," J Neurol Neurosurg Psychiatry 2003, 74: 811-813.
Antal et al., "Imaging artifacts induced by electrical stimulation during conventional fMRI of the brain," Neuroimage, Jan. 15, 2014; 85(0 3).
Hosoi et al., "Electrical stimulation of afferent vagus nerve induces IL-1β expression in the brain and activates HPA axis," Am J Physiol Regulatory Integrative Comp Physiol, 279: R141-R147, 2000.
Beekwilder et al., "Overview of the Clinical Applications of Vagus Nerve Stimulation," J Clin Neurophysiol 2010; 27(2): 130-138.
Pavlov et al., "The vagus nerve and the inflammatory reflex—linking immunity and metabolism," Nat Rev Endocrinol. Dec. 2012, 8(12): 743-54, Figure 1.
van Bree et al., "New therapeutic strategies for postoperative ileus," Nat Rev Gastroenterol Hepatol. Nov. 2012, 9(11): 675-83., Figure 1.
Hiraki et al., "The effect of vagus nerve stimulation during transient focal cerebral ischemia on chronic outcome in rats," J Neurosci Res. Apr. 2012, 90(4): 887-894.
Kampusch et al., "Expected Effects of Auricular Vagus Nerve Stimulation in Dystonia," Biomed Tech 2013; 58 (Suppl. 1) 2013.
Taylor et al., "An in vivo investigation in motor learning with the use of transcutaneous vagus nerve stimulation," Presented at Manchester Life Sciences PhD Conference 2013.
Abou-Setta et al., "Pain Management Interventions for Hip Fracture," Comparative Effectiveness Review No. 30 (Prepared by the University of Alberta Evidence-based Practice Center under Contract No. 290-02-0023.) AHRQ Publication No. 11-EHCO22-EF, Rockville, MD: Agency for Healthcare Research and Quality, May 2011.
Holloszy et al., "Adaptations of Skeletal Muscle to Endurance Exercise and Their Metabolic Consequences," J. Appl. Physiol.: Respirat. Environ. Exercise Physiol. 56(4): 831-838, 1984.
Baggish et al., "Athlete's Heart and Cardiovascular Care of the Athlete: Scientific and Clinical Update," Circulation, 2011, 123: 2723-2735.

Asher et al., "Auriculotherapy for Pain Management: A Systematic Review and Meta-Analysis of Randomized Controlled Trials," The Journal of Alternative and Complementary Medicine, 2010, pp. 1097-1108, vol. 16, No. 10.
Kelly, "Wearable Tech to Hack Your Brain," CNN Tech, Oct. 23, 2014, available at: http://www.cnn.com/2014/10/22/tech/innovation/brain-stimulation-tech/.
Manta, Stella et al, Optimization of vagus nerve stimulation parameters using the firing activity of serotonin neurons in the rat dorsal raphe, European Neuropsychopharmacology (2009) 19, pp. 250-255, 2008 Elsevier B.V. and ECNP.
Mcswiney, B.A. et al., The Response of Smooth Muscle to Stimulation of the Vagus Nerve., pp. 124-131, Department of Physiology, the University of Leeds.
Merrill, Daniel R. et al., Electrical stimulation of excitable tissue: design of efficacious and safe protocols, Journal of Neuroscience Methods 141 (2005), pp. 171-198, Elsevier B.V.
Nemeroff, Charles B. et al., VNS Therapy in Treatment-Resistant Depression: Clinical Evidence and Putative NeurobiologiGal Mechanisms, Neuropsychopharmacology (2006) 31, pp. 1345-1355, 2006 Nature Publishing Group.
Olofsson, Peder S. et al., A Stimulating Concept: Bioelectronic Medicine in Inflammatory Disease, Department of Biomedical Sciences, 2014, pp. 30-33, The Feinstein Institute for Medical Research, New York, United States of America.
Olofsson, Peder S. et al., Single-Pulse and Unidirectional Electrical Activation of the Cervical Vagus Nerve Reduces Tumor Necrosis Factor in Endotoxemia, Bioelectron Med 2, 2015, pp. 37-42, The Feinstein Institute for Medical Research, Published Online(www.bioelecmed.org).
Pecanha De Oliveira, Tiago et al., Post-Exercise Cardiac Full Vagal Reactivation: Initial Proposal and Influence of Physical Training, Journal of the American Society of Exercise Physiologists, Dec. 2012, pp. 103-111, vol. 15 No. 6, ASEP organization.
Raedt, Robrecht et al., Increased hippocampal noradrenaline is a biomarker for efficacy of vagus nerve stimulation in a limbic seizure model, J. Neurochem. (2011) 117, pp. 461-469, Journal of Neurochemistry, 2011, International Society for Neurochemistry.
Schauerte, Patrick et al., Ventricular Rate Control During Atrial Fibrillation by Cardiac Parasympathetic Nerve Stimulation: A Transvenous Approach, Journal of the American College of Cardiology, pp. 2043-2050, vol. 34, No. 1, 1999, Published by Elsevier Science Inc.
Sellaro, Roberta et al., Transcutaneous Vagus Nerve Stimulation Enhances Post-error Slowing, Journal of Cognitive Neuroscience 27:11, pp. 2126-2132, 2015 Massachusetts Institute of Technology, Leiden University, USA.
Shepherd, Robert K. et al., Electrical stimulation of the auditory nerve: II. Eject of stimulus waveshape on single ¢ bre response properties, Hearing Research 130 (1999), pp. 171-188, 1999 Elsevier Science B.V.
Shetake, Jai A. et al., Pairing tone trains with vagus nerve stimulation induces temporal plasticity in auditory cortex, Journal, Experimental Neurology 233 (2012) pp. 342-349, 2011 Elsevier Inc.
Silberstein MD, Stephen D. et al., Chronic migraine headache prevention with noninvasive vagus nerve stimulation, The EVENT Study, Journal, Neurology, pp. 1-11, 2016 American Academy of Neurology.
Smith, Jody et al., What Happens in the Vagus Nerve Doesn't Stay There, Research Says, 2015 HW, LLC d/b/a EmpowHER Media, p. 4, Published on EmpowHER.
Stanley, Jamie et al., Cardiac Parasympathetic Reactivation Following Exercise: Implications for Training Prescription, Sports Med (2013) 43: pp. 1259-1277, Springer International Publishing Switzerland 2013.
Stanley, Jamie et al., The effect of post-exercise hydrotherapy on subsequent exercise performance and heart rate variability, Eur J Appl Physiol (2012) 112: pp. 951-961, Jun. 28, 2011, Springer-Verlag 2011.
Steenbergen, Laura et al., Transcutaneous vagus nerve stimulation (tVNS) enhances response selection during action cascading pro-

(56) References Cited

OTHER PUBLICATIONS cesses, European Neuropsychopharmacology (2015) 25, pp. 773-778, 2015 Elsevier B.V. and ECNP.

Terry Jr, Reese S. et al., Vagus Nerve Stimulation Therapy for Epilepsy, 2014 The Author(s) pages 139-160, Chapter 7, Licensee InTech.

Yamakawa, Kazuma et al., Electrical Vagus Nerve Stimulation Attenuates Systemic Inflammation and Improves Survival in a Rat Heatstroke Model, Plos One, pp. 1-7, vol. 8, Issue 2, e56728, PLOS ONE.

Yin, Jieyun et al, Gastrointestinal Electrical Neuromodulation for Functional Gastrointestinal Diseases, Obesity and Diabetes, Bioelectron Med 2:13—19, 2015, pp. 13-19, Jan. 28, 2015. Bioelectronic Medicine.

Zhang, MD, Youhua et al., Chronic Vagus Nerve Stimulation Improves Autonomic Control and Attenuates Systemic Inflammation and Heart Failure Progression in a Canine High-Rate Pacing Model, Article, 2009, pp. 692-699, 2009 American Heart Association, Inc.

Bahmer, et al., Recording of electrically evoked auditory brainstem responses after electrical stimulation with biphasic, triphasic and precision triphasic pulses, Hearing Research, 259 (2010), pp. 75-85, 2009 Elsevier B.V.

Bain, et al., Non-Invasive Neuromodulation of the Central Nervous System: Opportunities and Challenges: Workshop Summary, The National Academies of Sciences, Engineering, Medicine, 6 x 9 Paperback (2015), 118 pages, The National Academy of Sciences, Washington, DC.

Barnett, Anthony et al., Using Recovery Modalities between Training Sessions in Elite Athletes Does it Help?, Sports Med 2006; 36 (9): pp. 781-796, 2006 Adis Data Information B.V.

Ben-Menachem, E. et al., Surgically implanted and non-invasive vagus nerve stimulation: a review of efficacy, safety and tolerability, European Journal of Neurology, 2015, 22: pp. 1260-1268, published by John Wiley & Sons Ltd on behalf of European Academy of Neurology.

Berthoud, et al., Functional and chemical anatomy of the afferent vagal system, Autonomic Neuroscience: Basic and Clinical 85 (2000), pp. 1-17, 2000 Elsevier Science B.V.

Bonaz,Bruno et al., Anti-inflammatory properties of the vagus nerve: potential therapeutic implications of vagus serve stimulation, The Journal of Physiology, 000.0 (2016), pp. 1-10, 2016 The Authors. The Journal of Physiology, the Physiological Society.

Borland, M.S. et al., Cortical Map Plasticity as a Function of Vagus Nerve Stimulation Intensity, Brain Stimulation 9 (2016), pp. 117-123, 2015 Elsevier Inc.

Brock, C. et al., A Report on 2 Studies of the Effects of non-invasive Vagus Nerve Stimulation (nVNS) on Autonomic and Inflammatory Parameters in Healthy Humans, Poster, http://vnsociety.com/wp-content/uploads/2015/11/Brock-2015-WCI-Poster-A-Report-on-2-Studies-of-the-Effects-of-nVNS-on-Autonomic-and-Inflammatory-Parameters-in-Healthy-Humans.pdf.

Buchheit, Martin et al., Monitoring endurance running performance using cardiac parasympathetic function, Eur J Appl Physiol (2010) 108: pp. 1153-1167, Springer-Verlag 2009.

Busch, Volker et al., The effect of transcutaneous vagus nerve stimulation on pain perception e An experimental study, Brain Stimulation 6 (2013) pp. 202-209, 2013 Elsevier Inc.

Capone, Fioravante et al., The effect of transcutaneous vagus nerve stimulation on cortical excitability, J Neural Transm (2015) 122: pp. 679-685, Springer-Verlag Wien 2014,.

Clinical Trials, et al., Nervana, NCT01569789: Effects of Auricular Vagus Nerve Stimulation on the Pro-Inflammatory Cytokine Response in Healthy Adults, PowerPoint, Clinical Trials PPT 8.2015.

Cooke, Martin et al., The foreign language cocktail party problem: Energetic and informational masking effects in non-native speech perception, J. Acoust. Soc. Am., 123 (1), pp. 414-427, 2008 Acoustical Society of America.

Cyberonics, Inc., et al., Implantable Neurostimulator-Implemented Method for Enhancing Post-Exercise Recovery through Vagus Nerve Stimulation, Report Information from ProQuest, Jul. 11, 2016 18:59, pp. i, ii, 1-7, 2016 ProQuest LLC.

Czura, Christopher J. et al., Vagus Nerve Stimulation Regulates Hemostasis in Swine, NIH PA, Author Manuscript, Shock. Jun. 2010; 33(6): pp. 608-613., National Institutes of Health, PMC Aug. 13, 2010.

Davidovics, Natan S. et al., Effects of Biphasic Current Pulse Frequency, Amplitude, Duration and Interphase Gap on Eye Movement Responses to Prosthetic Electrical Stimulation of the Vestibular Nerve, NIH PA, Author Manuscript, Feb. 2011; 19(1): pp., 84-94, National Institutes of Health, IEEE Trans Neural Syst Rehabil Eng. 2011.

De Ferrari, Gaetano M. et al., Chronic vagus nerve stimulation: a new and promising therapeutic approach for chronic heart failure, European Heart Journal (2011) 32, pp. 847-855, The Author 2010, European Society of Cardiology.

Doucet, Barbara M. et al., Neuromuscular Electrical Stimulation for Skeletal Muscle Function, Yale Journal of Biology and Medicine 85 (2012), pp. 201-215. Copyright © 2012.

Ellrich, Jens et al., Transcutaneous Vagus Nerve Stimulation, European Neurological Review, 2011;6(4): pp. 262-4, Touch Briefings 2011,.

Engineer, Navzer D. et al., Directing neural plasticity to understand and treat tinnitus, Hearing Research 295 (2013), pp. 58-66, 2012 Elsevier B.V.

Extreme Biometrics, et al., ExtremeBiometrics Control Human PerformanceTM, Powerpoint slides, pp. 1-10, Motor Sports.

Fang, et al., Transcutaneous Vagus Nerve Stimulation Modulates Default Mode Network in Major Depressive Disorder, Biological Psychiatry Feb. 15, 2016, pp. 79:266-273, 2016 Published by Elsevier Inc on behalf of Society of Biological Psychiatry.

Frangos, Eleni et al., Non-invasive Access to the Vagus Nerve Central Projections via Electrical Stimulation of the External Ear: fMRI Evidence in Humans, Brain Stimulation 8 (2015), pp. 624-636, 2015 Elsevier Inc.

Ghacibeh, Georges A. et al., Effect of vagus nerve stimulation on creativity and cognitive flexibility, Epilepsy & Behavior 8 (2006), pp. 720-725, 2006 Elsevier Inc.

Gold, MD, PHD, Michael R. et al., Vagus Nerve Stimulation for the Treatment of Heart Failure, Journal of the American College of Cardiology, 2016, pp. 149-158, vol. 68, No. 2, Published by Elsevier, 2016 by the American College of Cardiology Foundation.

Goldstone, B.W. et al., The Role of the Vagus Nerve in Cardiac Adaptation to Exercise, Pflfigers Arch. 325, (1971) pp. 113-124, by Springer-Verlag 1971.

Guillem, Francois et al., Are cholinergic enhancers beneficial for memory in schizophrenia? An event-related potentials (ERPs) study of rivastigmine add-on therapy in a crossover trial, Progress in Neuro-Psychopharmacology & Biological Psychiatry 30 (2006) pp. 934-945, 2006 Elsevier Inc.

He,Wei et al., The auriculo-vagal afferent pathway and its role in seizure suppression in rats, BMC Neuroscience 2013, 14:85, pp. 1-9 Research Article, BioMed Central Ltd.,.

Hofmann, Lorenz et al., Modified pulse shapes for effective neural stimulation, Original Research Article, Sep. 28, 2011, pp. 1-10, vol. 4, Article 9, Frontiers in Neuroenginneering.

Huang, Christie Q. et al., Electrical Stimulation of the Auditory Nerve: Direct Current Measurement in vivo, IEEE Transactions on Biomedical Engineering, (1999) pp. 461-470, vol. 46, No. 4, April 1999, 1999 IEEE.

Hyvärinen, Petteri et al., Transcutaneous Vagus Nerve Stimulation Modulates Tinnitus-Related Beta— and Gamma-Band Activity, Article in Ear and Hearing— Nov. 2014, pp. 1-10, PubMed, • Ear & Hearing • Copyright © 2014 by Lippincott Williams & Wilkins• Printed in the U.S.A.

Iacono, Maria I. et al., MIDA: A Multimodal Imaging-Based Detailed Anatomical Model of the Human Head and Neck, Research Article, 2015, pp. 1-35, Published: Apr. 22, 2015, PLOS ONE, Denmark.

(56) References Cited

OTHER PUBLICATIONS

Ingvalson, Erin M. et al., Bilingual speech perception and learning: A review of recent trends, International Journal of Bilingualism, 2014, pp. 35-47, vol. 18(1) , © The Author(s) 2012, University of Maryland on May 2, 2016.

Jacobs, Heidi I. et al., Transcutaneous vagus nerve stimulation boosts associative memory in older individuals, Neurobiology of Aging 36 (2015), pp. 1860-1867, 2015 Elsevier Inc.

Kampusch, Stefan et al., Modulation of Muscle Tone and Sympathovagal Balance in Cervical Dystonia Using Percutaneous Stimulation of the Auricular Vagus Nerve, Artificial Organs 2015, pp. E202-E212, vol. 39, No. 10, Copyright © 2015 International Center for Artificial Organs and Transplantation and Wiley Periodicals, Inc.

Koopman, Frieda A. et al., Vagus nerve stimulation inhibits cytokine production and attenuates disease severity in rheumatoid arthritis, Article, 2016, pp. 1-6, Edited by Ruslan Medzhitov, Yale University School of Medicine, New Haven, CT, and approved Jun. 1, 2016, PNAS Early Edition.

Kraus, Thomas et al., CNS Bold fMRI Effects of Sham-Controlled Transcutaneous Electrical Nerve Stimulation in be Left Outer Auditory Canal— A Pilot Study, Brain Stimulation 6 (2013), pp. 798-804, 2013 Elsevier Inc.

Lecumberri, Maria L. et al., Non-native speech perception in adverse conditions: A review, Speech Communication 52 (2010), pp. 864-886, 2010 Elsevier B.V.

Lee, Steven W. et al., Chronic cyclic vagus nerve stimulation has beneficial electrophysiological effects on healthy hearts in the absence of autonomic imbalance, Physiological Reports ISSN 2051-817X, pp. 1-8, vol. 4, Iss. 9, e.12786, 2016 published by Wiley Periodicals, Inc. on behalf of the American Physiological Society and The Physiological Society. 2016.

Lengeris, Angelos et al., The effect of native vowel processing ability and frequency discrimination acuity on the phonetic training of English vowels for native speakers of Greek, J. Acoust. Soc. Am. 128 (6), Dec. 2010, pp. 3757-3768, vol. 128, No. 6, 2010 Acoustical Society of America.

Levine, Yaakov A. et al., Neurostimulation of the Cholinergic Antiinflammatory Pathway in Rheumatoid Arthritis and Inflammatory Bowel Disease, Bioelectronic Medicine, 2014, pp. 34-43, Published Online (www.bioelecmed.org) Dec. 2, 2014.

Lewis, M.E. et al., Vagus nerve stimulation decreases left ventricular contractility in vivo in the human and pig heart, Journal of Physiology (2001) 534.2, pp. 547-552, J. Physiol.

Li, Meihua et al., Vagal Nerve Stimulation Markedly Improves Long-Term Survival After Chronic Heart Failure in Rats, Journal of the American Heart Association, Jan. 6, 2013, 2004; 109, pp. 120-124, 2004 American Heart Association,.

Lynch, Cheryl L. et al., Functional Electrical Stimulation, Closed-Loop Control of Induced Muscle Contractions, IEEE Control Systems Magazine, Apr. 2008, pp. 40-50.

Manta, Stella et al, Enhancement of the function of rat serotonin and norepinephrine neurons by sustained vagus serve stimulation, J Psychiatry Neurosci 2009;34(4): pp. 272-80., 2009 Canadian Medical Association.

\* cited by examiner

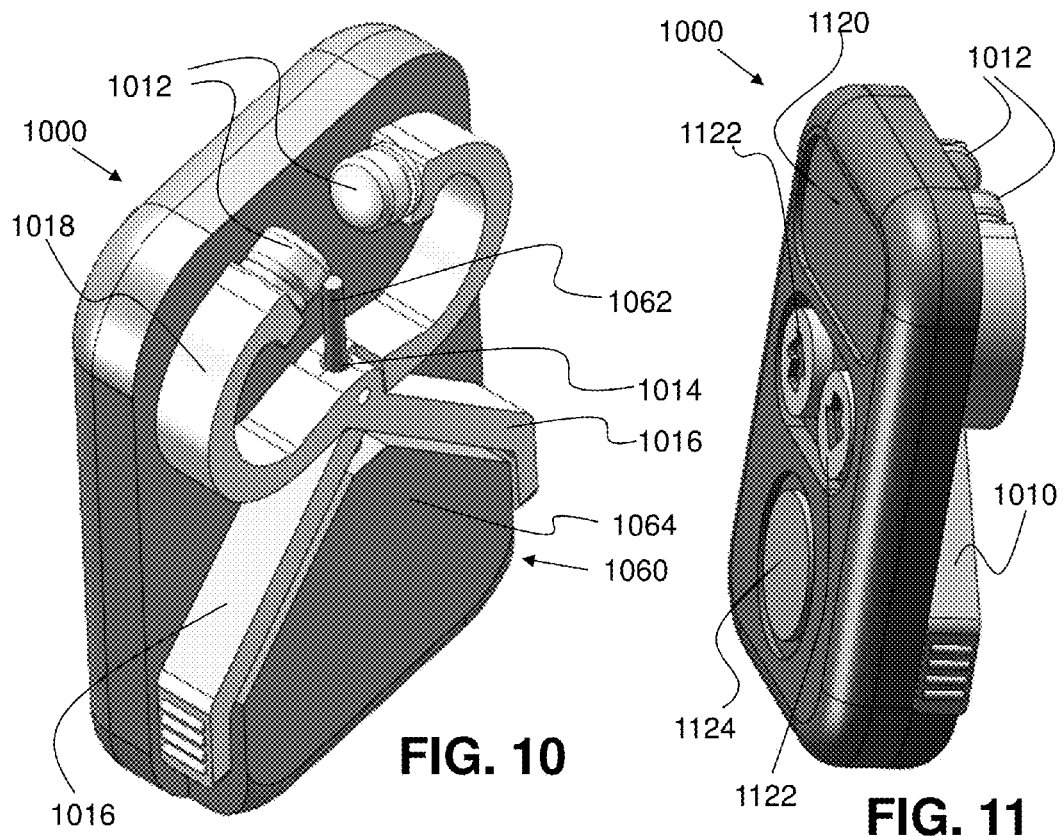

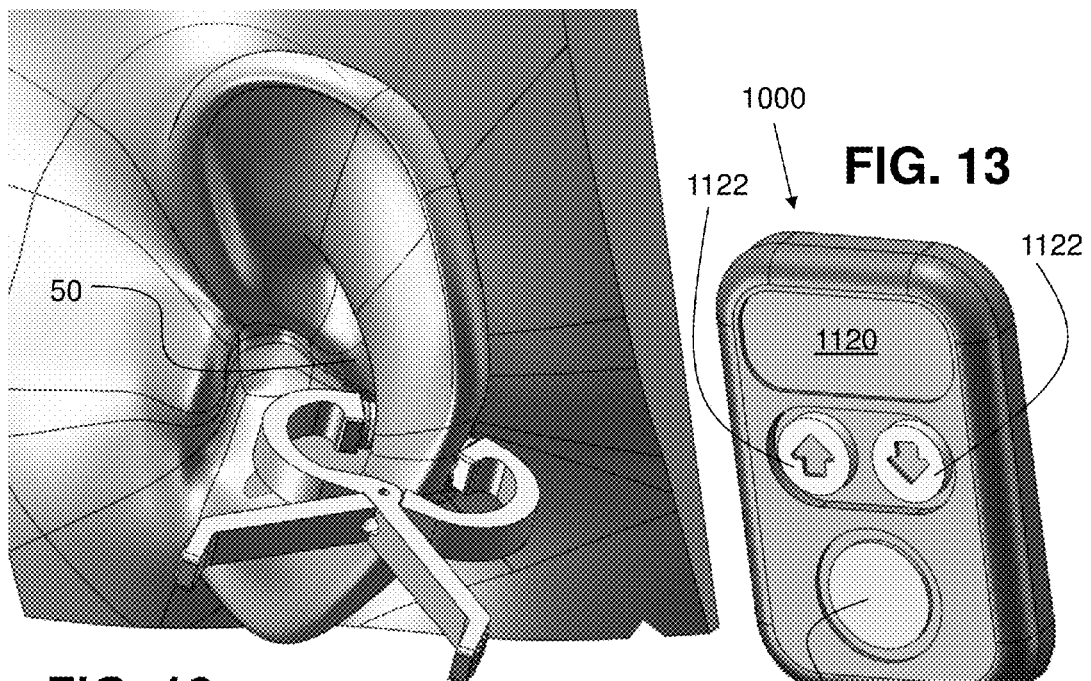
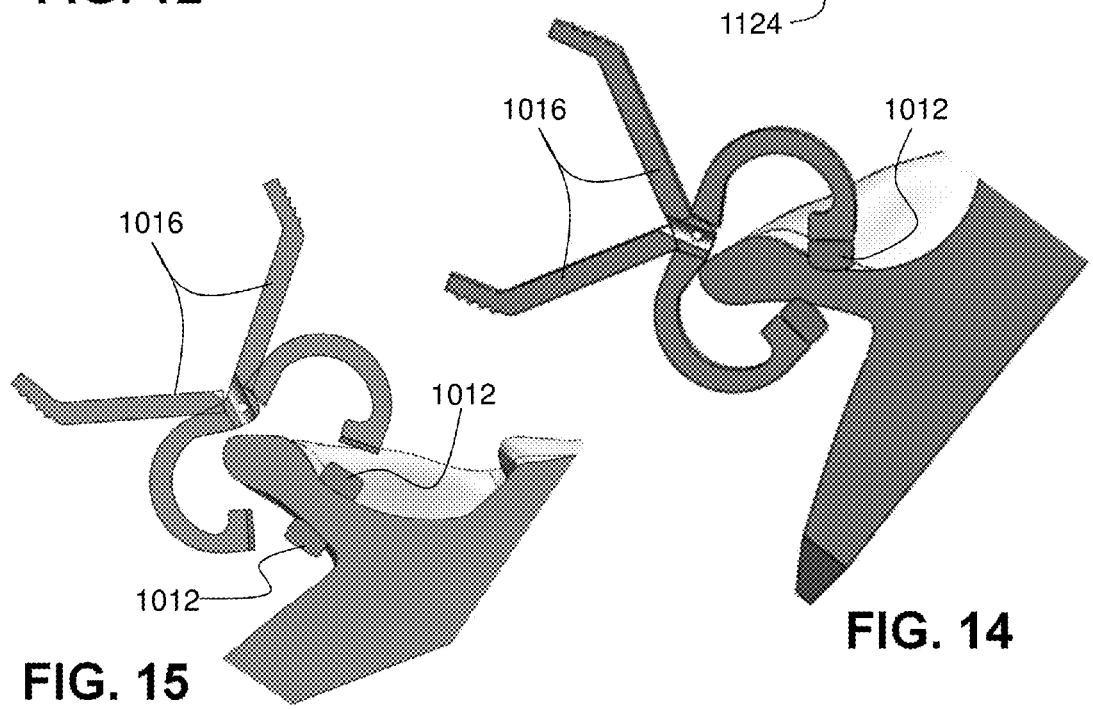
FIG. 12
FIG. 13
FIG. 14
FIG. 15

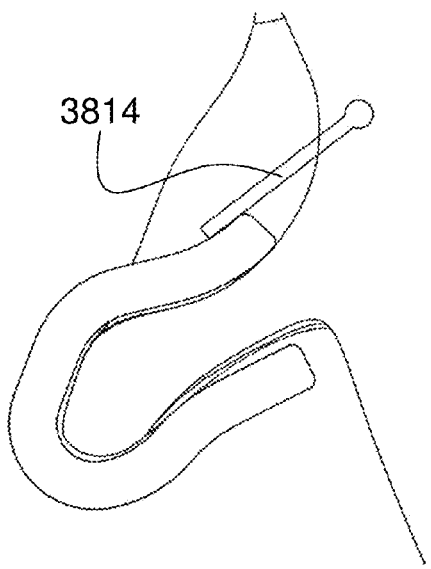
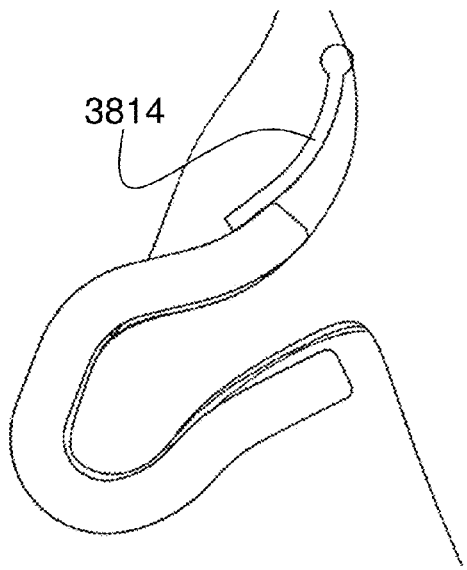
FIG. 38          FIG. 39
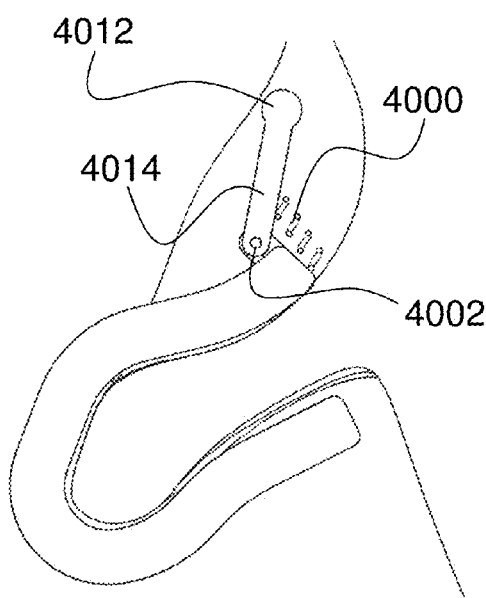
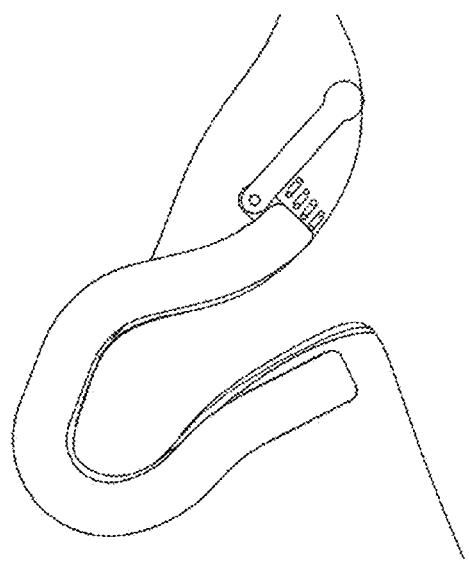
FIG. 40          FIG. 41

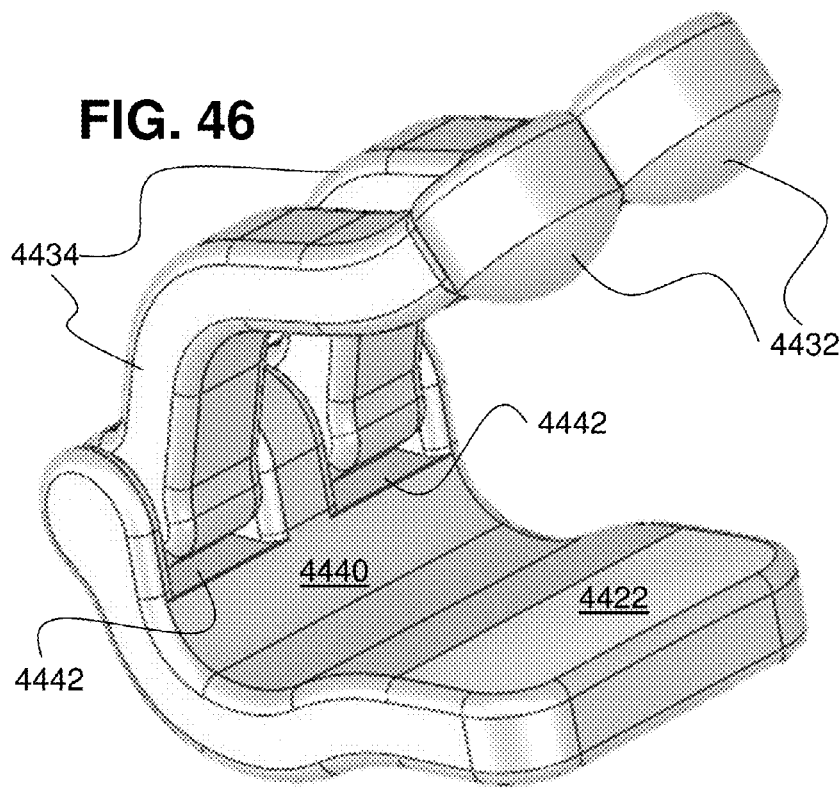
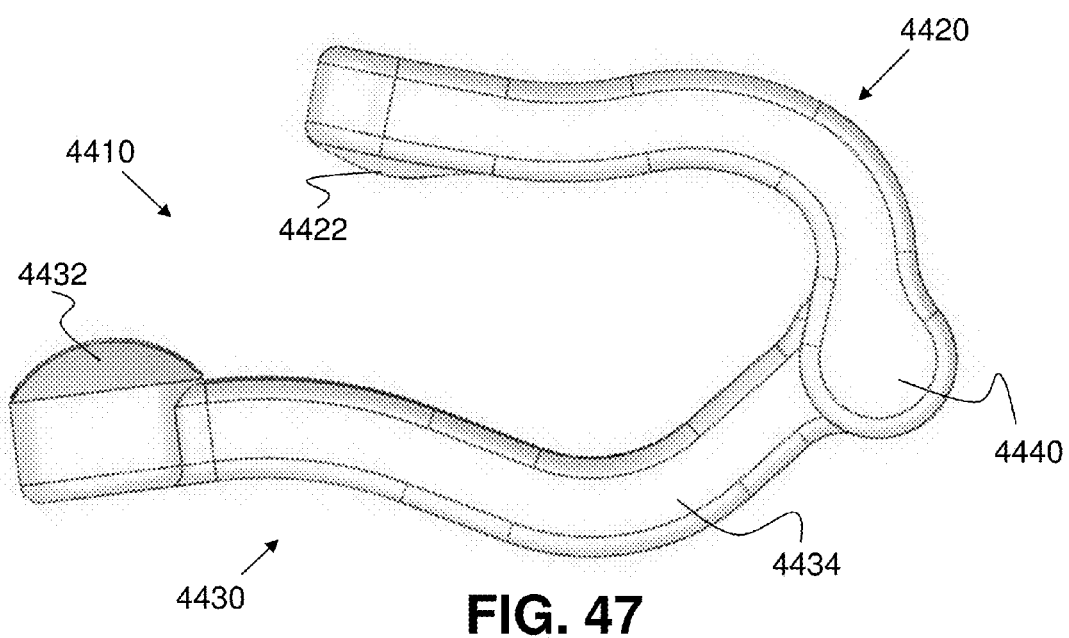

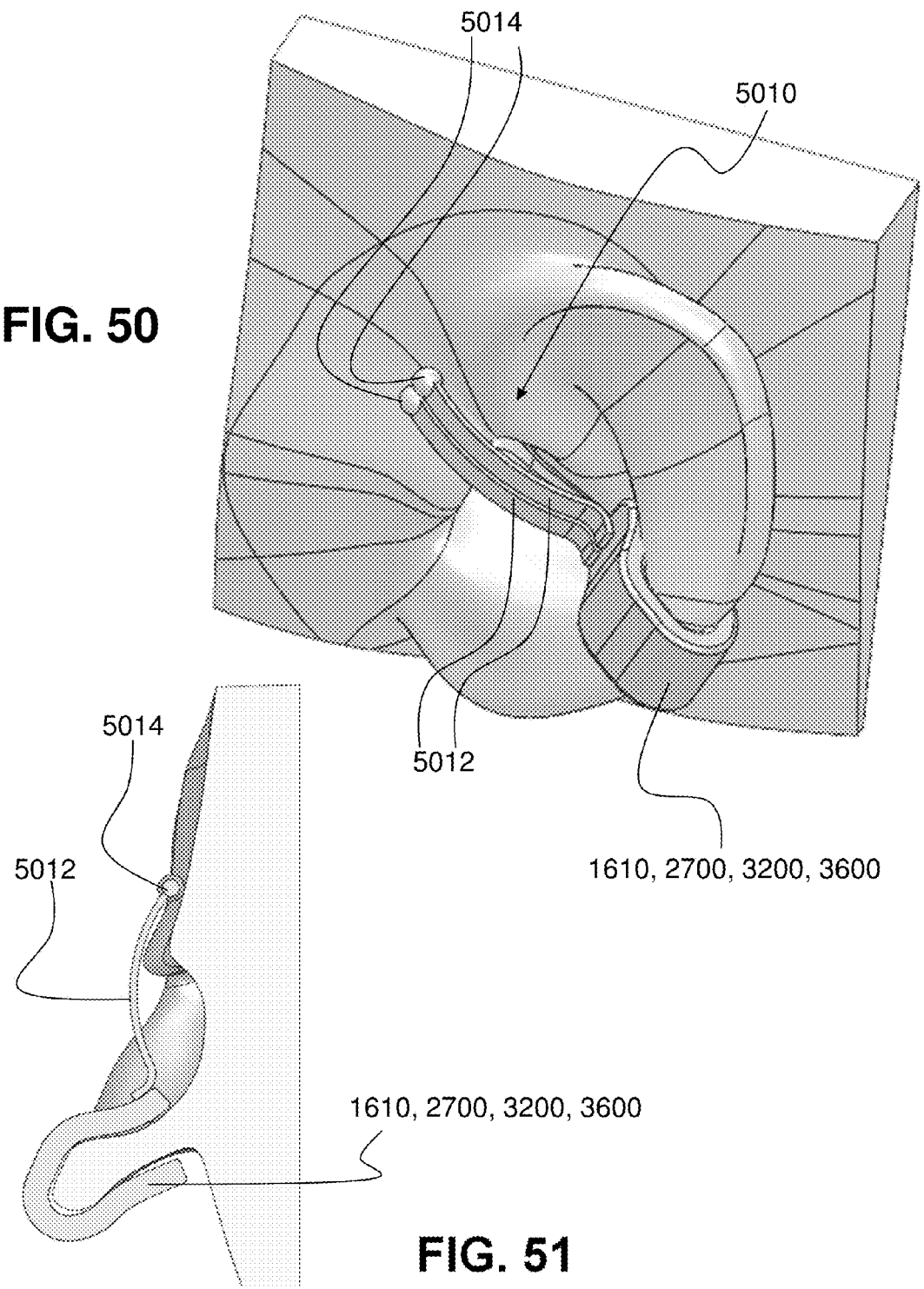

FIG. 52
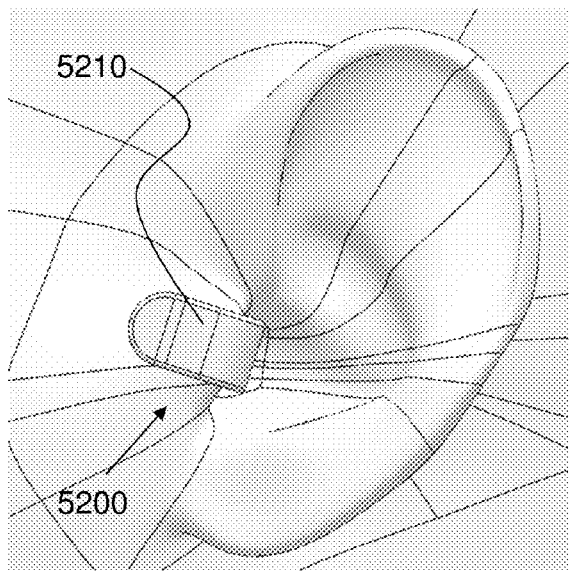
FIG. 53
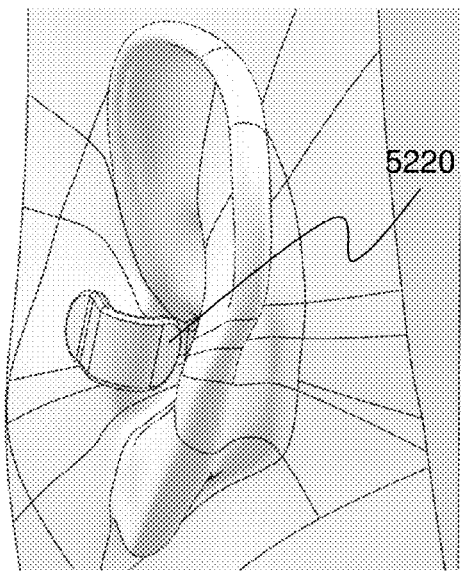
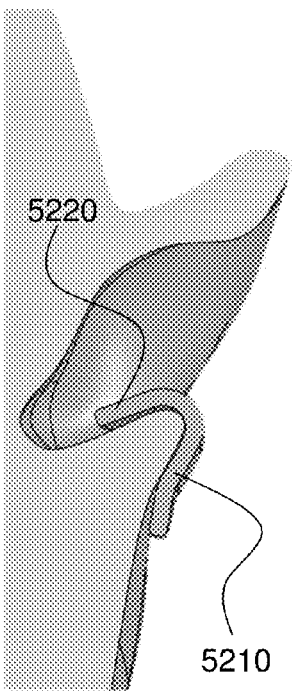
FIG. 54
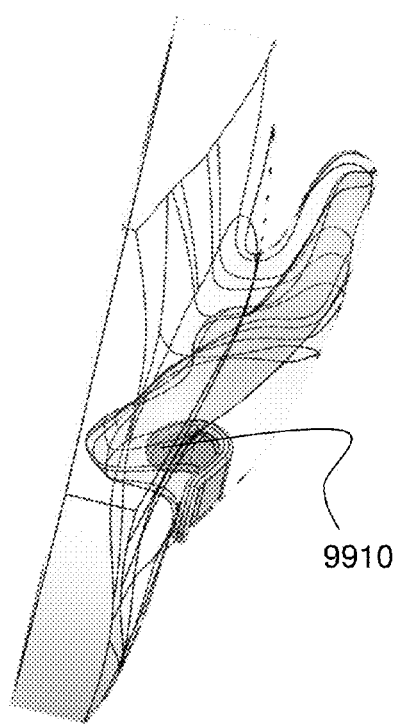
FIG. 55

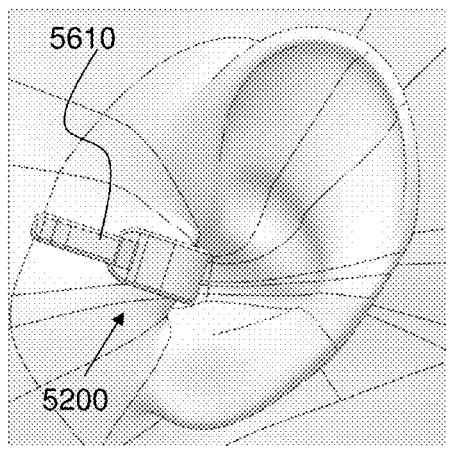
FIG. 56
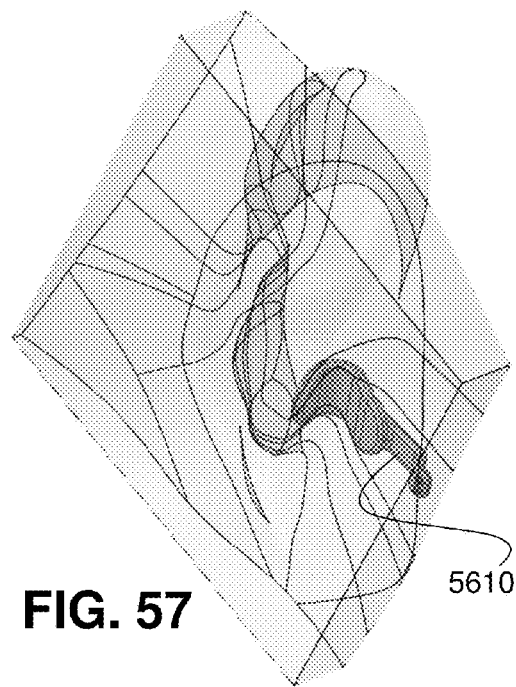
FIG. 57
FIG. 58
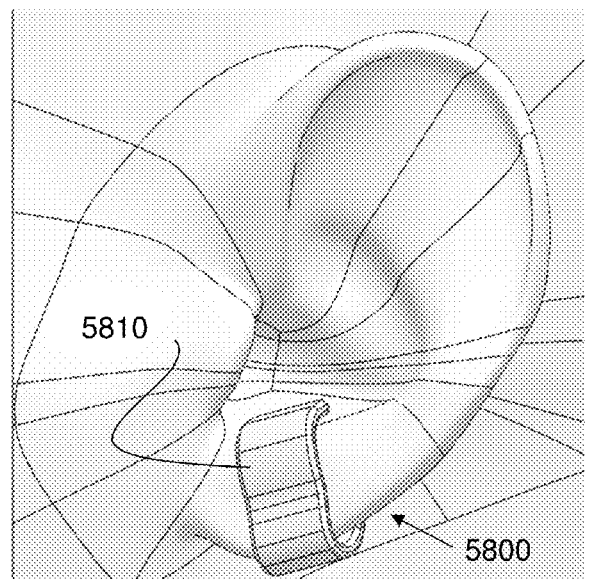
FIG. 59
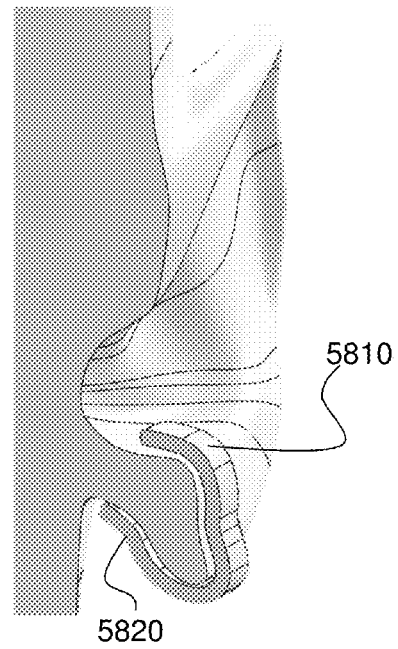

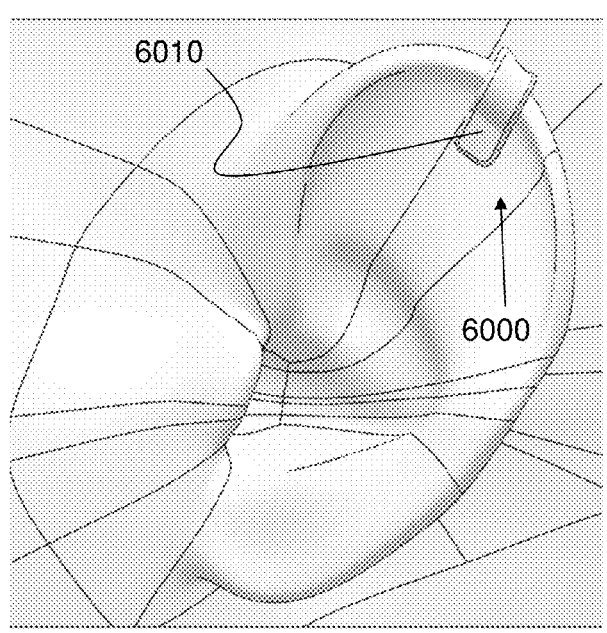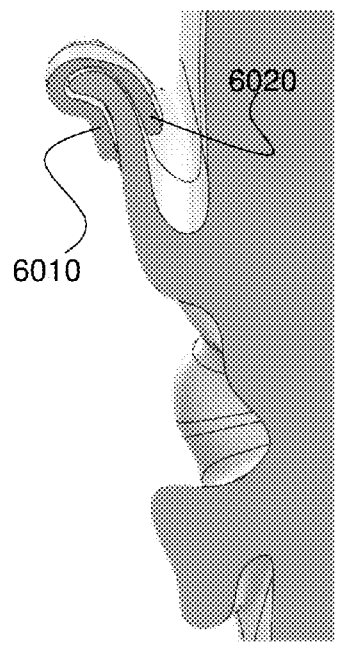
FIG. 60  FIG. 61
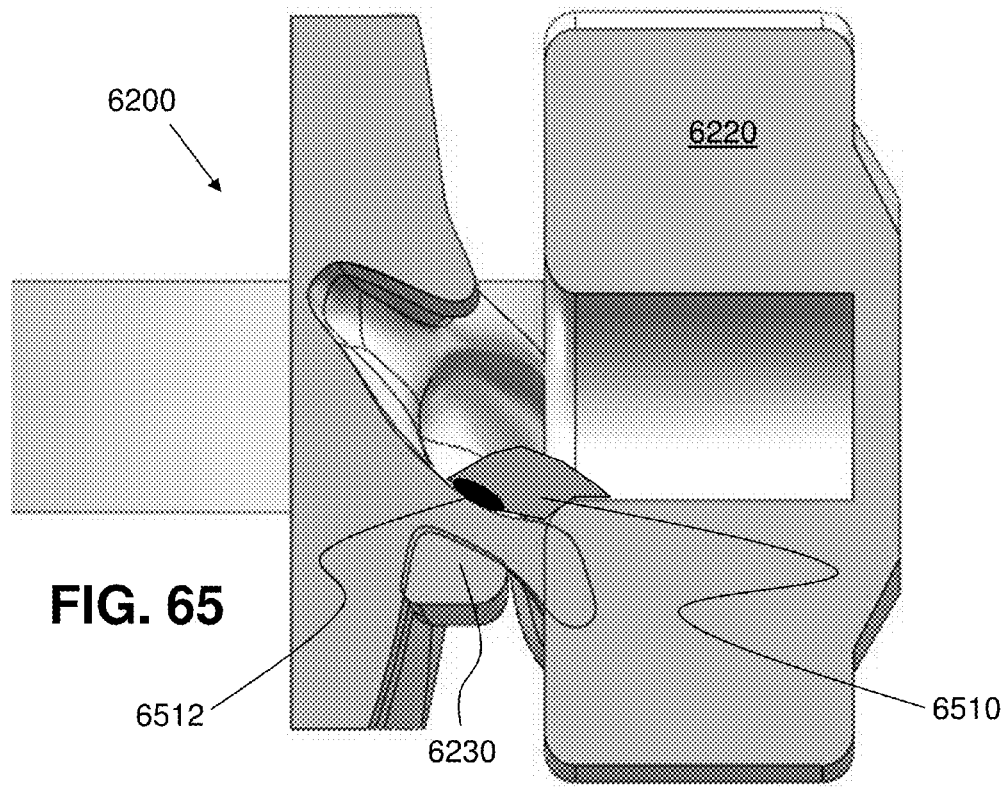
FIG. 65

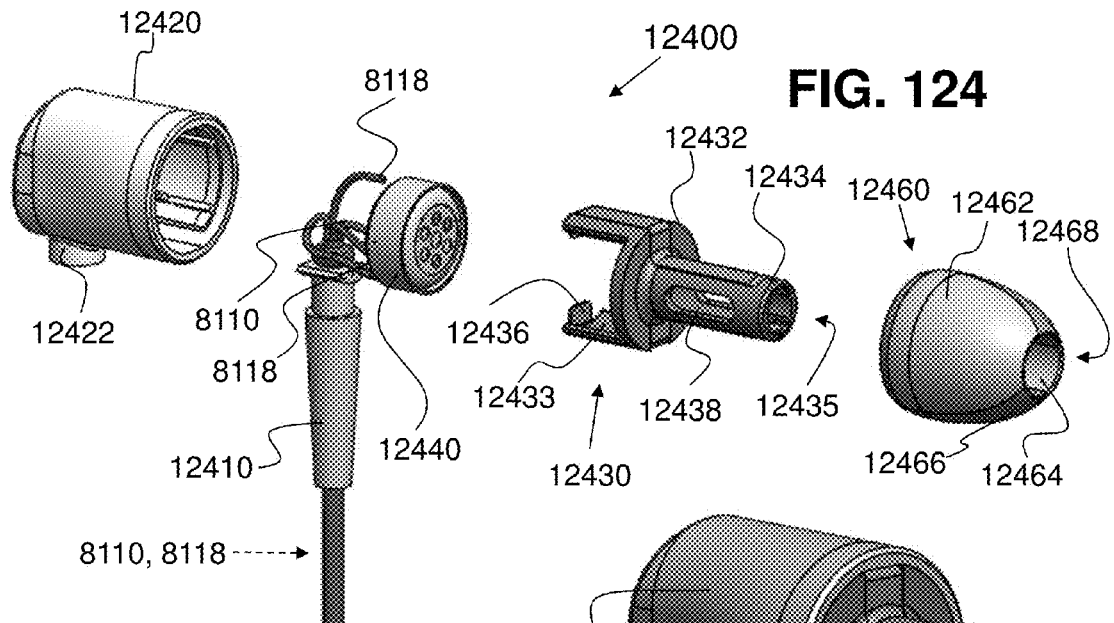
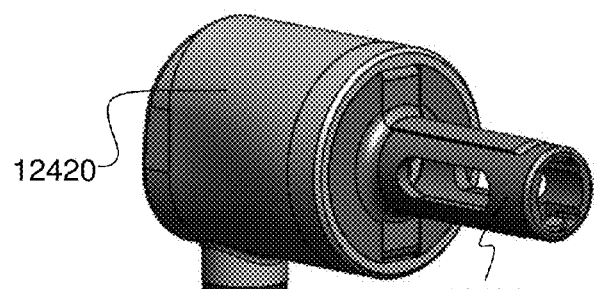
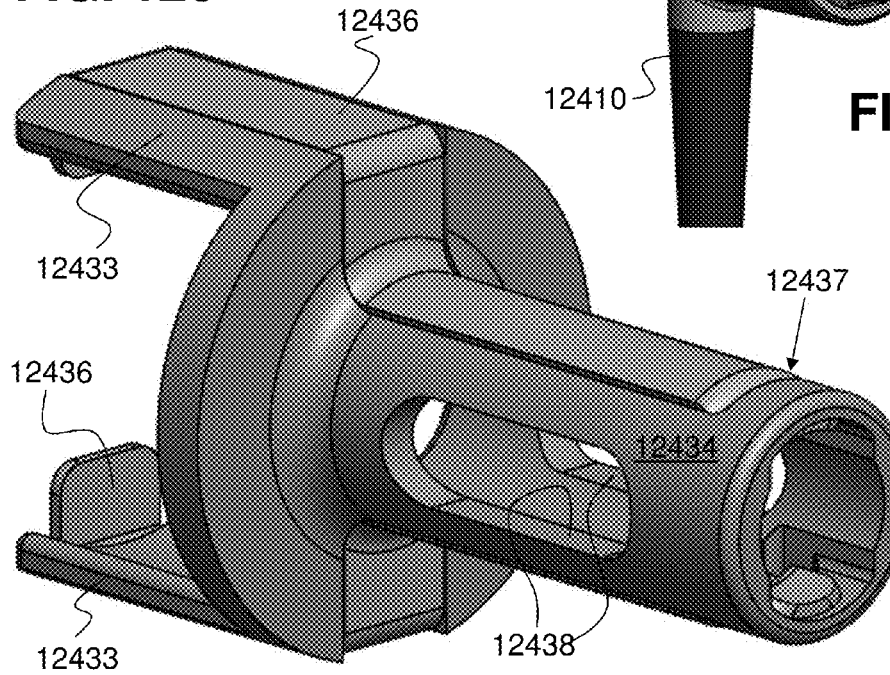

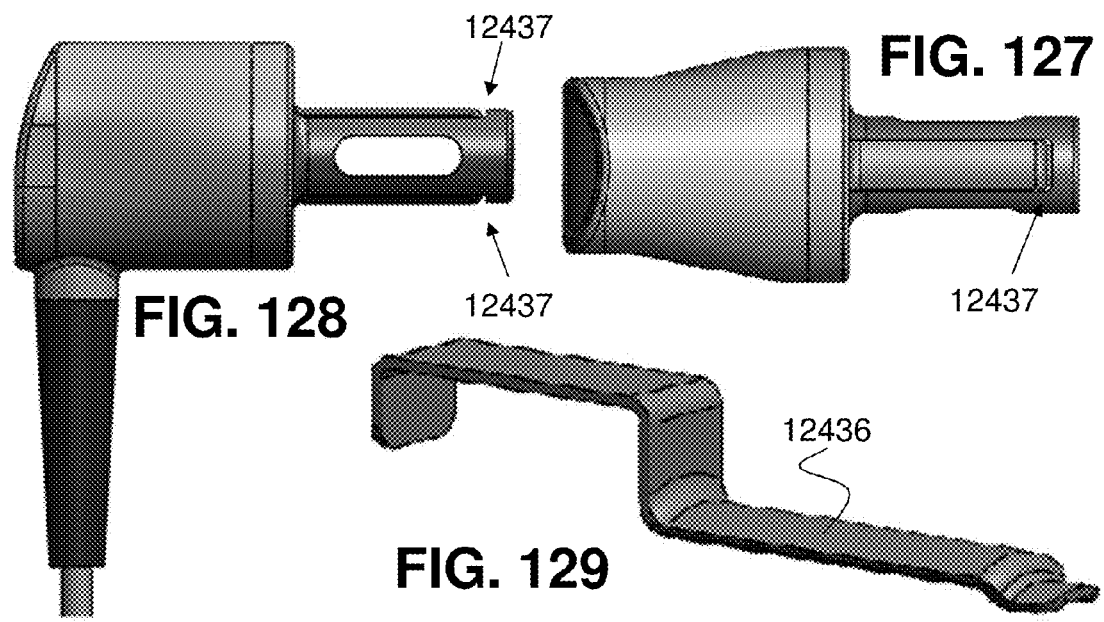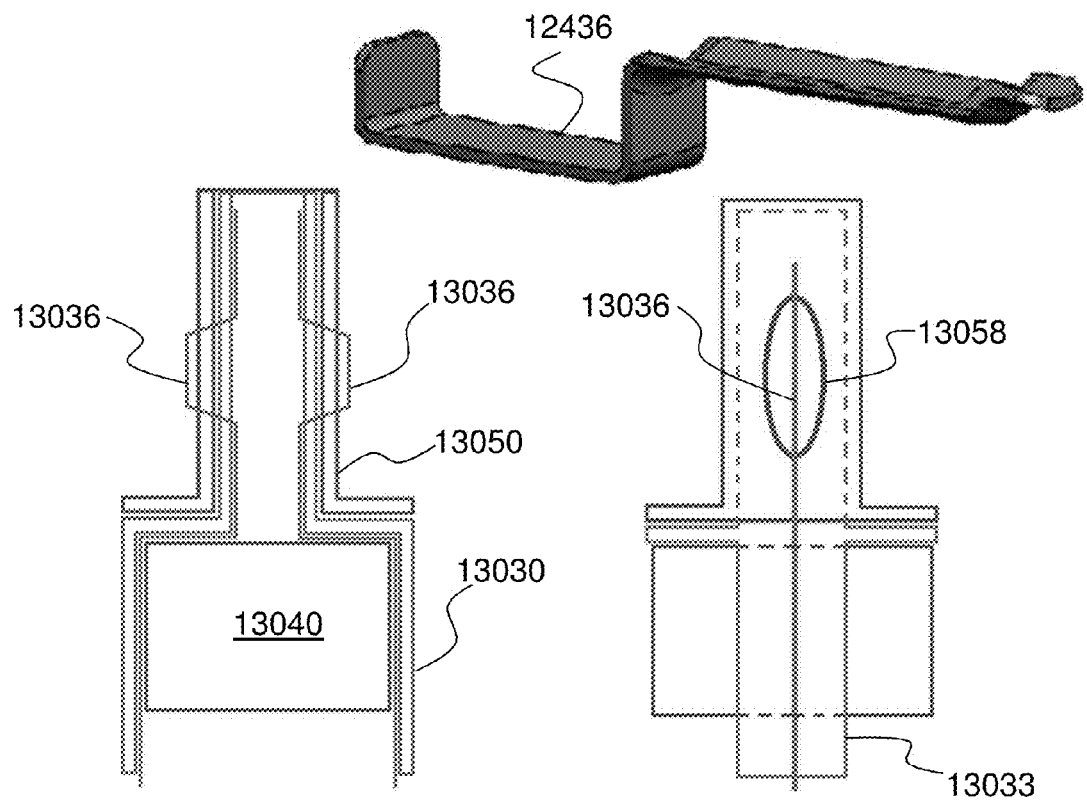

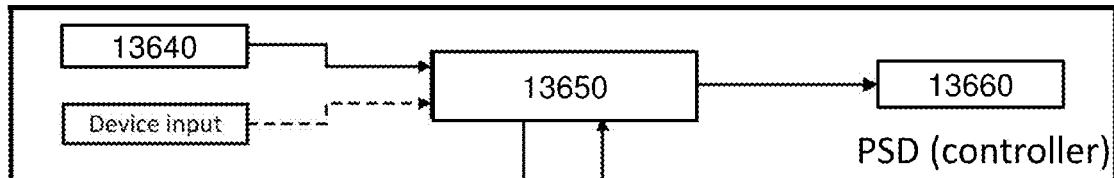
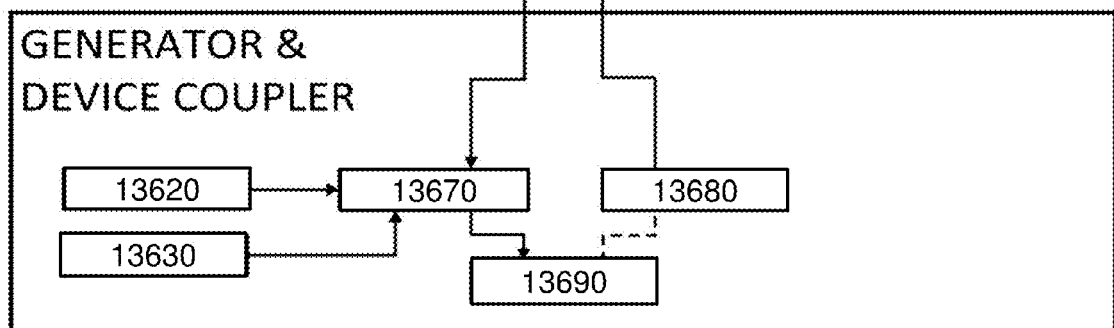
FIG. 138
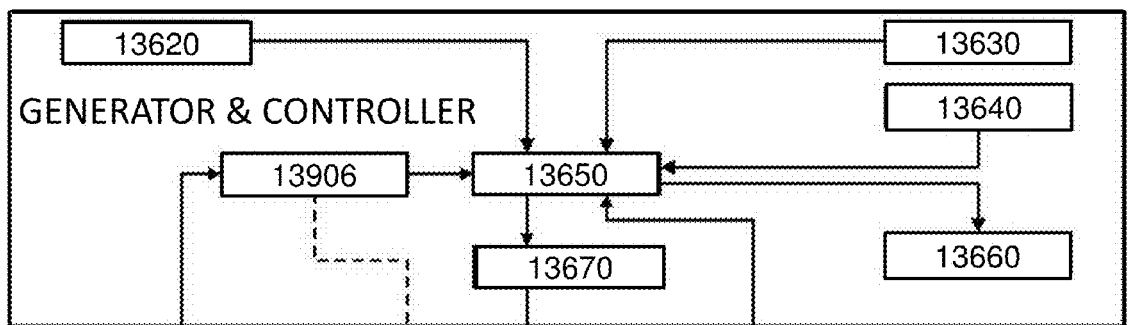
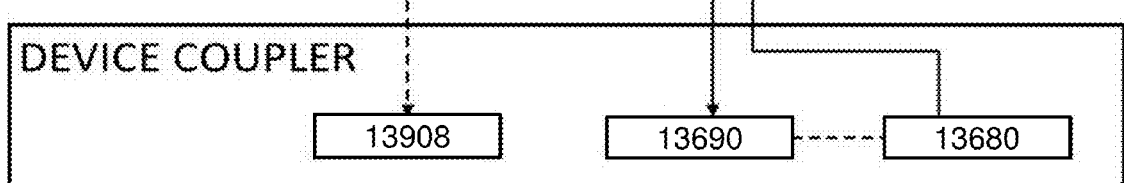
FIG. 139

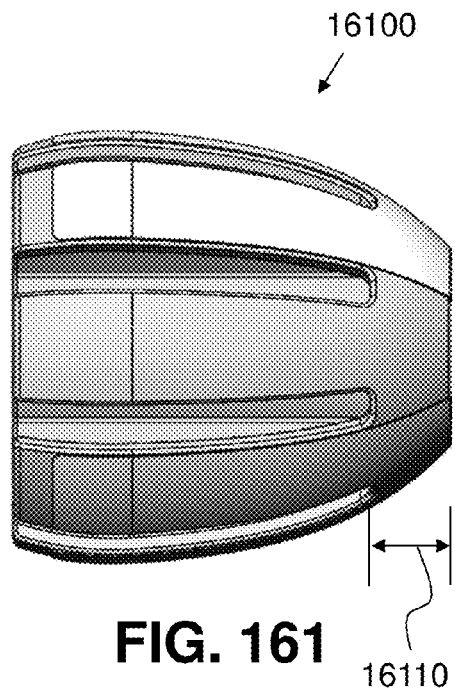
FIG. 161
FIG. 162
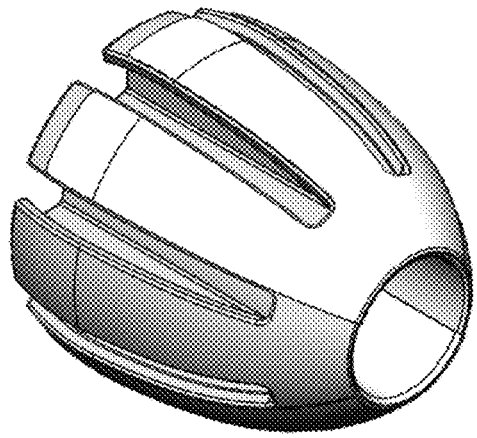
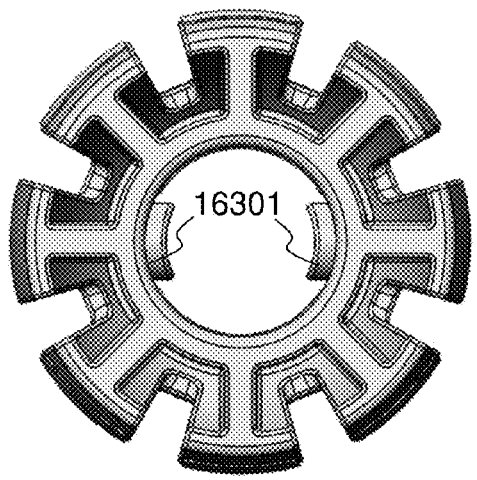
FIG. 163
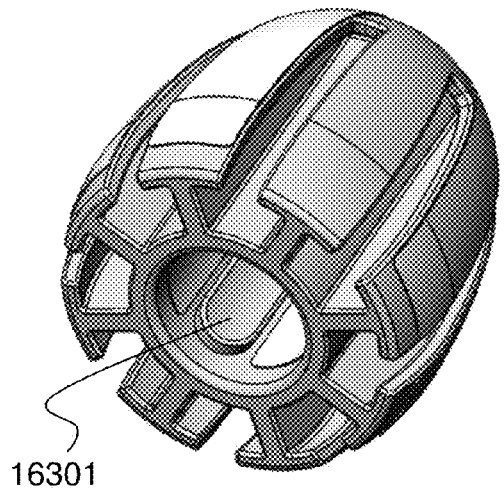
FIG. 164

TRANSCUTANEOUS ELECTROSTIMULATOR AND METHODS FOR ELECTRIC STIMULATION

CROSS-REFERENCE TO RELATED APPLICATIONS

This application claims the priority, under 35 U.S.C. §119, of U.S. Provisional Patent Application Nos. 62/011,985, filed Jun. 13, 2014, and 62/121,759, filed Feb. 27, 2015; the prior applications are herewith incorporated by reference herein in their entireties.

STATEMENT REGARDING FEDERALLY SPONSORED RESEARCH OR DEVELOPMENT

Not applicable

FIELD OF THE INVENTION

The present invention lies in the field of electrical stimulation devices. The present disclosure relates to methods of electrical stimulation of anatomic structures such as nerves, blood vessels, muscles, connective tissue, glands, individual organs, and organ systems and devices that accomplish such stimulation using modulated electric current applied directly or indirectly to tissue through external (non-invasive) or minimally invasive measures. In particular, the present disclosure relates to methods and devices that use transcutaneous and percutaneous methods of stimulating nerves to cause an array of therapeutic benefits, including those dependent upon where the stimulation is directed.

BACKGROUND OF THE INVENTION

It is known that the use of electric current to stimulate nerves and other anatomic structures can have positive therapeutic benefits. The alteration of nerve activity through the delivery of electrical stimulation has been defined as neuromodulation or neurostimulation, which will be used interchangeably herein along with electrostimulation. One significant use is for control of pain. Prior to such uses, for many decades, only medications were available. Neuromodulation devices began with implantable systems and moved to transcutaneous ones.

Historically, neuromodulation devices have most effectively accomplished therapeutic results by invasive measures. More specifically, the patient has an electrode or coil surgically implanted directly onto the nerve being targeted for stimulation and also has a signal generator surgically implanted under the skin. The signal generator is connected to the stimulation electrode and passes current to the electrode. Medtronic, for example, developed a line of Deep Brain Stimulation (DBS) implants under the names Soletra® and Kinetra®, but they are no longer sold. Some of these implants that are currently being sold use the trade name Activa® and mitigate symptoms of movement disorders, such as Parkinson's Disease. These devices are implanted typically in patients who are not able to use drugs for treatment.

Another system includes both implanted and external devices. In such a configuration, the patient has an electrode or coil surgically implanted directly onto the nerve being targeted for stimulation, and a signal generator separate from the electrode or coil is used to stimulate transcutaneously at the coil site by placing an active electrode on the skin in proximity to the implant. The powered signal generator passes electromagnetic radiation or magnetic flux to, thereby, excite the passive coil and induce it to emit its own electromagnetic emission. These systems employ induction measures for nerve stimulation, referred to as IMNS.

One type of neuromodulation using these implanted devices is vagus nerve stimulation, a procedure that stimulates the vagus nerve with electrical impulses. The vagus nerve (Cranial Nerve X) originates from the brainstem as two separate nerves, which travel down the neck and chest and coalesce into one nerve with multiple branches that innervate organs in the thorax and abdomen. Vagus nerve stimulation can be used to treat epilepsy when other treatments have not worked adequately, for example. Vagus nerve stimulation has also been used as a treatment for depression, and is being studied to treat other conditions such as multiple sclerosis, migraine, weight loss, motion disorders, insomnia, management of pain, obesity, and Alzheimer's disease, to name a few. Historically, with vagus nerve stimulation, a stimulation device is surgically implanted at or about the vagus nerve and a signal generator is surgically implanted under the skin, for example, near the clavicle in the chest. A wire is threaded under the skin connecting the signal generator to the stimulation device at the vagus nerve. When activated, the signal generator sends electrical signals along the vagus nerve, which can either travel to the brainstem and have therapeutic effects on the brain, travel down the vagus to affect various end-organs that are supplied by this nerve, block physiologic nerves signals traveling along the vagus, or send signals simultaneously to the brain and to one or more end-organs normally supplied by the vagus or to the brain only.

Electrostimulation can be used on any nerve or organ to have various therapeutic benefits. Directing modulated current to any cranial nerve could be used to affect the brain due to their natural anatomic connection to the brainstem. For example, electrostimulation of the trigeminal nerve or its branches may be able to block the perception of pain of the head and face or mitigate these symptoms by causing endorphin release from the electrical signal that travels up to the brain.

Cyberonics, Inc., sells a set of vagus nerve stimulators, each being an implantable device. They are sold under the trade names AspireHC™, Pulse™, and Demipulse™. Cyberonics received FDA approval for treatment of epilepsy with their implants in 1997. Any implantable device carries the risks associated with anesthesia such as stroke and death, as well as the risk of damage to vital structures surrounding the vagus and vocal cord paralysis, and the risk of infection at the surgical site. If the device were to break or need to be adjusted, another surgery would be required. Additionally, batteries that power the implanted generators for these devices eventually wear down and must be replaced, requiring surgery with associated risks for each generator change.

Another implanted device uses induction as a means to send a signal to an implanted device that is surgically placed on the vagus nerve. A removable collar is considered the device charger and is worn around the patient's neck. Therapy is planned and programmed from a portable electronic tablet. With such a device, the risks of surgery, as listed above, still exist, in addition to the unsightly and cumbersome nature of a dog-collar style necklace.

Less invasive devices that exist use transcutaneous needle arrays. One example of such a system is disclosed in U.S. Patent Publication No. 2013/0150923 to Schnetz et al., and is sold by Biegler GmbH under the trade name P-STIM®. A significant drawback of such systems is that the needle electrodes break the skin, causing pain and the consequent patient aversion, as well as an increasing risk of infection.

Non-invasive devices that are as or more effective would be desirable, for example, one that is utilized transcutaneously. Some devices employ Vagus Nerve Stimulation (VNS) transcutaneously in an attempt to reproduce the effects of implantable devices. For example, electroCore developed a transcutaneous VNS device that looks like a stun-gun and is placed on the neck over the vagus nerve. When activated, the device provides electric stimulation to the neck when a patient feels the onset of a seizure. electroCore's device is sold under the name gammaCore®. Due to the depth of the vagus nerve at that treatment location, such devices place a large electrical signal directly to the carotid artery when in use. Patients experience significant intolerance to such high levels of electrical energy, as well as incur the possibility of closing the artery, or dislodging plaque or a clot, if sufficient pressure is applied over the treatment period. Additionally, it is known that electrical energy supplied to blood vessels can cause vasoconstriction. Thus, there is the dangerous possibility that the physical pressure exerted on the carotid could be enhanced by the electrical energy and shut the artery during treatment. In addition, significantly more current is needed to traverse more interposed tissue, which is accompanied with an increase in discomfort and can adversely affect other structures.

In contrast to the electroCore device, Cerbomed GmbH developed a transcutaneous VNS device under the name NEMOS®. The cell-phone-like controller connects to a non-adjustable earpiece that places two electrodes on the skin of the concha of the ear at two specific points. The earpiece serves as scaffolding that retains the position of the electrodes and maintains constant contact forces of the electrodes against the skin of the target area within the concha of the ear. The earpiece is retained with an "earbud-like" component that resides in the ear canal inferiorly and under the "conchal ridge" superiorly. Retention is dependent upon constant vertical spring forces that have to be substantially strong enough to avoid movement of the apparatus. The force required to accomplish this is poorly tolerated over the prolonged required treatment periods because of the very thin skin of the outer ear canal that the device is contacting, as well as the high degree of sensitivity of the ear in this location. Such apparatuses in or about the ear canal can impair hearing and negate the ability to use earphones for simultaneously listening of music. Additionally, the superior retention point of the apparatus has a very thin skin, has minimal subcutaneous "padding," and is very non-compliant. Further, the surface area of contact of the retention device is limited in comparison to the force required to retain the device, making the retention forces very concentrated and painful. The limited surface area contact causes high resistance, poor signal transmission, and increased pain. If the spring force was reduced to gain comfort, the earpiece would no longer be retained well and the electrode contact against the skin would become suboptimal or lost completely. Further, the superior and inferior anchoring points only lend to placing the electrodes at a specific location on the ear. This location may not be ideal for the therapeutic benefit that such devices are intended to have. Therefore, the Cerbomed earpiece design does not lend itself to electrode placement at any other anatomic locations about the ear. This apparatus is not resistant to motion from routine human activity, such as walking quickly, running, collision with others and other objects, such as tree branches, crowds, wind, etc. Furthermore, the cord interfacing with the earpiece is disposed of inferiorly and applies a downward force not only due to its own weight but also when it gets caught or snagged on other objects. The vertically grounded retention elements of the earpiece submit to these forces and easily dislodge and subsequently disrupt proper contact or dislodge the necessary electrode interfacing with the skin.

Transcutaneous VNS uses the fact that the auricular branch of the vagus nerve (ABVN) supplies the skin of the concha in the human ear. The NEMOS® generator applies electrical signals that are known in the art to these two points. To overcome the resistance of the skin, this device provides a very high level of energy that patients find difficult to tolerate.

Another neuromodulation device for treatment of migraines takes the form of a headband and is sold by Cefaly-Technology, Inc. It is known that most headaches and migraines involve the trigeminal nerve. Its superior branch (supra-orbital) ends at the exit of the eye socket, underneath the skin of the forehead. The Cefaly® headband connects to an adhesive electrode on the forehead. Through the electrode, the headband generates modulated electrical signals to stimulate the nerve endings of the trigeminal nerve. Neuromodulation of the trigeminal nerve with Cefaly® helps reduce the frequency of migraine attacks. Efficacy of this device relies on maintaining proper contact to the skin during the entire treatment duration and this is why the Cefaly® headband has significant negative characteristics. The adequacy of maintaining electrical contact is very inconsistent and can vary based on the storage temperature of the electrode, the ambient temperature during application and use, the stability over time of the adhesive, relative humidity, skin thickness, skin oil levels, thickness of the underlying tissue, and potential allergies to the substances within the adhesive. Also, the surface area of the electrode is large, and resides on the forehead, making it unsightly, hot, and visually disruptive in certain locations such as the workplace. Electrode removal can be painful as it strips underlying hair from the forehead. It is also cumbersome to apply a large adhesive bandage to one's own forehead and then be required to interface it with a generator as a multistep process. Finally, the device causes painful muscle contractions during use.

Current transcutaneous devices have not achieved good results for a multitude of reasons. First, current transmitted through the skin in order to target an anatomic structure inside the body results in poor signal strength to the target structure, poor localization of the target structure, and difficulty with signal transmission through the barrier of the skin and surrounding structures. Further, the high current has collateral physiological effects to the surrounding non-targeted structures. In addition, the degree of user coupler apposition to the skin is not maintained as a constant by present devices. This leads to variation in impedance, which can adversely affect the degree of transmission of the electromagnetic signal through the skin and, therefore, change the effectiveness of the signal in reaching the target structure. Moreover, maintenance of position at the location where the user coupler is in contact to the external portion of the body has been a challenge due to variability of adhesives that adhere to skin and due to discomfort of any devices that use strong springs or other mechanical measures to maintain position. Additionally, fixation of the user couplers that are secured secondarily to a structure remote from the targeted skin interface location frequently lose their indexing due to body motion and environmental contact. Loss of position on the skin by the user coupler leads to the signal not being maintained on the targeted internal structure, which adversely leads to ineffectiveness of the device. Furthermore, optimal locations at which stimulator user couplers are recommended to be placed on the body surface are constantly changing due to ongoing and evolving scientific research, thus making obsolete user couplers that are designed only for a specific anatomic location. For systems that do not include a coupler, the user then becomes the coupling mechanism for the device, requiring steady hands to hold the device in a precise location to deliver the electrical signal to the desired underlying nerve structure throughout the duration of the therapy.

User couplers of prior art neuromodulation devices and systems are not scalable to differing anatomies, require anatomies to be similar and/or consistent, are not universal, do not maintain consistent and adequate contact during daily activities, are unsightly, and are uncomfortable, and, when used about the ear, the prior art devices obstruct the auditory canal, are dependent upon obstructing the ear canal, and preclude other auditory canal systems. With regard to the generator elements of the prior art, they are not modulated or subject to external input, they are not synchronized with audio signals, and there are no features to improve patient tolerance.

As can be seen, there is a need for systems and methods that provide an external, transcutaneous stimulator that maintains constant signal transmission to the desired target, maintains electrodes at constant pressure and constant location for maximum efficacy, maintains position of the user coupler on the body's interface location, and can be modified easily to place electrodes at alternate interface locations without the need for changing device hardware.

It is well known that effectiveness of central nervous system (CNS) stimulation by sending electrical signals through the cranial, peripheral, or central nerves that are remote from the brain has been demonstrated to treat various conditions such as epilepsy, depression, obesity, systemic inflammatory disorders, depression, sleep disorders, tinnitus, poor concentration, attention defecit disorders, heart disease, arrhythmias, pain, and chronic pain, to name a few. Studies have shown that effectiveness, as well as effectiveness for any given disease or disorder, relates to the type of electrical signal generated (i.e., wave type/wave geometry, pulse width, dwell time, using pulse bursts, pulse duration, power, and patterns of administration of therapy such as varying the amplitude of the current with or without variations of some or all of the aforementioned parameters). A certain minimal power threshold must be met to have a therapeutic benefit. As an upper power threshold has not been established, it is well accepted that there exists a "therapeutic range" of power that, on the low end, is the minimal power requirement to have any documentable therapeutic benefit. Increasing the power of the electronic signal above that therapeutic threshold appears to have a greater benefit. The problem facing advancing neuromodulation devices and methods is whether or not an individual patient can tolerate the discomfort associated with the delivery of a signal delivered at the power necessary to maximize therapeutic benefit.

Due to the inconvenience of the application process of current transcutaneous neuromodulation devices and the inability to deliver therapy in a discrete way, users may choose to delay therapy until they have privacy and a dedicated amount of time for the treatment. This additionally limits access to non-pharmacologic therapies that can treat a multitude of chronic diseases, symptoms, and conditions.

It would be beneficial to provide systems and methods for allowing a patient to tolerate uncomfortable electronic signals delivered. Thus, a need exists to overcome the problems with the prior art systems, designs, and processes as discussed above.

SUMMARY OF THE INVENTION

The invention provides systems and methods of electrostimulation that overcome the hereinafore-mentioned disadvantages of the heretofore-known devices and methods of this general type and that accomplish electrostimulation using modulated electric current applied directly or indirectly to human or animal anatomic targets through external (non-invasive) measures. In particular, the invention provides neuromodulation methods and devices by transcutaneously stimulating anatomic targets to cause an array of therapeutic benefits depending on where the stimulation is directed. Various embodiments described herein provide electrostimulation at areas on the same side of the cranium, for example, a pair of electrodes on the left or right side of the user's head. Other embodiments can have electrodes placed on both sides of the user's head but each respective electrode pair (or set) is only on one side of the user's head. Finally, further embodiments can place the two or more poles of a respective electrode pair or set on opposing sides of the user's head to deliver trans-cranial electrical stimulation.

There are additional advantages to transcutaneous measures that can consistently, reliably, and universally deliver electrical signals for neuromodulation. One benefit provided by such transcutaneous measures includes instances where surgical implantation is impractical and/or could not be predicted as a future need, such as pain mitigation for an injured soldier, for example. In this circumstance, it is advantageous to be able to effectively connect electrodes to a soldier who is on the battlefield with ease, reliability, and resistance to environmental conditions, especially motion, and have the electrical signal be well-tolerated by the subject and be consistently effective. Furthermore, the known positive effects that VNS has on mood elevation and enhanced concentration are effects that may be beneficial in situations that are not otherwise anticipated or require only intermittent therapy rather than the long-term therapy, such as provided by an implantable device. An example of this benefit could be understood in the military, in general, because keeping mood, morale, and concentration up is either more or less difficult depending on the situation. For example, if a sniper just lost a fellow soldier or friend to an improvised explosive device, it may be difficult for that soldier to have the will or concentration to continue to discharge his/her duties as effectively as before. Having a device available that can be interfaced quickly to that soldier, which not only will enhance his/her mood but increase concentration when the need arises to take an accurate shot at the enemy, is clearly advantageous. Other soldiers may have fluctuations in mood or concentration that can mitigated on an "as needed" basis with a transcutaneous device.

One exemplary system and method herein utilizes a non-implanted signal generator connected (by wire or wirelessly) to a user coupler located on the user's ear. As used herein, a user coupler, a patient coupler, an electrode coupler, a user coupling device, or a device coupler all are devices that place the electrodes adjacent the tissue to be electrically stimulated. In one exemplary embodiment, the user coupler places electrodes adjacent the auricular branch of the vagus nerve. In other embodiments, the user coupler places electrodes adjacent to the trigeminal nerve. Various advantages of the user couplers described herein is that they are able to be used on varying overall ear anatomies by taking advantage of various anatomical features including consistent anatomical features that are universal across a large portion of the population, they are able to maintain consistent and adequate contact during daily activities, they have a progressive look, they are comfortable, and they are not dependent on occluding the auditory canal to allow other auditory canal systems (e.g., speakers for music) to function simultaneously.

Each of the prior art attempts to retain a user coupler have failed either because it was designed to fit only one particular anatomical location and the progression of the technology made such a design obsolete or the retention device was just too uncomfortable for daily use or was designed for specific anatomic geometries that are quite variable causing poor fit, poor retention, and poor contact in a large portion of the population. In contrast, the user coupler configurations described herein are comfortable and can be used in the future even with improved or different theories of use created. For example, as discoveries are made demonstrating that electrically stimulating new or different points on or in proximity to the ear have increased efficacy or new benefits, it would be advantageous to use the same coupling measures to serve as a universal fixation allowing electrode contact with any location on or near the ear with minor modification to the electrode "extensions" or "booms."

The user couplers, therefore, are independent of future research in the field of electrode placement for neuromodulation. In the future, other points may be identified as beneficial and, therefore, the user couplers can be modified to target such other points. The structure of the ear that is targeted by exemplary embodiments of the device and methods described herein maximize retention to place the electrode user coupler in a strategic location, for example, to access all areas of the concha of the ear and its surrounding structures with use of electrode booms or to access the ear canal. In exemplary embodiments, the electrode locations are radially disbursed from a strategically located fixation point on the helix of the ear to facilitate excellent electrode contact in all potential target locations of the ear and surrounding structures.

The various configurations of the user couplers utilize either or both of form-fitting and force-fitting connectors. A form-locking or form-fitting connection is one that connects two elements together due to the shape of the elements themselves, as opposed to a force-locking connection, which locks the elements together by force external to the elements. In exemplary embodiments of the user couplers described herein, a form-fitting clip follows anatomical structures of the mid-helix or the ear canal that are substantially similar over vast patient populations. In addition to such form-fitting structures, force-fitting structures provide a connection adjacent the electrode locations that uses a mechanical or magnetic force to retain the user coupler in place. One example is a pair of attractive magnets or a magnet-ferrous pair. The form-fitting and force-fitting embodiments can be used together if desired in a particular application.

Other embodiments include a positioning and retention structure that serves to maintain the user interface members and electrodes about specific areas of the target anatomy, the target anatomy being points where compression and/or electrical stimulation is intended to be targeted for a desired effect. Anatomical structures targeted with the systems and methods described herein include a nerve, a series of nerves, a bundle of nerves, blood vessels, muscular structures, and/or organs. Some of the targeted nerves include all of the cranial and facial nerves including, but not limited to, peripheral, central, sensory, motor, sensorimotor, and autonomic nerves and all of their branches, in particular, the vagus nerve, the trigeminal nerve, the auricular nerve, the occipital nerve, the auriculotemporal nerve, and the trochlear nerve. In particular, embodiments herein, the trigeminal or vagus nerves are used. This is not to be understood as limited to these nerves and it is to be understood as being equally interchangeable with any cranial nerve, its branches, or blood vessels of the head or neck. Some of the targeted arteries include all of the cranial and facial arteries including, but not limited to, the temporal, auricular, maxillary, occipital, and external carotid arteries and all of their branches. As used herein, a facial artery is meant to include the artery that is coursing anterior to the tragus.

Critical areas of the systems and methods described herein directly contact the user. There is one contacting member that connects the user couplers containing electrodes so that the connection directs the contact points and maintains the contact points for consistent signal delivery. This connecting structure may generate dynamic and static forces and/or torques ideally suited to maintain position and pressure of the apparatus about specific points of the human anatomy. In one exemplary embodiment, the contacting member is a headband or a halo-like device that contains two user couplers interfacing with the ear canals bilaterally and making contact with a cutaneously accessible portion of the vagus nerve. User couplers may also contain speakers with removably attachable ear interface points that contain electrodes on one or both user couplers. The speaker component contains an electrical interface point that allows electrode to be interfaced with a speaker component. A removably attachable component may have characteristics like malleability for comfort or may contain no electrodes at all. The halo may contain rigid, semi-rigid, malleable, spring-like or stretchable material and may contain hinges with passive, ratchet-like, frictional, spring loaded, or magnetic hinge points to size the halo properly to individuals with different head geometries, ear positions, and ear canal geometries. The halo provides varying degrees of inward force to achieve and maintain adequate coaptation of the electrodes to the target structure, in this case, the ear canal. The halo may have telescoping components that adjust in length or circumference of one or more parts of the structure to optimize fit and maintain contact between electrode member and target organ for signal delivery. Frames that contain contact points are connected to other contact points through a common structure. This structure is customizable in length, angulation, and orientation to optimize contact between the electrodes and the target structure as well as a position for the duration of therapy. Some contact points may be just for indexing and not for signal delivery. Contact points may or may not contain electrodes. In addition, contact points may contain speakers and have disposable tips.

One exemplary embodiment of the signal generator delivers a specific electromagnetic signal at a predetermined or variable current, frequency, and impulse rate and duration through a conduit that directs the signal to a location remote from the generator to at least one user coupler, which user coupler includes an electrode that serves as the electrically positive contact point. Additionally, there is a least one other electrode serving as the ground or electrically negative point that tracks through the conduit and back to the generator to complete the circuit. This configuration is not to be understood as limited to the specific orientation described. In such embodiments, it is to be understood that, where multiple electrodes are used, polarity can be switched at any time. In an exemplary embodiment, polarity can be switched rapidly so that one electrode delivering current will not be more uncomfortable than another, which could occur if the polarity of the electrodes always remained the same.

In exemplary embodiments, at least one of the electrodes contains a magnet and the other of the electrodes contains ferrous material or an oppositely charged magnet allowing the electrodes to be in reciprocal positions on or about the skin such that the target structure to be stimulated is within the electromagnetic field generated by the signal generator. The magnetic user couplers disclosed serve as improvements over present non-invasive, transcutaneous devices because each user coupler includes two oppositely charged magnets (or magnetically attractive materials) with integrated electrodes that are included in each separate circuit that is conveying a transcutaneous energy emission to the user. All electrodes mentioned herein can be of either polarity, as the generator can deliver alternating polarity. The magnetic electrodes are placed in reciprocal locations with respect to the user's surface anatomy, overlying a site that contains the structure to be targeted. Targeted structures may be a nerve, a series of nerves, a bundle of nerves, blood vessels, muscular structures, and/or organs. Using electrodes integral to magnetic couplers results in an improved ease of placement with minimal training. The placement onto an anatomic site is easily and precisely reproducible, allows for tissue compression to reduce signal impedance, and resists movement of the electrodes off of their intended location due to constant magnetic retention forces.

Wind, rain, moisture, environmental contact, and user motion are factors that can cause electrodes to be moved inadvertently off their intended location on the body, thus making the electrodes no longer an effective stimulating device for the target location. The systems and methods described herein secure such electrodes in a manner to resist and prevent inadvertent movement due to any environmental influence. One exemplary method for delivering electromagnetic neural stimulation to a person that addresses such factors comprises placing a user coupler having a positive electrode onto the target skin location and placing a negative (ground) electrode in the reciprocal position where a position of both electrodes is maintained by the magnetic field of the two magnets or a magnet and a ferrous material. After tissue compression between the magnets is maximized, which occurs after a relatively short period of time, impedance of the circuit is maintained because the magnetic field is constant. With pressure and distance at the electrode interface point maintained for a time consistent with therapy duration, the impedance remains substantially constant and ensures a consistent and predictable dose of electromagnetic signal at the target structure. Due to the maintained magnetic forces and the tissue compression and indentation, the user coupler resists straying from its original position, which movement may arise from sweat, user activity, or inadvertent environmental contact. If, however, the user coupler(s) did stray from its/their prescribed location, they can be easily repositioned by the user merely by placing the electrodes back onto the area of visual skin compression, resulting in an instantaneous restoration of compressive forces without the electrodes enduring any decrement of forces and, therefore, maintaining the original impedance and signal at the target structure.

In yet another aspect, multiple user couplers containing oppositely charged electrodes emanate from the electro-stimulation conduit, thereby allowing multiple electromagnetic signals to be transmitted through the skin to target one or more structures. This configuration allows the generator to power multiple pairs of electrodes to stimulate multiple anatomic locations selectively or simultaneously. If new or different anatomic locations are discovered to be useful for the treatment of different ailments, this user coupler system can be placed easily onto different external anatomic locations to maximize the device's therapeutic benefit. Parallel or sequential therapies can also be administered, i.e., both nerve stimulation and vasoconstriction or one then the other, in one therapeutic period. All of the systems and methods described herein with regard to electrostimulation of nerves are also applicable for vasoconstriction or vasodilation treatments.

Other exemplary embodiments include a generator that sends a signal to one or more user couplers including one or more electrode points or pairs, each electrode delivering a distinct and independently adjustable signal. Once one or more of the user couplers are connected to the body surface, the generator uses a sensing circuit to determine the electrical properties of the target stimulation area such as impedance, resistance, capacitance, inductance, and any version of an equivalent circuit such as RC, LC, and LRC. For example, the generator uses a sensing circuit to determine the impedance at the electrode-skin surface interface site. Once the generator determines the impedance level, the generator increases power delivered to the specific electrode or electrodes that have an impedance level deemed too high based upon a pre-programmed software algorithm. In users with electrode impedance levels that are too low, the generator may, conversely, individually lower power to the individual electrode or electrodes to achieve proper signal strength delivered to the targeted structure. In other embodiments where multiple electrodes are present, the generator can send no signal through the high-resistance electrodes and only send signals through electrodes where the resistance is acceptable. The generator may also give a visual or audible output to the user if the effectiveness of the signal cannot be mitigated by generator adjustments. In these instances, the user may need to tighten, reposition, or add conductive gel in order to achieve proper signal transmission. In the case of embodiments with multiple user couplers, each electrode pair, or each individual electrode in the case of a common ground, will remain constant or individually be given progressively increasing power based on the individual impedance of each electrode. This allows the proper signal strength to be delivered to the target structure or structures in circumstances where increased impedance is registered by the impedance circuit contained within the generator. Levels of electrical properties may occur in individuals with variations in thickness or character of their skin or with skin contaminants, moisture level, or general tissue thickness related to genetics, adipose content, amount of circulating blood volume, electrolyte levels in the serum, muscle size, moisture content, as well as environmental factors such as rain, amount of compression imparted on the skin by the magnetic retention forces, and exogenous conductive or non-conductive materials such as dielectric compounds or exogenous topically applied substances such as cosmetics or pharmaceuticals.

In another exemplary embodiment, systems and methods include user couplers that have multiple, integrated electrodes that use a common or individual grounding points. In such an embodiment, the "array" of electrodes is applied to the body surface as one unit. The array comprises multiple electrodes that are positioned in a predetermined geometry so that the electrodes come in contact with the targeted body surface location in a predictable, predetermined geometry.

This is advantageous in situations where it is desirable and most effective to stimulate a target structure with multiple electrodes positioned at separate sites. Application of the user coupler including electrode arrays can be more efficient, reproducible, and accurate during its application as opposed to placing multiple, individual electrodes to a specific body surface that is in direct proximity or "signal proximity" to the organ being targeted by the signal. Other advantages of having the electrode array is the ability to sweep the signal among the various electrodes in different patterns, which increases user tolerance because there is not a continuous signal at fixed locations, and may have a treatment benefit by covering a broader area. Further embodiments of generators configured to function with such arrays may include measures for determining electrical properties at the distinct locations of the electrodes contained in the array and that respond by adjusting the signal strength to an increasing or decreasing level to maximize the signal's strength to the structure being targeted. Additionally, inputs derived from a plurality of user data may serve to modify which individual electrodes the generator inputs a greater or lesser signal. For example, if the generator is sending signals to a electrode array, or to multiple, individual electrodes, user response to effectiveness of therapy may cause the generator to increase the signal to one or more electrodes, decrease to one or other electrodes, or even stop sending a signal completely to one or more electrodes to optimize treatment effect to the structure being targeted. The user may be prompted by a visual or audible queue, for example, to input whether the user is experiencing proper effectiveness for any given therapy. If the user is inputting user interface data consistent with inappropriate effectiveness, the generator may change the signal strength or character at one or more electrode sites. In addition to the described user tolerance/comfort features, the user coupler may contain a mechanical vibration device that transmits vibrations to the target location. Vibration on sensory surfaces is known to distract a user from sensing pain and sometimes causes numbness. As such, the systems and methods described herein can be augmented with a vibration system that administers vibrations or compression independently or in synchronization with electrostimulation or inputs from devices such as audio.

As an additional feature of this feedback embodiment, the generator can be provided with measures to respond to user input to optimize effectiveness of treatment and the generator and/or user couplers can measure and optimize electrode signals by having sensors integral or separate from the user couplers to measure at least one or more of heart rate, respiratory rate, blood pressure skin/tissue moisture levels, oxygen saturation, motion, head position, cardiac output and venous pressure, and/or to perform an electro-cardiogram and/or an electro-encephalogram and/or electromyography (EMG) and/or electrodermal activity (EDA), or the electrodes can sense and/or measure such parameters. The generator contains electronics and algorithms to measure these physiologic parameters and, in turn, adjust the signals through one or more of the electrodes that the generator is driving to optimize the response to treatment.

In another exemplary embodiment, the generator device includes an ability to change various qualities of the signal being generated. These qualities include number of signals transmitted (in embodiments with multiple pairs of electrodes), which pairs of electrodes are to be active (sent signals or off), amperage, voltage, amplitude, frequency, pulse duration, pulse type, and modulation type. The changes are accomplished by using an adjustment device and by confirming user inputs by audible or visual outputs.

Other exemplary embodiments include a user surge button that allows the user to receive a higher dose of stimulation emission to mitigate symptoms that may "breakthrough" a lower level of constant, pre-programmed emissions. For example, with a user whose treatment for chronic back pain is auricular transcutaneous neural stimulation, the user may have adequate pain control throughout the day at a predetermined generator setting, but, when lifting a heavy object, the user experiences a heightened level of pain (i.e., breakthrough pain). At the moment the breakthrough pain becomes apparent, the user depresses the user surge button to cause the generator to send an increased level of signal through the conduit, with subsequent increased stimulation of the target structure, thereby mitigating the user's breakthrough pain. This can apply to seizures as well if the user is cognizant of an aura.

In other exemplary embodiments, the software, circuit, or "chip" that determines device functionality (i.e., number of signal types, power, amplitude, frequency and pulse duration, selectability between user couplers) can be removably replaced with routines or chips having other functionality or can be reprogrammable at the factory, or through the use of an app where the device having the app communicates with the present systems or the device and can be integrated into the device itself. In an exemplary chip configuration, the chip can be removed and replaced into a specific socket or slot, or can be integrated into a sealed or partially sealed battery pack that contains the chip, where the act of simply removing an existing battery pack and replacing it with a new one having the same or different chip can instantaneously change or maintain device functionality. This configuration reduces manufacturing costs as well as reduces consumer costs as it is no longer necessary to produce distinctly different generator units with different functionality or require the consumer to replace the entire device to alter its functionality if that is desirable or indicated. The chip also can allow the same device to have expanded applications.

With the foregoing and other objects in view, there is provided, a transcutaneous electrostimulation device comprising an electrostimulation generator providing at an output a nerve electrostimulation signal, an electronic signal conduit conductively connected to the output of the electrostimulation generator, and an electrode coupler shaped to form fit an ear canal of a human ear and having at least one electrostimulation electrode conductively connected to the electronic signal conduit to receive the nerve electrostimulation signal and positioned at the at least one electrostimulation electrode coupler to contact tissue within an ear canal and apply the nerve electrostimulation signal to the tissue transcutaneously.

With the objects in view, there is also provided a transcutaneous electrostimulation device comprising an electrostimulation generator providing at an output a nerve electrostimulation signal, an electronic signal conduit conductively connected to the output of the electrostimulation generator, an audio source outputting audio signals, and an electrode coupler shaped to form fit an ear canal of a human ear and having at least one audio speaker connected to the audio source and receiving the audio signals for output into the ear canal when worn, having at least one electrostimulation electrode conductively connected to the electronic signal conduit to receive the nerve electrostimulation signal and positioned to contact tissue within an ear canal and apply the nerve electrostimulation signal to the tissue transcutaneously, and supplying the nerve electrostimulation signal while the audio signals are output.

With the objects in view, there is also provided a transcutaneous electrostimulation device comprising an audio source outputting audio signals, an electrostimulation generator providing at an output a nerve electrostimulation signal, an electronic signal conduit conductively connected to the output of the electro stimulation generator, an electrode coupler shaped to form fit an ear canal of a human ear and having at least one audio speaker connected to the audio source and receiving the audio signals for output into the ear canal when worn, having at least one electrostimulation electrode, conductively connected to the electronic signal conduit to receive the nerve electrostimulation signal, and positioned to contact tissue within an ear canal and apply the nerve electrostimulation signal to the tissue transcutaneously, and supplying the nerve electrostimulation signal while the audio signals are output, and the electrostimulation generator modulating the nerve electrostimulation signal based upon the audio signals.

In accordance with a further feature, the nerve electrostimulation signal is a vagus nerve electrostimulation signal.

In accordance with an added feature, the nerve electrostimulation signal is a trigeminal nerve electrostimulation signal.

In accordance with an additional feature, the electrode coupler comprises an earbud having an exterior surface and the at least one electrostimulation electrode comprises a conductive surface on a portion of the exterior surface such that, when the earbud is inserted within the ear canal, the at least one electrostimulation electrode contacts tissue within the ear canal.

In accordance with yet another feature, the earbud has a speaker assembly and the electronic signal conduit comprises a speaker conduit conductively connected to the speaker assembly and having a standard audio jack shaped to be inserted into a standard audio output to receive therefrom audio signals and an electrostimulation conduit conductively connecting the nerve electrostimulation signal to the conductive surface.

In accordance with yet a further feature, the electronic signal conduit is a wireless connection, the electrostimulation generator wirelessly transmits the nerve electrostimulation signal, and the electrode coupler has a receiver receiving the nerve electrostimulation signal, conductively connected to the at least one electro stimulation electrode, and providing the nerve electrostimulation signal to the at least one electrostimulation electrode.

In accordance with yet an added feature, there is provided an audio source outputting audio signals, the electrode coupler comprising at least one audio speaker connected to the audio source and receiving the audio signals for output into the ear canal when the electrode coupler is worn, and the electrostimulation generator sending the nerve electrostimulation signal to the electrode coupler while the audio signals are output.

In accordance with yet an additional feature, the electrostimulation generator modulates the nerve electrostimulation signal based upon the audio signals.

In accordance with again another feature, the at least one audio speaker is within the earbud and the electronic signal conduit comprises a speaker conduit conductively connected to the at least one audio speaker and having a standard audio jack shaped to be inserted into a standard audio output to receive therefrom audio signals and an electrostimulation conduit conductively connecting the nerve electrostimulation signal to the conductive surface.

In accordance with again a further feature, the electrostimulation generator receives the audio signals from the audio source and modulates the nerve electrostimulation signal based upon the audio signals.

In accordance with a concomitant feature, the at least one audio speaker is one of wirelessly connected to the audio source and directly connected to the audio source.

Although the invention is illustrated and described herein as embodied in systems and methods of transcutaneous electronic tissue stimulation, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Additional advantages and other features characteristic of the present invention will be set forth in the detailed description that follows and may be apparent from the detailed description or may be learned by practice of exemplary embodiments of the invention. Still other advantages of the invention may be realized by any of the instrumentalities, methods, or combinations particularly pointed out in the claims.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the present invention. Advantages of embodiments of the present invention will be apparent from the following detailed description of the exemplary embodiments thereof, which description should be considered in conjunction with the accompanying drawings in which:

FIG. 10 is a rear perspective view of a transcutaneous vagus nerve stimulation system with an electrode application device in a docked state;

FIG. 11 is a perspective view of the system of FIG. 10 from in front of a right side thereof;

FIG. 12 is a fragmentary, perspective view of the electrode application device of FIG. 10 clipped onto a left ear of a user;

FIG. 13 is a perspective view of the system of FIG. 10 from in front of a right side thereof;

FIG. 14 is a fragmentary, perspective and laterally cross-sectional view of the electrode application device of FIG. 12 viewed from above the user with the application device in a docked and implanting state of the electrodes;

FIG. 15 is a fragmentary, perspective and laterally cross-sectional view of the electrode application device of FIG. 12 viewed from above the user with the application device in an undocked state of the electrodes post-implantation;

FIG. 38 is a fragmentary, horizontally cross-sectional view of the form-fitting electrode application device of FIG. 16 with another exemplary embodiment of an extending electrode assembly in an idealized non-flexed position;

FIG. 39 is a fragmentary, horizontally cross-sectional view of the form-fitting electrode application device of FIG. 38 with the extending electrode assembly in a flexed position;

FIG. 40 is a fragmentary, horizontally cross-sectional view of the form-fitting electrode application device of FIG. 16 with another exemplary embodiment of an extending electrode assembly in a held-open position;

FIG. 41 is a fragmentary, horizontally cross-sectional view of the form-fitting electrode application device of FIG. 16 with another exemplary embodiment of an extending electrode assembly in a natural closed position;

FIG. 46 is a perspective view of the form-fitting and force-fitting electrode application device of FIG. 44 in a partially open configuration;

FIG. 47 is a side elevational view of the form-fitting and force-fitting electrode application device of FIG. 44 in a closed configuration;

FIG. 50 is a fragmentary, side perspective view of an exemplary embodiment of an neurostimulator device with electrode booms extending to a trigeminal/temporal location;

FIG. 51 is a fragmentary, perspective and laterally cross-sectional view of the neurostimulator device of FIG. 50;

FIG. 52 is a fragmentary, side perspective view of an exemplary embodiment of a tragus neurostimulator device;

FIG. 53 is a fragmentary, rear perspective view of the tragus neurostimulator device of FIG. 52;

FIG. 54 is a fragmentary, perspective and laterally cross-sectional view of the neurostimulator device of FIG. 52;

FIG. 55 is a fragmentary, perspective, partially transparent, and laterally cross-sectional view of the neurostimulator device of FIG. 52;

FIG. 56 is a fragmentary, side perspective view of an exemplary embodiment of the tragus neurostimulator device of FIG. 53 with an electrode boom;

FIG. 57 is a fragmentary, perspective, partially transparent, and laterally cross-sectional view of the neurostimulator device of FIG. 56;

FIG. 58 is a fragmentary, side perspective view of an exemplary embodiment of an ear lobe neurostimulator device;

FIG. 59 is a fragmentary, front perspective and vertically cross-sectional view of the ear lobe neurostimulator device of FIG. 58;

FIG. 60 is a fragmentary, side perspective view of an exemplary embodiment of a superior helix neurostimulator device;

FIG. 61 is a fragmentary, rear perspective and vertically cross-sectional view of the superior helix neurostimulator device of FIG. 60;

FIG. 65 is a fragmentary, perspective and laterally cross-sectional view of an upper portion of the electrode headset device of FIG. 62 viewed from below;

FIG. 119 is a fragmentary, exploded, perspective view of an exemplary embodiment of an earbud-type neurostimulator device with a multi-electrode flower-shaped electrode coupler;

FIG. 120 is a fragmentary, enlarged, perspective view of a speaker housing stud of the earbud-type neurostimulator device of FIG. 119;

FIG. 121 is an enlarged, perspective view of the speaker housing stud of the earbud-type neurostimulator device of FIG. 119;

FIG. 122 is a fragmentary, perspective view of the earbud-type neurostimulator device of FIG. 116 in an assembled state;

FIG. 123 is a fragmentary, perspective view of the earbud-type neurostimulator device of FIG. 119 in an assembled state;

FIG. 124 is a fragmentary, exploded, perspective view of an exemplary embodiment of an earbud-type neurostimulator device with a multi-electrode flower-shaped electrode coupler;

FIG. 125 is a fragmentary, enlarged, perspective view of portions of the earbud-type neurostimulator device of FIG. 124 in an assembled state without an earbud;

FIG. 126 is an enlarged, perspective view of the speaker housing stud of the earbud-type neurostimulator device of FIG. 124;

FIG. 127 is an enlarged, top plan view of the earbud-type neurostimulator device of FIG. 125;

FIG. 128 is a fragmentary, enlarged, side elevational view of the earbud-type neurostimulator device of FIG. 125;

FIG. 129 is a perspective view of conductive leads of the earbud-type neurostimulator device of FIG. 124;

FIG. 130 is a diagrammatic side elevational view of an exemplary embodiment of an earbud-type neurostimulator device with an earbud removed;

Figures 132, 133:
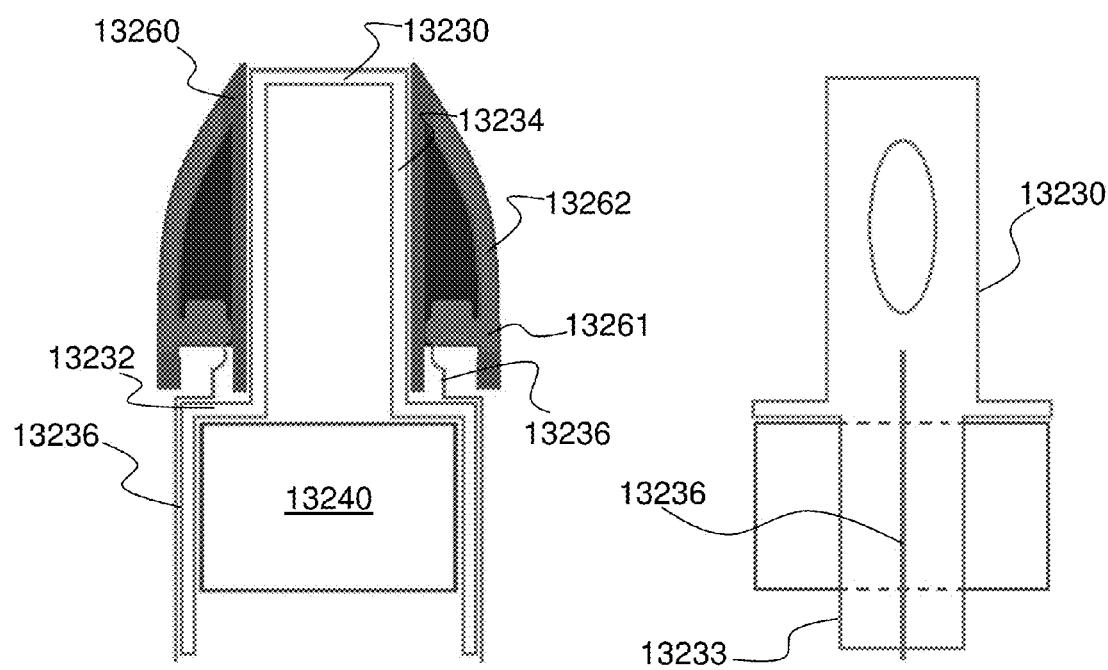
Figures 134, 135:
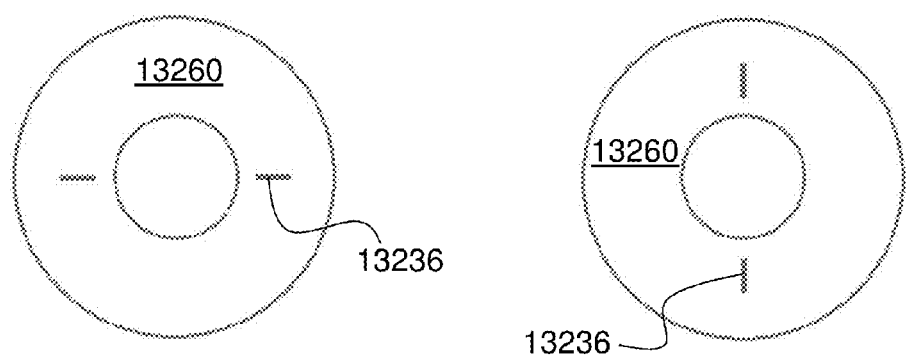
Figure 136:
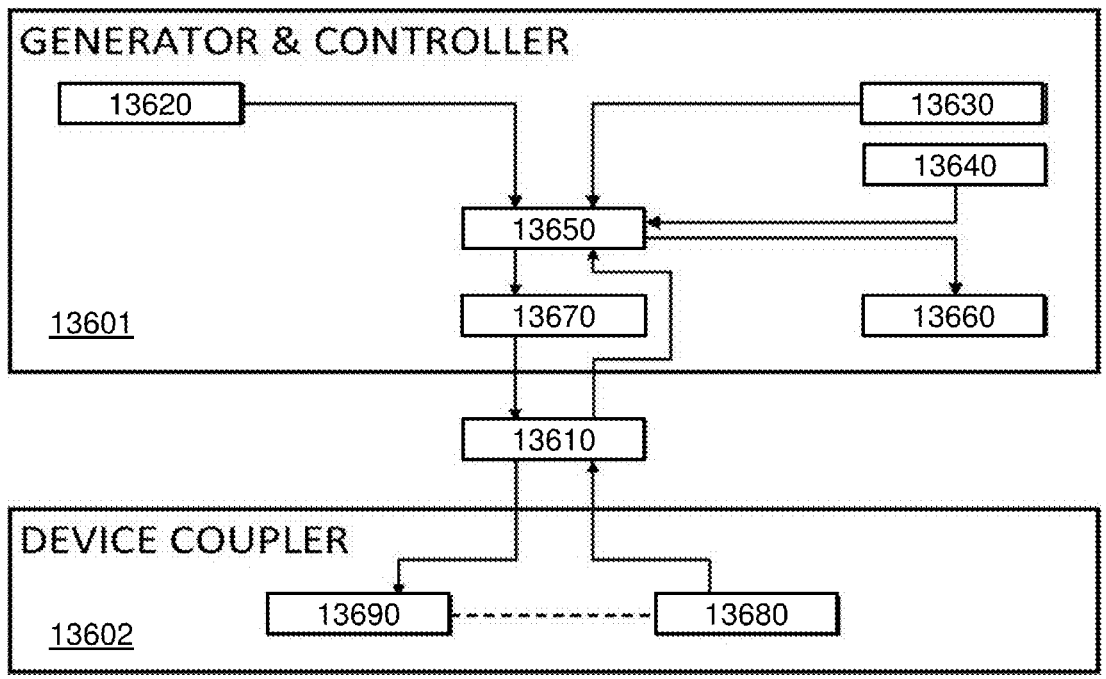
Figure 137:
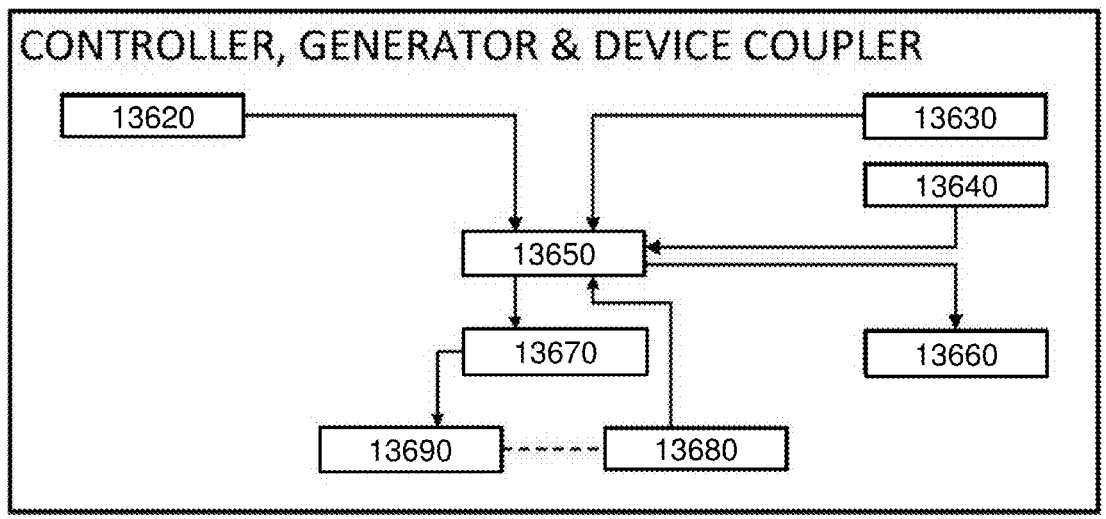
Figure 140:
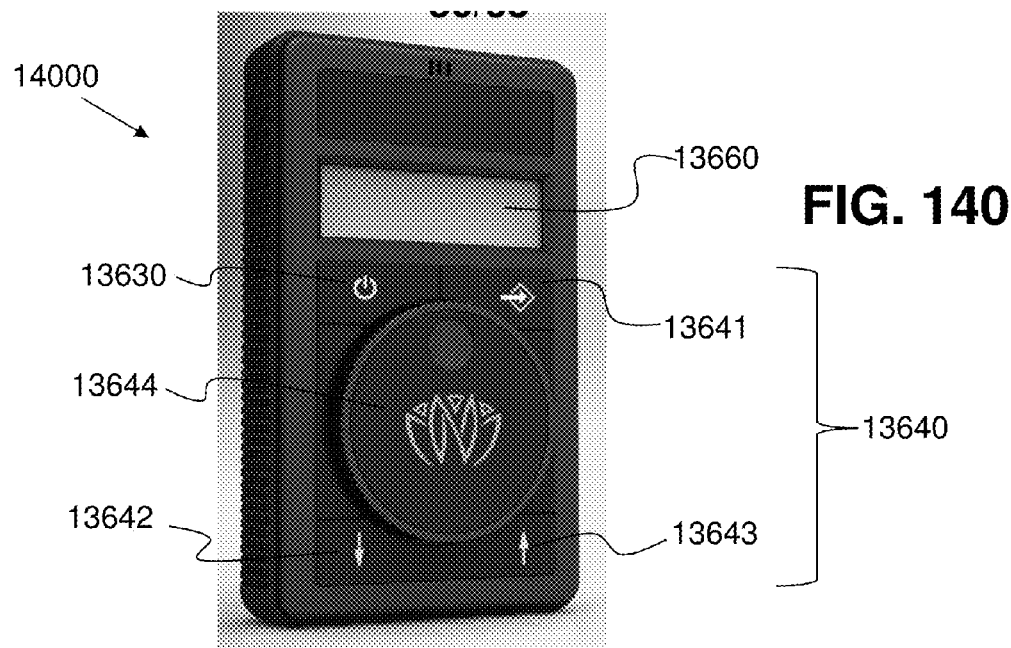
Figure 141:
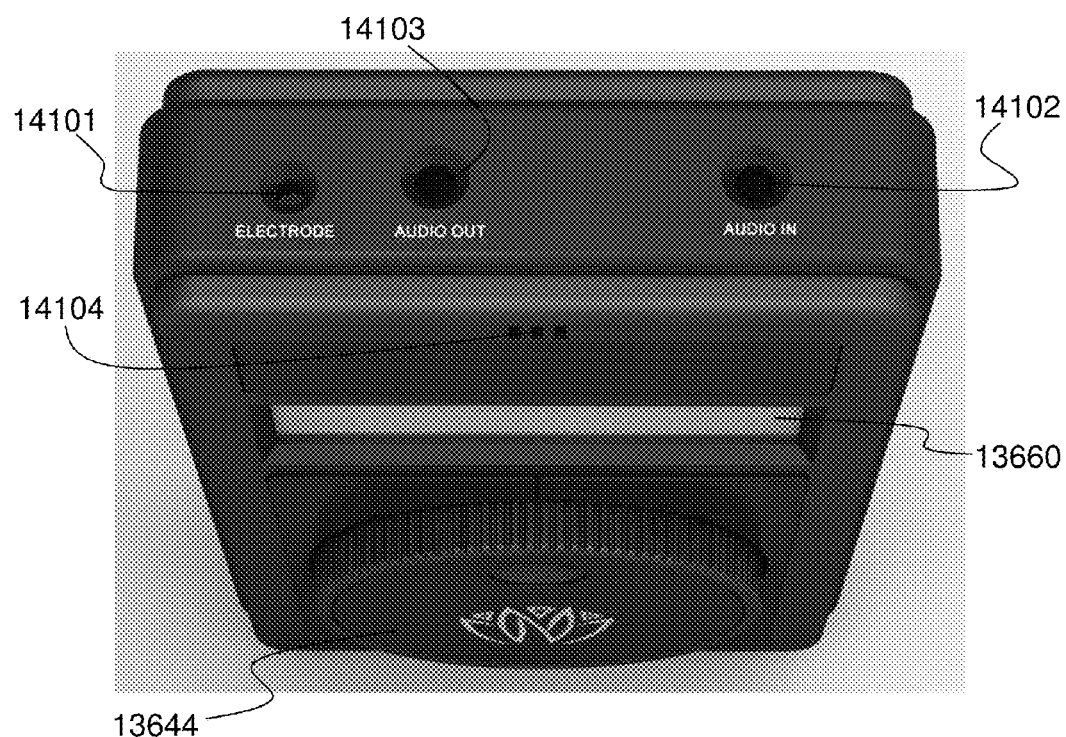
Figure 142:
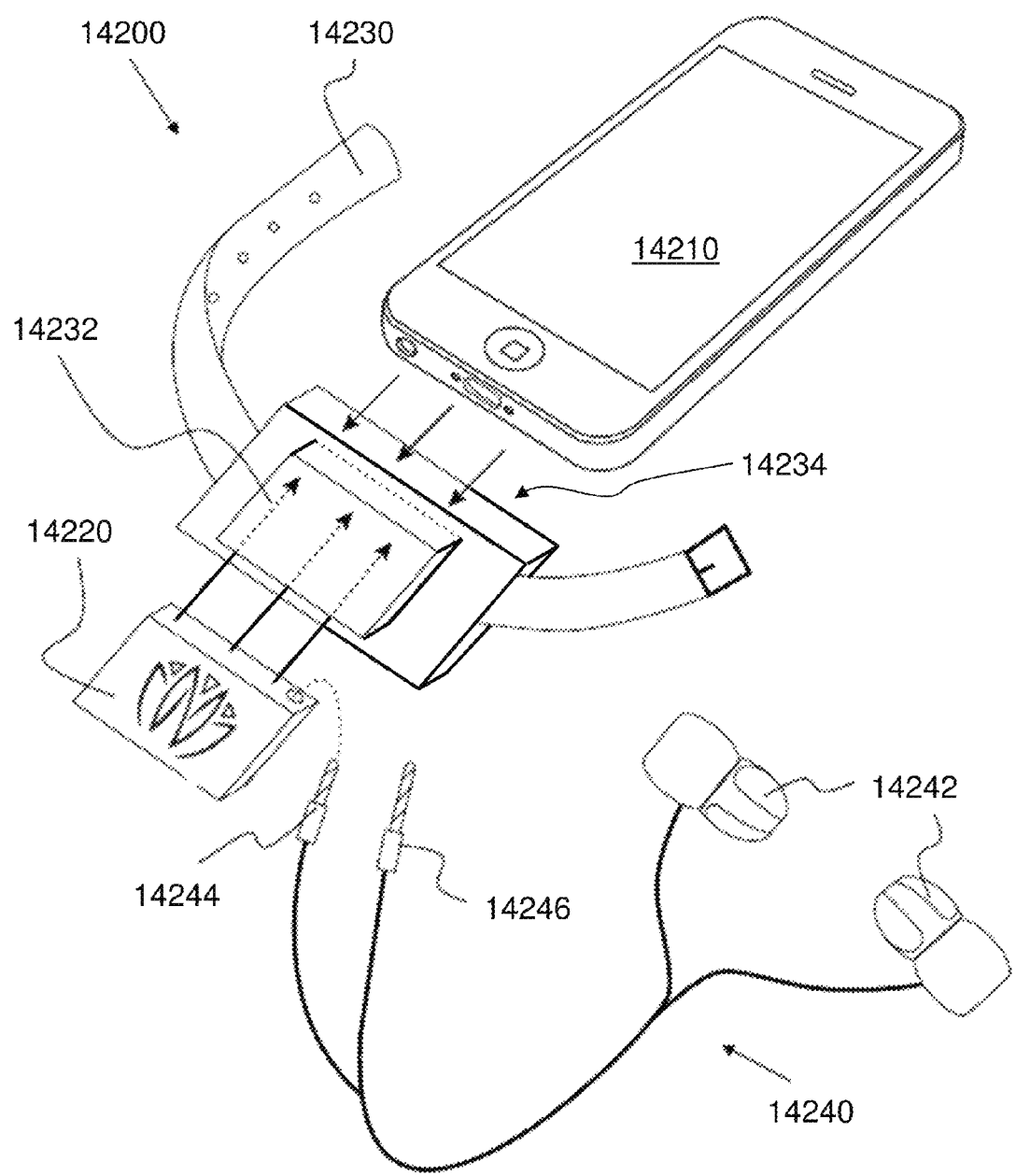
Figure 143:
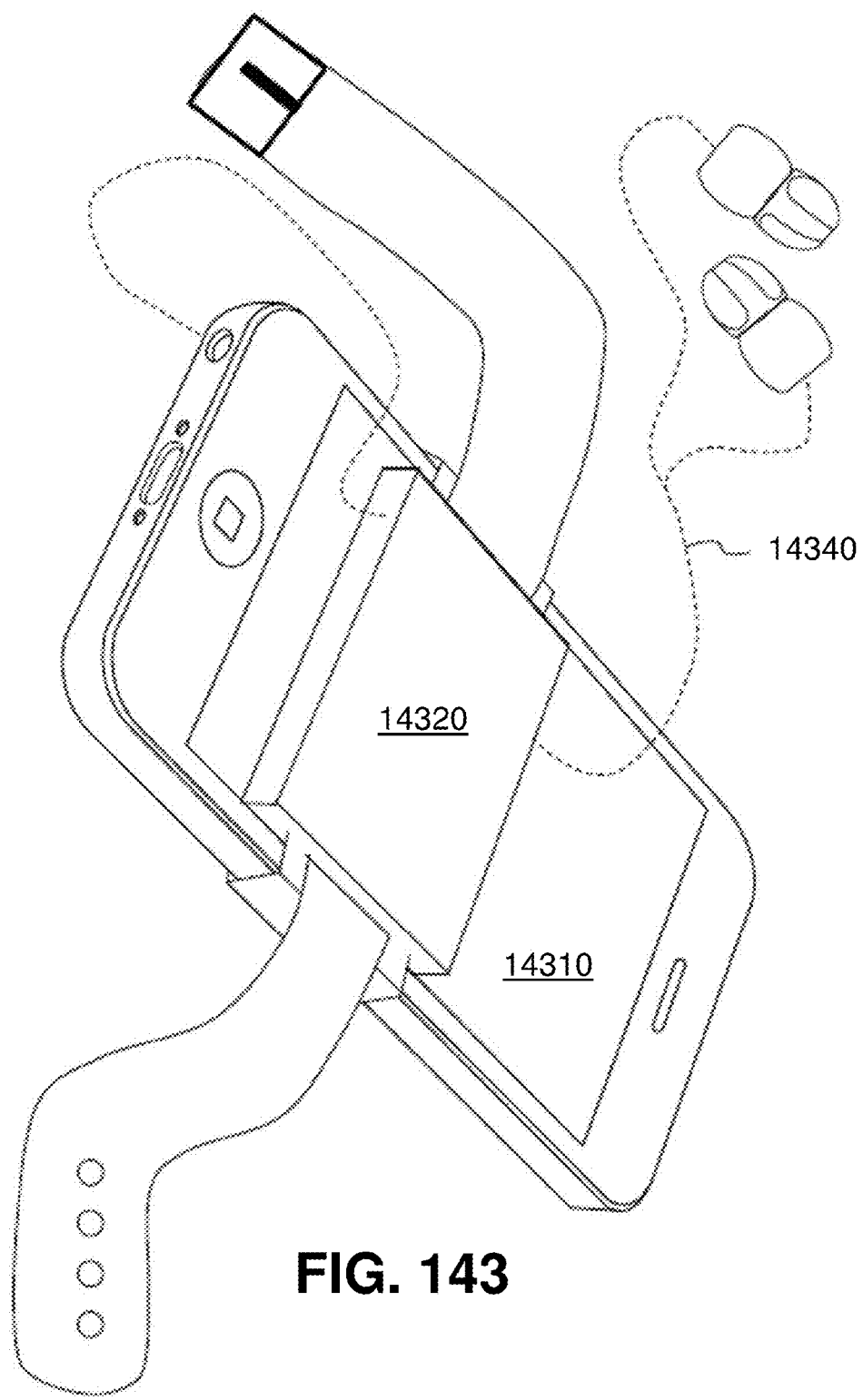
Figure 144:
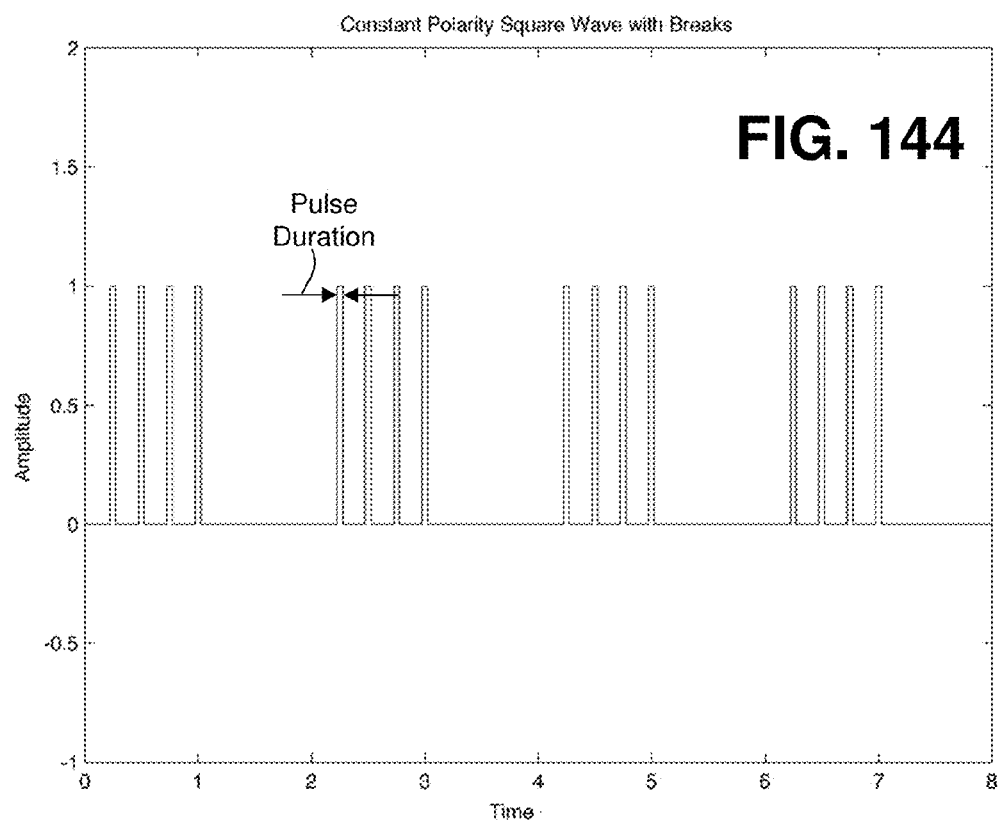
Figure 145:
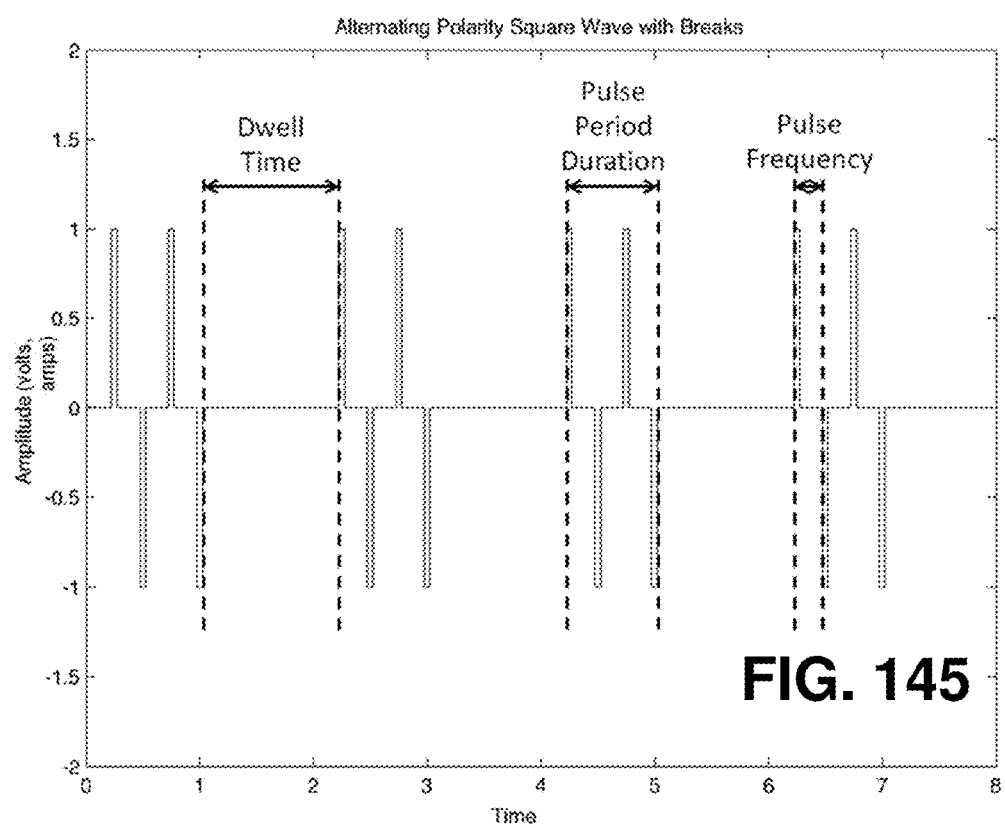
Figure 146:
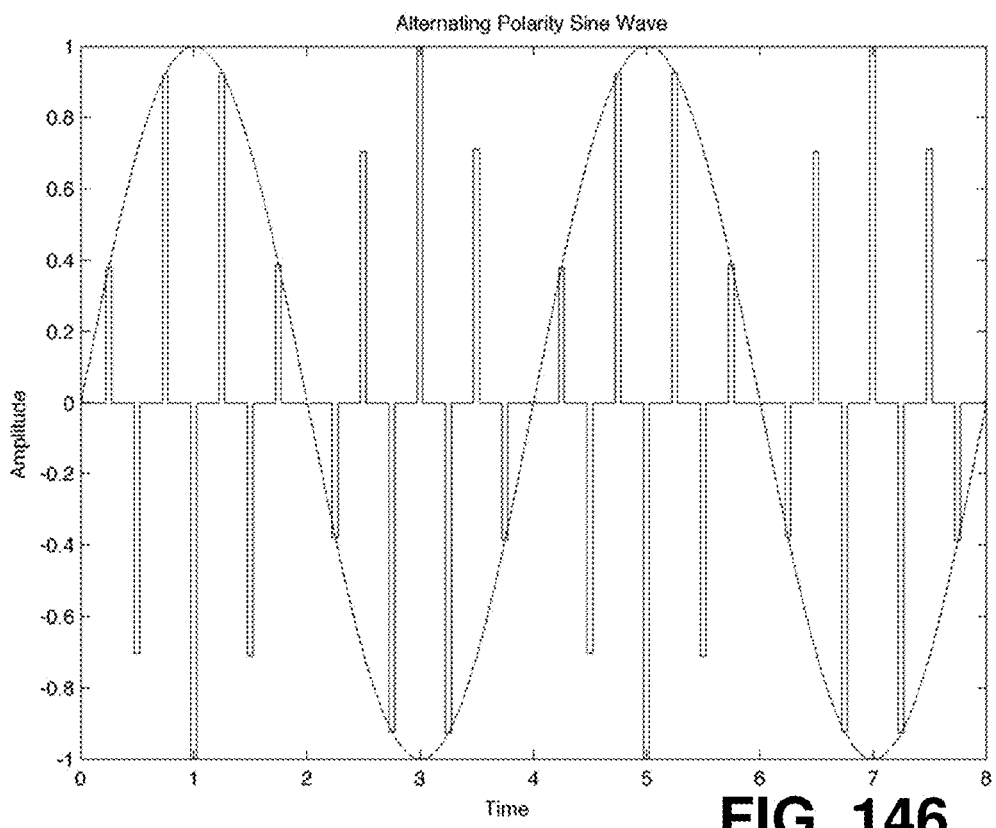
Figure 147:
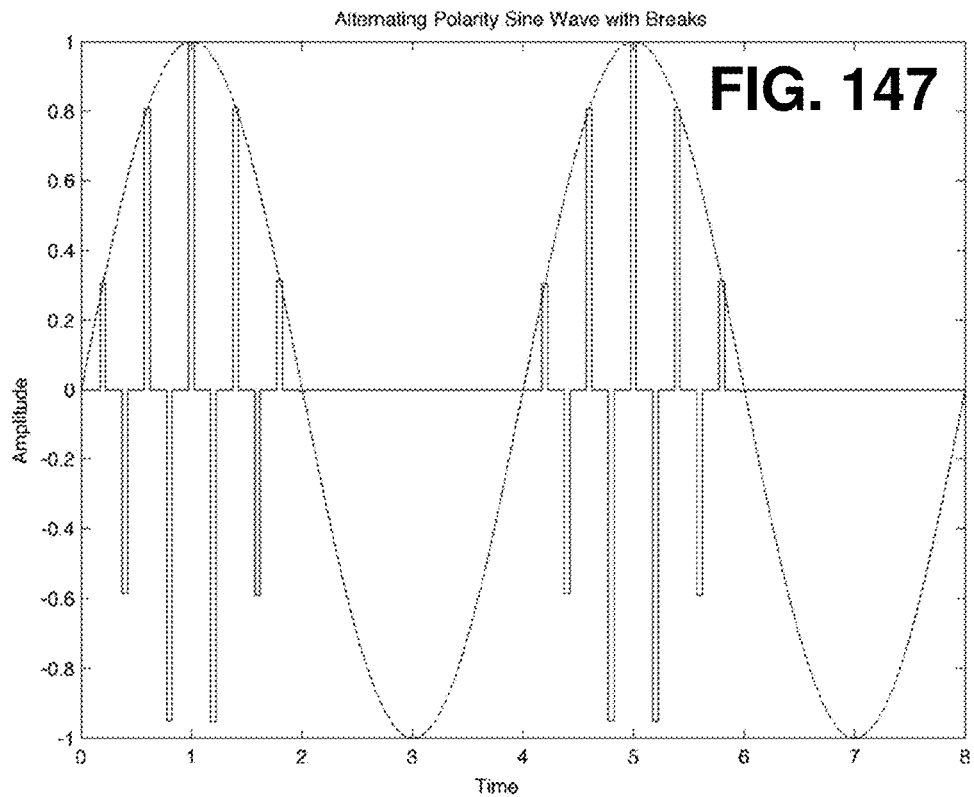
Figure 148:
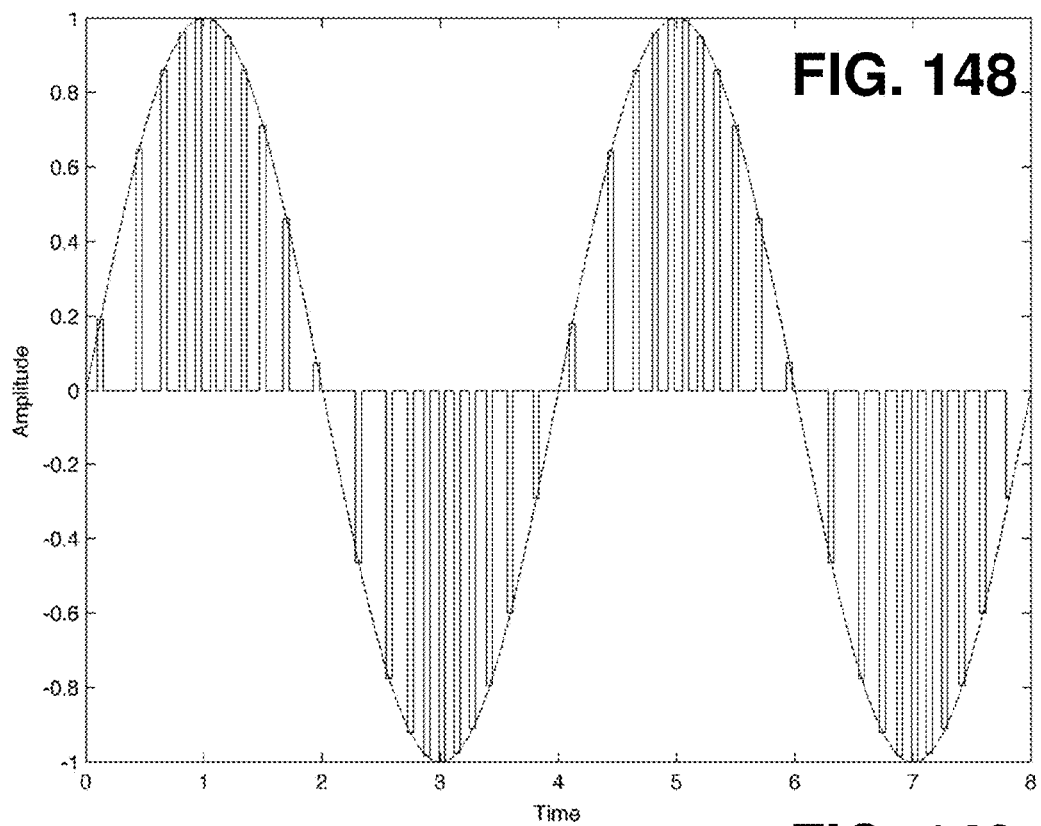
Figure 149:
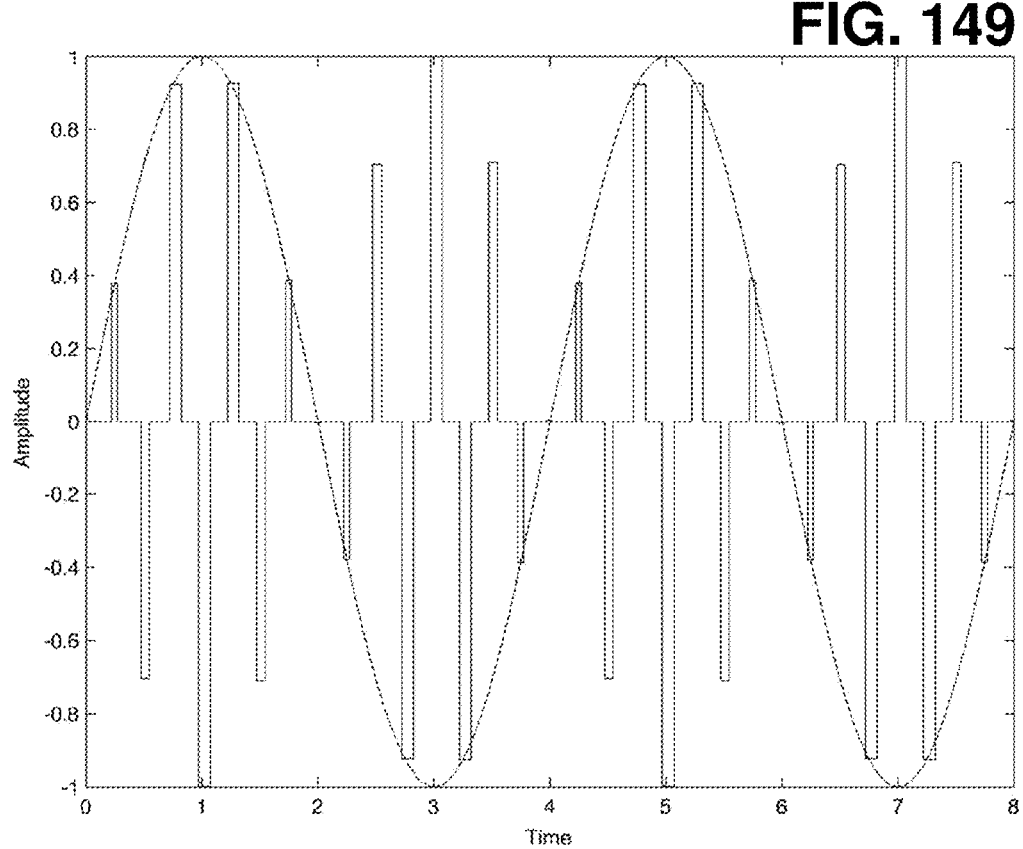
Figure 150:
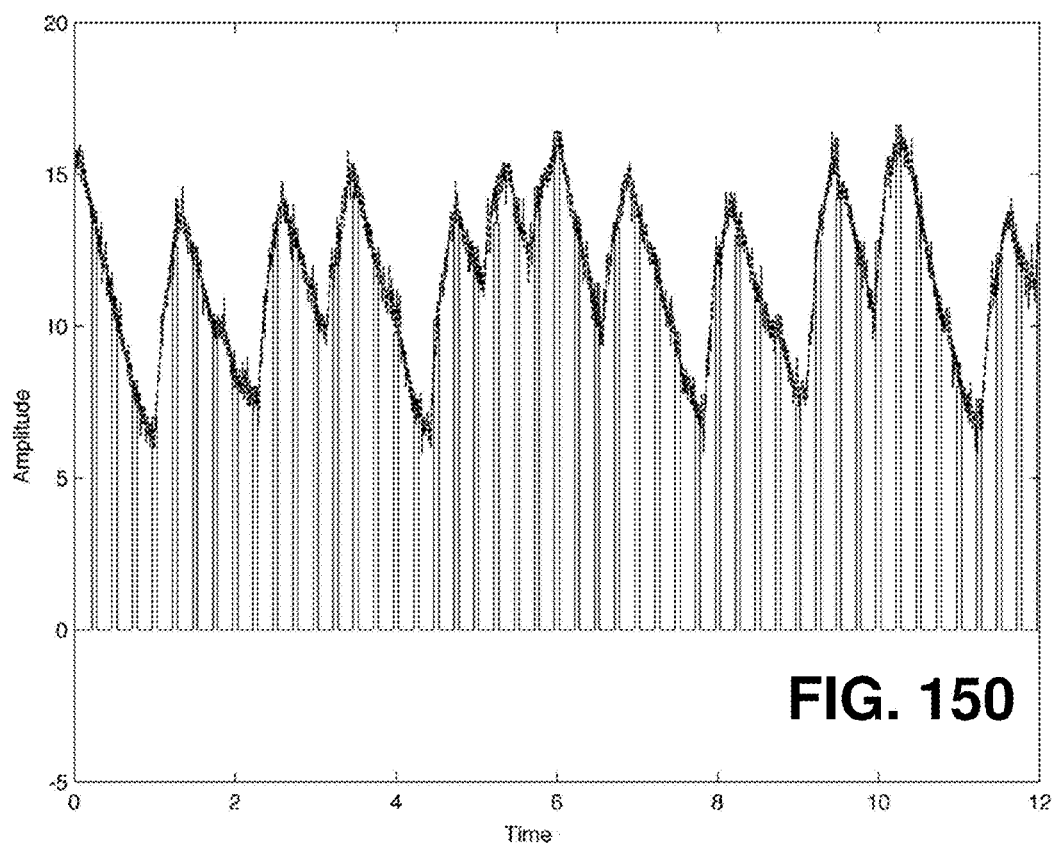
Figure 151:
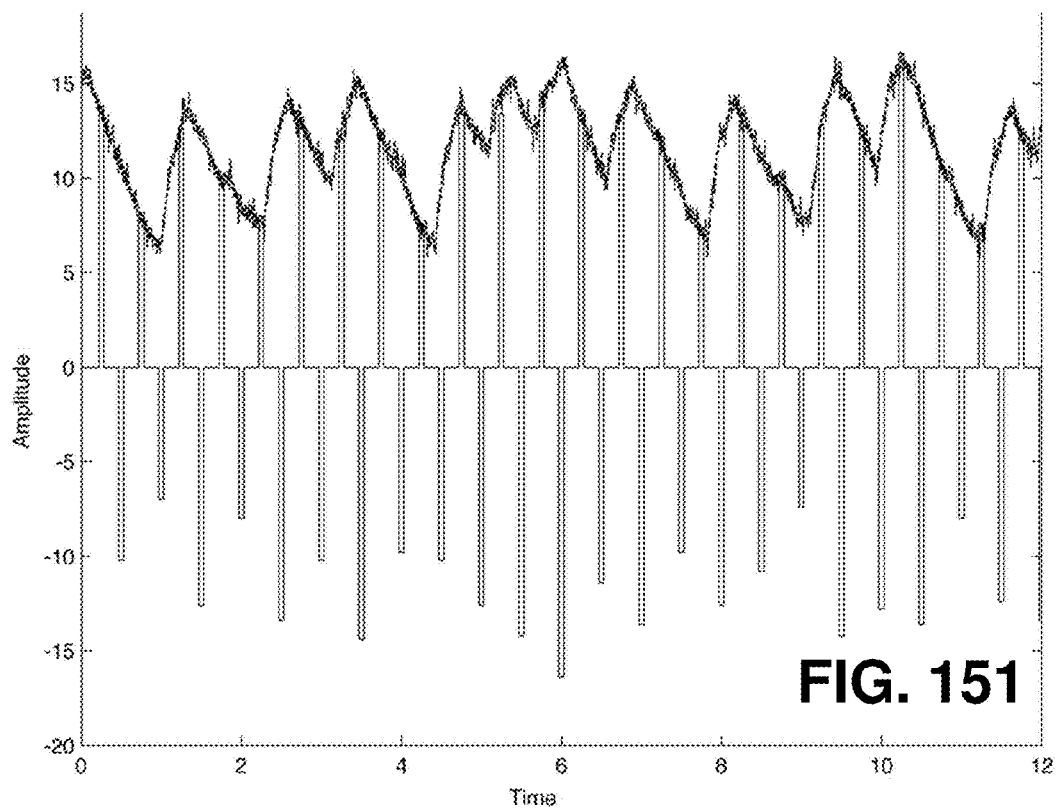
Figure 152:
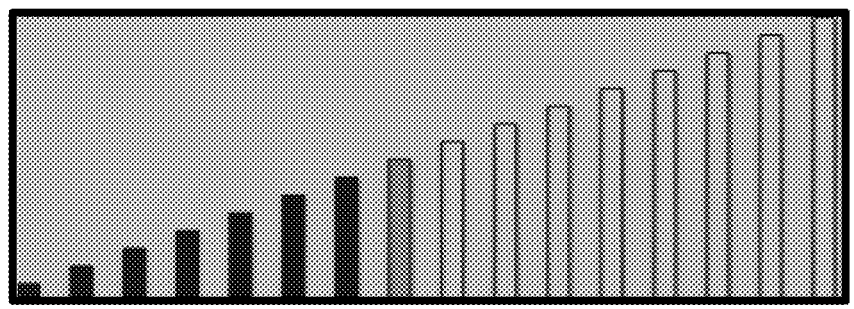
Figure 153:
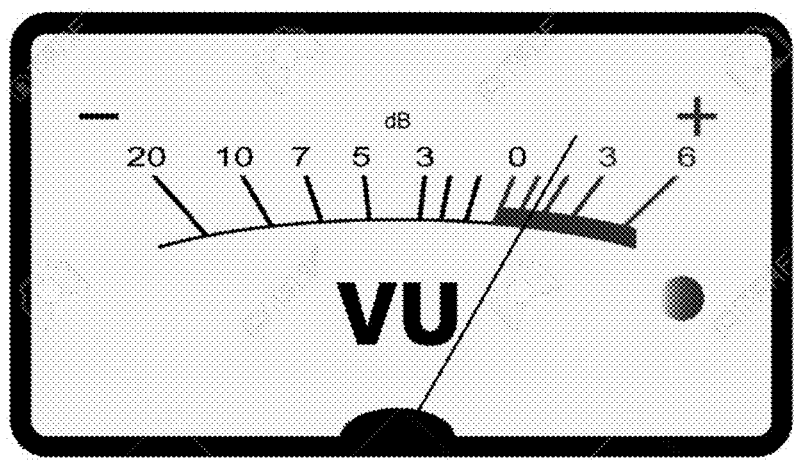
Figure 154:
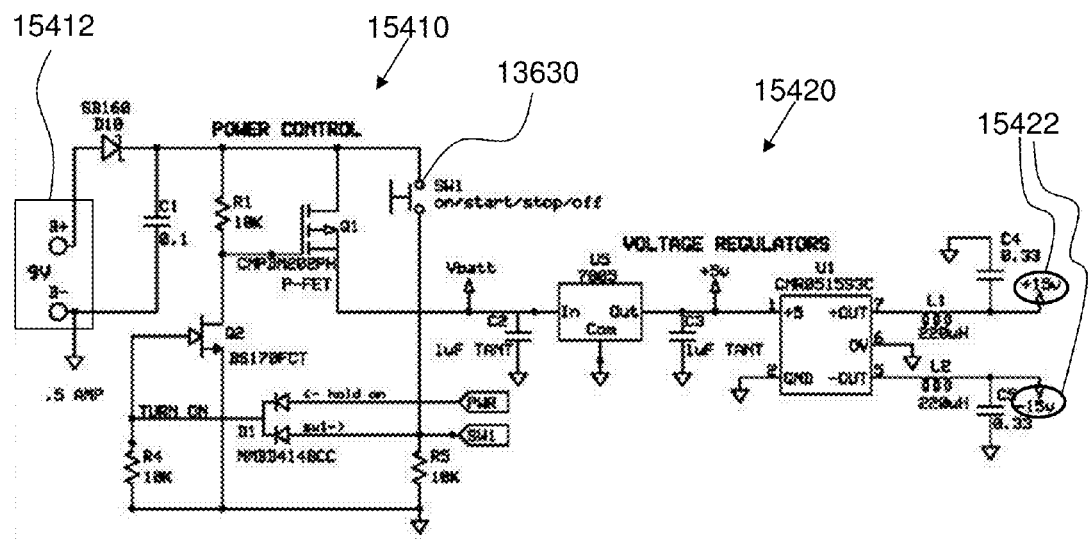
Figure 155:
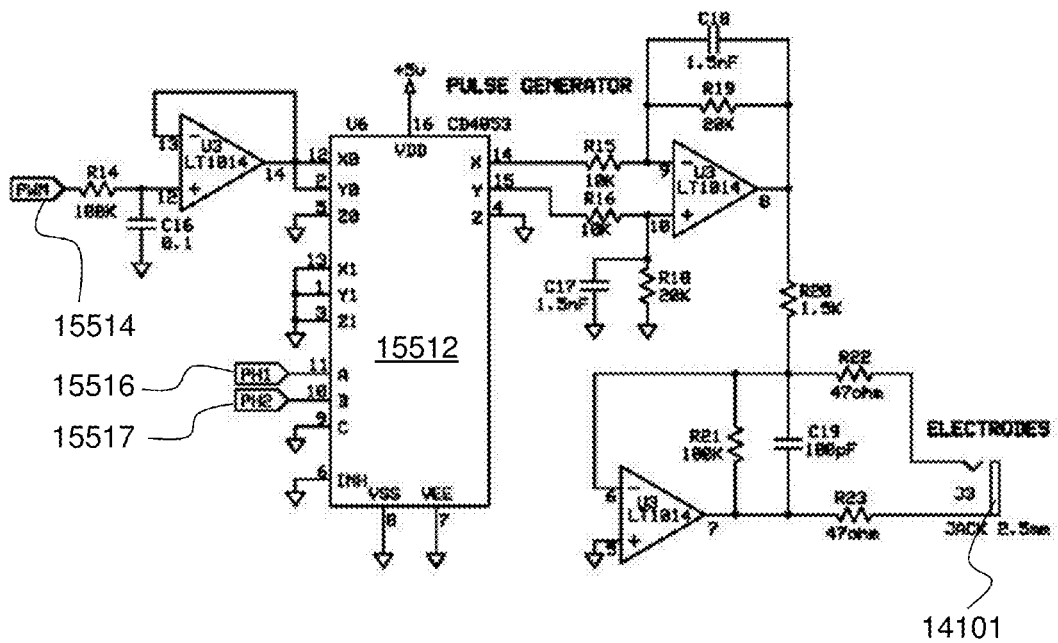
Figure 156:
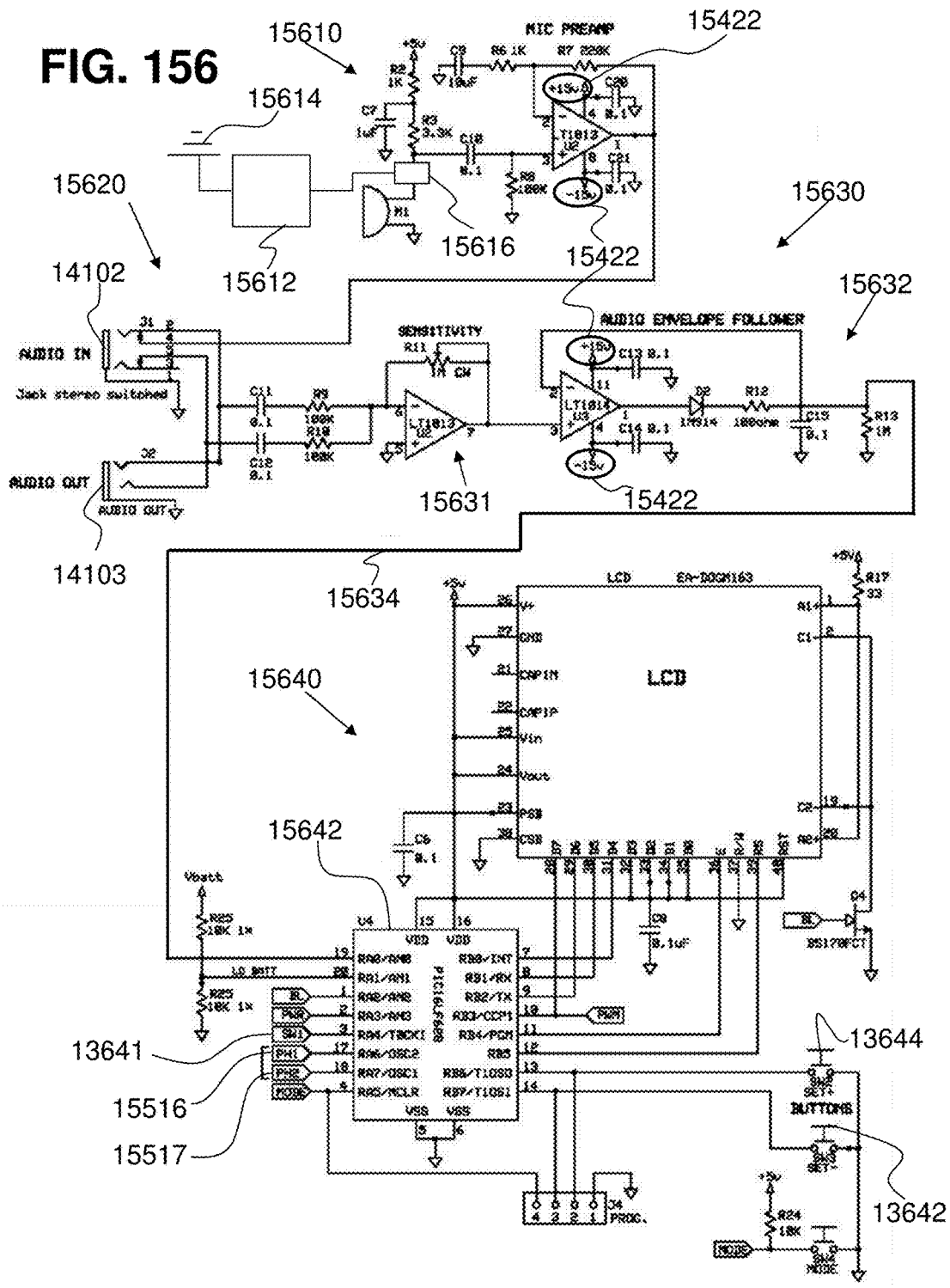
Figure 157:
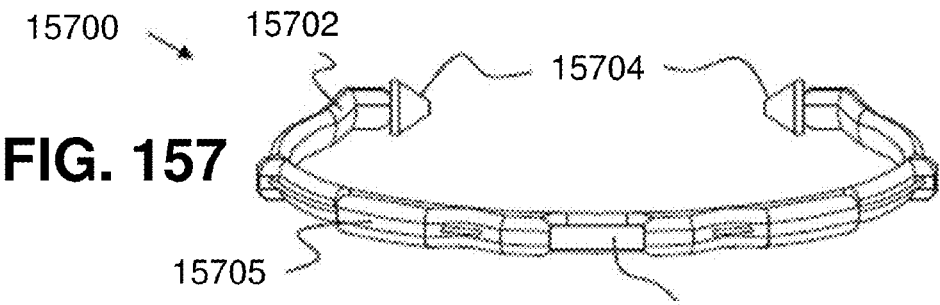
Figure 158:
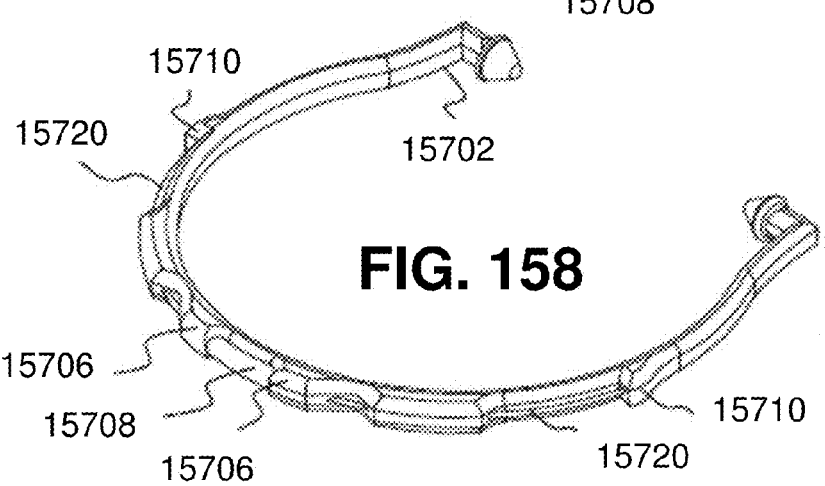
Figure 159:
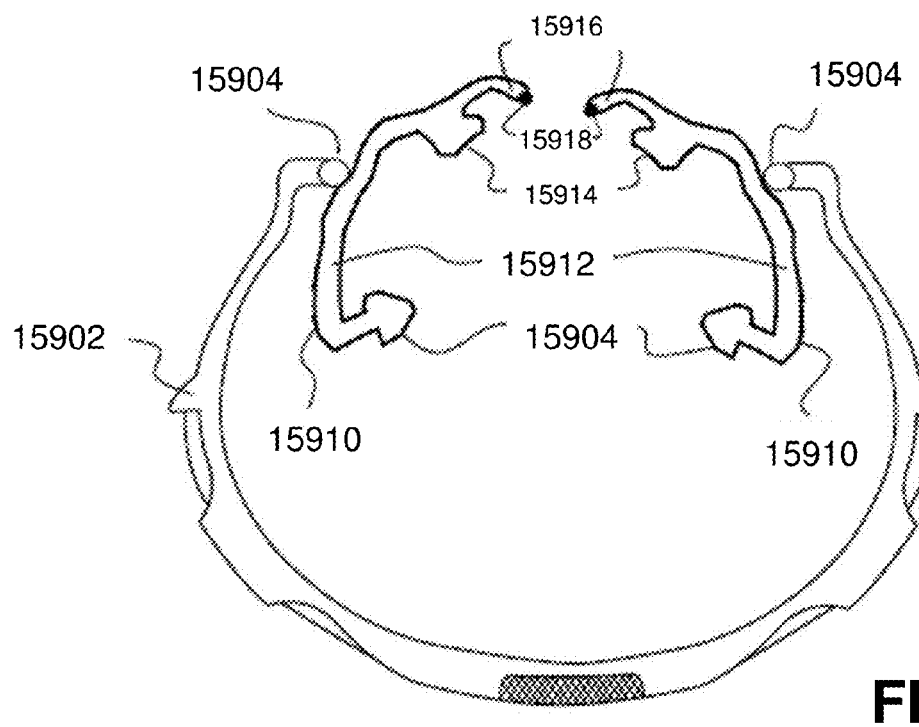
Figure 160:
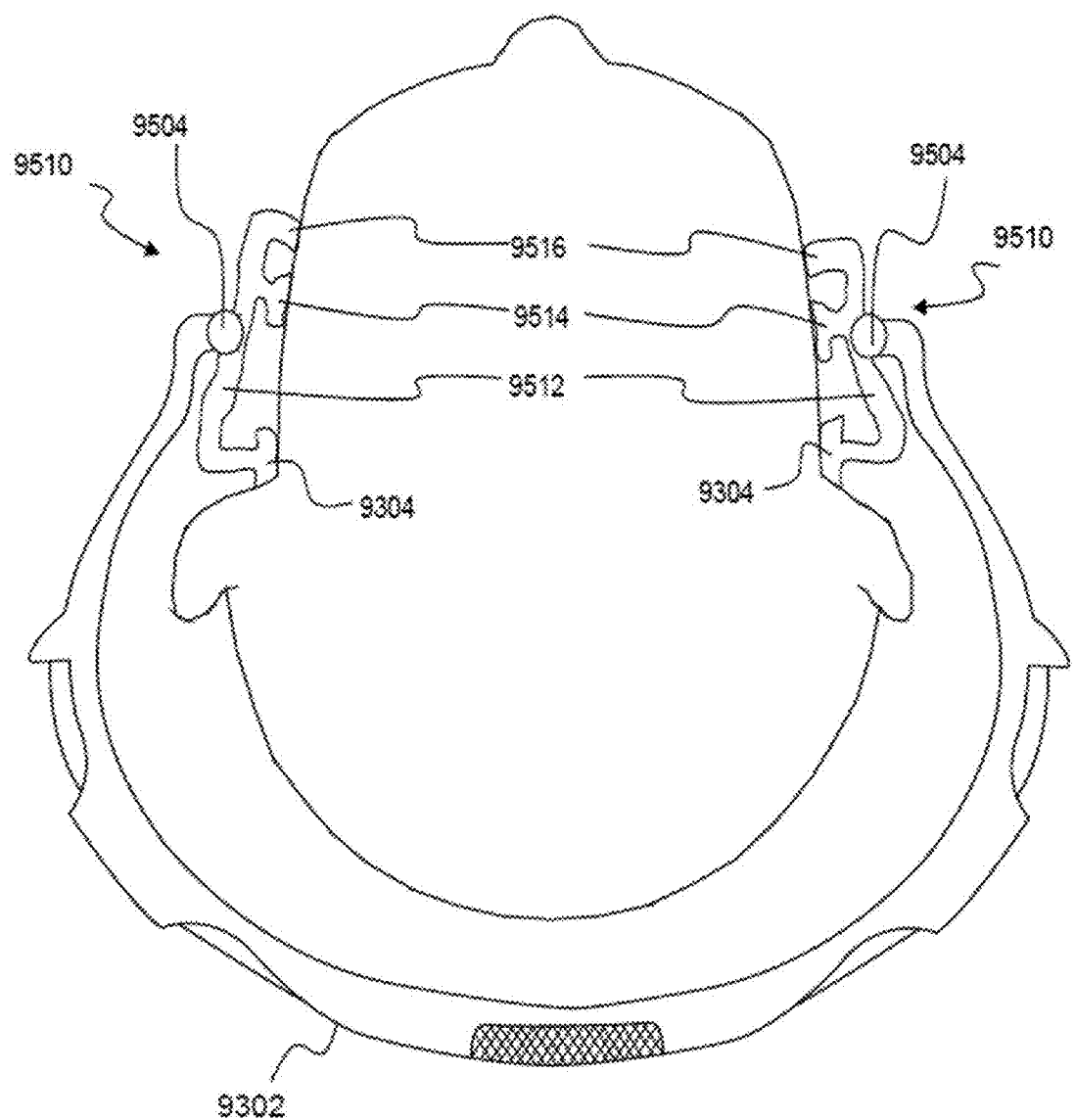
Figure 165:
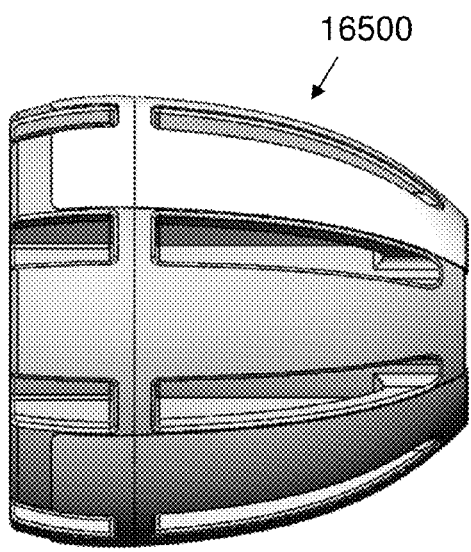
Figure 166:
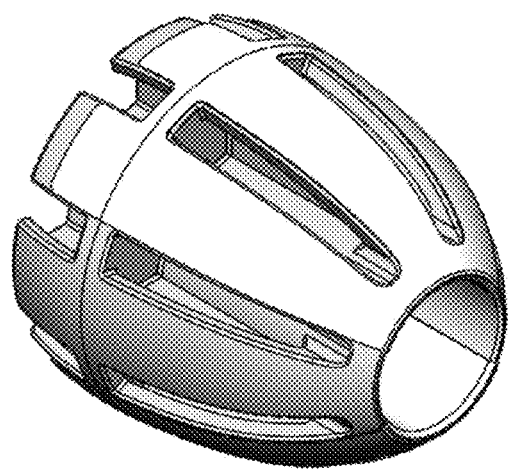
Figure 167:
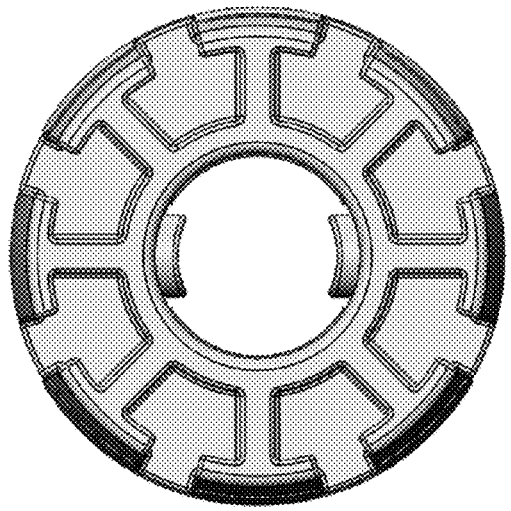
Figure 168:
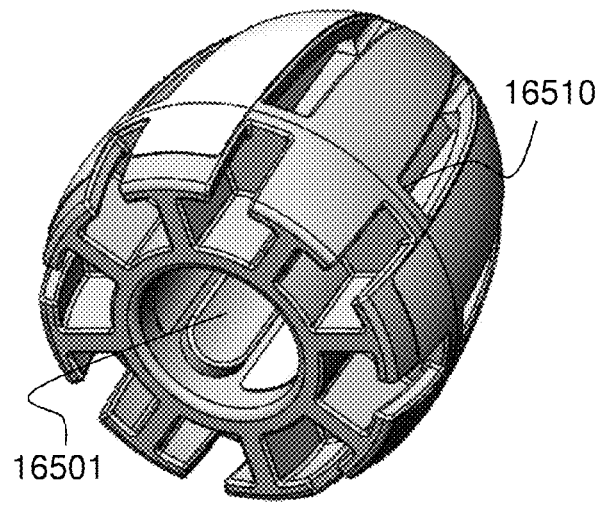

FIG. 131 is a diagrammatic side elevational view of the earbud-type neurostimulator device of FIG. 130 rotated ninety degrees;

FIG. 132 is a cross-sectional view of a an exemplary embodiment of an earbud-type neurostimulator device;

FIG. 133 is a side elevational view of the neurostimulator device of FIG. 132 rotated ninety degrees with the earbud removed;

FIG. 134 is a top plan view of the neurostimulator device of FIG. 132;

FIG. 135 is a top plan view of the neurostimulator device of FIG. 134 rotated ninety degrees;

FIG. 136 is a block circuit diagram of an exemplary embodiment of a signal and transmission architecture for providing neuromodulation with a combined generator and controller and a remote device coupler;

FIG. 137 is a block circuit diagram of an exemplary embodiment of a signal and transmission architecture for providing neuromodulation with a combined generator, controller and device coupler;

FIG. 138 is a block circuit diagram of an exemplary embodiment of a signal and transmission architecture for providing neuromodulation with a controller and a remote generator and device coupler;

FIG. 139 is a block circuit diagram of an exemplary embodiment of a signal and transmission architecture for providing neuromodulation with a combined generator and controller, a remote device coupler, and an audio source;

FIG. 140 is a front perspective view of an exemplary embodiment of an electrostimulation signal generation and transmission device;

FIG. 141 is a top perspective view of the device of FIG. 140;

FIG. 142 is a front perspective view of another exemplary embodiment of an electrostimulation signal generation and transmission device;

FIG. 143 is a front perspective view of a further exemplary embodiment of an electrostimulation signal generation and transmission device;

FIG. 144 is a graph of an exemplary embodiment of an electrostimulation process using an output of a constant polarity square wave with breaks;

FIG. 145 is a graph of an exemplary embodiment of an electrostimulation process using an output of an alternating polarity square wave with a constant pulse and breaks;

FIG. 146 is a graph of an exemplary embodiment of an electrostimulation process using an output of an alternating polarity modulated sine wave;

FIG. 147 is a graph of an exemplary embodiment of an electrostimulation process using an output of an alternating polarity modulated sine wave with breaks;

FIG. 148 is a graph of an exemplary embodiment of an electrostimulation process using a continuous square wave pulse having a sine wave modulated amplitude with a modulated frequency dependent upon amplitude;

FIG. 149 is a graph of an exemplary embodiment of an electrostimulation process using a continuous square wave pulse having a sine wave modulated amplitude at a constant frequency with no polarity group;

FIG. 150 is a graph of an exemplary embodiment of an electrostimulation process using an audio band amplitude modulated pulse output;

FIG. 151 is a graph of an exemplary embodiment of an electrostimulation process using an audio band amplitude modulated pulse output with breaks;

FIG. 152 is a diagrammatic illustration of an exemplary embodiment of a display;

FIG. 153 is a diagrammatic illustration of an exemplary embodiment of a display;

FIG. 154 is a circuit diagram of an exemplary embodiment of a power control and voltage regulation circuit for an electrostimulation device;

FIG. 155 is a circuit diagram of an exemplary embodiment of a pulse generation circuit for an electrostimulation device;

FIG. 156 is a circuit diagram of an exemplary embodiment of an audio input circuit, a sensitivity adjustment circuit and a display circuit for an electrostimulation device;

FIG. 157 is a rear perspective view of an exemplary embodiment of a trigeminal and temporal stimulator headband;

FIG. 158 is a perspective view from above a side of the trigeminal and temporal stimulator headband of FIG. 157;

FIG. 159 is a top plan view of the trigeminal and temporal stimulator headband of FIG. 157 with pivoting contact booms;

FIG. 160 is a top plan view of the headband of FIG. 157 in place on a user's head;

FIG. 161 is a side elevational view of an exemplary embodiment of an electrostimulation electrode earbud;

FIG. 162 is a perspective view from an audio out end of the electrostimulation electrode earbud of FIG. 161;

FIG. 163 is a plan view from a housing end of the electrostimulation electrode earbud of FIG. 161;

FIG. 164 is a perspective view from the housing end of the electrostimulation electrode earbud of FIG. 161;

FIG. 165 is a side elevational view of an exemplary embodiment of an electrostimulation electrode earbud;

FIG. 166 is a perspective view from an audio out end of the electrostimulation electrode earbud of FIG. 165;

FIG. 167 is a plan view from a housing end of the electrostimulation electrode earbud of FIG. 165; and FIG. 168 is a perspective view from the housing end of the electrostimulation electrode earbud of FIG. 165.

DETAILED DESCRIPTION OF THE INVENTION

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

It will be appreciated that embodiments of the invention described herein may be comprised of one or more conventional processors and unique stored program instructions that control the one or more processors to implement, in conjunction with certain non-processor circuits and other elements, some, most, or all of the functions of the devices and methods described herein. The non-processor circuits may include, but are not limited to, signal drivers, clock circuits, power source circuits, and user input and output elements. Alternatively, some or all functions could be implemented by a state machine that has no stored program instructions, or in one or more application specific integrated circuits (ASICs) or field-programmable gate arrays (FPGA), in which each function or some combinations of certain of the functions are implemented as custom logic. Of course, a combination of these approaches could also be used. Thus, methods and means for these functions have been described herein.

The terms "program," "software," "software application," and the like as used herein, are defined as a sequence of instructions designed for execution on a computer system or programmable device. A "program," "software," "application," "computer program," or "software application" may include a subroutine, a function, a procedure, an object method, an object implementation, an executable application, an applet, a servlet, a source code, an object code, any computer language logic, a shared library/dynamic load library and/or other sequence of instructions designed for execution on a computer system.

Herein various embodiments of the present invention are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Described now are exemplary embodiments. Referring now to the figures of the drawings in detail and first, particularly to FIG. 1, there is shown a first exemplary embodiment of an electrostimulator with a user coupler containing a pair of electrodes (indicated diagrammatically and circled with a dashed line). An electromagnetic pulse generator 1 includes the user surge button 2, which allows a user to direct the generator 1 (with a button depression) to impart a predetermined output signal of a pre-set duration of an increased or different signal modulation, i.e., if the user has a back pain flair after lifting, he/she is able to depress the user surge button 2 to have an "as needed" higher dose of stimulation. The generator 1 also includes a control 3 (e.g., a dial) that can turn on and off the generator 1 and/or alter settings in the device to provide variable and various settings. The generator 1 also can include a data screen or monitor 4 to provide visual indication or feedback to a user.

A conduit 5 for transmitting signals to the user coupling devices 8 is connected to the generator 1. Splitter conduits 6 supply dedicated signals to one or more pairs of the user couplers 8 (a second pair 8 being indicated with dashed lines). Each of the user couplers in this embodiment has a magnetic component 7 (i.e., a reciprocal magnetic element). In other words, each of the pair of couplers 8 has one of the reciprocal magnetic elements 7 that attract each other, thus creating and maintaining proper contact (and maintaining proper impedance) between the contact leads of the user couplers and the body surface. With two pairs of user couplers 8, signal can be applied to two different body surface sites. Other exemplary embodiments can include greater than these two pairs of user couplers 8 (or two sets of user couplers 8 and a common ground).

Figure 1:
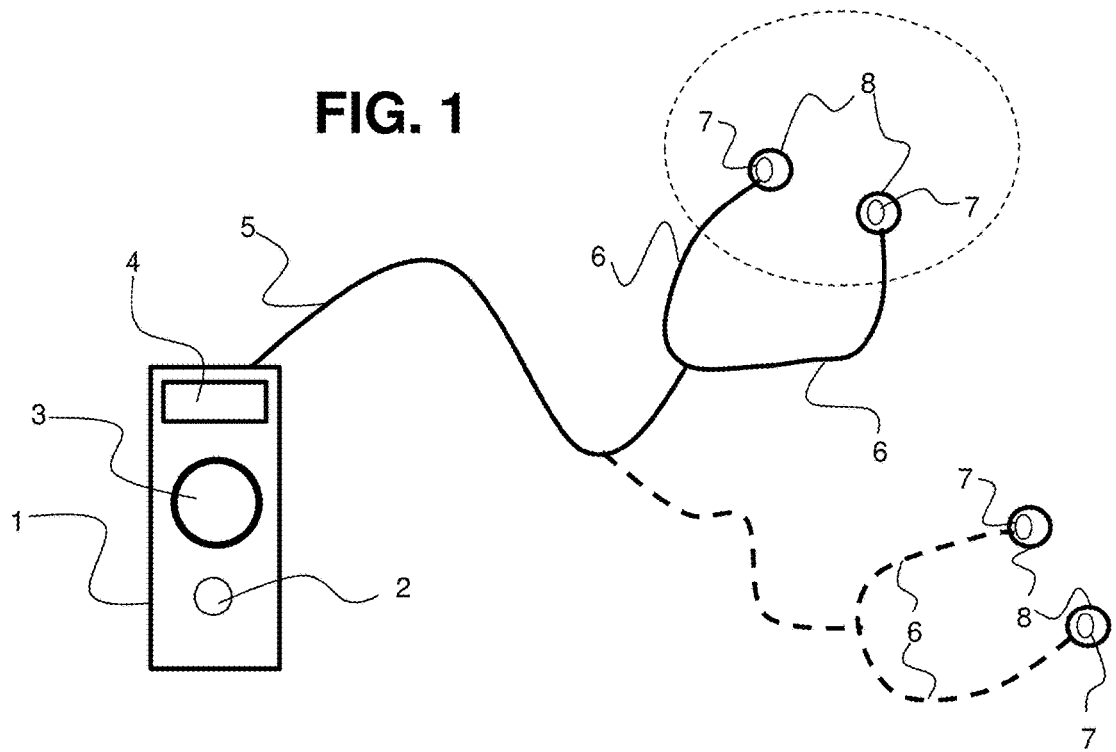
FIG. 1 is a diagrammatic representation of an electrostimulator with one pair of user couplers for application to one body surface site.
Figure 2:
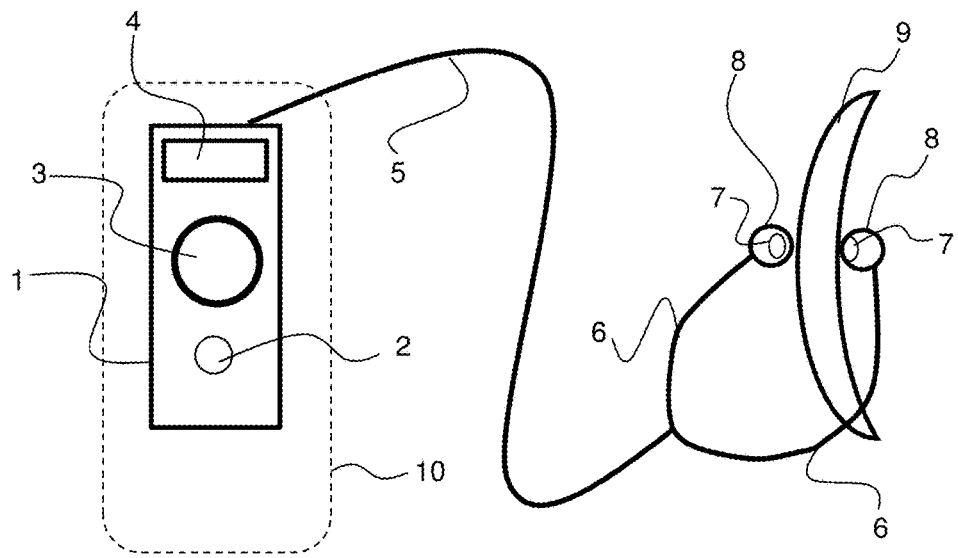
FIG. 2 is a diagrammatic representation of the device in FIG. 1 with its single pair of user couplers applied to a user target area about the ear.

FIG. 2 depicts the device of FIG. 1 with a single pair of user couplers applied to a user target area about the user's ear 9. The contact lead 5 transmits a signal(s) from the splitter conduit 6 to the user's body surface, here, about the ear 9. The user couplers are pressed and held against the skin of the ear 9 by the magnetic component 7 and, thereby, allow transmission of an electromagnetic signal through the user's body surface, thus affect the targeted structure.

In an exemplary embodiment, the user couplers can have a common ground locally or remotely (i.e., to the portion of the generator that would be in contact with the skin). Ground may have a heating device that causes increased blood flow or perspiration, thereby decreasing impedance and increasing signal transfer to the target structure.

In the exemplary embodiment shown, the generator 1 can be a stand-alone device. As an alternative, for example, the generator 1 can be a smartphone that has software for carrying out the signal transmission as an app on the smartphone, indicated diagrammatically with the dashed lines 10 in FIG. 2.

In the exemplary embodiment of FIG. 2, neuromodulation of the vagus nerve can occur for treating various conditions, such as for pain relief. Characteristics of the vagus nerve are that it is a cranial nerve having both efferent (motor) and afferent (sensory) transmission. The vagus nerve has been identified as a conduit towards treating conditions such as the sensations of pain, emotions (e.g., well-being, pleasure, depression), the ability to concentrate, the occurrence of seizures, and disorders of the limbic system.

Figure 3:
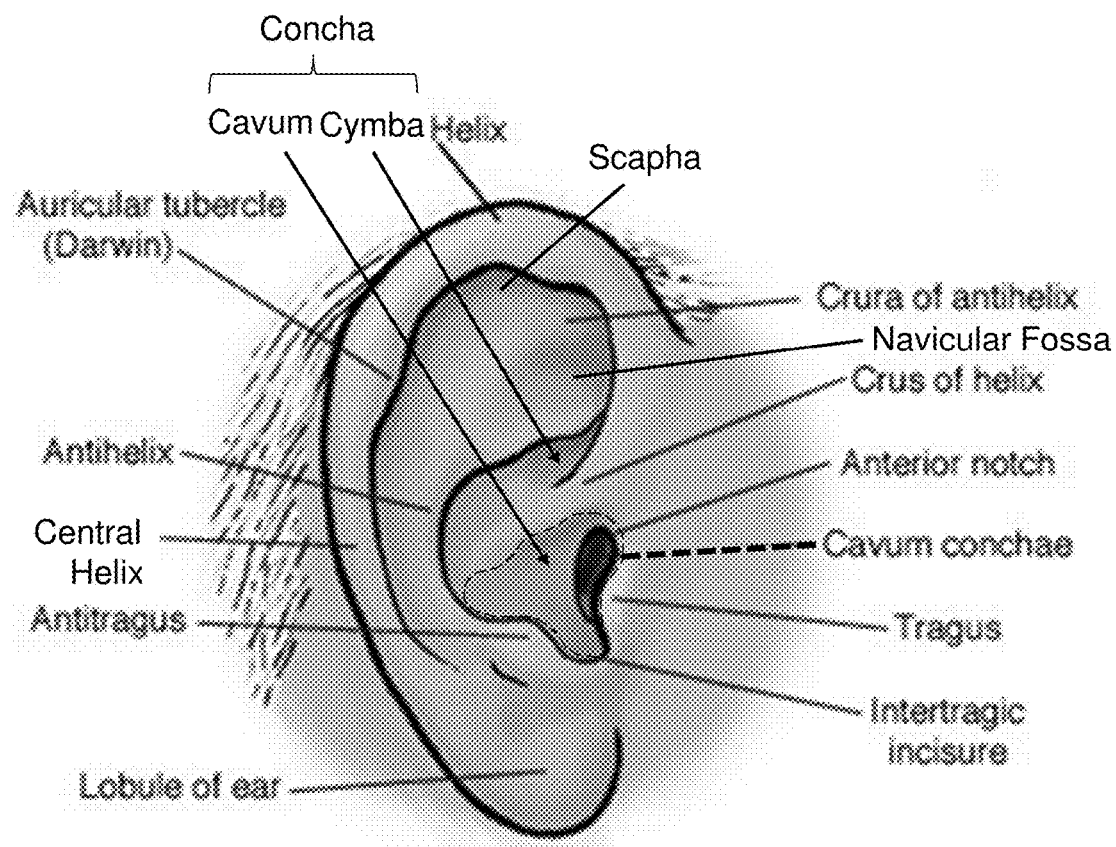
FIG. 3 is a fragmentary illustration of a right human ear with anatomy indications.

Such therapy utilizing the external (non-invasive) systems and methods described herein for the vagus nerve references a diagram of the human ear in FIG. 3. It is known that the vagus nerve has a branch that passes close to the concha of the ear. The concha forms a concave bowl shape and comprises the cymba above the crus of the helix and the cavum below the crus of the helix. The inventors have discovered that areas of the ear are particularly useful for applying neuromodulation to the vagus nerve: the concha and the posterior auricle (the back side of the ear opposite the concha) and a portion of the ear canal. The first two of these therapy regions are identified in FIGS. 4 and 5 with the conchal region 50 and the auricle region 60 highlighted.

Figure 4:
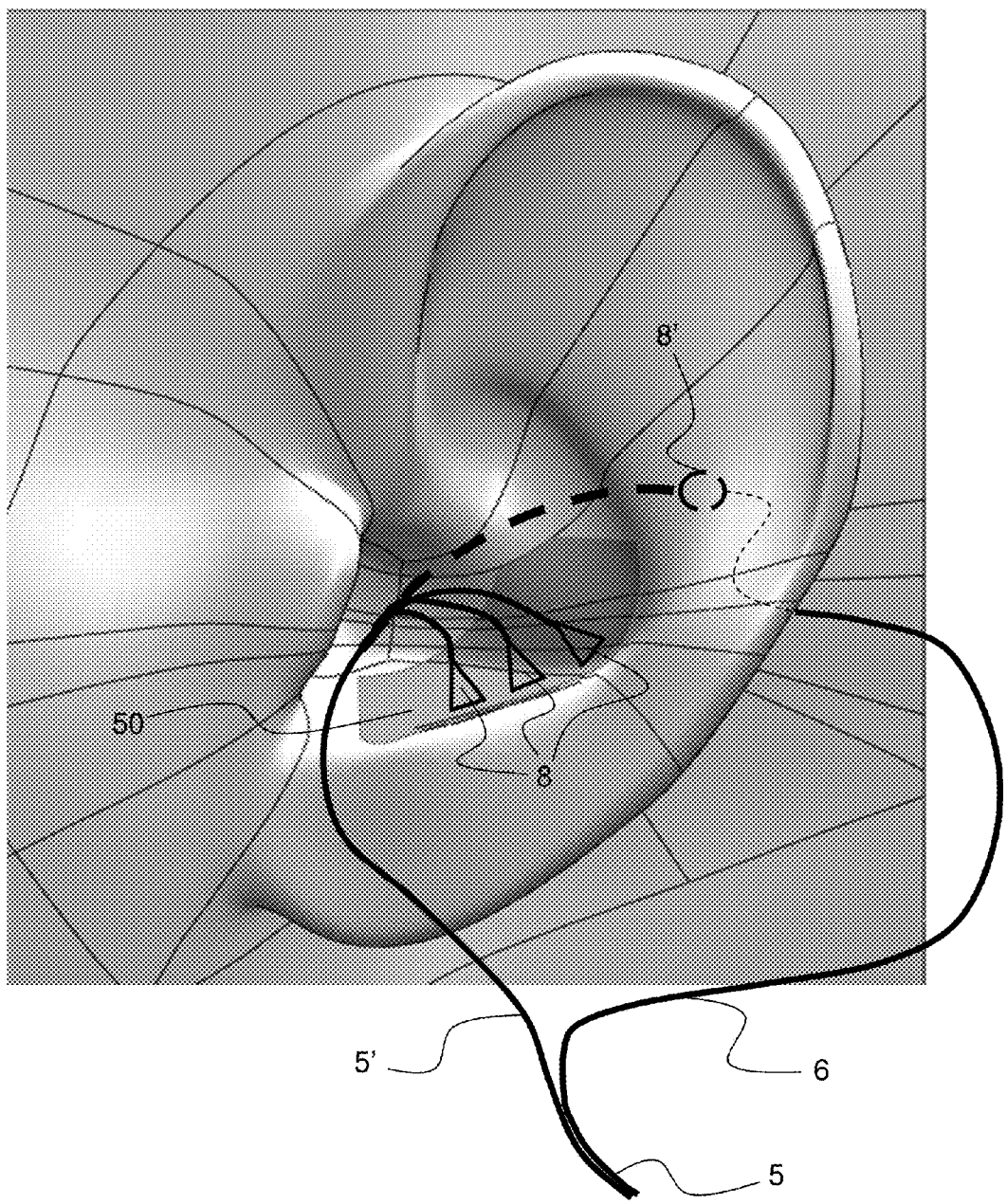
FIG. 4 is a fragmentary, side perspective view of the ear with exemplary embodiments of transcutaneous vagus nerve stimulation devices.
Figure 5:
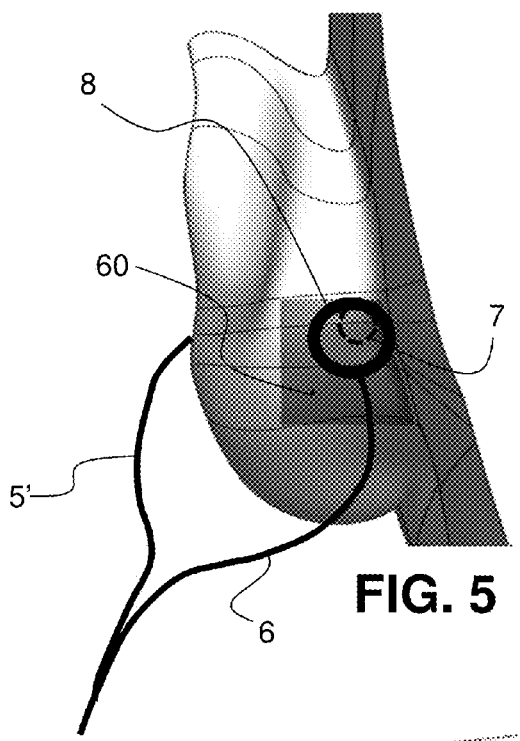
FIG. 5 is a fragmentary, rear perspective view of the ear of FIG. 4.
Figure 6:
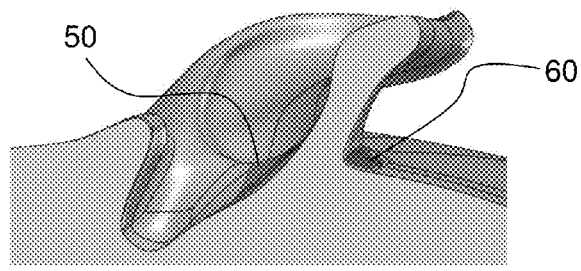
FIG. 6 is a fragmentary, lateral cross-sectional view of an upper portion the ear of FIG. 4 viewed from below.
Figure 7:
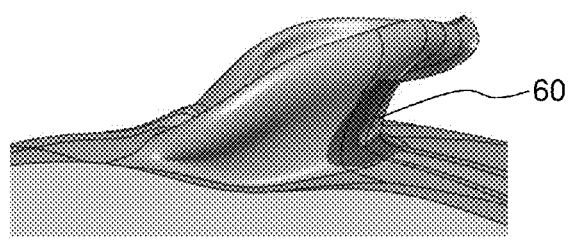
FIG. 7 is a fragmentary, bottom perspective view of the ear of FIG. 4.

A first exemplary embodiment of a system such as those described with regard to FIGS. 1 and 2 is illustrated in FIGS. 4 and 5. Therein, a conduit 5 for transmitting signals to the coupling devices is connected to the generator 1. One portion of the conduit 5' provides a positive side of the signal to electrodes 8 and another portion 6 of the conduit 5 supplies a negative or ground side of the signal to the electrodes 8. In the exemplary embodiment shown, there are three electrodes 8 on the positive side. There can be a corresponding set of three electrodes 8 on the negative side behind the ear (not illustrated) or there can be a single grounding electrode 8 behind the ear as shown in FIG. 4. Each of the electrodes 8 can have a magnetic component 7 (i.e., a reciprocal magnetic element) to secure to the surface of the ear. If there is a ferrous material 7 on the back side of the ear, a grounding electrode 8' could be present on the same side of the ear as the positive electrodes 8. Such a configuration is illustrated with a dashed line leading to the electrode 8' in FIG. 4. Each of the positive electrodes 8 can be supplied with the same or different signals. In the latter case, the generator 1 can apply a variable signal pattern that utilizes feedback from the user. When the signal is providing the user with a beneficial result, the generator 1 can be caused to retain the signal pattern currently being applied for the therapy period. When the signal is not providing the user with a beneficial result, the generator 1 can be caused to change the signal pattern currently being applied to a different signal pattern or, if there are multiple electrodes 8, to change how the electrodes apply the signal. For example, if a signal from one of the three electrodes 8 and electrode 8' are beneficial, then the electrode 8' can be paired with another of the three electrodes 8. Alternatively, the negative or ground and positive can be switched about to have a signal occur between two of the three electrodes 8. Alternatively or additionally, three different signals can be applied to each of the three electrodes 8. In this manner, if one or two or even all three of the signals being applied to a portion of the concha (through respective device couplers 8) achieve a beneficial result, the differing topographies and impedances of the ear can be rendered moot.

In an alternative exemplary embodiment, the grounding electrode 8' can be a position maintaining device (indicated in FIG. 4 with a large dashed line) connected to the conduit 5' (e.g., with a shielded piece of Nitinol). This Nitinol can have its own dedicated current supply, that, when applied, heats the wire and, therefore, bends the Nitinol towards the inner surface of the ear to move its contact point towards the skin, not only to enhance position maintenance, but also to decrease impedance.

The electrodes 8, 8' can take various forms. As describe above with regard to FIGS. 1 and 2, the user couplers can simply be a pair of electrodes. FIGS. 16 to 28, in comparison, show two different configurations.

Figure 8:
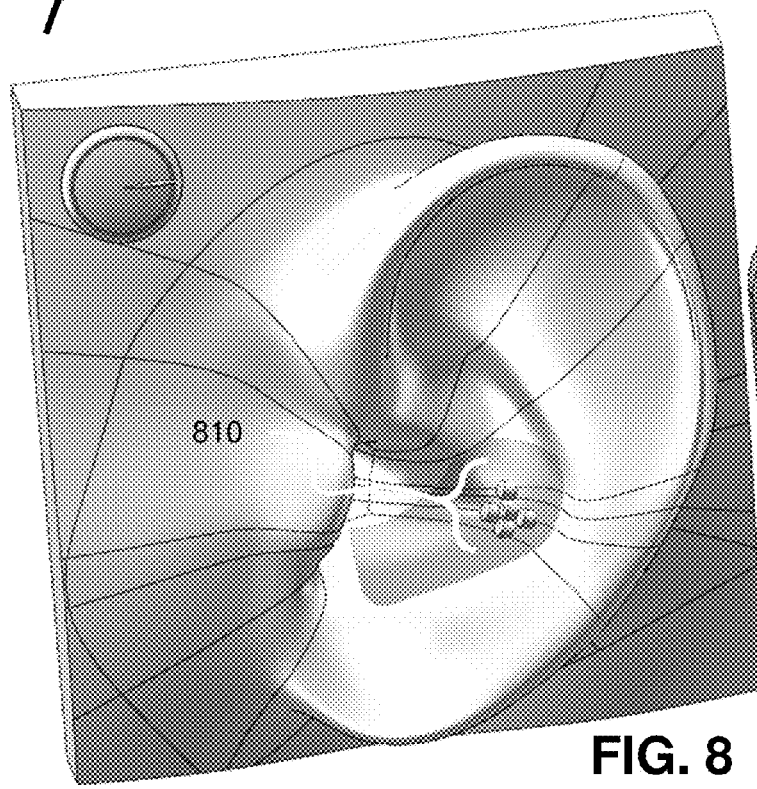
FIG. 8 is a fragmentary, side perspective and vertically cross-sectional view of the ear of FIG. 4 with an exemplary embodiment of a transcutaneous vagus nerve stimulation device.
Figure 9:
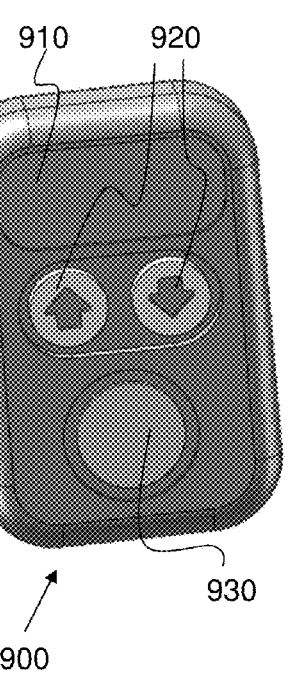
FIG. 9 is a front elevational view of an exemplary embodiment of a vagus nerve stimulation generator and control device.
Figure 16:
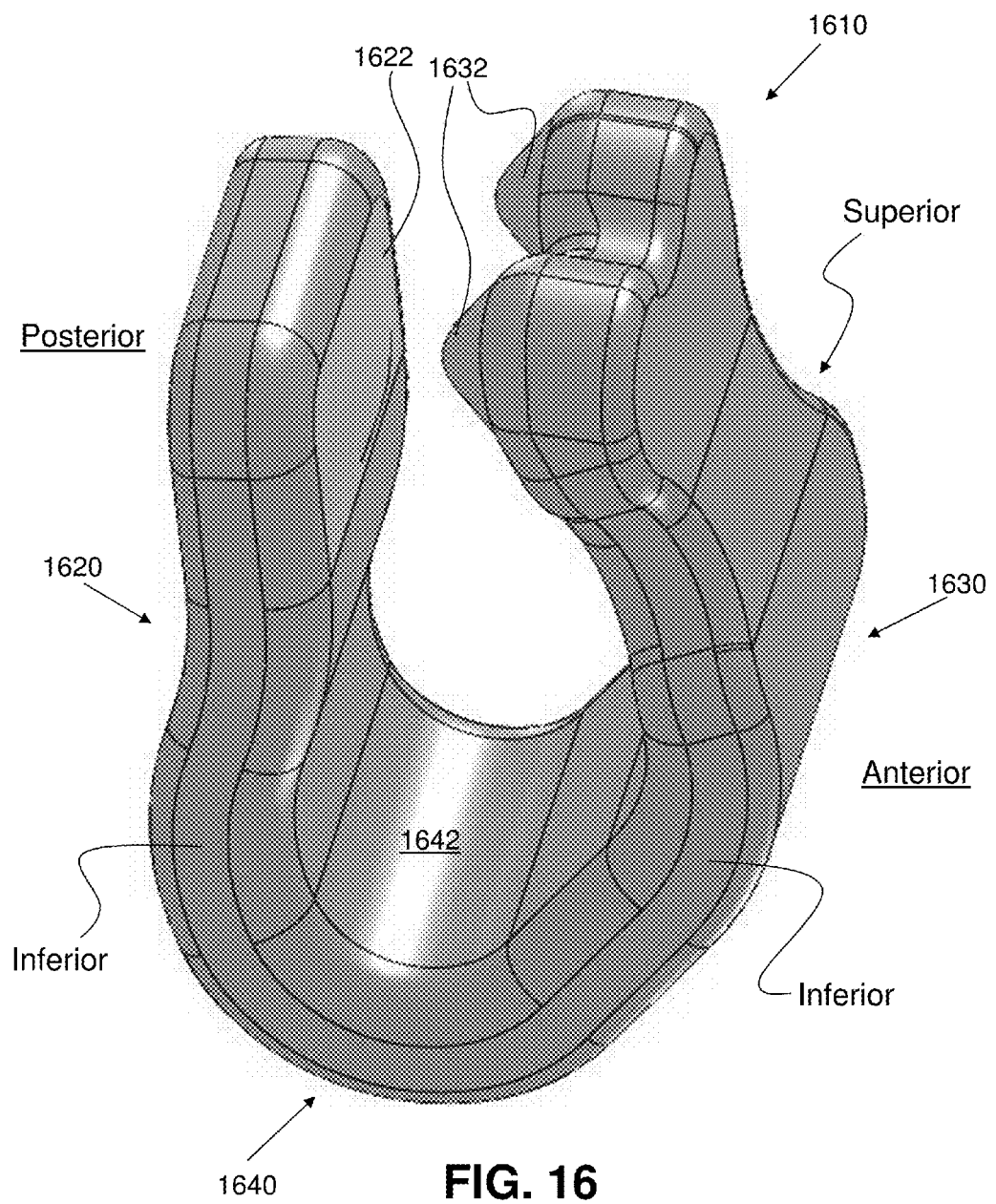
FIG. 16 is a perspective view of an exemplary embodiment of a form-fitting electrode application device.

In FIGS. 8 and 9, an array of three electrodes 810 are provided in the conchal region 50 and a single grounding electrode 820 is provided in the auricle region 60. Any of the herein-described signals can be provided to each of the electrodes 810, 820 to provide therapeutic benefit to the vagus nerve. An exemplary embodiment of the generator 900 is shown in FIG. 9. The generator 900 includes a display 910, control buttons 920, and a surge button 930.

In FIG. 8, an array of five electrodes 810 are provided in the conchal region 50 and a single grounding electrode (not illustrated) is provided in the auricle region 60. Any of the herein-described signals can be provided to each of the electrodes 810 to provide therapeutic benefit to the vagus nerve. An exemplary embodiment of the generator 900 is shown in FIG. 9. The generator 900 includes a display 910, control buttons 920, and a surge button 930.

In embodiments where a surge button is included, the generator can give a user control of "emergency" electrostimulation dosing. This is beneficial in instances where the individual is experiencing an aura (i.e., a harbinger to a seizure) and the user may not have the generator activated. By providing the surge button, even where the generator is turned off, the generator can be programmed to allow the user to transmit a high power signal expeditiously and avert a seizure using the surge button. Another use of the surge button occurs when the user is using the generator actively for therapy but results are not occurring. In such a case, the user may desire a dose of electrostimulation at higher power. The surge button affords the user the ability to receive that dose the moment the button is pressed, serving to override the current therapy and deliver a pre-programmed, higher dose of electrostimulation for a predetermined time. Other processes that can be carried out with the buttons of the generator include a continuous high-power signal to be delivered for the duration that the button is depressed. The actuation element could be in any form, whether a button, a switch, a voice command, a touch screen input, or a voice input. In an emergency situation, a "high dose" feature can also be activated based upon the generator sensing some physiologic data, through a variety of sensors that can be attached to the generator as needed (e.g., blood pressure, temperature, respiration) and the generator can respond by activating the override if the sensors reach a pre-programmed parameter or condition. In comparison, if the device is using one of the on-board algorithms, such as a "ramp up" algorithm that is described below, activating the generator in a standard manner will not give an immediate "high power signal".

FIGS. 10 to 15, in comparison, show a transcutaneous vagus nerve stimulation system having a VNS generator 1000 with a dockable electrode application device 1010. In this exemplary embodiment, the electrode application device 1010 can be wireless to have the electrodes 1012 communicate with the VNS generator 1000, for example, by Bluetooth® or Wi-Fi. Alternatively, connectivity between the VNS generator 1000 and the two electrodes 1012 of the electrode application device 1010 is wired, for example, like the embodiment of FIG. 1. The VNS generator 1000 includes a display 1120, control buttons 1122, and a surge button 1124. The VNS generator 1000 has a docking station 1060 that, in this exemplary embodiment, comprises a post 1062 extending from a docking block 1064. When the electrode application device 1010 is undocked, a non-illustrated bias device (such as a spring), biases the electrodes 1012 towards one another. In such a configuration, when placed on an ear, for example as shown in FIGS. 12, 14, and 15, the bias device compresses the two electrodes 1012 against opposing tissue of the conchal 50 and auricle 60 regions to attach the electrodes 1012 in place for therapeutic use. In this configuration where the electrodes 1012 are simply "button-like," the interior opposing surfaces of the electrodes 1012 have thereon a skin-fastening device (such as an adhesive) so that, when placed on the ear, the button electrodes 1012 stick to the exterior surfaces. When allowed to spring shut on the ear, the bias device forces the two electrodes 1012 towards one another to, thereby, fasten (temporarily) the electrodes 1012 on the ear until they are to be removed. Because the force that the skin-fastening device has on the ear is greater than the force keeping the electrodes 1012 on the electrode application device 1010, the electrodes 1012 separate from the electrode application device 1010 when the latter is moved away from the ear as shown in FIG. 15. One benefit to this embodiment is that it eliminates that pain that is caused by constant compression of a clipped device.

To dock the electrode application device 1010 at the VNS generator 1000, the user moves the proximal arms 1016 of the electrode application device 1010 towards one another to align the arms 1016 sufficiently to form a central port 1014 having an interior shaped correspondingly to the exterior shape of the post 1062, thereby allowing the electrode application device 1010 to be slid down the post 1062 and self-lock the electrode application device 1010 to the VNS generator 1000 with the distal arms 1018 separated for new electrode replacement.

The configuration of the electrode application device 1010 as a scissor allows either or both of the two sides to have more than one electrode. For example, one side can have two electrodes and the other can have one electrode or a grounding electrode. Alternatively, both sides can have three electrode pairs aligned with one another. Any configuration of electrodes to place at least one of the electrodes in one of the conchal 50 or auricle 60 regions is envisioned to supplement the embodiments described herein.

The configuration of the electrode application device 1010 is not limited to a scissor-type clamping action. The two sides of the electrode application device 1010 can be clamshell-shaped and spring loaded. In such a configuration, the opposing members have a one-hand operation for ease of placement by a user. Alternatively, the hinge can be configured like the bi-modal hinge of clip-on earrings.

The scissor configuration of the electrode application device 1010 is a force-locking device, as opposed to a form-locking device. The electrode application clip or Helix Cuff 1610 shown in FIGS. 16 to 18, 20 to 29, and 36 to 43, in comparison, is a form-fitting device. The Helix Cuff 1610 has a posterior portion 1620, an anterior portion 1630, and a bridge portion 1640 connecting the posterior and anterior portions 1620, 1630. Each of the posterior and anterior portions 1620, 1630 has a respective electrode or set of electrodes. In this exemplary embodiment, the posterior portion 1620 has a single grounding electrode 1622 and the anterior portion 1630 has a pair of positive electrodes 1632. Signals can be provided to the Helix Cuff 1610 either wirelessly, through a wire, or both (a wire being illustrated in FIG. 37).

Figure 17:
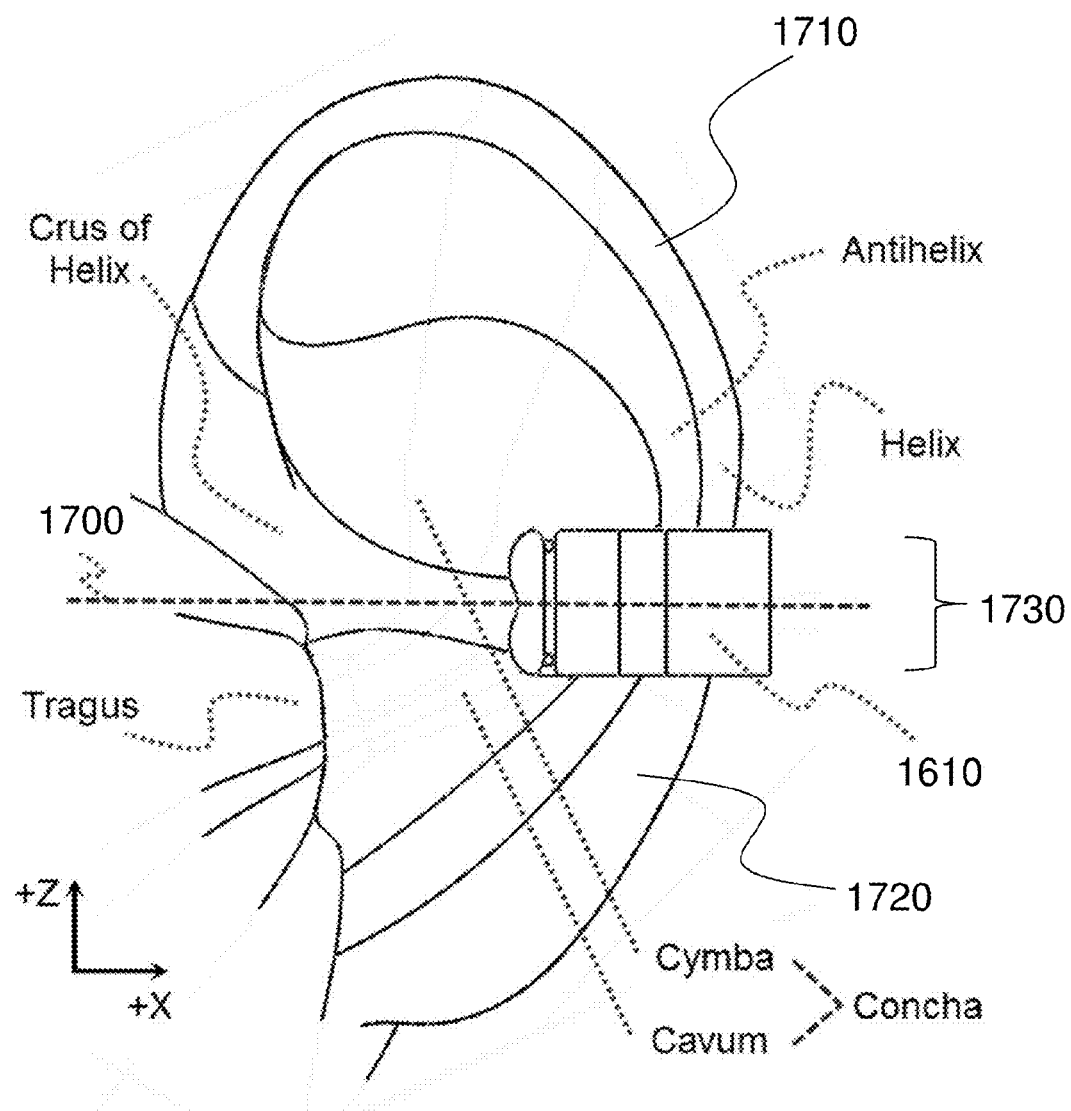
FIG. 17 is a fragmentary, diagrammatic view of a human left ear with the form-fitting electrode application device of FIG. 16 installed thereon.
Figure 18:
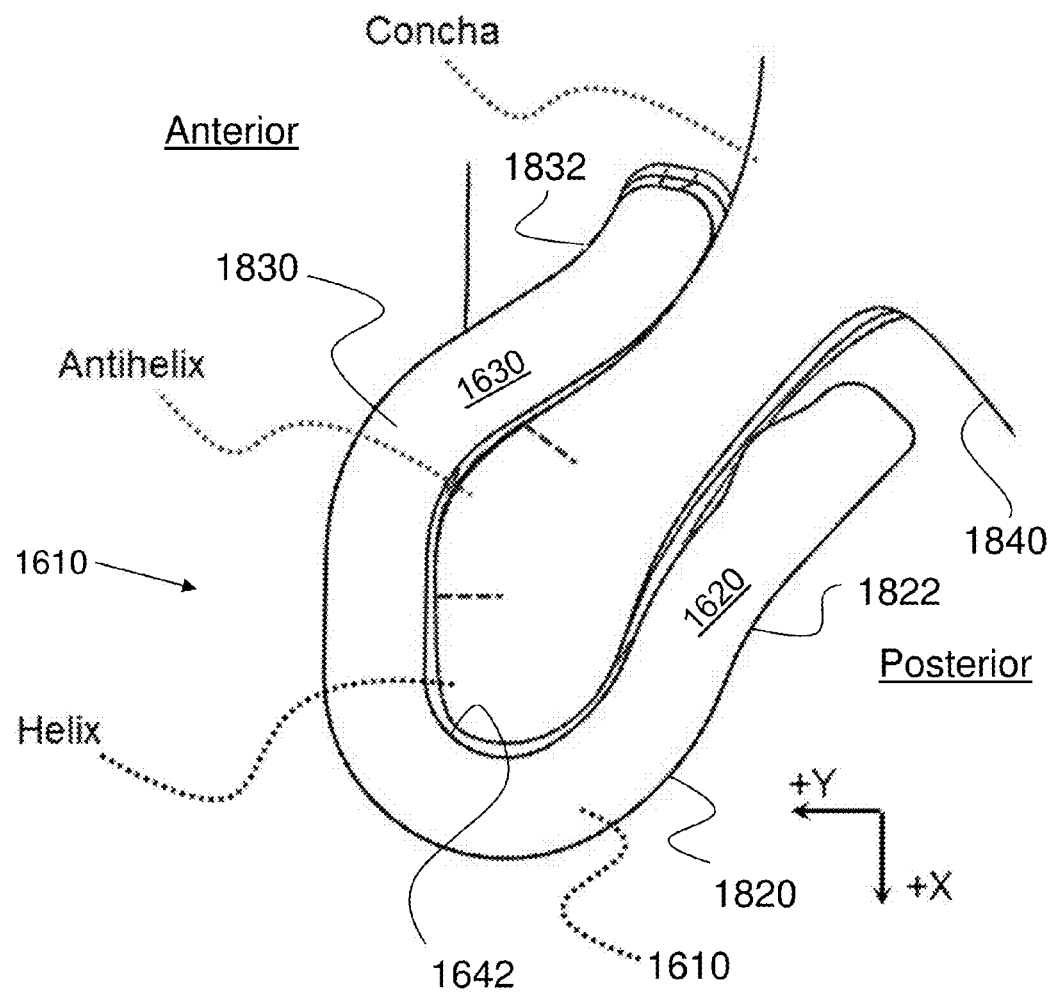
FIG. 18 is a fragmentary, horizontally cross-sectional view of the electrode application device of FIG. 16 installed on a human left ear.
Figure 19:
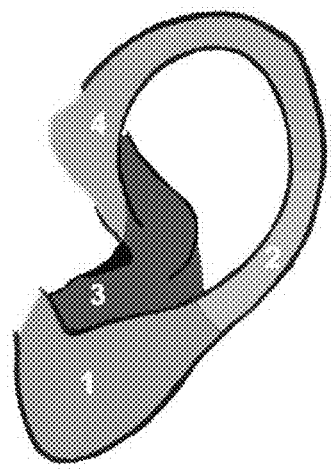
FIG. 19 is a fragmentary, diagrammatic view of a human left ear with respective nerve target locations.

Each of the posterior and anterior portions 1620, 1630 has a respective shape to fit the anatomy of an ear. Before describing the Helix Cuff 1610 in detail, it is beneficial to discuss the anatomy of a human ear with regard to FIGS. 3 and 17. Even though each person has his/her own particular shape and size for each ear (and the two ears of one person are different from one another), there is one common feature that is present on the helix of virtually every ear. In particular, the helix curves upwards and forward in an ovular shape towards the crus of helix. As the helix spirals downwards and then centrally inwards towards the concha, the end portion of the crus of helix defines an axis 1700 that divides an upper portion 1710 of the rear helix from a lower portion 1720 of the rear helix. Where the axis 1700 bisects the rear helix is a helix portion that is substantially straight. This straight helix portion is defined herein as the central helix 1730. It is the central helix 1730 that is present in virtually all shapes of a human ear. With this central helix 1730 discovered, the inventors shaped the Helix Cuff 1610 to fit the central helix 1730, the shape being a form-fit that retains, very comfortably, the Helix Cuff 1610 on the central helix 1730 of a human ear. FIG. 18 illustrates the Helix Cuff 1610 placed on the central helix 1730 and FIG. 19 illustrates a transverse cross-section of the Helix Cuff 1610 at the axis 1700.

The particular shape of the Helix Cuff 1610 facilitates attachment to an ear by following the perimeter of natural anatomical geometries. In this way, fixation occurs in each of the ±X, ±Y, and ±Z axes. The Helix Cuff 1610 is generally U-shaped and surrounds the anterior and posterior helix and antihelix. The valley 1642 of the U-shape rests up against the helix. The anterior portion 1630 has a first anterior curve 1830 that enters the concha and has a second anterior curve 1832 that curves in the opposite direction of the first anterior curve 1830. The length of the anterior portion 1620 of the U-shape can be as long as the anterior side of the helix, the antihelix, or the concha and, in an exemplary embodiment, extends approximately 15 to 25 mm, in particular, approximately 17 mm, from the valley 1642 of the Helix Cuff 1610. The posterior portion 1620 of the U-shape has a first posterior curve 1820 in the posterior direction to wrap around the helix and has a second posterior curve 1822 that curves in the opposite direction of the first posterior curve 1820. The length of the posterior portion 1620 of the U-shape can be as long as the posterior side of the ear to touch the head 1840 behind the ear or can be a distance therefrom, as is shown in FIG. 18. In an exemplary embodiment, the length of the posterior portion 1620 extends approximately 10 to 20 mm, in particular, approximately 13 mm from the valley 1642 of the Helix Cuff 1610.

The Helix Cuff 1610 has a vertical height (see FIG. 17) sufficient to have it remain within the substantially straight central helix 1730 and is, in this exemplary embodiment, substantially symmetric about the axis 1700. As will be described below, the Helix Cuff 1610 can be but need not be substantially symmetric about the axis 1700.

With the shape as described, movement of the Helix Cuff 1610 is restricted in every direction once installed at the central helix 1730 of the ear. In particular and with regard to FIG. 18, movement is restricted in the direction of the +X axis by the first anterior curve 1830. Tension of the Helix Cuff 1610 in the +X direction is borne by interior curved surface of the anterior portion 1630 of the Helix Cuff 1610 and the anterior concha surface and/or antihelix. Movement is restricted in the direction of the −X axis by the interior surface of most of the "U" shape of the Helix Cuff 1610 and, primarily, by the valley 1642. Tension of the Helix Cuff 1610 in the −X direction is borne by the interior surface of the "U" shape, e.g., the valley 1642, and the outer surface of the helix. Movement is restricted in the direction of the +Y axis by the interior surface of the posterior portion 1620. Tension of the Helix Cuff 1610 in the +Y direction is borne by the interior surface of the posterior portion 1620 and the posterior surface of the ear opposite the helix and antihelix. Movement is restricted in the direction of the −Y axis by the interior surface of the anterior portion 1630. Tension of the Helix Cuff 1610 in the −Y direction is borne by the interior surface of the anterior portion 1630 and the anterior surface of the helix, the antihelix, and/or the concha.

Movement with regard to the Z axis is described with reference to FIG. 17. In particular, movement is restricted in the direction of the +Z axis by the superior surfaces and edges of the Helix Cuff 1610. Tension of the Helix Cuff 1610 in the +Z direction is borne by the superior surfaces and edges on the Helix Cuff 1610 and the natural curvature of the helix and the antihelix in the −X direction and elevation of the crus of helix and the concha in the +Y direction. Movement is restricted in the direction of the −Z axis by the inferior surfaces and edges of the Helix Cuff 1610. Tension of the Helix Cuff 1610 in the −Z direction is borne by the inferior surfaces and edges of the Helix Cuff 1610 and the natural curvature of the helix and the antihelix in the −X direction and elevation of the crus of helix and the concha in the +Y direction. Similarly, any rotation of the Helix Cuff 1610 about the three axes is restrained by the same principals.

With such a shape, the Helix Cuff 1610 provides many beneficial features. First, for example, the Helix Cuff 1610 indexes to the attachment location, facilitating ease of self-application. The attachment location of the central helix is exposed completely to the user. Significantly, the attachment location at the central helix is a natural convergence point (e.g., axis 1700) for many anatomical features, such as the curves of the superior and inferior portions of the helix, the antihelix, and the concha. The user is able to easily identify the location by visually or tactilely following the crus of helix and the helix to helix's central straight section.

Second, the Helix Cuff 1610 is surprisingly comfortable and, after a short time, the user no longer feels its presence. This is because the measures for attaching the Helix Cuff 1610 to the ear use geometric constraints without applying constant pressure on the auricular surface. As is known, constant pressure on auricular surfaces is uncomfortable, such as the pressure exerted by clip-on earrings. In addition, the attachment zone of the Helix Cuff 1610 resides on an especially inactive nerve. For such a small part of the anatomy, four different sensory nerves connect to the external ear. As shown in the diagram of FIG. 19, these nerves are (1) the greater auricular nerve, (2) the lesser occipital nerve, (3) the auricular branch of the vagus nerve, and (4) the auriculotemporal nerve. The greater auricular nerve is a branch of the cervical plexus. It innervates the posteromedial, posterolateral, and inferior auricle (lower two-thirds both anteriorly and posteriorly). The lesser occipital nerve innervates a small portion of the helix. The auricular branch of the vagus nerve innervates the concha and most of the area around the auditory meatus. Finally, the auriculotemporal nerve originates from the mandibular branch of the trigeminal nerve. It innervates the anterosuperior and anteromedial aspects of the auricle. It is known that in the perimeter portion of the ear (sections 2 and 4) are less influential than the portion of the ear lobe (section 1) and that the lesser occipital nerve communicates with a zone that is less influential than the other three.

Figure 20:
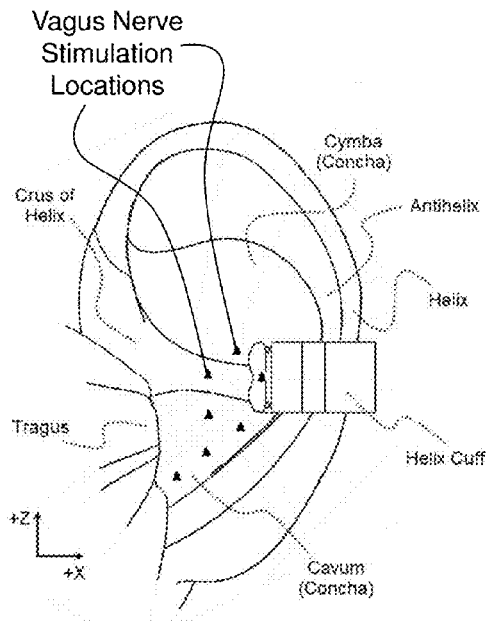
FIG. 20 is a fragmentary, diagrammatic view of the form-fitting electrode application device of FIG. 16 installed on an ear and indications of vagus nerve stimulation locations.
Figure 21:
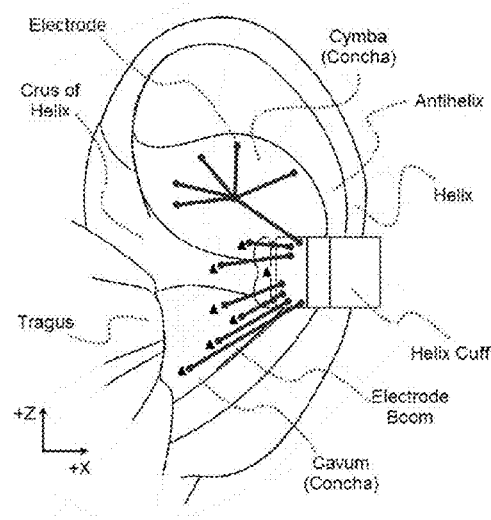
FIG. 21 is a fragmentary, diagrammatic view of the form-fitting electrode application device of FIG. 16 installed on an ear and diagrammatic representations of electrode booms to vagus nerve stimulation locations.

Third, the central helix is centrally situated for therapeutic target locations. As shown in FIGS. 17, 20, and 21, the Helix Cuff's 1610 central attachment location provides an optimum platform for therapeutic features such as electrodes and electrode booms (illustrated diagrammatically in FIG. 21 with lines projecting from the Helix Cuff 1610) that target strategic stimulation points (indicated by triangles). The attachment location about the crus of helix line (e.g., axis 1700) allows any boom(s) targeting auricular stimulation points to be short and not rely on additional support features other than the Helix Cuff 1610 itself, as will be described in further detail below. As the field of neuromodulation is evolving, a robust, universal platform that can easily target a particular location in the ear, such as that described herein, is desirable.

Figure 22:
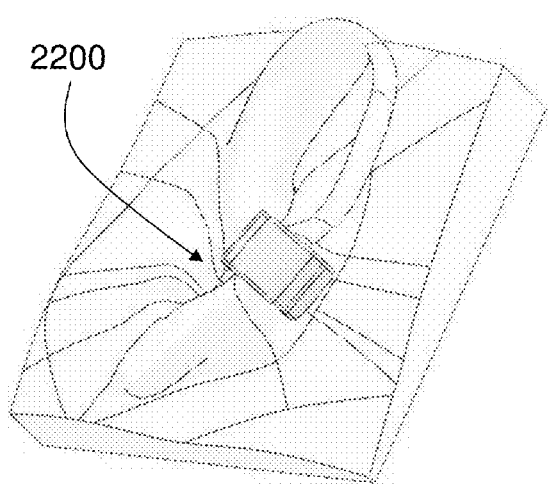
FIG. 22 is a fragmentary, perspective view of the form-fitting electrode of FIG. 16 on a left ear viewed from the below the rear of the ear.
Figure 23:
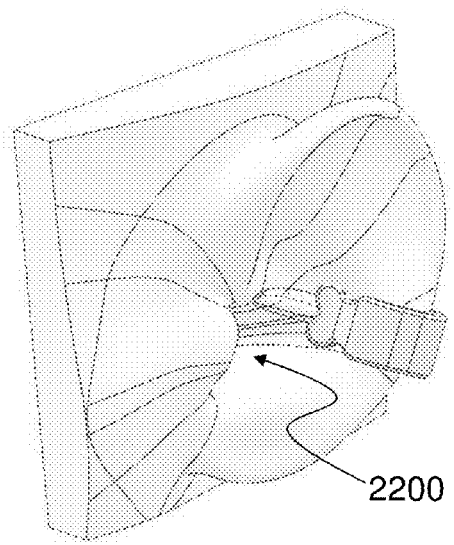
FIG. 23 is a fragmentary, perspective view of the form-fitting electrode of FIG. 16 on a left ear viewed from above a front of the ear.

Fourth, as shown in FIGS. 22 and 23, the Helix Cuff 1610 does not occlude the auditory canal 2200. This means that the Helix Cuff 1610 does not inhibit placement of a traditional audio ear bud or other auditory canal device and, as is described in further detail below, actually provides a platform for synergistic use of the neuromodulation devices and methods with traditional, personal, auditory transmission devices.

Finally, the Helix Cuff 1610 can be, in the exemplary embodiment illustrated, ambidextrous. One Helix Cuff 1610 can be placed on both ears with equal comfort and ease, independent of the particular geometries of the two ears. If a single coupler system is desired, an ambidextrous Helix Cuff 1610 is required. In the exemplary embodiments illustrated, the Helix Cuff 1610 is geometrically symmetric about each of the planes that are affected by right and left ear applications. While symmetric embodiments are illustrated herein, it is equally envisioned to customize one or more Helix Cuffs 1610 in a way that is tailored to a specific location site or to deliver neuromodulation at a particular location.

As mentioned, the electrodes need not be located solely on the outer surfaces of the Helix Cuff 1610. Electrode contact point(s) or surface(s) of the Helix Cuff 1610 can be located on any surface that contacts an auricular surface. The electrodes can be only ground/negative, only positive, or both. The shape of the electrodes can be varied, including, for example, spherical, hemispherical, pyramidal, columnar, and contoured to anatomical curvature. With regard to the exemplary configuration show in FIGS. 8, 24, and 25, there can be two positive anterior electrodes 1632 each having a pyramidal shape and one posterior ground electrode 1622 having a plate-like shape. Materials use for the electrode(s) include, for example, metals (e.g., biocompatible, hypoallergenic, precious), conductive polymers, conductive composites, conductive foams, and conductive coatings applied to a soft surface. Each of the electrodes can be shaped to receive a conductive pad, for example, a gel pad that is single or multiuse and can be user applied. Exterior contact surfaces of the electrodes can be textured, such as with serrations or barbs, to increase conductivity. In an exemplary embodiment where percutaneous connectivity is desired, the electrodes can be/have needles that pierce the surface of the skin. The surface of the electrodes can also be optimized for applied gel retention.

Figure 26:
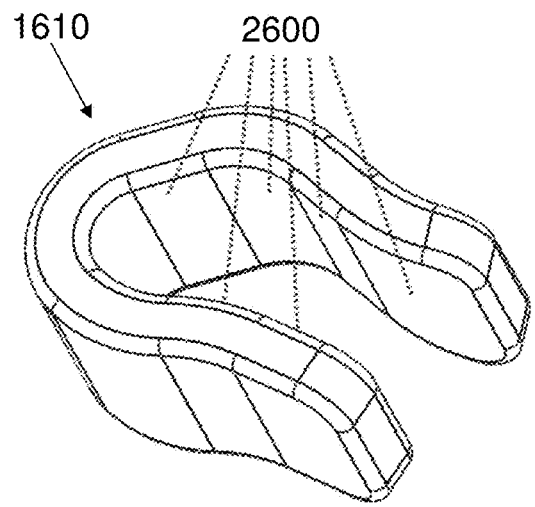
FIG. 26 is a perspective view of an exemplary embodiment of a form-fitting electrode application device.

Another exemplary configuration of electrodes is shown in FIG. 26, in which an array of surface electrode plates 2600 are disposed about the interior surfaces of the Helix Cuff 1610. Here, the electrode plates 2600 are disposed in a single line from the distal end of the interior anterior surface to the distal end of the interior posterior surface. As desired, the electrode plates 2600 can be disposed on the exterior surfaces and the distal ends. Further, the electrode plates 2600 are illustrated as a series of plates along one single line. Each of these plates can be divided into upper and lower (or left and right) halves in parallel (not illustrated) or they can be asymmetrically disposed plates about any of the exterior surfaces of the Helix Cuff 1610.

Figure 27:
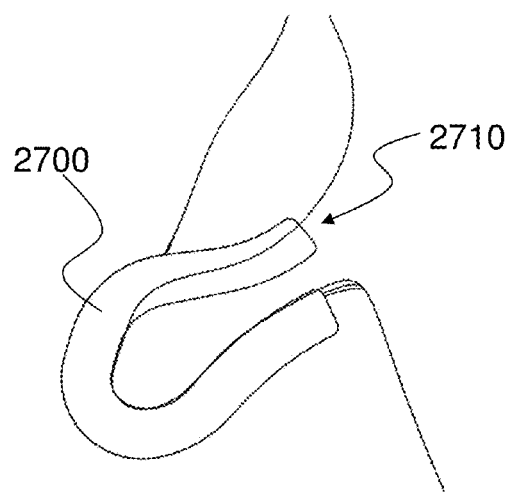
FIG. 27 is a fragmentary, horizontally cross-sectional view of an exemplary embodiment of a form-fitting and force-fitting electrode application device in a natural open configuration and displayed where an auricle would be located.
Figure 28:
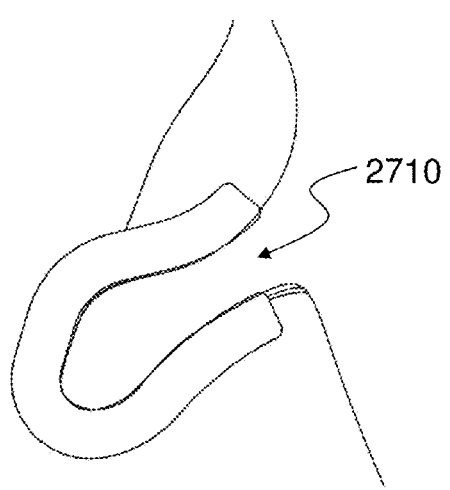
FIG. 28 is a fragmentary, horizontally cross-sectional view of the form-fitting and force-fitting electrode application device of FIG. 27 in a partially expanded configuration after installed on an auricle.
Figure 24:
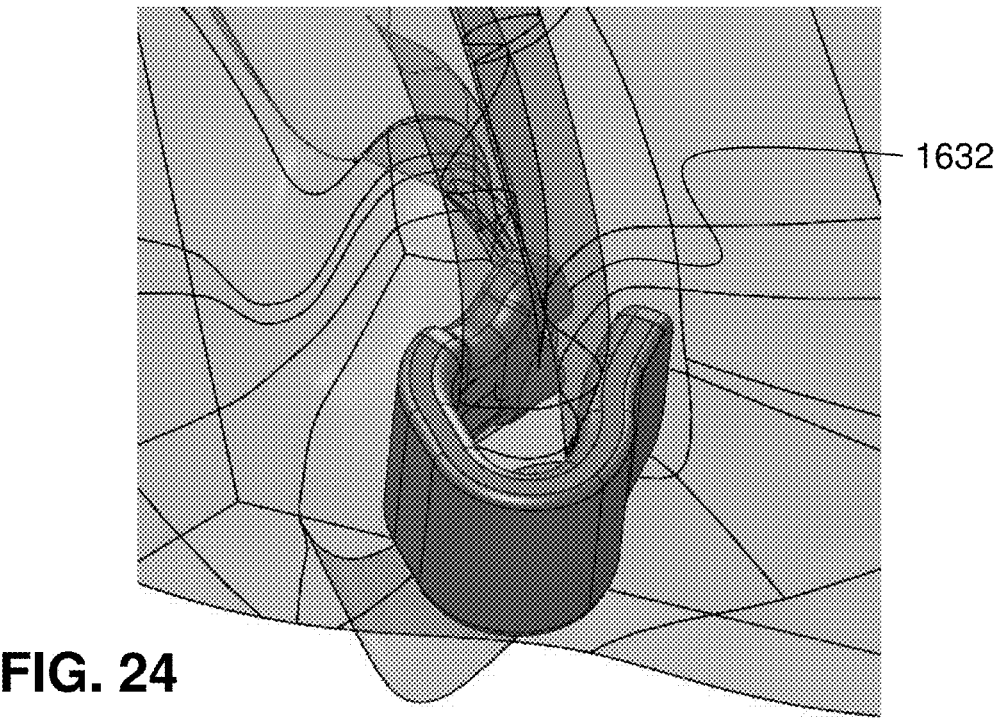
FIG. 24 is a fragmentary, partially transparent, perspective view of the form-fitting electrode of FIG. 16 on a left ear viewed from above the rear of the ear.
Figure 25:
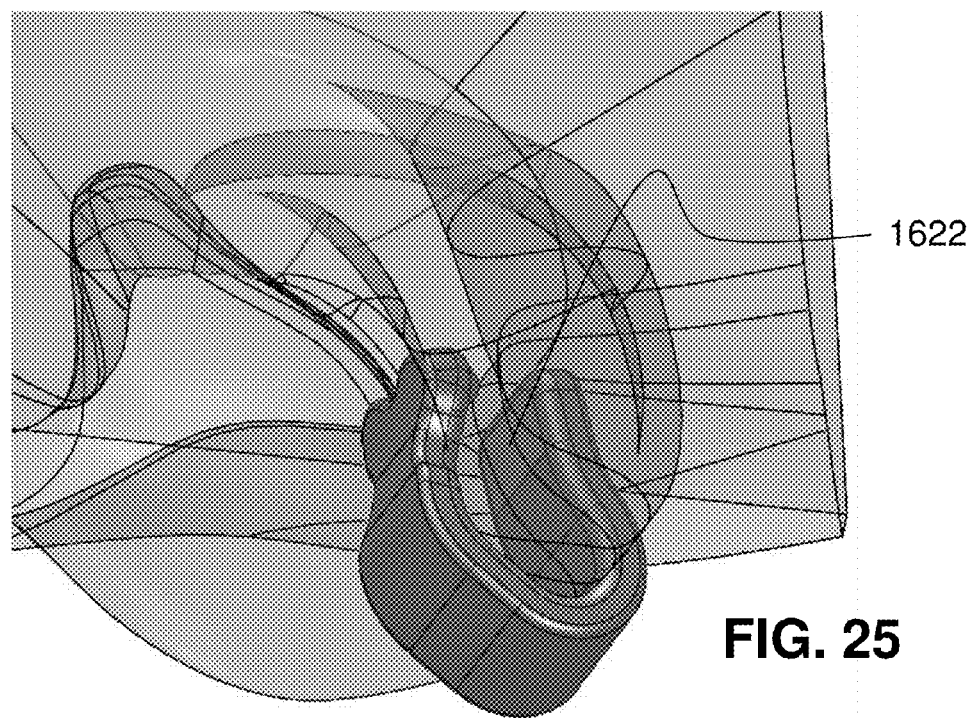
FIG. 25 is a fragmentary, partially transparent, perspective view of the form-fitting electrode of FIG. 16 on a left ear viewed from above the front of the ear.
Figure 29:
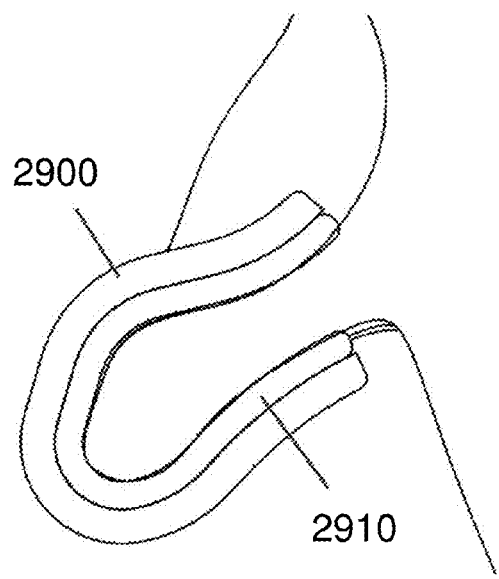
FIG. 29 is a fragmentary, horizontally cross-sectional view of an exemplary embodiment of a form-fitting electrode application device with a liner.

The Helix Cuff can also include some force-fitting features. For example, as shown in FIGS. 27 and 28, the Helix Cuff 2700 is, in its neutral state (FIG. 27), at a U-shape that is narrower than the auricle 2710. When attached, as shown in FIG. 28, the Helix Cuff 2700 flexes outwards and conforms to the geometry of the auricle 2712. Compression applied by the strength of the cuff is maintained in a comfortable pressure range. An adjustable clamp limiter can be implemented to limit continuing spring force from the spring clamp frame by a user adjustable or preset physical stop to govern the clamp gap dimension or a user adjustable or preset force limiting feature to govern clamping force. To enhance compression, if desired, magnets can be attached to the reciprocal inner surfaces of the U-shape.

Figure 30:
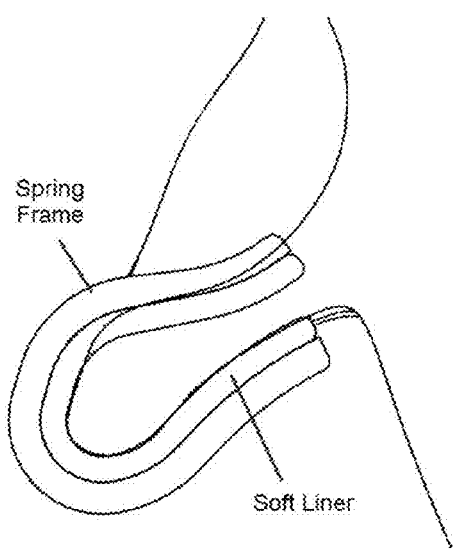
FIG. 30 is a fragmentary, horizontally cross-sectional view of an alternative embodiment of the form-fitting and force-fitting electrode application device of FIG. 29 in a natural open configuration and displayed where an auricle would be located.
Figure 31:
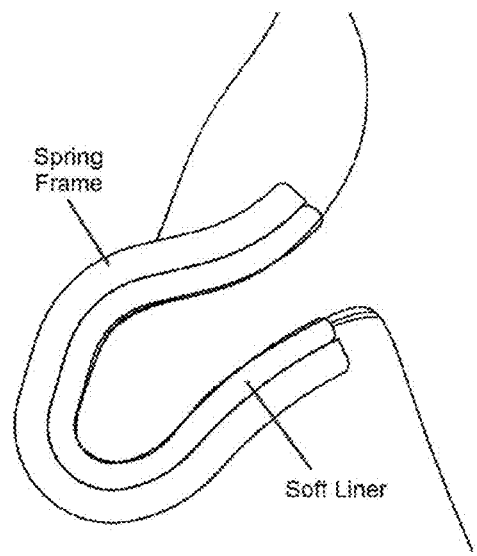
FIG. 31 is a fragmentary, horizontally cross-sectional view f the form-fitting and force-fitting electrode application device of FIG. 30 in a partially expanded configuration after installed on an auricle.
Figure 32:
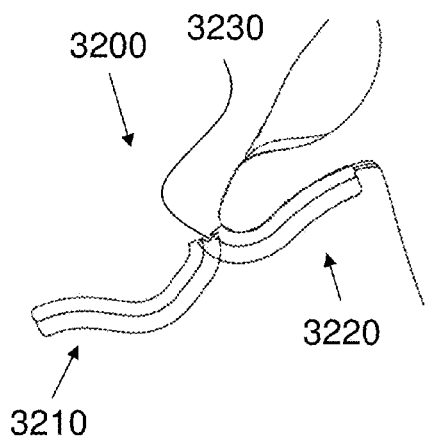
FIG. 32 is a fragmentary, horizontally cross-sectional view of an exemplary embodiment of a form-fitting electrode application device with a liner and a hinged frame in an open configuration.

Shapes and fit can be altered by use of material. In an exemplary embodiment, the Helix Cuff 1610, 2700 is composed of a low durometer material (e.g., between 10 and 70 on the Shore OO scale and, in particular, between 20 and 40). Such materials can include, thermopolymer/thermoset rubbers, foams and viscoelastic materials for example, silicone, polyurethane, and neoprene. Regardless of where the electrodes are placed on or at the Helix Cuff 1610, 2700, 2900, if desired, the interior surface can be coated with a soft liner 2910, such as that shown in FIG. 29, and, additionally or alternatively, can be combined with a Helix Cuff 2700 that is, in its neutral state, narrower than the auricle 2710 (FIG. 30) but expands when installed (FIG. 31) to maintain a comfortable range of pressure on the auricle. This relatively softer liner 2910 (relatively being defined with respect to its difference from the frame of the Helix Cuff 2700) can also have various dimensions indicative of different auricular size ranges (e.g., small, medium, large). If desired, a user can be provided with a liner insert 2910 that best fits the user's ear. The sizing liner 2910 can also be rigid.

The Helix Cuffs 1610, 2700, 2900 mentioned above are of a single part. In another exemplary embodiment, the Helix Cuff 3200 can have a two-part (e.g., clamshell) configuration 3210, 3220 that is connected together by a hinge 3230. In alternative embodiments, the Helix Cuff 3200 can be composed of a rigid frame 3210, 3220 with the central hinge 3230, an inner liner 3240, and reciprocal magnets 3250 to clamp the frame parts 3210, 3220 onto the auricle. The hinged frame 3210, 3220, 3230 can also contain a non-illustrated adjustable stop to limit the magnetic clamping force. Alternatively, the hinged frame 3210, 3220, 3230 can be a "floppy" unhinged component that uses the magnets 3250 to clamp onto the auricle.

An alternative to the hinge is a multi-modal spring clamp analogous to a clip-on earring. In such a configuration, the multimodal spring clamp is in a locked open position. When placed into an intermediate spring closing position, a spring closure takes over and presses the two halves into a closed position. Such a configuration aids in indexing and attachment onto an auricle. The multi-modal spring claim can be closed to a stop to limit compression or to continuously apply compression on the auricle.

As mentioned herein, for example with regard to FIG. 21, electrodes can extend away from the main body of the Helix Cuff 1610, 2700, 2900, 3200 to contact various vagus nerve stimulation locations within the ear, in particular, within the concha and ear canal. Such electrodes can be integral with or removably added to the main body of the Helix Cuff 1610, 2700, 2900, 3200. Electrode booms can be disposed directionally in all planes to satisfy connection direction between the Helix Cuff and a target location for neuromodulation. Electrode booms generally contain three main features: a structural member or beam, an electrical conduit, and an end effector (e.g., an electrode and/or a sensor). These features can be combined into a single part and that part can be integral with or removably connected to the Helix Cuff.

FIGS. 36 to 39, for example, illustrate one exemplary embodiment of a Helix Cuff 3600 with an electrode boom assembly 3610 comprised of an electrode 3612, an electrode connector 3614, and an electrical conduit 3616 conductively connecting the electrode 3612 to the generator (through an electronic conduit 3718) or to a contact at the Helix Cuff 3600 that is, in turn, connected to the generator 3720, which is shown only diagrammatically. The electrode boom assembly 3610 is used to target specific stimulation locations and/or to sense a particular position on the anterior or posterior surface of the auricle.

Figure 36:
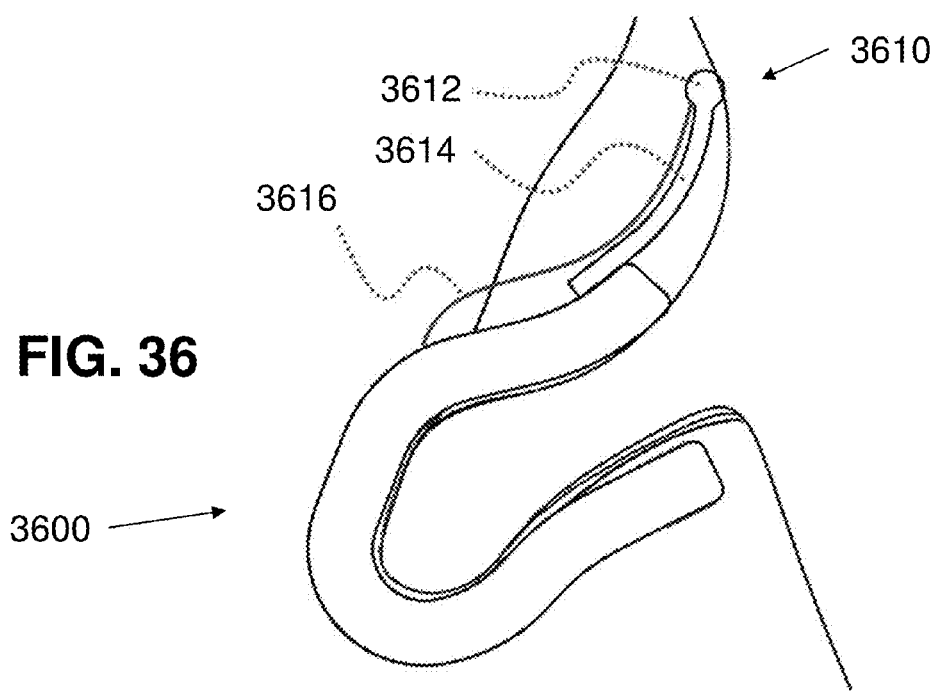
FIG. 36 is a fragmentary, horizontally cross-sectional view of the form-fitting electrode application device of FIG. 16 with an exemplary embodiment of an extending electrode assembly.
Figure 37:
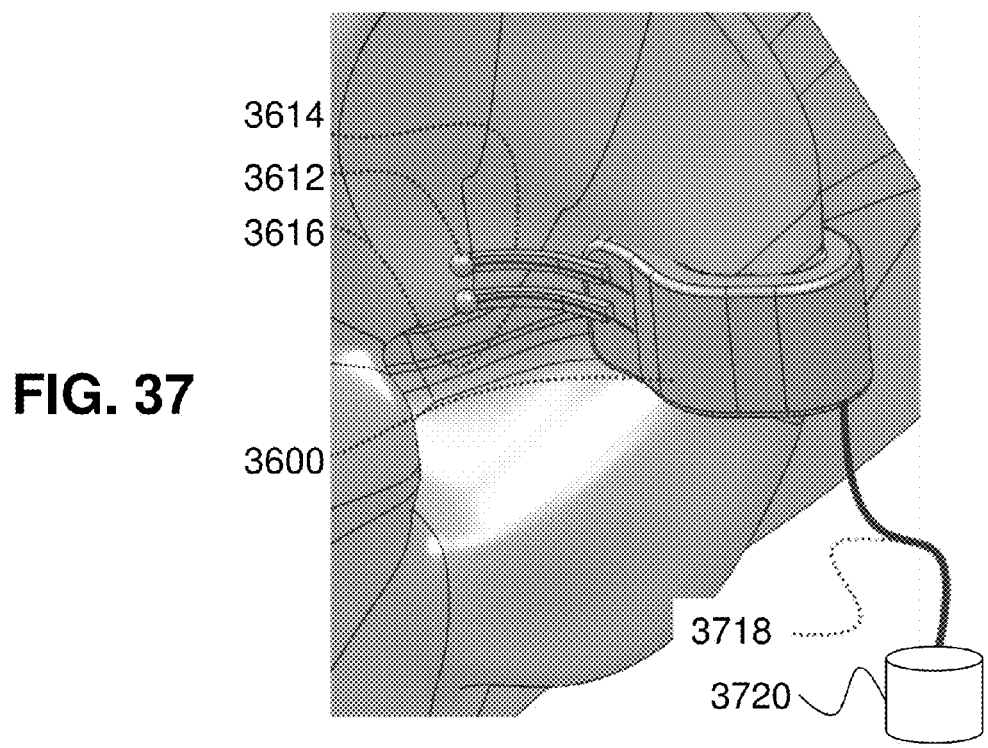
FIG. 37 is a fragmentary, perspective view of the form-fitting electrode application device of FIG. 36 with an exemplary embodiment of an electrode conduit and generator.

The electrode connectors 3614 shown in FIGS. 36 and 37 are rigid beams having a particular shape. In an alternative embodiment, the electrode connectors can be a flex spring 3814 having a natural position that interferes with the auricle when the Helix Cuff 3600 is installed. Such a configuration flexes to comply with auricular geometry. The electrode connector 3814 can be of shape memory and super elastic, for example. In another alternative embodiment, the electrode connectors 4014 can be connected to the Helix Cuff 3600 by a spring pivot hinge comprising a pivot 4000 and a spring 4002. The spring 4002 provides a force to press the contact point of the electrode 4012 to the surface of the auricle. The electrode connector 4014 can be locked in open position, can continuously provide a force, and/or can have an adjustment device to limit the applied force. The beam of the electrical connector 4014 can be rigid or it can flex. In the latter case, the flexing beam can provide the force-limiting feature. The hinge point of the pivot hinge can be a lockable universal joint. The electrical connector 4014 need not be a beam. It can be a flexing wire lead with an electrode(s) at its end(s). Likewise, the electrode conduit can be a wire or conductive support member. Further, the electrode connector 4014 can be surface conforming, of a soft foam rubber extension of the Helix Cuff that contours to targeted auricular surface.

Figure 33:
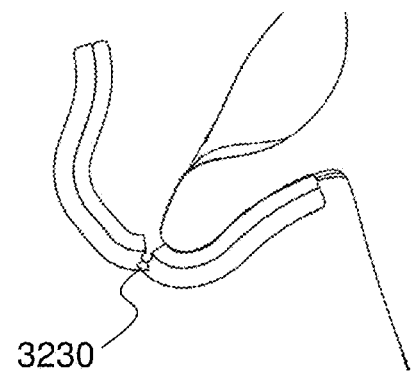
FIG. 33 is a fragmentary, horizontally cross-sectional view of the form-fitting electrode application device of FIG. 32 with the hinged frame in a partially closed configuration.
Figure 34:
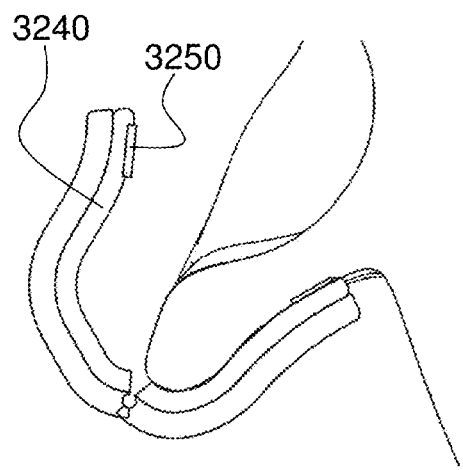
FIG. 34 is a fragmentary, horizontally cross-sectional view of the form-fitting electrode application device of FIG. 32 with the hinged frame in a partially closed configuration and with a magnetic closure.
Figure 35:
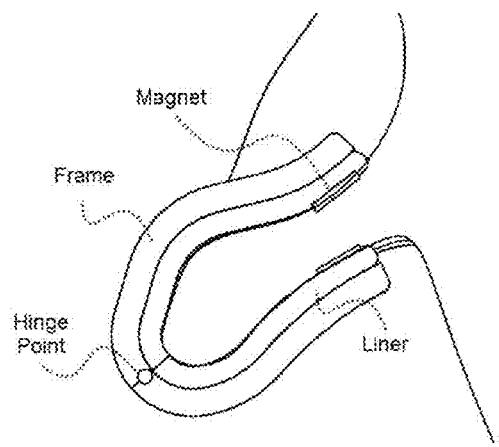
FIG. 35 is a fragmentary, horizontally cross-sectional view of the form-fitting electrode application device of FIG. 34 with the hinged frame in a closed configuration.
Figure 42:
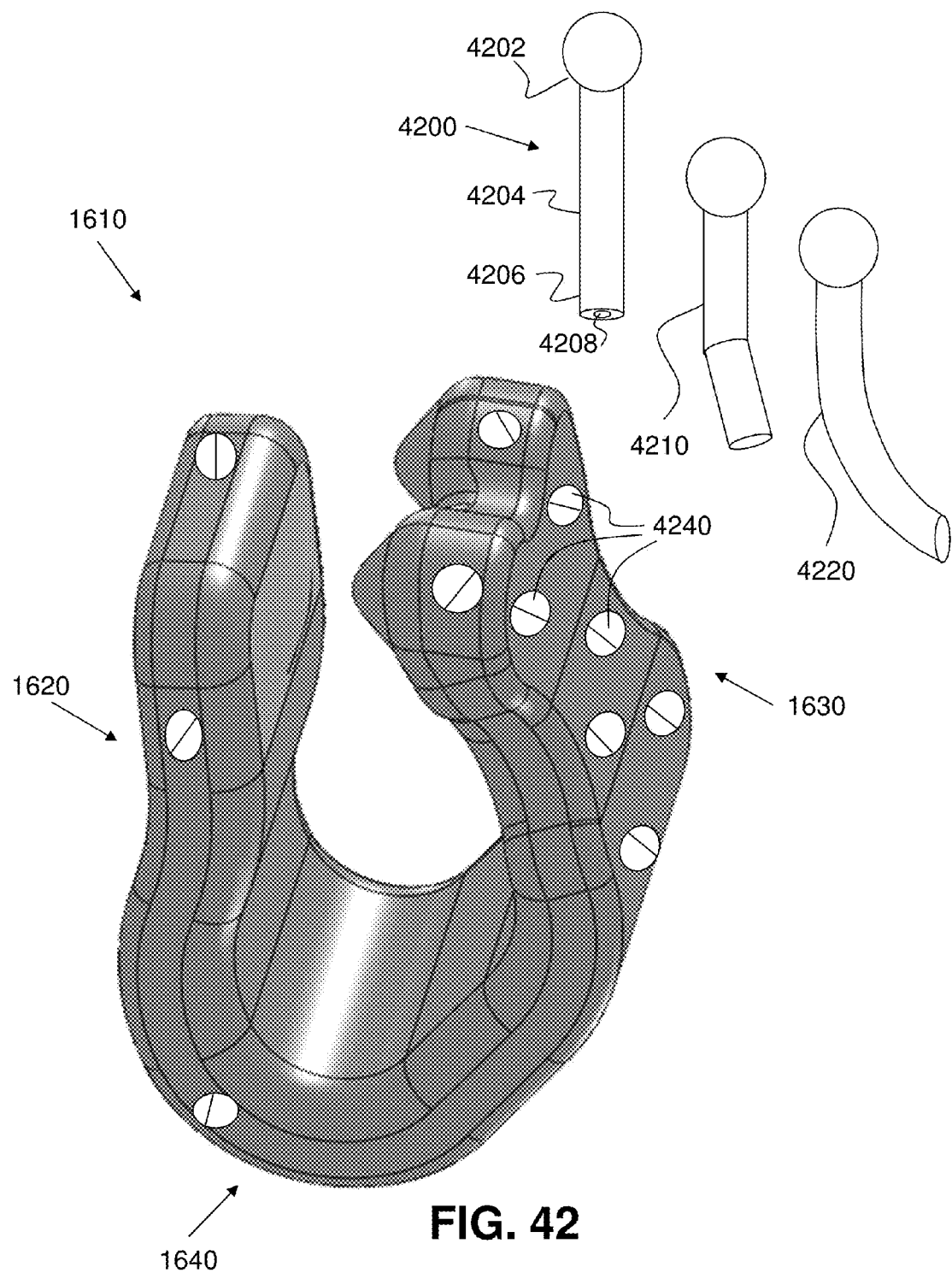
FIG. 42 is a perspective view of an exemplary embodiment of a form-fitting electrode application device with boom connection areas.

In an exemplary embodiment that can be applied to all instances where an electrode boom is desired, any version of the Helix Cuff 1610, 2700, 2900, 3200, 3600 can be provided with insertable boom members 4200, 4210, 4220, examples of which are diagrammatically shown in FIG. 42. These are not the only shapes for the boom, and variations are equally possible. Explanation of the first exemplary boom member 4200 is made and is equally applicable to every configuration of a boom member. The boom member 4200 comprises a distal electrode 4202, a boom 4204, and a contact stub 4206. The entire boom member 4200 can be electrically conductive or a non-illustrated internal conductor can connect the conductive distal electrode 4202 to the proximal end surface of the contact stub 4206, at which is a conductor 4208 for receiving the signal. The boom members 4200, 4210, 4220 connect conductively to the Helix Cuff 1610, 2700, 2900, 3200, 3600 through blind holes 4240 that are disposed anywhere on the outside surfaces of the Helix Cuff 1610, 2700, 2900, 3200, 3600. Exemplary locations for the blind holes 4240 are illustrated in FIG. 42, although many other locations are possible. What is relevant is that the blind holes 4240 be disposed at the surface of the Helix Cuff 1610, 2700, 2900, 3200, 3600 (e.g., orthogonally or at an angle thereto) to place the distal electrode 4202 at a treatment location on the tissue to be treated (e.g., at the locations shown in FIGS. 33, 34, 50). Thus, for example, the blind holes 4240 can be disposed on any of the surfaces of the posterior portion 1620, anterior portion 1630, bridge portion 1640, or on the inferior, superior, and/or edge surfaces, as shown in FIG. 42. These blind holes 4240 can have an electrically conductive interior surface that makes electric contact with any portion of the outer surface of the contact stub 4206 or they can have a distal conductor disposed at the bottom surface of the blind hole 4240 (e.g., a protrusion in the shape of a pyramid or hemisphere).

Figure 43:
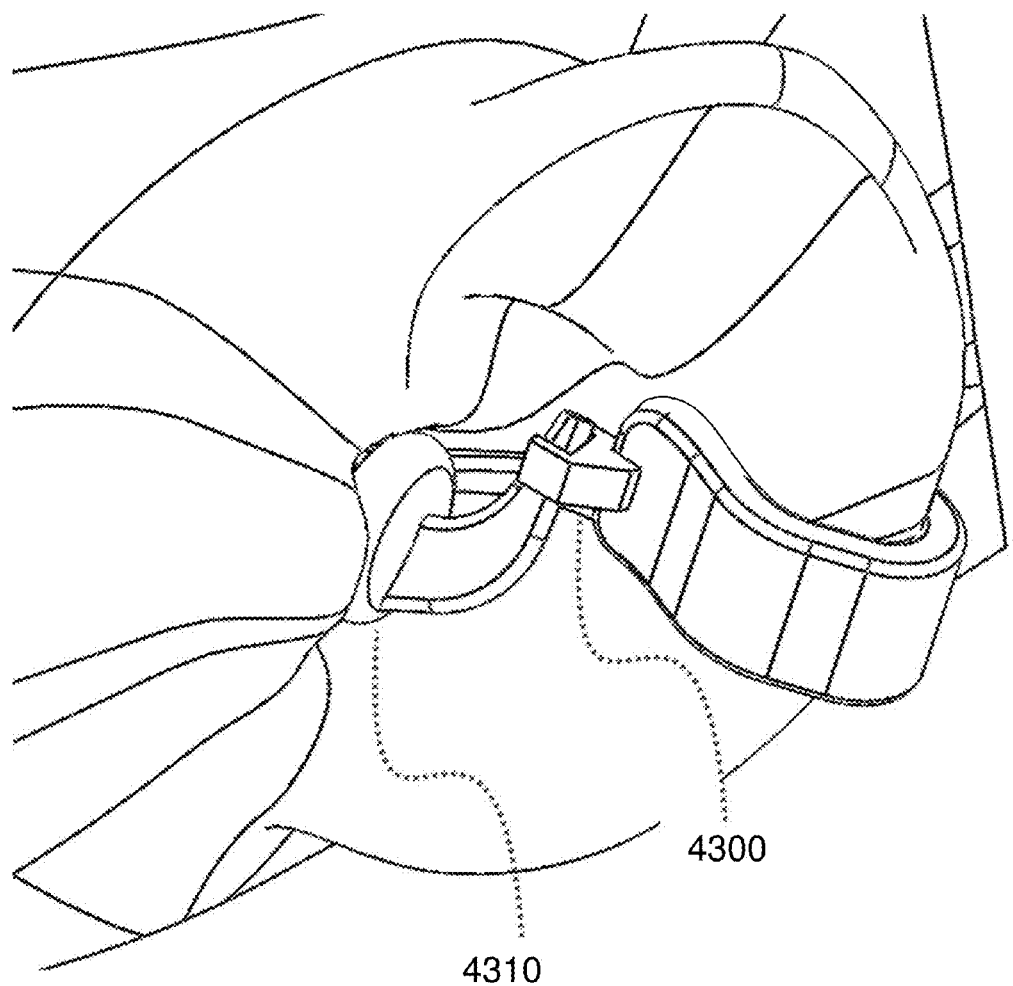
FIG. 43 is a fragmentary, perspective view of the form-fitting electrode application device of FIG. 16 with an exemplary embodiment of an earbud assembly.
Figure 44:
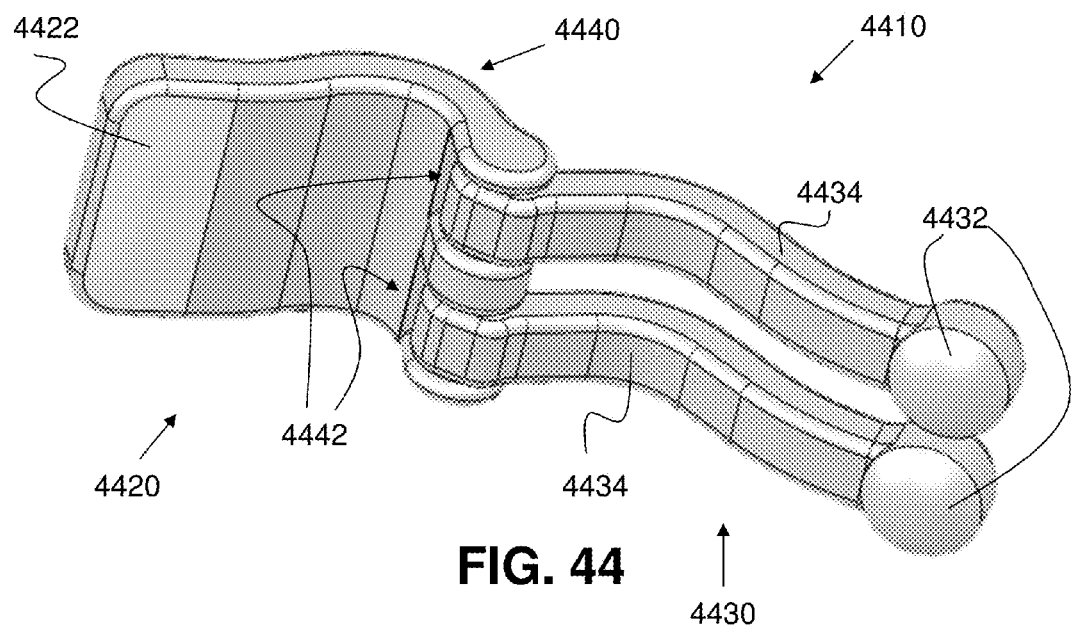
FIG. 44 is a perspective view of a form-fitting and force-fitting electrode application device in an open configuration.
Figure 45:
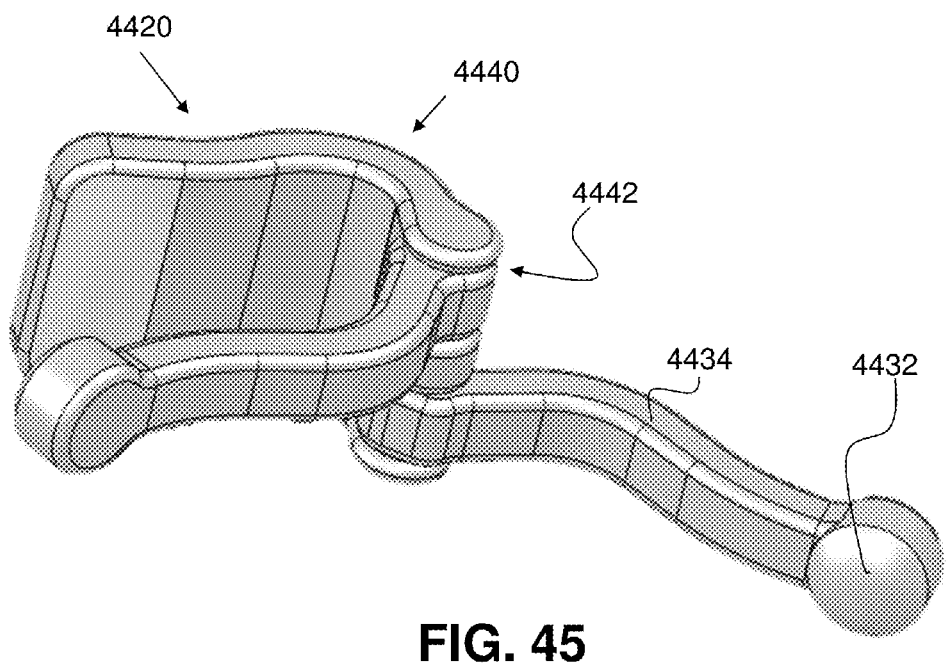
FIG. 45 is a perspective view of the form-fitting and force-fitting electrode application device of FIG. 44 in a partially open configuration.
Figure 48:
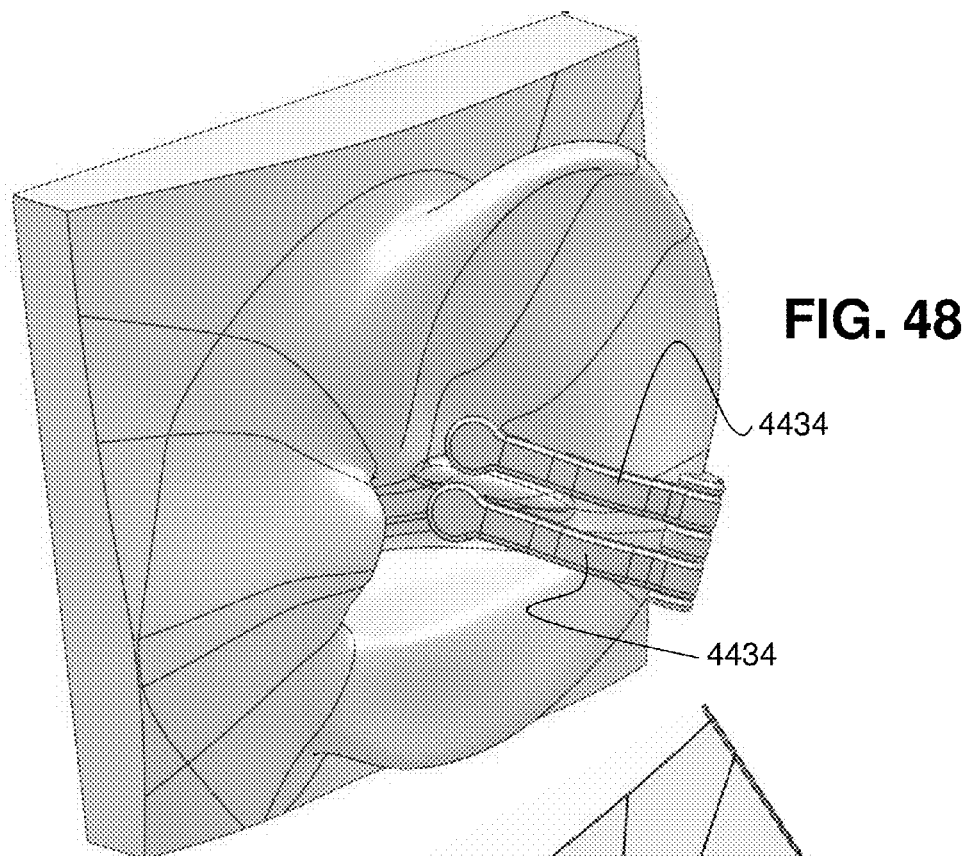
FIG. 48 is a fragmentary, perspective view of the form-fitting and force-fitting electrode application device of FIG. 44 closed on an ear and viewed from above the front of the ear.

Because the Helix Cuff 1610, 2700, 2900, 3200, 3600 does not interfere with the auditory canal, any standard set of earbuds can be used at the same time. The earbuds can be entirely separate from the Helix Cuff 1610, 2700, 2900, 3200, 3600 or they can, as shown in FIG. 43, removably attached to the Helix Cuff 1610, 2700, 2900, 3200, 3600. In particular, an earbud retention device 4300 is part of or removably attached to the Helix Cuff 1610, 2700, 2900, 3200, 3600. Earbud restraint is a known disadvantageous issue with simple earbud designs. By attaching the earbuds 4310 to the Helix Cuff 1610, 2700, 2900, 3200, 3600 (e.g., removably), earbud restraint issues are eliminated.

Figure 49:
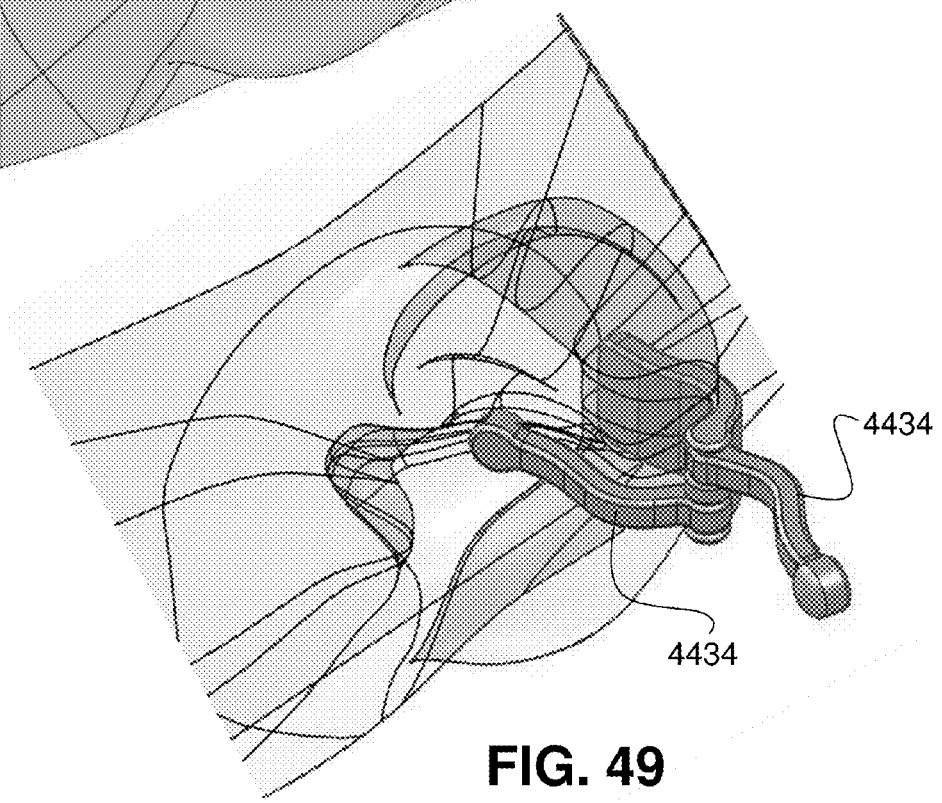
FIG. 49 is a fragmentary, partially transparent, perspective view of the form-fitting and force-fitting electrode application device of FIG. 44 on an ear and in a partially closed configuration.
Figure 62:
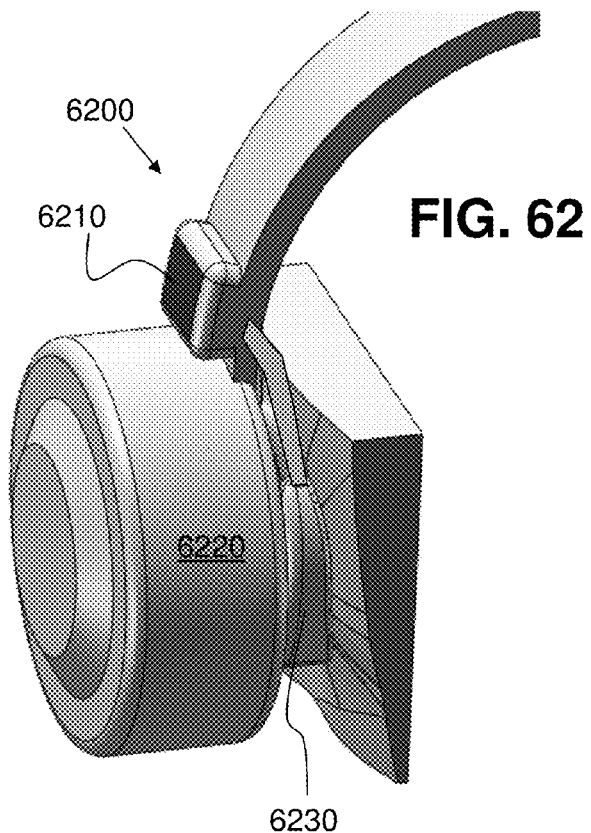
FIG. 62 is a fragmentary, perspective view of an exemplary embodiment of an electrode headset device.
Figure 63:
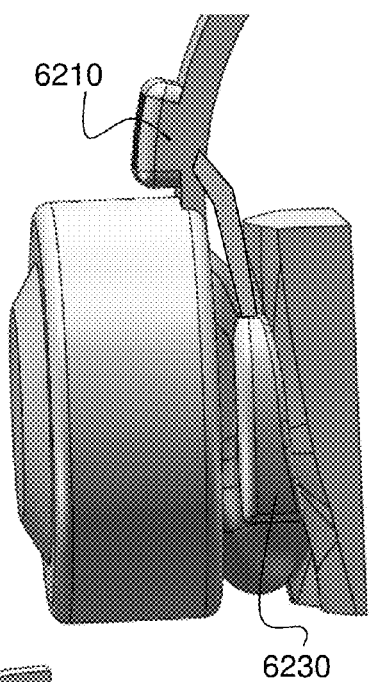
FIG. 63 is a fragmentary, perspective view of the electrode headset device of FIG. 62.
Figure 64:
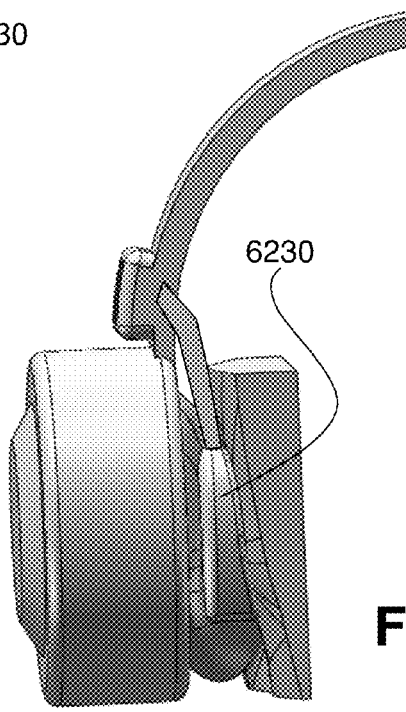
FIG. 64 is a fragmentary, perspective view of the electrode headset device of FIG. 62.

The embodiment of the electrode application clip 1610 of FIGS. 16 to 18, 20 to 26, 29, and 36 to 43 is connected to the ear only by a form-fitting connection. In contrast, the electrode application clip 4410 of FIGS. 44 to 49 is connected to the ear by both a form-fitting and force-fitting connection. More specifically, the interior shape of the both the outer and inner portions 4420, 4430 have approximately the same interior shape of the outer and inner portions 1620, 1630. The outer portion 4420 is, in this exemplary embodiment, one piece and has an inner electrode 4422 (e.g., ground/negative). The inner portion 4430 in this embodiment, however, is not one piece and is not fixed. Two outer arms 4434 each have a respective positive electrode 4432 and each are independently connected pivotally to the bridge 4440. The pivoting connection can be provided by an interior axle about which the arms pivot or can be provided by protrusions/depressions that are present but not illustrated between the proximal ends of each arm 4434 and the interior surfaces of two slots 4442 present at the bridge 4440, one for each of the arms 4434. Openable closeability of the arms 4434 can be provided merely from friction of the opposing elements themselves (which can be dependent upon the material(s) of the arms 4434 and the slots 4442 of the bridge 4440) or it can be provided by separate devices present within the arms 4434 or within the bridge 4440. Such closing devices can include springs or pivots, for example, that bias the arms 4434 in the closed position, shown in FIG. 47. As each of the arms 4434 can close down upon the ear independently, customized placement and well as customized comfort can be achieved. For example, as shown in FIG. 49, only one of the arms 4434 can be closed and used during therapeutic treatment if desired. FIG. 49 illustrates the process of clipping the electrode application clip 4410 to an ear. First, the outer portion 4430 is placed against the rear/posterior surface of the ear and then the two arms 4434 are moved to place the inner surfaces of the arms 4434 against the concha of the ear.

Electrodes are not limited to placement or extension within the concha of the ear. Electrodes can be placed at other portions at or around the ear as well. As shown in FIGS. 50 and 51, the Helix Cuff 1610, 2700, 2900, 3200, 3600 is provided with two electrode booms 5010 (comprising an electrode 5012, an electrode connector 5014, and a non-illustrated electrical conduit). The booms 5010 extend across the tragus to touch a temporal location near or at the area of the trigeminal nerve.

As set forth above, the central helix is one beneficial location for providing an electrode stimulation clip, such as the Helix Cuff. Other areas of the ear are also beneficial locations for providing an electrode stimulation clip. One exemplary alternative embodiment is shown in FIGS. 52 to 55, in which the electrode stimulation clip is a Tragus Cuff 5200. All of the features of the Helix Cuffs described herein are equally applicable to the Tragus Cuff 5200. This means, for example, that the Tragus Cuff 5200 can be a form fit to a shape of a person's tragus or can be a form and force fitting shape for the tragus. Electrodes can be placed on the Tragus Cuff 5200. In the exemplary configuration illustrated in FIGS. 52 to 55, electrodes on the interior sides of either the anterior 5210 or posterior 5220 portions of the Tragus Cuff 5200 can be used to deliver electrostimulation to the temporal region and/or to the trigeminal nerve. Shown in FIG. 55, for example, is a plate-type electrode 5510 on the posterior side of the tragus near the auditory canal. Similarly, electrodes extend from the Tragus Cuff 5200 on booms 5610 or other extension features, such as those illustrated in FIGS. 56 and 57, for example.

Another exemplary alternative embodiment is shown in FIGS. 58 and 59, in which the electrode stimulation clip is a Lobe Cuff 5800. All of the features of the Helix Cuffs described herein are equally applicable to the Lobe Cuff 5800. This means, for example, that the Lobe Cuff 5800 can be a form fit to a shape of a person's ear lobe or can be a form and force fitting shape for the ear lobe. Electrodes (not illustrated) can be placed on the Lobe Cuff 5800. In the exemplary configuration illustrated in FIGS. 58 and 59, electrodes on the interior sides of either the anterior 5810 or posterior 5820 portions of the Lobe Cuff 5800 can be used to deliver electrostimulation to the ear lobe, to the temporal region, to the trigeminal nerve, and/or to the concha. Similarly, electrodes can extend from the Lobe Cuff 5800 on booms or other extension features, for example.

Still a further exemplary alternative embodiment is shown in FIGS. 60 and 61, in which the electrode stimulation clip is a Superior Helix Cuff 6000. All of the features of the Helix Cuffs described herein are equally applicable to the Superior Helix Cuff 6000. This means, for example, that the Superior Helix Cuff 6000 can be a form fit to a shape of a person's superior helix or can be a form and force fitting shape for the superior helix. Electrodes (not illustrated) can be placed on the Superior Helix Cuff 6000. In the exemplary configuration illustrated in FIGS. 60 and 61, electrodes on the interior sides of either the anterior 6010 or posterior 6020 portions of the Superior Helix Cuff 6000 can be used to deliver electrostimulation to the helix and/or to the concha. Similarly, electrodes can extend from the Superior Helix Cuff 6000 on booms or other extension features, for example.

Further exemplary embodiments include headphone-like or earbud devices that have integrated electrodes, with or without an independent power source, that, when the headphones/earbuds are connected to the audio source, such as a smartphone, that audio source has a software application serving as the user interface and signal generator. But, these devices need not be solely purposed as neurostimulators. The earbuds/headphone can also be dual-purpose devices where the earbuds and connected smartphone act as both an audio device and as a neurostimulator device. Various exemplary embodiments of such devices are depicted in FIGS. 43, 62 to 66, 67 to 72, 81 to 135, 142, 143, and 161 to 168.

First, FIGS. 62 to 65 show a dual-purpose headphone and electrostimulation device 6200 with an attached generator and controller 6210 and user coupler integrated into the ear contact ring 6220. The ear contact ring 6220 is traditionally foam or soft material and covers most of the auricle and can house single electrode arrays or electrode pair arrays. Electrodes 6510 can protrude from or be shaped surfaces on the ear contact ring 6220 with conductive-coated areas 6512 or rigid conductive components. Additionally, a compliant or rigid contouring electrode carrier 6230 (for ground or a reciprocal polarity) is shown on the posterior side of the auricle. The power source between headphone and the electrostimulation generator can be shared.

Figure 66:
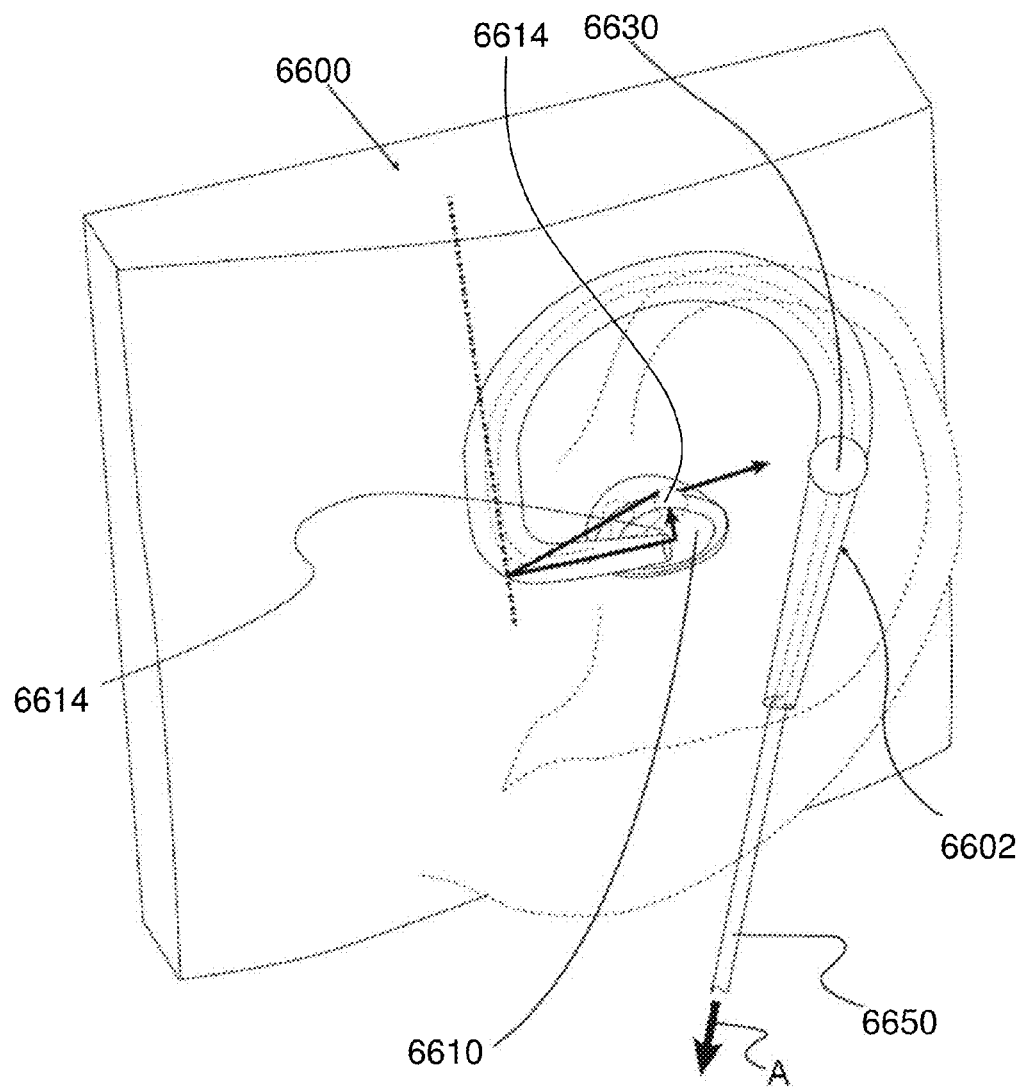
FIG. 66 is a fragmentary, partially transparent, perspective view of an exemplary embodiment of an over-the-ear electrode headset device viewed from a side of the ear.

An alternative exemplary embodiment shown in FIG. 66 is an over-the-ear electrode device 6600 that does not have integrated speakers (although addition of speakers is an option). This electrode device 6600 has an ear cuff 6602 that positions the positive electrode(s) 6614 disposed at a distal end 6610 within the concha (see the transparent distal end of the ear cuff 6602 in FIG. 66) and the negative or grounding electrode(s) 6630 on a surface of a proximal end of the ear cuff 6602 behind the ear. The ear cuff 6602 can be of soft silicone defining an electrode supply conduit, which conduit can be malleable to provide stiffness and/or shape forming features. The form fit of the curved ear cuff 6602 provides sufficient force to keep the electrodes 6614, 6630 in contact with the ear surfaces and sufficient resistance to prevent the ear cuff 6602 from moving about the ear. For example, when the signal supply conduit 6650 becomes tangled or is pulled or jerked, those forces are absorbed by the ear and not by the distal portion of the ear cuff 6602 that houses the electrode 6614. Nonetheless, additional securing devices can be provided. For example, a magnetic device pair can be place with one part (not illustrated) on the distal end 6610 having the positive electrode(s) 6614 and the other part opposing the first part on the proximal end of the cuff 6602. For example, the negative electrode 6630 can also be the second magnetic part. It is noted, thereby, that the embodiment of FIG. 66 illustrates the property of utilizing the curve of the ear to accept and hold all forces imparted by the environment on the signal supply conduit 6650 that would tend to move the electrodes or the electrode devices away from the intended stimulation targets, for example, as depicted by arrow A in FIG. 69. This configuration for the signal supply conduit is equally applicable for any of the non-wirelessly supplied electrode device configurations described herein, including but not limited to each of the Helix Cuffs 1610, 2700, 2900, 3200, 3600, 4410, 5200, 5800, 6000 and to each of the earbuds 8130, 9130, 9430, 9510, 10060, 11660, 12460, 13260, 14242, 16100, 16500.

Figure 67:
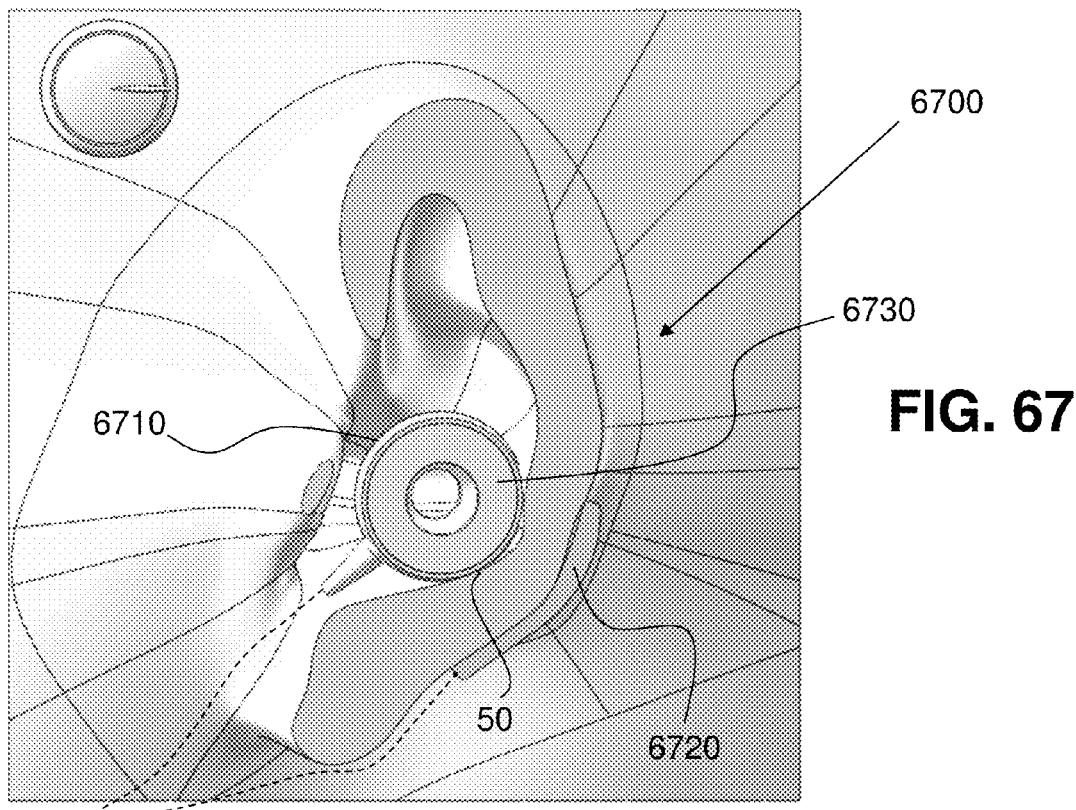
FIG. 67 is a fragmentary, side perspective and sagitally cross-sectional view of an exemplary embodiment of a dual-purpose, earbud/neurostimulator device with leads and speaker removed.
Figure 68:
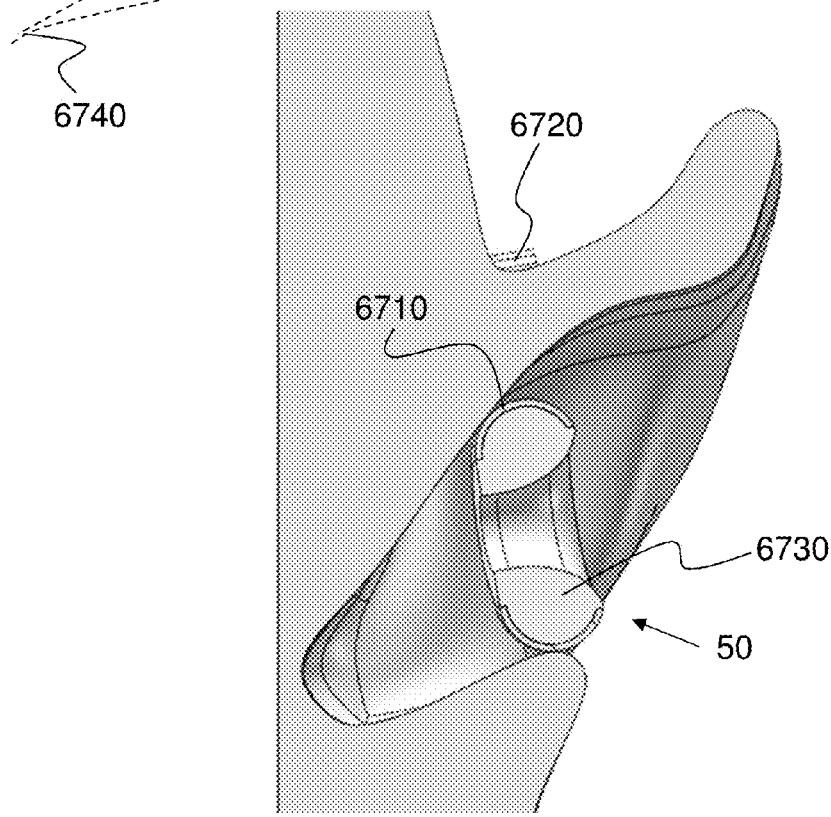
FIG. 68 is a fragmentary, side perspective and coronally cross-sectional view of the earbud/neurostimulator device of FIG. 67.

FIGS. 67 to 70 illustrate various embodiments of dual-purpose earbud/neurostimulator devices. The first exemplary embodiment of a dual-purpose earbud/neurostimulator device 6700 is shown in FIGS. 67 and 68. Here, the central audio speaker is not shown for purposes of clarity. The earbud base 6730 houses an external positive electrode 6710 that surrounds at least a portion of the outside surface of the base 6730 for secure adhesion and, in particular, places the positive electrode 6710 in direct contact with the conchal region 50 of the ear. Behind the ear, in the auricle region 60, is a negative or ground electrode 6720. These two electrodes can be connected together by a non-illustrated clip or other device that wraps around the helix of the ear or they can have corresponding magnetically coupling counterparts. Supply leads 6740, for both electrodes and the speaker of the earbud, are shown diagrammatically in FIG. 67 with dashed lines.

Figure 69:
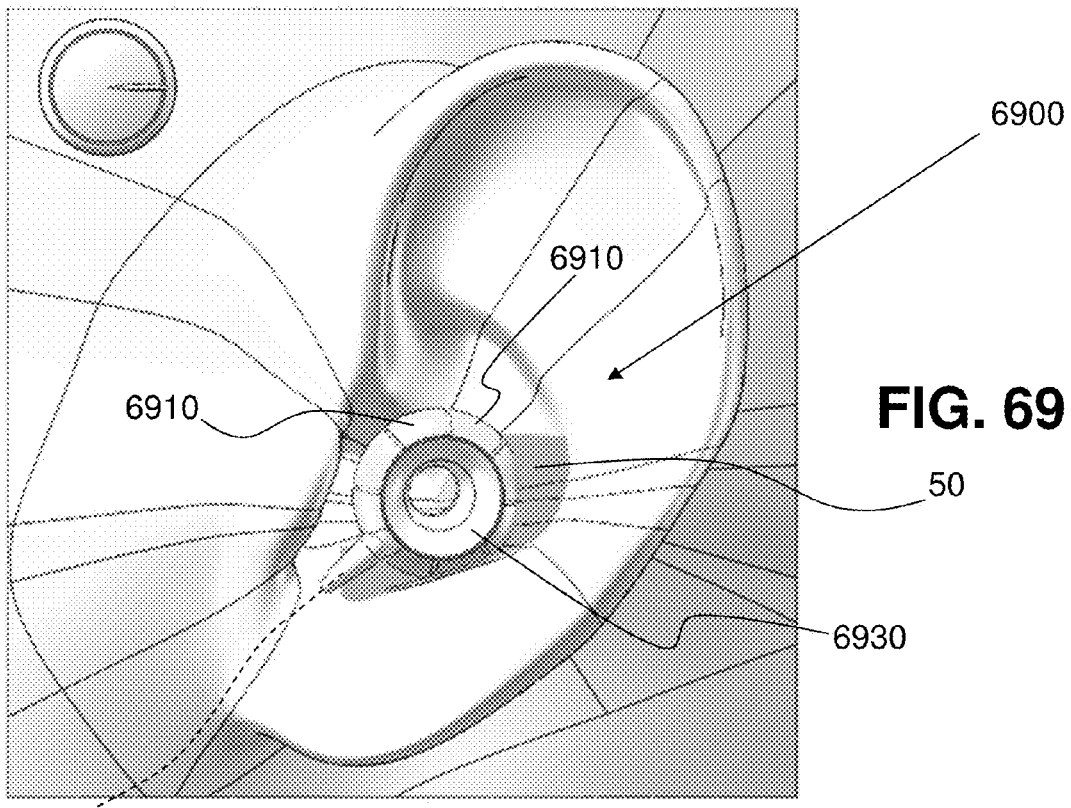
FIG. 69 is a fragmentary, side perspective view of an exemplary embodiment of a dual-purpose, earbud/neurostimulator device with leads and speaker removed for clarity.
Figure 70:
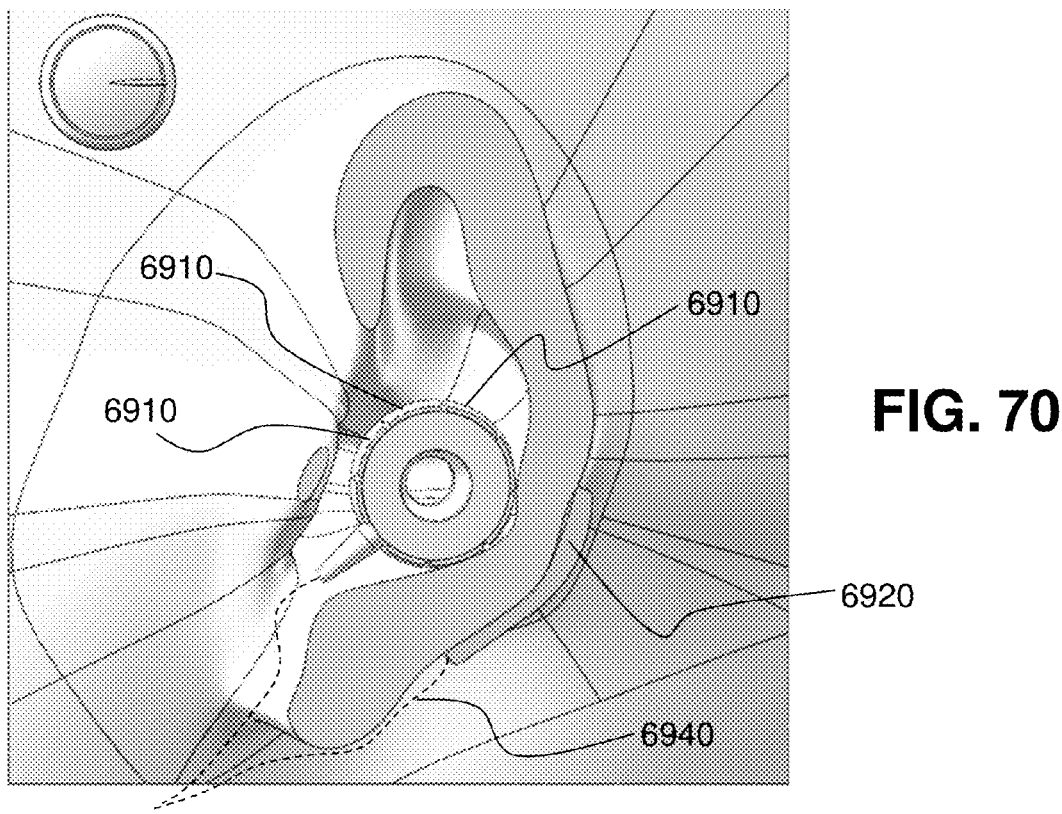
FIG. 70 is a fragmentary, side perspective and sagitally cross-sectional view of the earbud/neurostimulator device of FIG. 69.

A second exemplary embodiment of a dual-purpose earbud/neurostimulator device 6900 is shown in FIGS. 69 and 70. Again, the central speaker is not shown for purposes of clarity. The earbud base 6930 houses a set of external positive electrodes 6910 that surrounds at least a portion of the outside surface of the base 6930 for secure adhesion and, in particular, places at least one of the positive electrodes 6910 direct contact with at least one portion of the conchal region 50 of the ear. Behind the ear, in the auricle region 60, is a negative or ground electrode 6920. The front and rear electrodes can be connected together by a non-illustrated clip or other device that wraps around the helix of the ear or they can have corresponding magnetically coupling counterparts. Supply leads 6940, for both electrodes and the speaker of the earbud, are shown diagrammatically in FIG. 70 with dashed lines.

Figure 71:
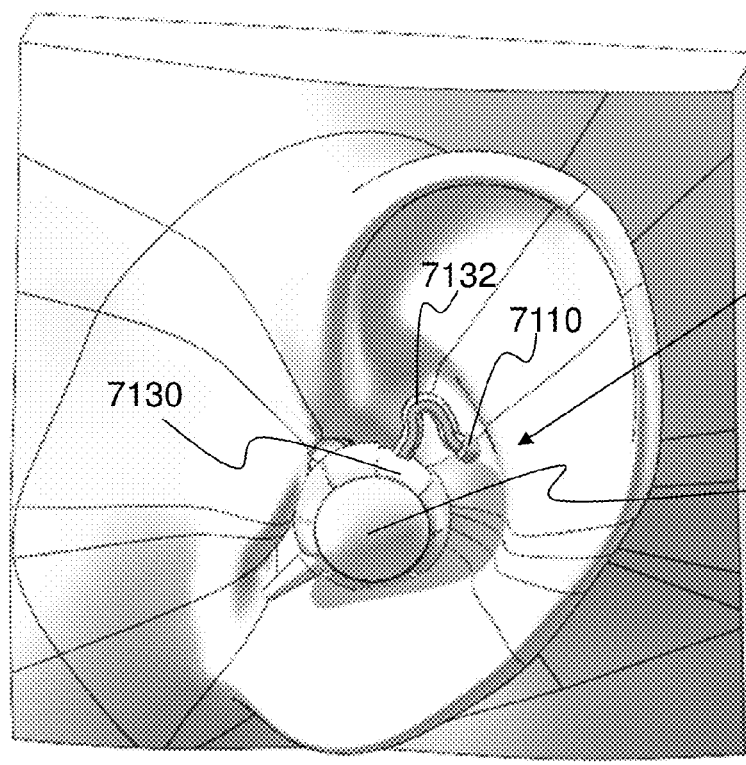
FIG. 71 is a fragmentary, side perspective view of an exemplary embodiment of a dual-purpose, earbud/neurostimulator device with leads and speaker removed for clarity.
Figure 72:
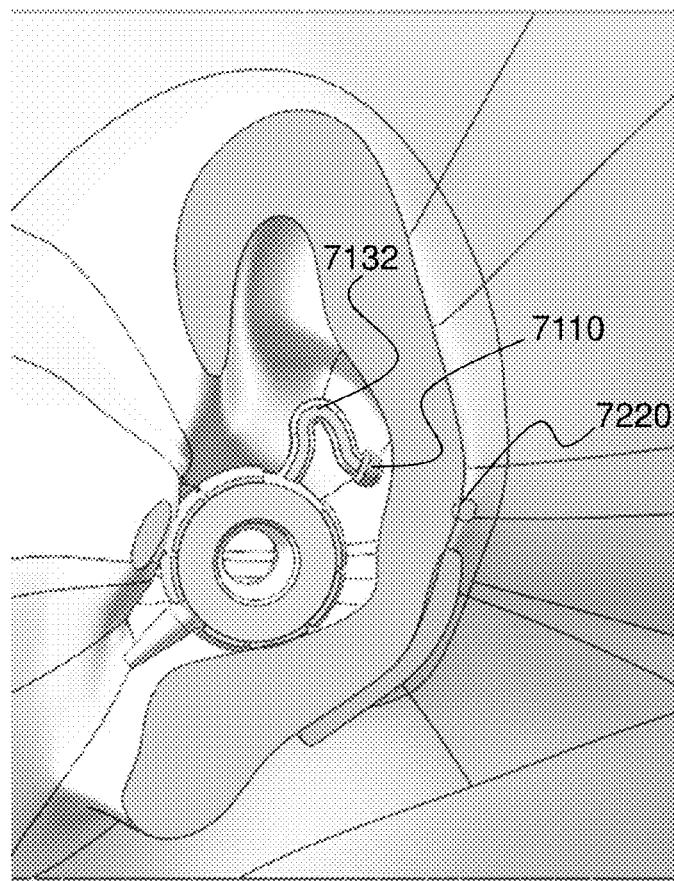
FIG. 72 is a fragmentary, side perspective and sagitally cross-sectional view of the earbud/neurostimulator device of FIG. 71.

A further exemplary embodiment of a dual-purpose earbud/neurostimulator device 7100 is shown in FIGS. 71 and 72. The central speaker 7102 is shown in FIG. 71 but is removed for purposes of clarity in FIG. 72. This exemplary embodiment is similar to the embodiment shown in FIGS. 69 and 70 except for the addition of an electrode extension 7132 extending to the conchal region 50, which extension 7132 placed a/another positive electrode 7110 thereon with a bias force, for example, from the curved shape of the extension 7132. Also provided is a corresponding negative/ground electrode 7220 disposed at the auricle region 60 of the ear.

Figure 73:
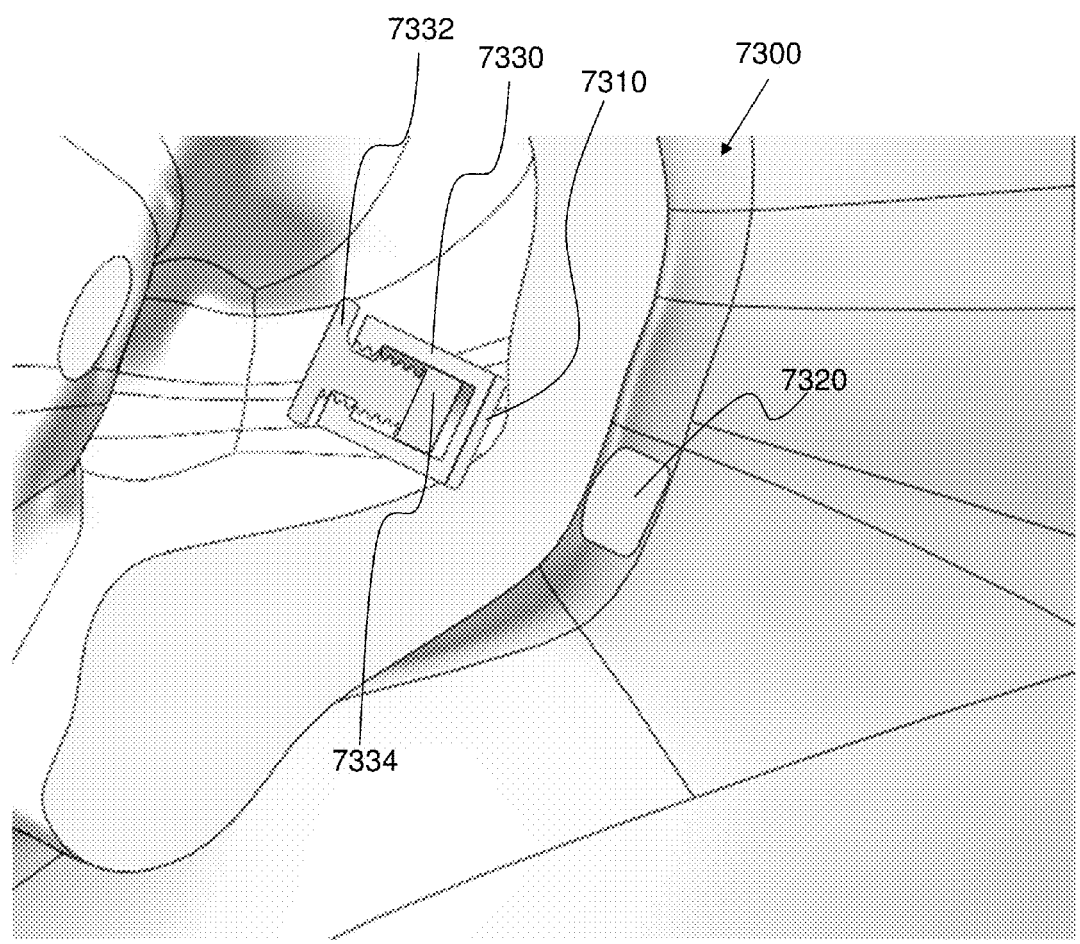
FIG. 73 is a fragmentary, side perspective and sagitally cross-sectional view of an exemplary embodiment of an adjustable magnetic attachment force neurostimulator device.

FIG. 73 illustrates a user coupler 7300 including a first body 7330 holding a magnetic component as well as an electrode 7310 that serves as the electrically positive contact point at the conchal 50 region of the ear. Additionally, there is a least one other magnetic electrode 7320 serving as the ground or electrically negative point that tracks through a non-illustrated conduit and back to the generator to complete the circuit. The electrode 7320 is placed at the auricle 60 region of the ear. At least one of the electrodes contains a magnet and the other of the electrodes contains ferrous material or an oppositely charged magnet allowing the electrodes to be in reciprocal positions on or about the skin such that the target structure to be stimulated is within the electromagnetic field generated by the signal generator. By turning the screw 7332 attached to the magnet 7334, a distance between the magnetic attraction point is decreased or increased, thereby adjusting clamping force tight or loose against the ear.

Figure 74:
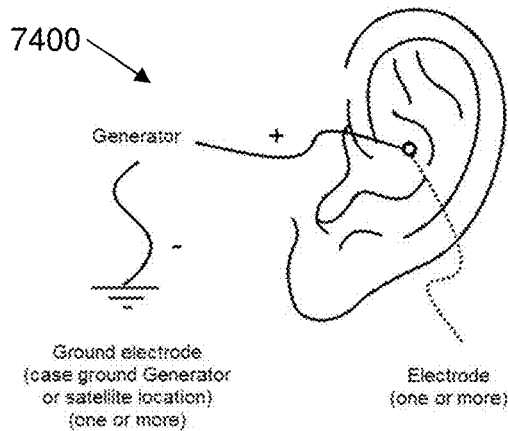
FIG. 74 is a diagrammatic illustration of a exemplary embodiment of placement of an electrode configuration.
Figure 75:
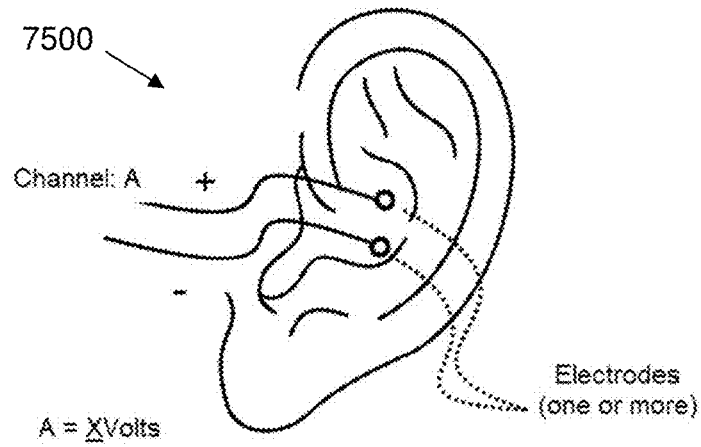
FIG. 75 is a diagrammatic illustration of a exemplary embodiment of placement of another electrode configuration.
Figure 76:
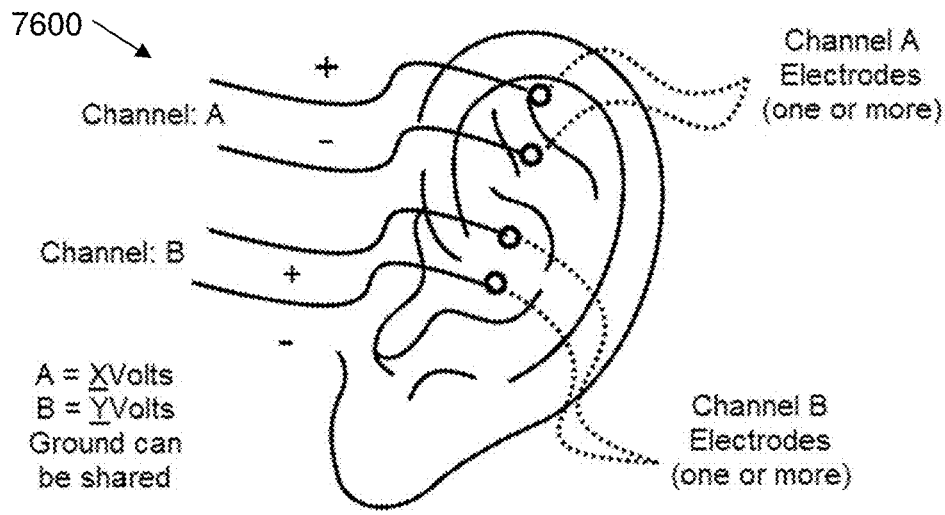
FIG. 76 is a diagrammatic illustration of a exemplary embodiment of placement of another electrode configuration.
Figure 77:
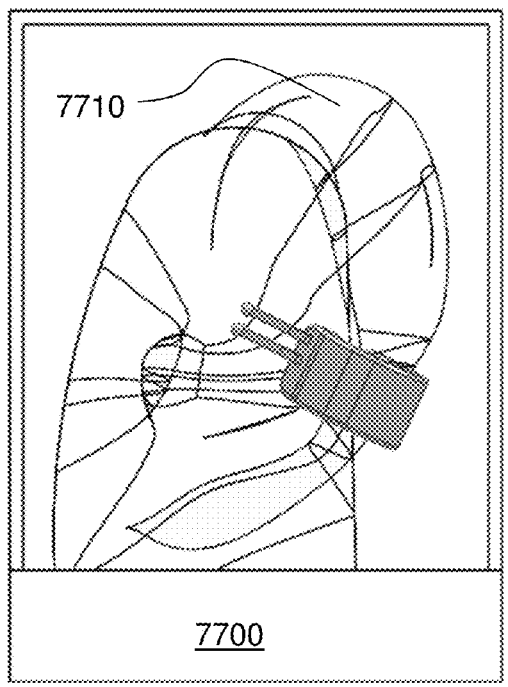
FIG. 77 is a front elevational view of an exemplary embodiment of a neurostimulator device within a packaging/charging station.
Figure 78:
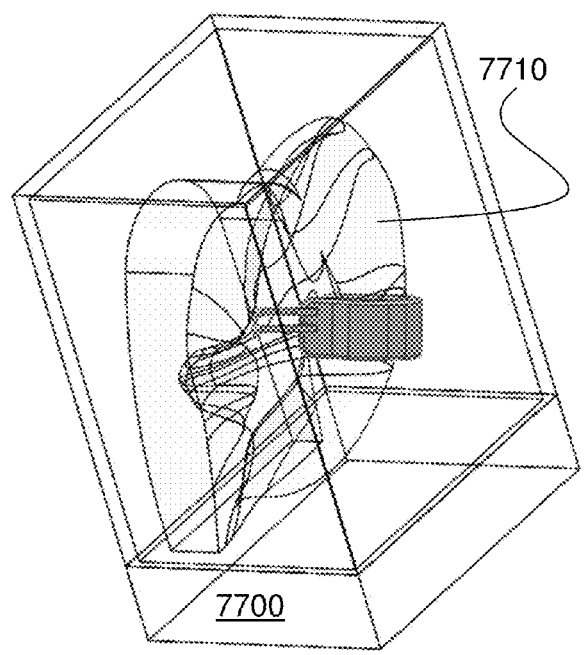
FIG. 78 is a front perspective view of the neurostimulator device and packaging/charging station of FIG. 77 viewed from the right side thereof.
Figure 79:
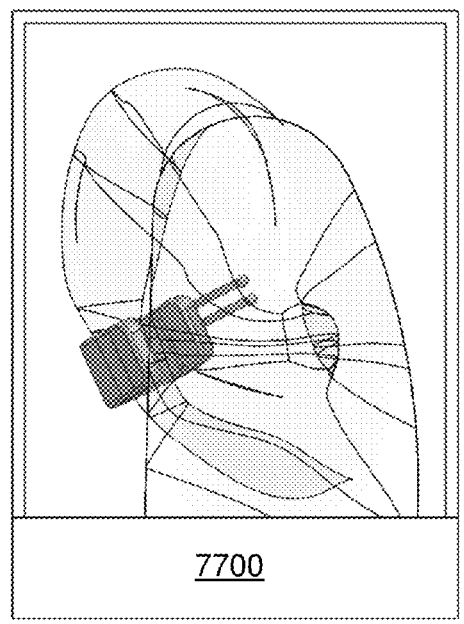
FIG. 79 is a rear elevational view of the neurostimulator device and packaging/charging station of FIG. 77.
Figure 80:
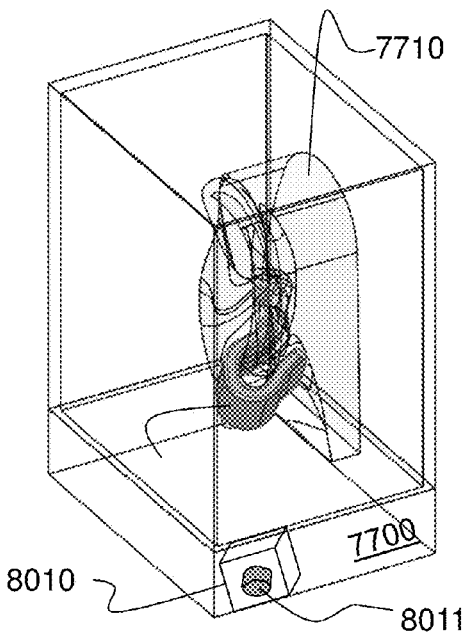
FIG. 80 is a front perspective view of the neurostimulator device and packaging/charging station of FIG. 77 viewed from the left side thereof.

As described above, application of neurostimulation to an auricle can occur in various ways. Electrode arrays can be placed on anterior or posterior auricular surfaces, for example. The three configurations 7400, 7500, 7600 for electrodes illustrated in FIGS. 74 to 76 are a subset of some basic configurations for electrode arrays. In particular, in the first exemplary configuration 7400 in FIG. 74, one or more electrodes are placed in the concha and a grounding electrode is placed at another portion of the user's body, for example, at the posterior side of the auricle. In the second exemplary configuration 7500 in FIG. 75, both positive and negative electrodes (or electrode arrays) are placed in the concha. In the third exemplary configuration 7600 in FIG. 76, one or more electrode pairs are placed in the concha and scapha.

FIGS. 77 to 80 show an exemplary embodiment of a user coupler in a packaged state. Even though this user coupler is similar to the embodiment illustrated in FIGS. 50 and 51, the configuration of packaging 7700 illustrated herein is applicable to all of the various user coupler embodiments described herein. The user coupler is fixed to the packaging 7700 by an attachment device 7710, such as a scale model of an ear or other target anatomy. Benefits of this attachment device 7710 include a complete constraining of the user coupler to protect it from transportation damage with a simultaneous instruction to the user of a correct target location, as well as to show what a correct application of the user coupler should look like. The packaging 7700 can be fully or partially clear to provide the consumer with an unobstructed view of the user coupler as well as the ear model 7710. One or more of the features of the systems and methods described herein, such as audio-synchronized pulsing lights, can be activated (for example by a power module 8010 having an on/off switch 8011) while the user coupler is in the packaging 7700. Another exemplary feature of the packaging 7700 is that the attachment device 7710 can also be a user coupler storage dock and/or charging dock when not in use.

Other exemplary embodiments of a dual-purpose earbud/neurostimulator device move neuromodulation into the ear canal. Such devices take advantage of the fact that the vagus nerve and branches thereof are close to and at the inner surfaces of the ear canal. By placing electrodes inside the ear canal, more direct access to the vagus nerve becomes possible. Various configurations of such devices are first shown in FIGS. 81 to 92.

Figure 81:
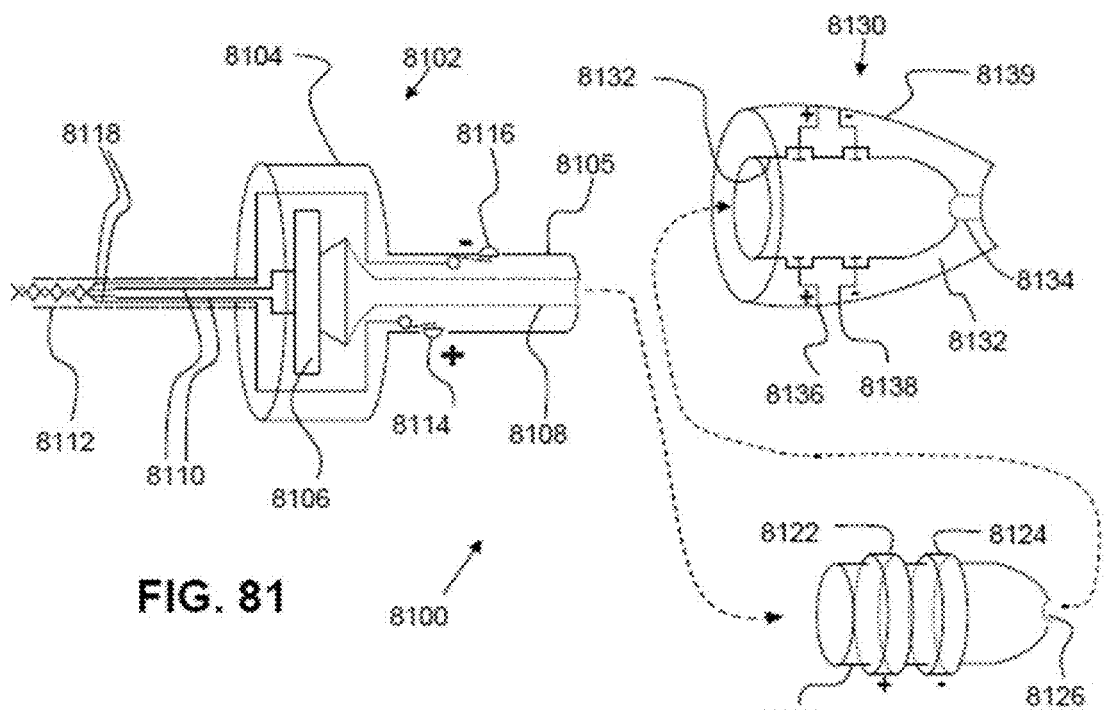
FIG. 81 is an enlarged, exploded, partially cross-sectional and partially hidden perspective view of an exemplary embodiment of a dual-purpose earbud/neurostimulator device.
Figure 82:
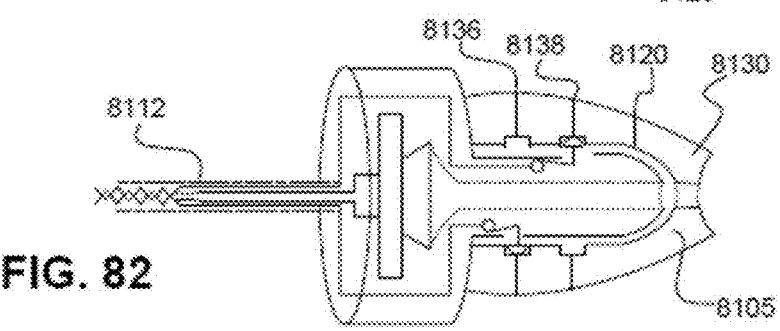
FIG. 82 is an enlarged, partially cross-sectional and partially hidden perspective view of the earbud/neurostimulator device of FIG. 81 in an assembled state.

With these characteristics in mind, reference is first made to FIGS. 81 to 84. In FIG. 81, a dual-purpose earbud/neurostimulator device 8100 is shown in an exploded view and FIG. 82 shows the parts in their assembled form. At the center is an electrode and audio platform 8102. The platform 8102 has a body 8104 that is relatively stiff as in other typical earbud devices. The body 8104 can be made of, for example, polycarbonate, polyethylene (LDPE), high density polyethylene (HDPE), polypropylene (PP), polystyrene (PS), polyvinyl chloride (PVC), and Polytetrafluoroethylene (PTFE). The body 8104 houses the electronic components of the device 8100. In particular, an internal audio speaker 8106 is aligned to project sound through an audio canal 8108 and out to the user when the device 8100 is placed in the user's ear canal. The audio canal 8108 can be of any acoustically beneficial shape and is shown only diagrammatically in FIGS. 81 and 82 with dotted lines. The audio speaker 8106 has electrical connections 8110 that extend back to the generator and/or audio device through a cable 8112, diagrammatically shown with dashed lines. Audio signals are transmitted through the electrical connections 8110 from the generator and/or audio device as these can be separate or integral components. The body 8104 also contains positive and negative/ground electrode supplies 8114, 8116 that electrically connect to the generator though stimulation supply lines 8118. In the exemplary embodiment, the positive and negative/ground electrode supplies 8114, 8116 have bias devices that allow movement of the physical electrical connection portion towards and away from a central longitudinal axis of the body 8104. These bias devices are shown diagrammatically in FIGS. 81 and 82. By applying an outward bias, the outer electrical connection surfaces are assured to keep contact with their respective counterparts on the insert 8120, which is slipped onto the sound canal stub 8105 of the body 8104.

Even though the insert 8120 can be integral with the relatively soft ear piece 8130 or integral with the body 8104, it is separate in this exemplary embodiment. The insert 8120 is hollow and has an interior cavity shaped to fit snugly on the sound canal stub 8105 of the body 8104. The insert 8120 has circumferential positive and negative connection bands 8122, 8124 each having an interior surface that is electrically conductive and, when the insert 8120 is installed on the stub 8105, respective electrical connectivity is established between the interior surface of each band 8122, 8124 and the electrode supplies 8114, 8116. If desired, the bands 8122, 8124 can be collinear with the interior surface of the insert 8120 or they can be offset, either inwards or outwards, to form a positive removable connection between the electrode supplies 8114, 8116 when connected together. The bands 8122, 8124 have a respective electrically conductive exterior surface that insulated from one another. This electrically conductive exterior surface also can be offset, either inwards or outwards. The exterior offset can be offset in the same direction as the interior surface or it can be opposite the offset of the interior surface so that there are either rings extending outwards from both surfaces of the insert 8120 or there are grooves extending inwards from each inner and outer surface. The distal end of the insert 8120 has an audio port 8126 that permits passage of audio sound. The insert 8120 is made of a material that can easily create the circumferential electrically conductive bands 8122, 8124 and keep them electrically isolated and insulated from one another. For example, the insert is of pvc, rubber, PEEK, or latex.

The outermost part of the device 8100 is the ear piece 8130, sometimes referred to as an earbud. As with conventional ear pieces, the ear piece 8130 is soft to be comfortable when inserted within the ear canal of a user. Thus, the ear piece 8130 is relatively softer than the body 8104. The ear piece 8130 defines an inner cavity 8132 into which the insert 8120 is placed in use. The inner cavity 8132 has a corresponding shape to the exterior of the insert 8120 and, in an exemplary embodiment, is sufficiently tight to prevent the ear piece 8130 from falling off of the insert 8120 or the body 8104 when in use. In an exemplary embodiment, the softness of the ear piece 8130 is such that the inner cavity 8132 can stretch a little to be press-fit over the insert 8120 when the insert 8120 is on the stub 8105 and that stretch acts as a bias to retain both the insert 8120 and the ear piece 8130 on the body 8104. The ear piece 8130 is formed with a sound channel 8134 that permits audio from the speaker 8106 to exit and pass through to enter the user's ear canal. The inner cavity 8132 contains positive and negative/ground connection areas 8136, 8138 at the inner surface thereof to electrically contact the exterior surfaces of the bands 8122, 8124 on the insert 8120 when the ear piece 8130 is installed thereon. The connection areas 8136, 8138 can be simple printed electrical pads or rings or can be more complex, such as pogo pins. In any embodiment, the connection areas 8136, 8138 pass through the material of the ear piece 8130 and exit to the exterior surface 8139. The ear piece 8130 is made of a material that can have electrical connections on the inner surface of the inner cavity 8132, can pass from the inner cavity 8132 through the material and to the exterior surface 8139, and can extend over an area on the exterior surface 8139 of the ear piece 8130. The connection areas 8136, 8138 in FIG. 81 are shown as inwardly extending, even though this is diagrammatic. As an alternative to inwardly extending areas, the areas can be collinear with the surface or they can extend inwardly as protrusions away from the surface of the inner cavity 8132. If the protrusions are soft as well as being the conductive connection areas 8136, 8138, then the protrusions can act as bias measures to press against the bands 8122, 8124 and, thereby, maintain electrical connectivity.

Figure 83:
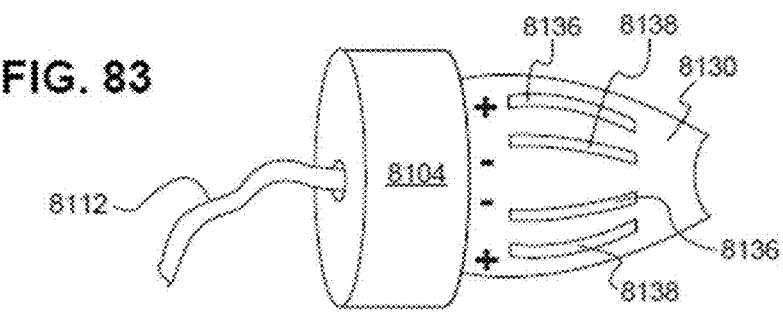
FIG. 83 is an enlarged, side perspective view of the earbud/neurostimulator device of FIG. 81 in the assembled state.
Figures 84, 85, 86:
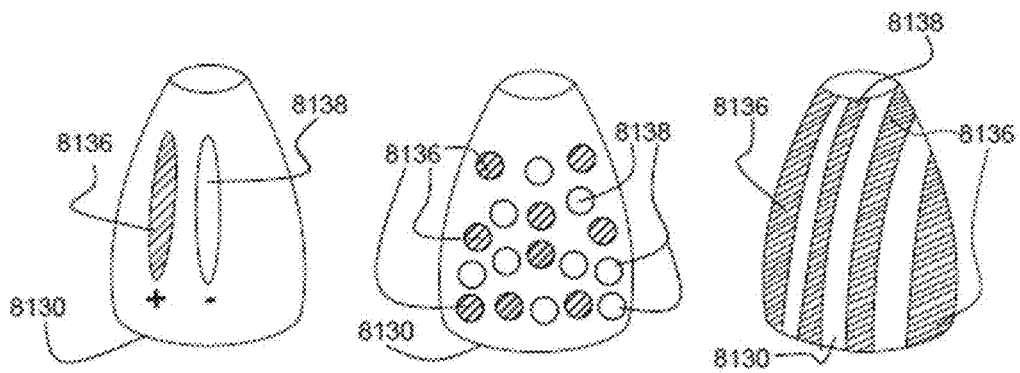
FIG. 84 is an enlarged, side perspective view of an exemplary embodiment of the ear piece of the earbud/neurostimulator device of FIG. 81.
FIG. 85 is an enlarged, side perspective view of an exemplary embodiment of the ear piece of the earbud/neurostimulator device of FIG. 81.
FIG. 86 is an enlarged, side perspective view of an exemplary embodiment of the ear piece of the earbud/neurostimulator device of FIG. 81.
Figures 87, 88:
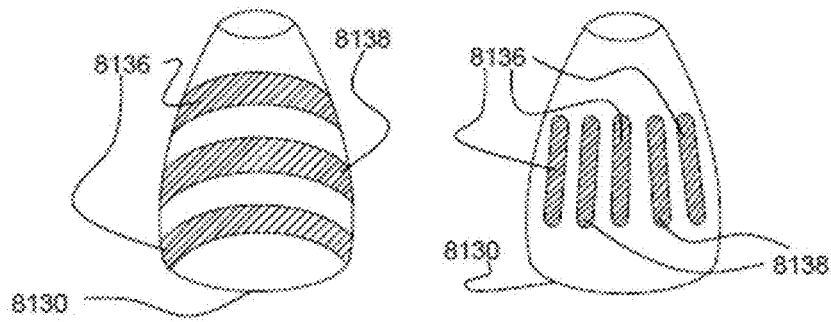
FIG. 87 is an enlarged, side perspective view of an exemplary embodiment of the ear piece of the earbud/neurostimulator device of FIG. 81.
FIG. 88 is an enlarged, side perspective view of an exemplary embodiment of the ear piece of the earbud/neurostimulator device of FIG. 81.
Figures 89, 90:
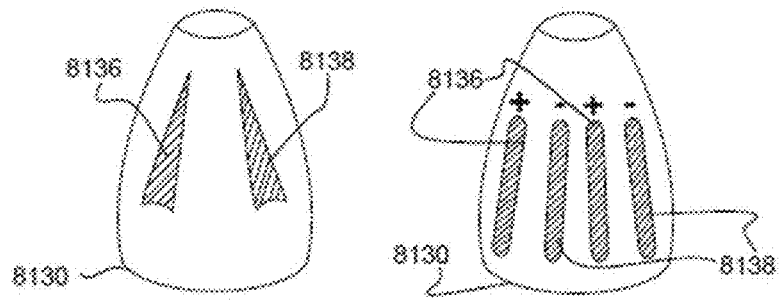
FIG. 89 is an enlarged, side perspective view of an exemplary embodiment of the ear piece of the earbud/neurostimulator device of FIG. 81.
FIG. 90 is an enlarged, side perspective view of an exemplary embodiment of the ear piece of the earbud/neurostimulator device of FIG. 81.
Figure 91:
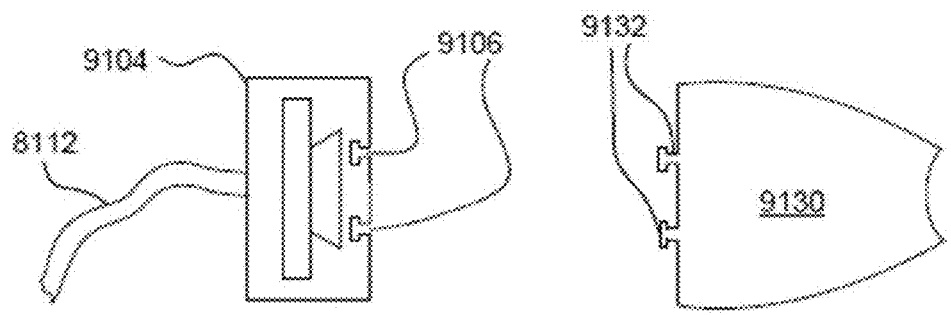
FIG. 91 is an enlarged, exploded, partially hidden, side perspective view of another exemplary embodiment of a dual-purpose earbud/neurostimulator device.

Neuromodulation electrodes on the exterior surface 8139 of the ear piece 8130 can take any form. One exemplary embodiment is shown in FIG. 83, in which there are two pairs of connection areas 8136, 8138, each having a positive and a negative/ground. Other exemplary embodiments are shown in FIGS. 84 to 90. In FIG. 84, there is one pair of connection areas 8136, 8138, each in the form of strips. In FIG. 85, the connection areas 8136, 8138 are many, are in the form of circular pads, and are spread out over the entirety of the exterior surface of the ear piece 8130. In FIG. 86, the connection areas 8136, 8138 are in the form of longitudinal strips circumferentially spread out over the entirety of the exterior surface of the ear piece 8130, with the number of the connection areas 8136, 8138 being different. Here, the number of positive electrode areas 8136 is greater than the number of negative/ground electrode areas but they can be reversed. In FIG. 87, the connection areas 8136, 8138 are in the form of circumferential rings or bands alternating from the base to the tip on the exterior surface of the ear piece 8130, with the number of the connection areas 8136, 8138 being different. Here, the number of positive electrode areas 8136 is greater than the number of negative/ground electrode areas but they can be reversed. In FIG. 88, the connection areas 8136, 8138 are in the form of small longitudinal strips circumferentially spaced around the exterior surface of the ear piece 8130. The number of the connection areas 8136, 8138 are shown as being different but they can be the same in number or can be any number of each. In FIG. 89, there is one pair of connection areas 8136, 8138, each in the form of a triangle. Finally, in FIG. 90, there are pairs of strip-shaped connection areas 8136, 8138 around the circumference of the ear piece 8130, each pair having one positive between two negative/ground. It is noted that each of the exemplary embodiments of the neuromodulation electrodes shown on the exterior surface 8139 of the ear piece 8130 shown and described herein is merely exemplary. The electrodes can be in any shape or number.

Figure 92:
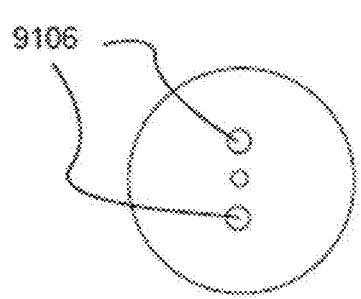
FIG. 92 is an enlarged, top plan view of the body of the device of FIG. 91 with a first exemplary embodiment of a connection configuration.
Figure 93:
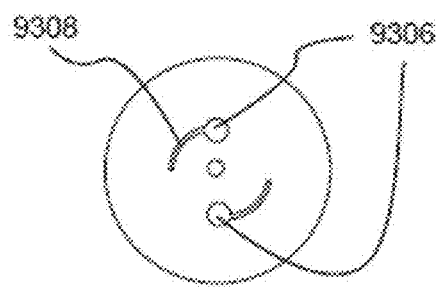
FIG. 93 is an enlarged, top plan view of the body of the device of FIG. 91 with a second exemplary embodiment of a connection configuration.

The ear piece 8130 and the body 8104 connect in a so-called pin-and-bore form fit. Another exemplary embodiment for connecting these two parts is shown in the diagrammatic representations of FIGS. 91 to 93. The body 9104 is similar to the body 8104 except there is no stub 8105. Instead, the body 9104 has connection ports 9106 into which connectors 9132 of the ear piece 9130 are removably inserted. FIG. 92 shows a single direction connection in which the connectors 9132 insert longitudinally directly into the connection ports 9106 to removably hold the ear piece 9130 to the body 9104 (e.g., with a press-fit). FIG. 93, in contrast, shows a multi-direction connection in which the connectors 9132 first insert longitudinally into the connection ports 9306 and, then, the ear piece 9130 is twisted (here, counterclockwise) to permit the distal head of the connectors 9132 to be captured within tracks 9308 of the connection ports 9306, similar to a bayonet mount. If the heads of the connectors 9132 form the electrical connection between the electrode supplies 8114, 8116 of the body 9104 for delivering the neuromodulation signals, then this connection mechanism provides a very stable and positive electrical connection while, at the same time, allows the user to rotate the ear piece 9130 with respect to the body 9104 to better align the external electrodes (not illustrated) with the person's unique vagus nerve anatomy at the ear canal. It is noted that the removable connection between the body 9104 and the ear piece 9130 can take any form and, therefore, the connection therebetween is not limited to the exemplary embodiments shown and described. It is noted that many of the parts of the body 9104 and the ear piece 9130 that are similar to the embodiment of FIGS. 81 to 83 have not been described or shown for clarity, but the descriptions are equally applicable.

Figure 94:
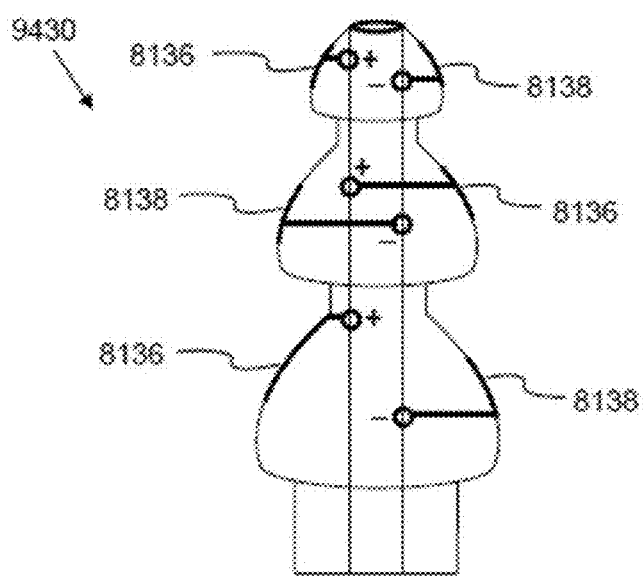
FIG. 94 is an enlarged, cross-sectional view of an exemplary embodiment of the ear piece of the earbud/neurostimulator device of FIG. 81.

FIG. 94 illustrates another exemplary embodiment of the ear piece for the earbud/neurostimulator device. This ear piece 9430 is one that protrudes further into the ear canal and provides an improvement in the sealing of the outer surface of the ear piece 9430 to the surface of the ear canal due to the staggered umbrella shapes. With the increased sealing of the ear canal to the outer surfaces of the ear piece 9430, this configuration of the ear piece 9430 can be used in moist or wet environments, such as when swimming or bathing.

Figures 95, 96, 97:
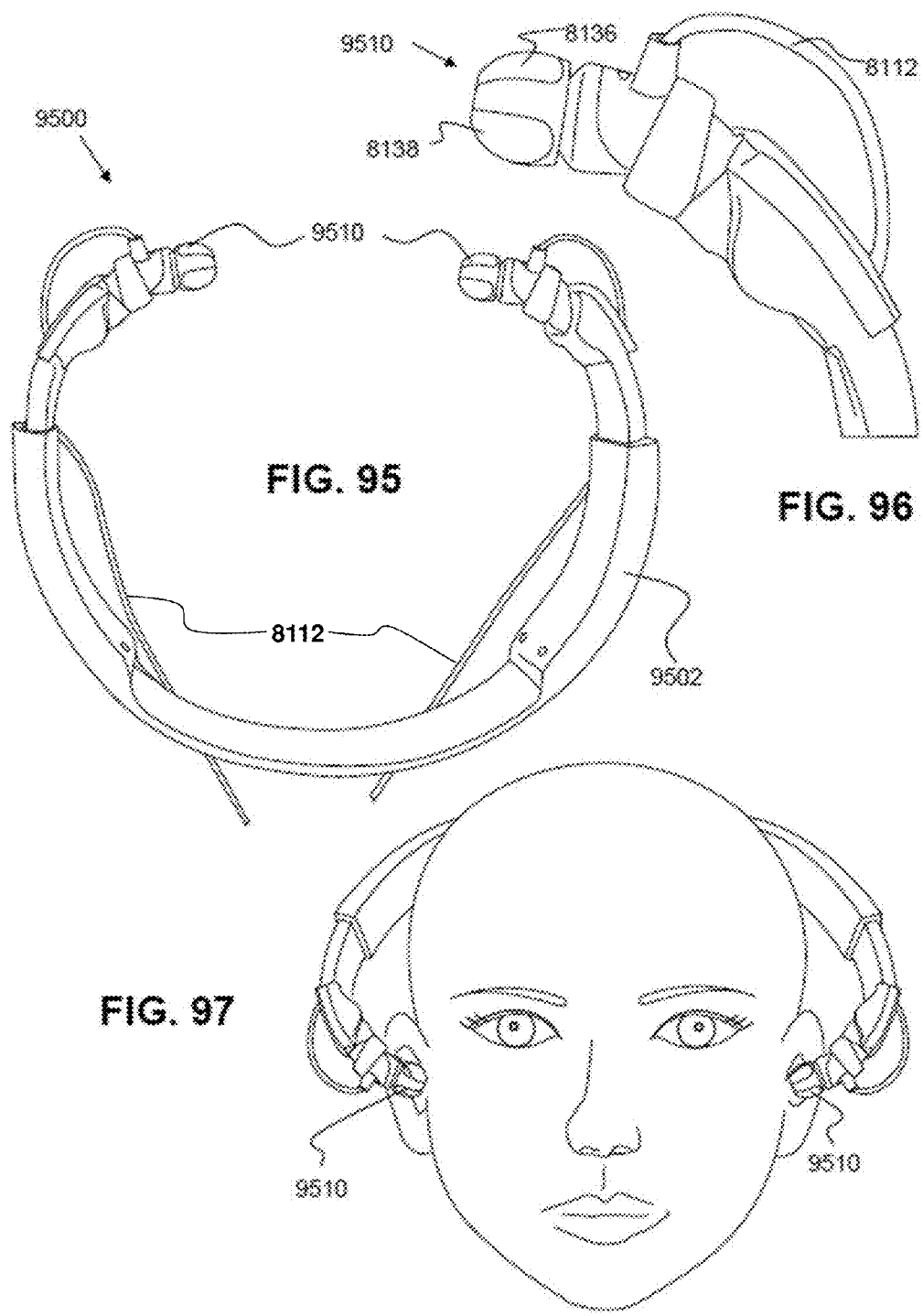
FIG. 95 is a top plan view of an exemplary embodiment of a headband earbud/neurostimulator device.
FIG. 96 is a fragmentary, enlarged top plan view of a distal end of the device of FIG. 95 with an earbud/neurostimulator device.
FIG. 97 is a diagrammatic perspective view of the device of FIG. 95 worn about a user's head.

FIGS. 62 to 65 illustrate an over-the-head configuration of a neurostimulator device 6200. In that embodiment, the ear contact ring 6220 cups over most or all of the ear. The ear contact ring 6220 can be replaced with ear pieces on either side. FIGS. 95 to 97 illustrates such an embodiment of a neuromodulation device 9500 with a C-shaped headband 9502 having distal ends. An earbud/neurostimulator device 9510 is placed at one or both of the distal ends of the headband 9502. When worn, each of the earbud/neurostimulator devices 9510 fits into a respective ear canal of a user. Each of the earbud/neurostimulator devices 9510 in FIG. 95 has electrode contacts 8136, 8138 for delivering neurostimulation to both ear canals. While electrode contacts 8136, 8138 are shown on both of the earbuds, only one of the earbuds can have the electrode contacts 8136, 8138 in a desirable alternative exemplary embodiment. Neurostimulation signals are provided to the earbud/neurostimulator device(s) 9510 through a cable 8112. The neurostimulation device 9500 can be worn about the back of a user's head as shown in FIG. 97 or it can be rotated about the axis between the user's ears to place the headband under the user's chin (not illustrated). Beneficial to this embodiment of the neurostimulation device 9500 is that the headband can be of a material with spring-back properties such that, when the C-shape of the headband 9502 is opened to fit on the user's head, the spring-back of the C-shape provides an inwardly directed force on the earbud/neurostimulator device 9510 to press it into the ear canal and improve contact of the electrode contacts 8136, 8138 with the inner surfaces of the ear canal.

Figure 98:
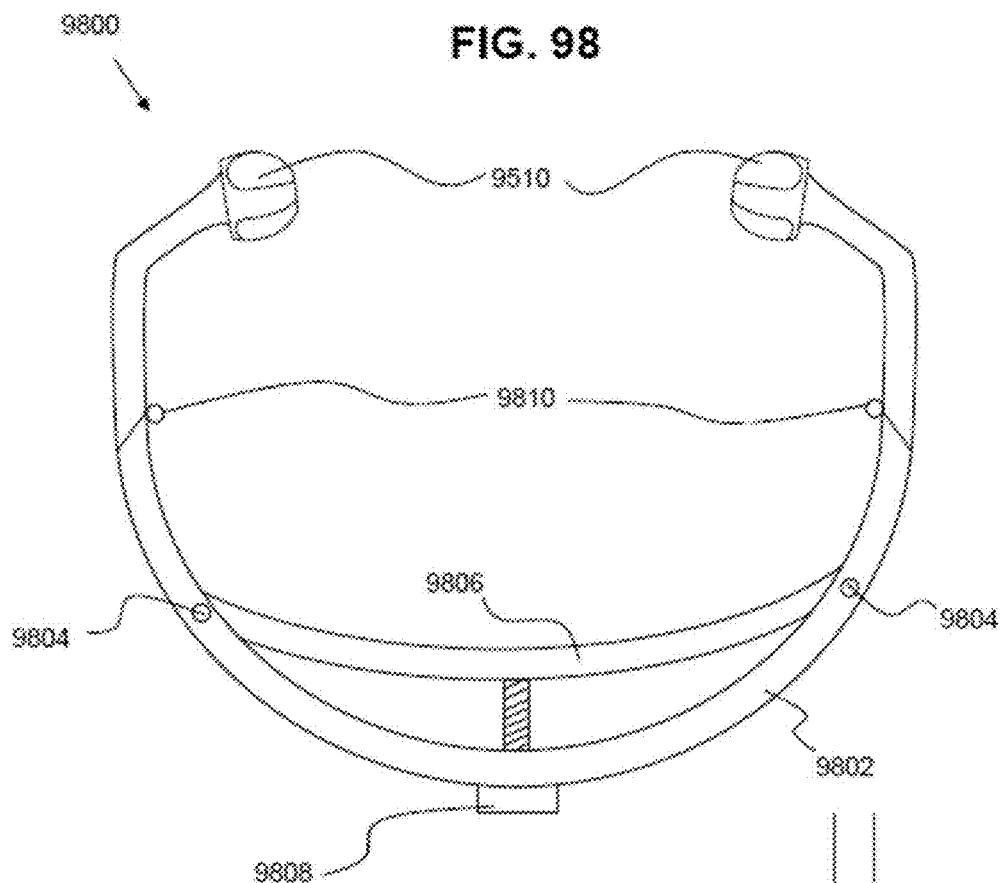
FIG. 98 is a top plan view of an exemplary embodiment of another headband earbud/neurostimulator device.

While the material of the headband 9502 can flex or be of a spring-back nature, mechanical devices can also be employed to press the distal earbud/neurostimulator device against and into a user's ear canal. One exemplary headband neurostimulation device 9800 is shown in FIG. 98, in which a headband 9802 includes pivot points 9804 at which a flex bar 9806 is mounted. The midpoint of the headband 9802 has a threaded throughbore in which is threaded an adjustment screw 9808. As such, when the screw 9808 is tightened, it presses against the centerpoint of the flex bar 9806, moving the centerpoint of the headband 9802 away from the flex bar 9806 and, thereby, causing the two earbud/neurostimulator devices 9510 to move towards one another. As headbands that wrap around a user's head are large and not easily stored, the headband 9802 can be provided with fold points 9810 that retain the shape of the headband 9802 when moved outwards as shown but also allow the distal ends to rotate and fold inwards for easy storage when removed from a user's head. Other portions of the headband neurostimulation device 9800 are similar to the exemplary embodiments described herein and are, therefore, not repeated.

Figure 99:
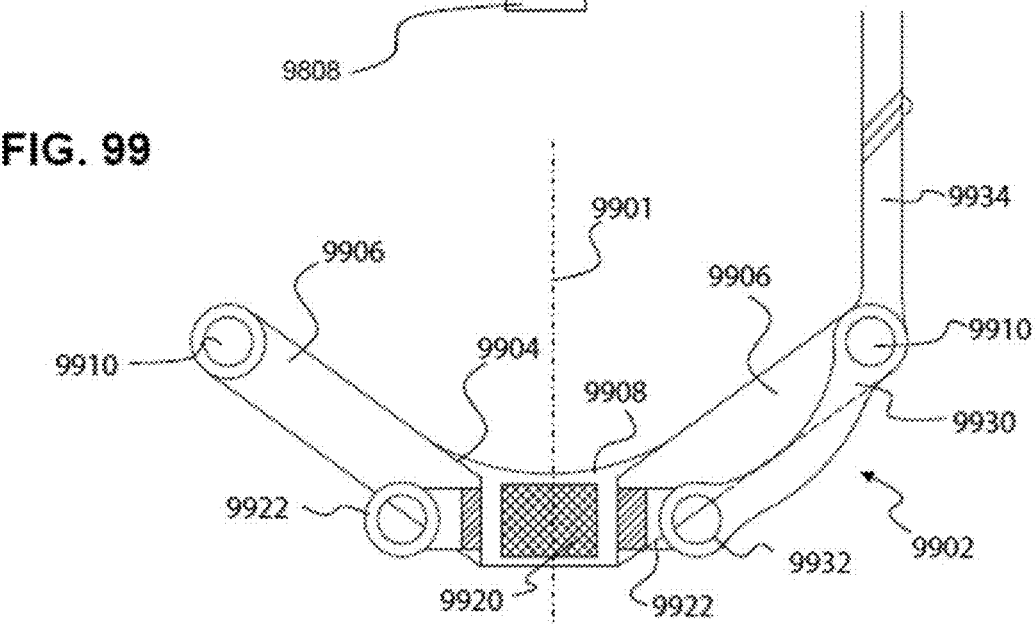
FIG. 99 is a top plan view of an exemplary embodiment of a further headband for an earbud/neurostimulator device.

Similar functions can be accomplished by the embodiment of the headband 9902 shown in FIG. 99. This headband 9902 has a main body 9904 having two outwardly projecting arms 9906 and a center point at which is located a spindle holder 9908. A hollow spindle 9920 is mounted in the spindle holder 9908 in a freely rotatable manner such that opposing cams 9922 threaded into the hollow of each of the opposing sides of the spindle 9920 can move inwards and outwards together as the spindle 9920 is spun in either direction. The distal ends of the cams 9922 are each connected to a first end 9932 of a pivot bar 9930, which pivot bar 9930 is pivotally connected to a respective distal end of an arm 9906 at a pivot point 9910. In such a configuration, as the cams 9922 are moved inwards, the first end 9932 moves towards the spindle 9920 and the second end 9934 moves away from a centerline 9901 of the headband 9902. When the spindle 9920 is spun in the opposite direction, the cams 9922 move outwards and the second ends 9934 close and move towards the centerline 9901.

The earbud embodiments shown in FIGS. 81 to 99 are just a few exemplary configurations for providing electrostimulation to the ear canal. The configuration of FIGS. 81 to 83 and 91 to 93 envision earbuds that can be utilized as stand-alone earbuds without headbands or they can be used with headbands, such as those illustrated in FIGS. 95 to 99. The general concept of the stand-alone electrostimulation earbuds is to provide a speaker in a housing that cooperates with an earbud having external electrical contacts to deliver electrostimulation to the surface of the ear canal while providing acoustic signals (such as music, white noise, an audio book, auditory pre-set patterns, and the like) into the ear canal through an acoustic delivery channel or port. Exemplary embodiments of stand-alone electrostimulation earbuds are shown starting with FIG. 100.

Figure 100:
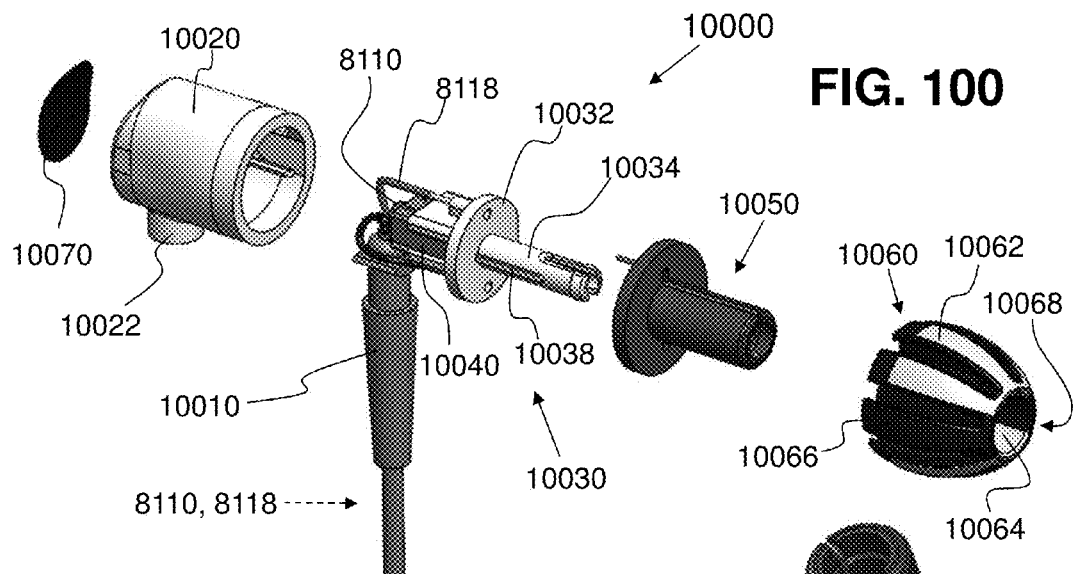
FIG. 100 is a fragmentary, exploded, perspective view of an exemplary embodiment of an earbud-type neurostimulator device with a multi-electrode flower-shaped electrode coupler.

FIG. 100 depicts a first exemplary embodiment of a stand-alone electrostimulation earbud 10000. Starting from the bundle of electrical leads, including two 8110 for the speaker and two 8118 for the electrostimulation signal, a strain relief 10010 guides the leads into a speaker housing 10020 and is fixed within an entry port 10022. The speaker housing 10020 is semi-rigid and can be made of plastic, for example, ABS. The speaker housing 10020 can be 3D printed if desired and forms an encasement for a device that holds a speaker therein. In particular, an internal hollow of the speaker housing 10020 receives a speaker housing stud 10030, in which is held a speaker assembly 10040. The exemplary embodiment of the speaker housing stud 10030 shown in FIG. 100 is shaped to hold a rectangular cuboid speaker assembly 10040, such as the Sonion 2356, which is about 11 mm to 12 mm in maximum width. Thus, the outer diameter of the speaker housing 10020 can be as little as about 14 mm. The speaker leads 8110 pass through the interior of the speaker housing 10020 and are electrically connected to the speaker assembly 10040. Connection of the electrostimulation leads 8118 will be explained below. Finally, the rear of the speaker housing 10020 can be shaped to provide a space for a decal or sticker 10070 printed with a trademark thereon or the space can form the logo itself, for example, by raised bosses or lowered channels, which logo can be back lit by, for example, an LED that pulses and/or changes colors with the electrostimulation signal.

When installed at the speaker housing 10020, the speaker housing stud 10030 has a flange 10032 that, together with the strain relief 10010 and the speaker assembly 11040, substantially seal off the interior of the speaker housing 10020 from the environment. At its rear side, the speaker housing stud 10030 has a speaker encasement 10031, best shown in FIG. 101, that securely holds the speaker assembly 10040 at the speaker housing stud 10030. At its front side, the speaker housing stud 10030 has a core-assembly stud 10034. The core-assembly stud 10034 has various features. First, sound from the speaker assembly 10040 needs to be communicated to the user. In the particular exemplary embodiment of FIGS. 100 to 103, the interior hollow of the core-assembly stud 10034 forms a sound channel that communicates sound from the speaker assembly 10040 to the user's inner ear. A second feature holds an earbud core assembly 10050 to the core-assembly stud 10034 when the earbud core assembly 10050 is connected thereto. In the particular exemplary embodiment of FIGS. 100 to 103, the core-assembly stud 10034 has a split mushroom end 10036 that is able to compress inwards when the earbud core assembly 10050 is being installed thereon and then spring outwards when the surface of interior bore 10052 of the earbud core assembly 10050 enlarges. The enlarged diameter portion 10054 of the interior bore 10052 of the earbud core assembly 10050 can be seen in the right side of FIG. 101 and in FIG. 103 and the split mushroom end 10036 is shown seated in that expanded area in FIG. 102. A third feature of the core-assembly stud 10034 clocks the earbud core assembly 10050 to a pre-set installation orientation. In the particular exemplary embodiment of FIGS. 100 to 103, the core-assembly stud 10034 has at least one clocking ridge 10038 and, preferably, two clocking ridges 10038 on opposing sides of the core-assembly stud 10034. This clocking feature will be described in further detail below.

The flange 10032 has two electrical contacts that provide an electrical conduit for electrostimulation arriving through the electrostimulation leads 8118. As will be explained in the embodiments herein, this conduit can take various forms. One exemplary configuration for the electrostimulation leads 8118 shown in FIGS. 100 to 103 is an electrically conductive bore or via 10033 on the earbud (or front) side of the flange 10032. Each lead 8118 is connected to the bore 10033 at the rear side of the flange 10032 in any way, for example, by soldering or press-fitting. On the opposite side of the flange 10032, the bore 10033 provides an orifice in which a conductor is slidably received.

The earbud core assembly 10050 is semi-rigid and can be made of plastic, for example, ABS. The earbud core assembly 10050 can be 3D printed if desired and forms the structural support for the earbud 10060. The earbud core assembly 10050 also has various features. First, the central bore 10052 receives the core-assembly stud 10034 therein. The expanded portion 10054 is located at distal end of the central bore 10052 such that, when the core-assembly stud 10034 is temporarily locked therein, the distal end of the core-assembly stud 10034 does not protrude from the distal end of the earbud core assembly 10050. Although, if desired, the distal end can protrude therefrom. It is noted that the earbud 10060 is most likely a disposable part and, therefore, is envisioned to be replaced (although it can be reusable). Thus, it must be able to be removed from either or both of the speaker housing stud 10030 and the earbud core assembly 10050. If desired, the earbud core assembly 10050 can also be disposed along with the earbud 10060 or it can be retained for use with a replacement earbud 10060.

Figures 101, 103:
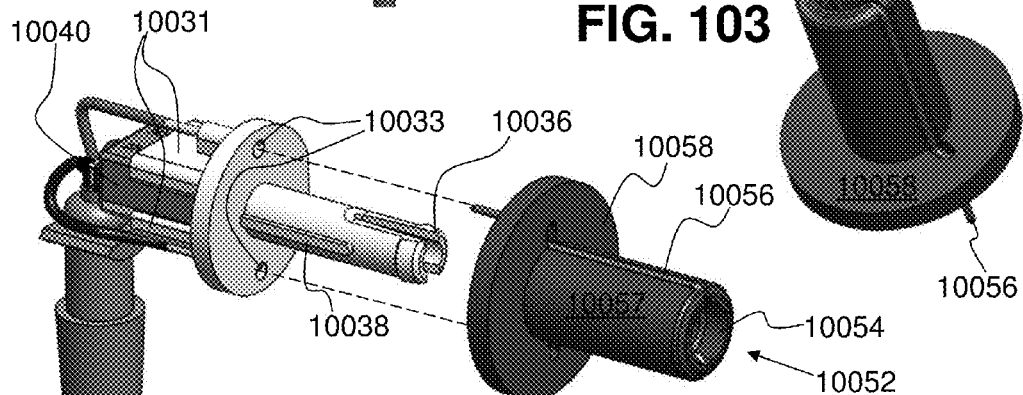
FIG. 101 is a fragmentary, enlarged, exploded, perspective view of portions of the earbud-type neurostimulator device of FIG. 100 including a strain relief, a speaker assembly, a speaker housing stud, and an earbud core assembly.
FIG. 103 is an enlarged, perspective view of the earbud core assembly of the earbud-type neurostimulator device of FIG. 100.
Figure 102:
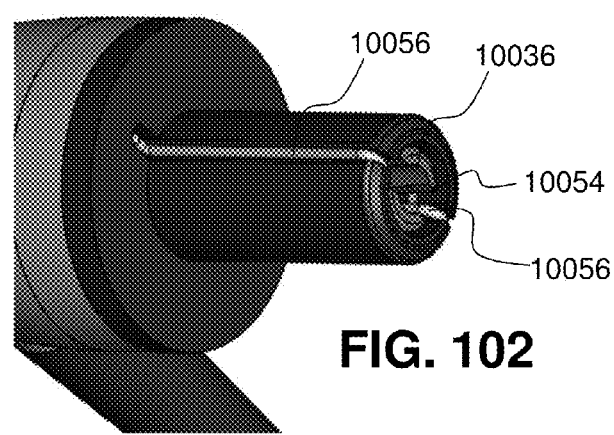
FIG. 102 is a fragmentary, enlarged, perspective view of the earbud-type neurostimulator device of FIG. 100 with the earbud core assembly installed on the speaker housing stud.

The earbud core assembly 10050 also has a set of electrostimulation conductors 10056 that, in this exemplary embodiment, are on opposing sides but they can be disposed at any two (or more) locations about the exterior surface of the earbud core assembly 10050. The conductors 10056 each project entirely through a flange 10058 of the earbud core assembly 10050 to form two rearward projecting extensions that can be inserted into respective ones of the bores 10033 when the earbud core assembly 10050 is correctly rotated (i.e., clocked) in an installation position. To provide this clocking, the interior surface of the central bore 10052 has a non-illustrated groove that extends from the rear side of the flange 10058 starting from an open funnel shape necking down to a shape that exactly matches the exterior shape of the clocking ridges 10038. The length that the clocking ridges 10038 extend away from the flange 10032 of the speaker housing stud 10030 is set so that the rearward projecting extensions of the conductors 10056 are prevented from coming into contact with the flange 10032 unless and until the two clocking ridges 10038 are within the corresponding grooves of the central bore 10052. In this way, the conductors 10056 automatically and assuredly enter the bores 10033 and make electrical contact with the leads 8118. The conductors 10056 are shown as round wires but they can be of any polygonal shape, including hexagonal, triangular, and square, for example. As shown in FIG. 103, the conductors 10056 use their shape to remain fixed on the body of the earbud core assembly 10050. From the earbud side of the earbud core assembly 10050, the conductors 10056 pinch the distal end of the stud 10057 of the earbud core assembly 10050 with a 180-degree bend. Then, the conductors 10056 travel along the length of the stud 10057 in a groove that keeps the conductors 10056 resting therein but still projecting out from the outer surface of the stud 10057. The conductors 10056 then bend approximately 90 degrees outwards and then 90 degrees rearward to project through the flange 10058 and extend out the rear side thereof. In order to make contact with conductive surfaces 10062, 10064 of the earbud 10060, it is important, in this exemplary embodiment, for the conductors 10056 to protrude from the outer surface of the stud 10057. Any part or all of the portion of the conductors 10056 that extend along the exterior of the stud 10057 can be bent outwards to produce a bias that insures conductive connection to conductive interior surfaces 10062, 10064 of the earbud 10060.

The earbud 10060 is the part that provides electrostimulation from the generator to the ear canal. In an exemplary embodiment, a body 10066 of the earbud 10060 is made of silicone and, therefore, it is flexible and soft enough to place in a user's ear canal without discomfort. The earbud 10060 is envisioned to be disposable (although it can be reusable). The earbud 10060 has eight leaves or tines. The number of tines is not significant as long as a first portion of the outer surface of the earbud 10060 can conduct one part (positive/negative/ground) of the electrostimulation and another different second portion of the outer surface of the earbud 10060 insulated from the first portion can conduct the other part (negative/ground/positive) of the electrostimulation. In the embodiment where eight tines are present, an adjacent set of three of the tines conduct the first part of the signal and an adjacent set of three different tines conduct the other part of the signal, the two individual remaining tines separating and insulating the two sets of three. The earbud 10060 has an interior lumen 10068 that is sized to fit snugly but removably on the stud 10057 of the earbud core assembly 10050. Because the component inserted into an ear achieves the best fit if it is made of a conformal or malleable material, the electrode/s disposed on the tissue contact surface of the earbud 10060 is/are malleable as well across various surface area shapes and curvatures. Another characteristic of the electrode/s is that they are durable, do not functionally impair the earbud's ability to conform properly to the user's anatomy, and are pragmatic/efficient to manufacture. With these characteristics in mind, there are a number of different types of materials and processes that can be used.

In various exemplary embodiments of the electrodes, to minimize restriction of the malleability of the earbud, current supplied thereto is advantageously conducted through a conduit within the inner lumen, out the lumen at the apex of the earbud, and continuing onto the outer surface of the earbud where tissue contact is to occur. One exemplary process for manufacturing this conductive path is to mask off all areas that are to remain non-conductive and then to spray or dip the masked earbud into the conductive liquid. After curing or drying, the masking is removed, leaving only the conduit portion of the electrode/s in the inner lumen contiguous with the electrode/s on outside surface of the earbud.

Masking, as used herein, can be defined as coating the earbud on areas where the conductive liquid will not adhere and then rendering these areas non-conductive after the insert is sprayed, dipped, or silk screened, for example.

Another exemplary embodiment to provide conductivity to the electrode-tissue interface is by coating a portion of the interior lumen 10068 adjacent the first conductor 10056 and then extending that coating around the end of the lumen (to the right in FIG. 100) and onto the outer surface or tissue contact area of the patient coupler to form the one or more conductive surface 10062. These conductive tissue contact areas may have various configurations, geometries, surface areas, or branching. Similarly, a portion of the interior lumen 10068 adjacent the second conductor 10056 may be coated and this coating is extended around the end of the lumen and onto another location of the tissue contact area of the coupler that is not in contact with the other coating(s) to form the second conductive surface 10064.

One way to apply the conductive coating is with an adhesive tape manufactured by 3M, the tape having a conductive surface on one side and a silicone adhesive on the other, although other methods and devices are equally applicable as well. As used herein, the conductive coating may be conductive inks, liquids, gels, glues, powders, foils, tapes, curable liquids, metallic materials, or other conductive malleable materials (conforming non-conductive materials that have conductive elements "blended" in them during their original manufacturing process rendering them conductive). Thus, the word "coating" is to be broadly interpreted and not limited to only a single embodiment. Other ways to apply the conductive coating include, for example, spray coating, silk screening/screen printing, dip coating, and manual painting, with an understanding that the coating geometry is highly specific. Thus, depending on the configuration on which the coating is to be applied, consideration is given to the level of precision present during the application process. In addition to a viscous coating, thin conducting strips (such as aluminum foils) can be adhered to the earbud to create conducting paths that function as electrodes.

In this exemplary embodiment, there are two distinct areas of conductive coatings: one serving as positive and the other serving as ground, each of the coating trifurcating and covering an exterior portion of three tines for each current path. The location of the trifurcated portions of the conductive surfaces on the outer surface of the tines is positioned to be the location of the tissue contact areas. If two or more separate and electrically distinct coatings are used, they will be electrically insulated from each other by a separation or other insulating device.

The earbud itself can be manufactured by using at least two "halves" of a conductive malleable material (e.g., conductive silicone) with at least one insulation component that is made of the same material but without conductive properties. One exemplary form of this configuration is a sandwich with the two halves of the conductive material separated by a laminate of the insulating material, the insulating material approximating the flexibility or other key properties of the conductive (electrode) halves.

In one exemplary molding process for manufacturing the earbuds, cast aluminum or resin molds are created to the specifications of the earbud. Liquid material is injected into the mold and is allowed to set, after which the conductive elements are added externally in any of the herein mentioned ways, for example, by painting on a coating, by taping a negative image off and dipping the molded bud into conductive coating, or by physically applying conductive adhesive foil to the bud.

Figure 104:
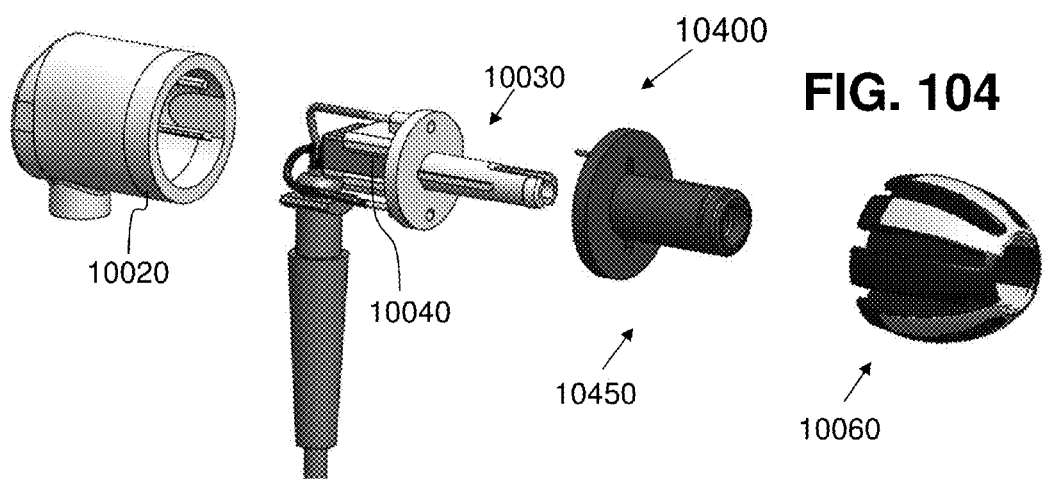
FIG. 104 is a fragmentary, exploded, perspective view of an exemplary embodiment of an earbud-type neurostimulator device with a multi-electrode flower-shaped electrode coupler.

FIG. 104 depicts a second exemplary embodiment of a stand-alone electrostimulation earbud 10400. The strain relief, speaker housing, speaker housing stud, speaker assembly, and ear bud are all similar to the embodiment of FIG. 100 and, therefore, will not be described in further detail as the descriptions herein are applicable to the instant embodiment. What is different is the earbud core assembly 10450. In the particular exemplary embodiment of FIGS. 104 to 107, the portion of the earbud core assembly 10450 that is different is how the electrostimulation conductors 10456 travel and are attached to the stud 10457 of the earbud core assembly 10450. With this one exception, all other attributes of the earbud core assembly 10450 are similar to the earbud core assembly 10050 and, therefore, are not repeated here.

The electrostimulation conductors 10456 in this exemplary embodiment are on opposing sides but they can be disposed at any two (or more) locations about the exterior surface of the earbud core assembly 10450. The conductors 10456 each project entirely through a flange 10458 of the earbud core assembly 10450 to form two rearward projecting extensions that can be inserted into respective ones of the bores 10033 when the earbud core assembly 10450 is clocked in the installation position. As described above, to provide this clocking, the interior surface of the central bore 10452 has at least one groove 10753 that extends from the rear side of the flange 10458. In contrast to the an open funnel shape necking down to a shape that exactly matches the exterior shape of the clocking ridges 10038, this groove 10753 has a shape substantially matching the groove 10438. Also, in FIGS. 104 to 107, there is only a single groove 10753, even though more are envisioned. The length that the clocking ridge 10438 extends away from the flange 10032 of the speaker housing stud 10030 is set so that the rearward projecting extensions of the conductors 10456 (e.g., bottom of FIG. 107) are prevented from coming into contact with the flange 10032 unless and until the clocking ridge 10438 is within the groove 10753 of the central bore 10452. In this way, the conductors 10456 automatically and assuredly enter the bores 10033 and make electrical contact with the leads 8118. The conductors 10456 are shown as round wires but they can be of any polygonal shape, including hexagonal, triangular, and square, for example.

Figure 105:
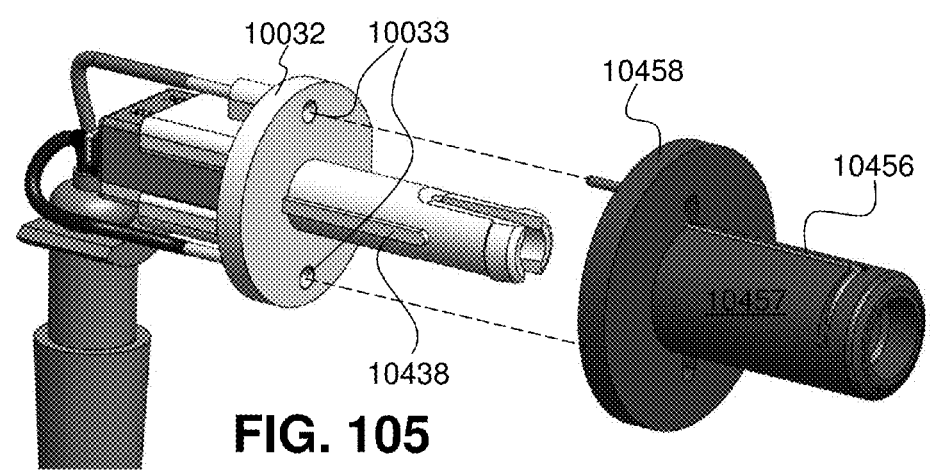
FIG. 105 is a fragmentary, enlarged, exploded, perspective view of portions of the earbud-type neurostimulator device of FIG. 104 including a strain relief, a speaker assembly, a speaker housing stud, and an earbud core assembly.
Figure 106:
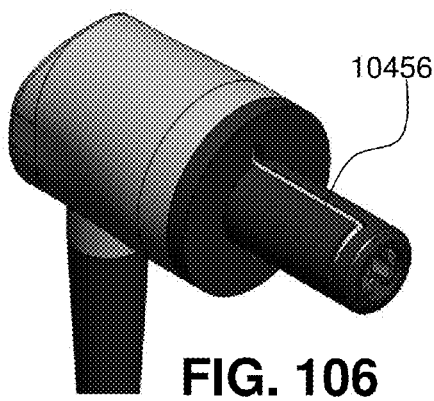
FIG. 106 is a fragmentary, enlarged, perspective view of the earbud-type neurostimulator device of FIG. 104 with the earbud core assembly installed on the speaker housing stud.
Figure 107:
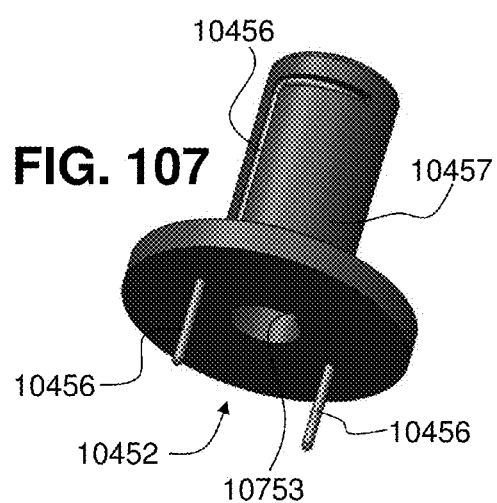
FIG. 107 is an enlarged, perspective view of the earbud core assembly of the earbud-type neurostimulator device of FIG. 104.

As shown especially in FIGS. 105 and 107, the conductors 10456 use their shape to remain fixed on the body of the earbud core assembly 10450. From the earbud side of the earbud core assembly 10450, the conductors 10456 reside in a circumferential groove within the central bore 10452 to have the core-assembly stud 10034 trap the conductors 10456 therein when the core assembly 10030 is installed within the earbud core assembly 10450. The conductors 10456 then radially pass outwards through the material of the stud 10457 to exit at the outer surface and travel circumferentially along a portion of the outside surface of the stud 10457. When transitioning from the interior of the stud 10457 to the exterior, the conductors 10456 can make a 180-degree bend or can make an S-like bend. The conductors 10456 then make a 90-degree bend away from the direction of the earbud 10060 and travel along a longitudinal length of the stud 10457 in a groove that keeps the conductors 10456 resting therein but still projecting out from the outer surface of the stud 10457. The conductors 10456 then bend approximately 90 degrees radially outwards and then 90 degrees rearward to project through the flange 10458 and extend out the rear side thereof. To make contact with conductive surfaces 10062, 10064 of the earbud 10060, it is important for the conductors 10456 to protrude from the outer surface of the stud 10457. In this regard, any part or all of the portion of the conductors 10456 that extend along the exterior of the stud 10457 can be bent outwards to produce a bias that insures conductive connection to conductive interior surfaces 10062, 10064 of the earbud 10060 or a portion can be made thicker in a radially outwards direction.

Figure 108:
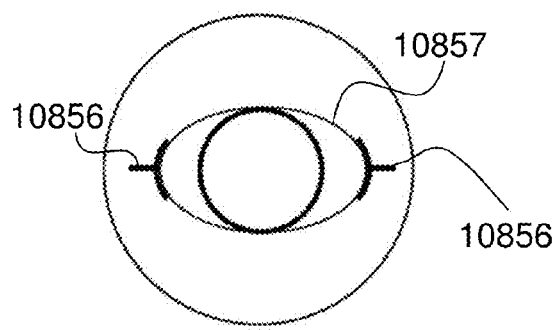
FIG. 108 is a top plan view of an exemplary embodiment of an electrode coupling subassembly for the multi-electrode coupler of FIG. 100.
Figure 110:
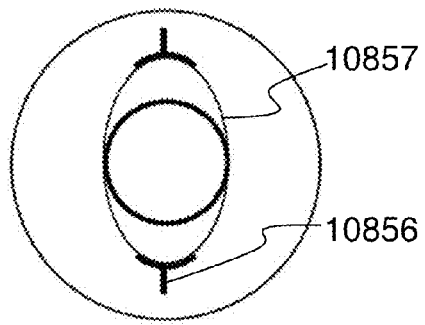
FIG. 110 is a top plan view of the electrode coupling subassembly of FIG. 124 rotated ninety degrees.
Figure 109:
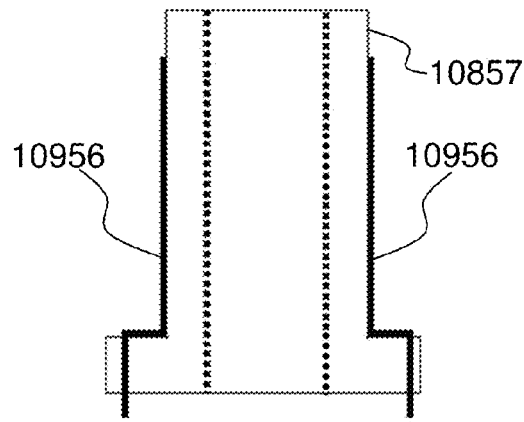
FIG. 109 is a side elevational view of the electrode coupling subassembly of FIG. 124 with a differently shaped conductor.
Figure 111:
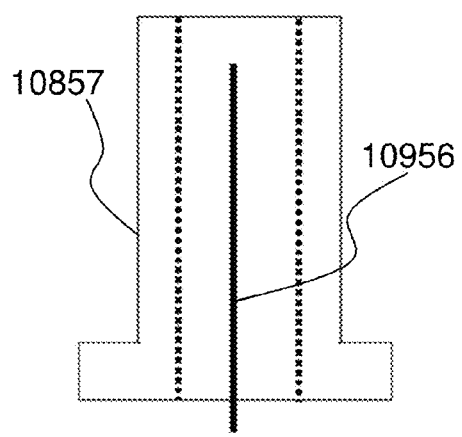
FIG. 111 is a side elevational view of the electrode coupling subassembly of FIG. 126 with the conductor of the subassembly of FIG. 109.
Figure 112:
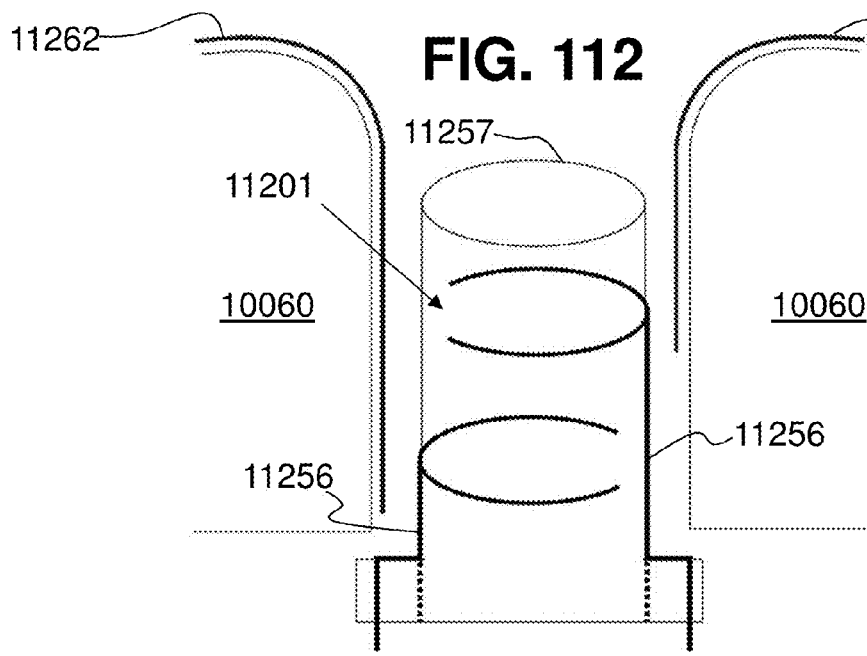
FIG. 112 is a partially cross-sectional, partially perspective view of an exemplary embodiment of an electrode coupling subassembly for the multi-electrode coupler of FIG. 100.

Other different embodiments for making electrical contact between the electrostimulation conductors and the electrostimulation leads 8118 are shown in FIGS. 108 to 112. In particular, FIGS. 108 to 111 illustrate an embodiment of an earbud core assembly 10850 that has a stud 10857 with an ovular exterior shape instead of circular. In this exemplary embodiment, it is the shape of the stud 10857 that provides the clocking feature, thereby making the clocking bosses/grooves unnecessary. In FIGS. 109 and 111, the conductors 10956 are wires having a polygonal shape. In contrast, FIGS. 108 and 110 show the conductors as being attached to the exterior and extending away from the surface of the stud 10857. Like the previous embodiments above, the embodiment of an earbud core assembly 11250 in FIG. 112 has a circular stud 11257. The conductors 11256, in contrast, have circumferential extents attached to the exterior of the stud 11257 at different longitudinal lengths along the circular stud 11257 that do not circumferentially overlap one another. Likewise, the interior conductive portions 11262, 11264 of the conducting sections 10062, 10064 of the earbud 10060 extend into the interior core of the earbud 10060 at different lengths so that there is only one orientation that successfully makes electrical contact. It is noted that this embodiment allows for a small range of clocking of the earbud core assembly 11250 to the earbud 10060, which range is defined and delimited by the size of the gap 11201 between each of the circumferential extents of the conductors 11256.

Figure 113:
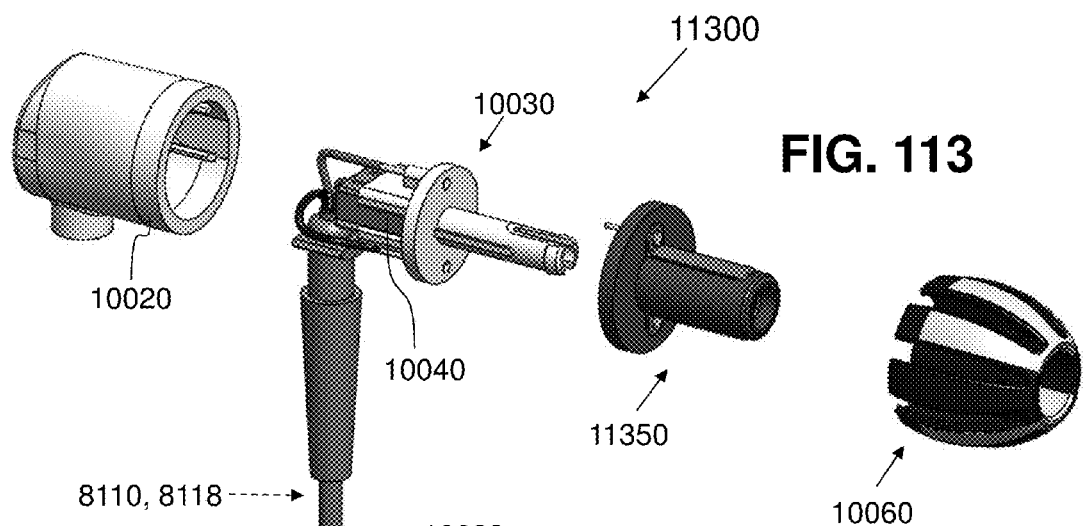
FIG. 113 is a fragmentary, exploded, perspective view of an exemplary embodiment of an earbud-type neurostimulator device with a multi-electrode flower-shaped electrode coupler.
Figure 114:
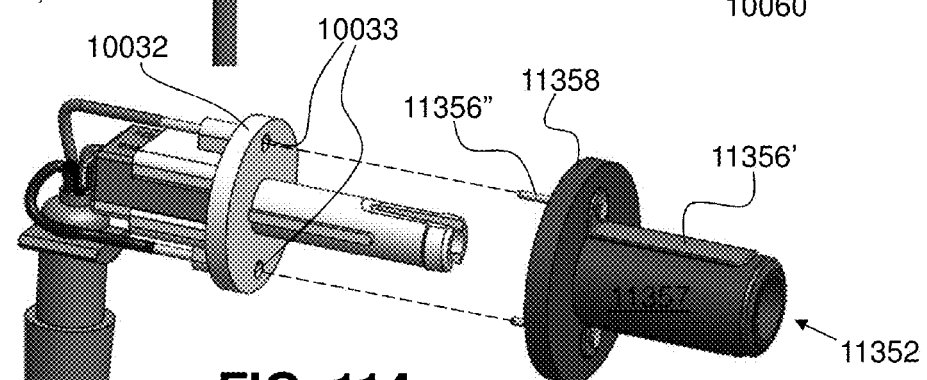
FIG. 114 is a fragmentary, enlarged, exploded, perspective view of portions of the earbud-type neurostimulator device of FIG. 113 including a strain relief, a speaker assembly, a speaker housing stud, and an earbud core assembly.
Figure 115:
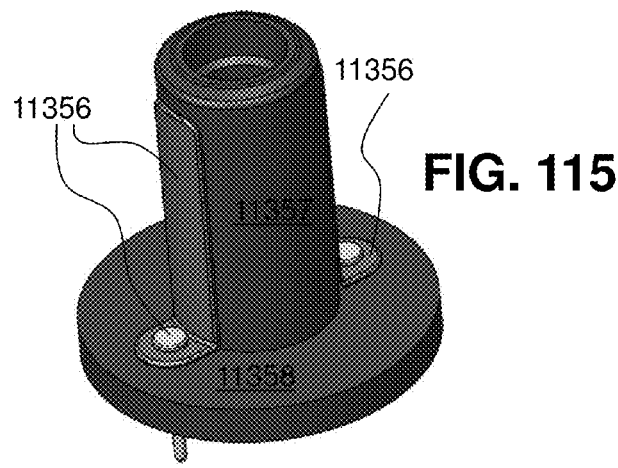
FIG. 115 is an enlarged, perspective view of the earbud core assembly of the earbud-type neurostimulator device of FIG. 113.

FIG. 113 depicts a third exemplary embodiment of a stand-alone electrostimulation earbud 11300. The strain relief, speaker housing, speaker housing stud, speaker assembly, and ear bud are all similar in this embodiment and, therefore, will not be described in further detail as the descriptions herein are applicable to the instant embodiment. What is different is the earbud core assembly 11350. In the particular exemplary embodiment of FIGS. 113 to 115, the portion of the earbud core assembly 11350 that is different is how the electro stimulation conductors 11356 travel and are attached to the stud 11357 of the earbud core assembly 11350. With this one exception, all other attributes of the earbud core assembly 11350 are similar to at least the earbud core assembly 10050 and, therefore, are not repeated here.

The electrostimulation conductors 11356 in this exemplary embodiment are on opposing sides but they can be disposed at any two (or more) locations about the exterior surface of the earbud core assembly 11350. Instead of a single conductor projecting entirely through the flange 11358 of the earbud core assembly 11350 to form the two rearward projecting extensions that can be inserted into respective ones of the bores 10033 when the earbud core assembly 10450 is clocked in the installation position, here, each conductor is formed from a set of two parts. A first part 11356' of each of the two-part conductors 11356 is surface conducting plate having a curved shape corresponding to the outer circumference of the stud 11357 and having a 90-degree bent portion that is shaped to abut the flange 11358. This bent portion has a throughbore that receives the second part 11356" of the conductor 11356, which is a pin or nail that pierces the throughbore and the flange 11358 to secure the first part to the earbud core assembly 11350. The ends of the pins are the conductive portions that enter the bores 10033 and make conductive contact for receiving the electrostimulation. As described herein, to provide clocking, the interior surface of the central bore 11352 has at least one groove that extends from the rear side of the flange 11358. As in other embodiments, the length that the clocking ridge 10438 extends away from the flange 10032 of the speaker housing stud 10030 is set so that the rearward projecting extensions of the conductors 11356 are prevented from coming into contact with the flange 10032 unless and until the clocking ridge 10438 is within the groove of the central bore 11352. In this way, the conductors 11356 automatically and assuredly enter the bores 10033 and make electrical contact with the leads 8118. The pins 11356" of the conductors 11356 are shown as round but they can be of any polygonal shape, including hexagonal, triangular, and square, for example.

The embodiments shown in FIGS. 100 to 107 and 113 to 115 house a rectangular shaped speaker assembly 10040. Another kind of speaker assembly is one that is coin-shaped, these structures are round and have diameters of between 8 mm and 16 mm. The following embodiments illustrate earbud-type neurostimulator devices that house such coin-shaped speaker assemblies. Some of the features that are present in these embodiments are substantially similar to ones in previous embodiments and, in such cases, will have the same or similar reference numerals. Other features may be similar but new reference numerals are used to identify the features in these embodiments. Such differences, however, does not mean that the features cannot be combined or exchanged with other similar features described above or below. Indeed, any feature of one embodiment can be and is considered to be interchangeable and/or combinable as one of ordinary skill in the art would make such changes or combinations.

Figure 116:
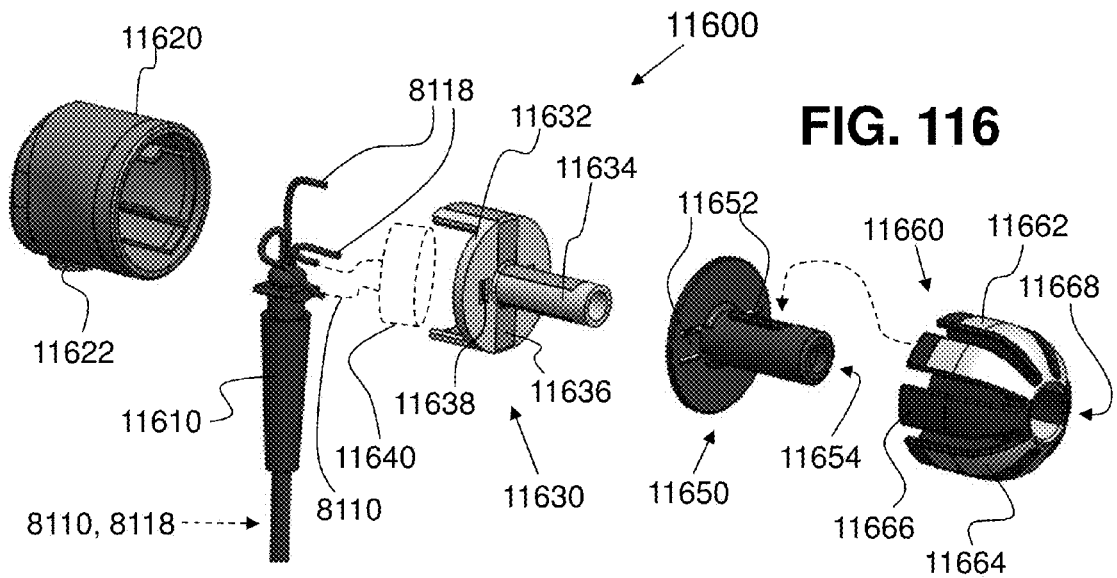
FIG. 116 is a fragmentary, exploded, perspective view of an exemplary embodiment of an earbud-type neurostimulator device with a multi-electrode flower-shaped electrode coupler.

FIG. 116 depicts a first exemplary embodiment of a stand-alone electrostimulation earbud 11600 for a coin-shaped speaker assembly. Starting from the bundle of electrical leads, including two 8110 for the speaker and two 8118 for the electrostimulation signal, a strain relief 11610 guides the leads into a speaker housing 11620 and is fixed within an entry port 11622. The speaker housing 11620 is semi-rigid and can be made of plastic, for example, ABS. The speaker housing 11620 can be 3D printed if desired and forms an encasement for a device that holds a speaker therein. In particular, an internal hollow of the speaker housing 11620 receives a portion of a speaker housing stud 11630, in which is held a speaker assembly 11640 (depicted with dashed lines). An overall length of the speaker housing stud 11630 is approximately 15 mm and an outer maximum diameter is about 13 mm. The exemplary embodiment of the speaker housing stud 11630 shown in FIG. 116 is shaped to hold a coin-shaped speaker assembly 11640 that is approximately 10 mm in diameter. Thus, the outer diameter of the speaker housing 11620 can be as little as about 12 mm but, here, is about 13 mm. The speaker leads 8110 (depicted with dashed lines) pass through the interior of the speaker housing 11620 and are electrically connected to the speaker assembly 11640. Connection of the electrostimulation leads 8118 will be explained below. Finally, the rear of the speaker housing 11620 can be shaped to provide a space for a decal or sticker printed with a trademark thereon or the space can form the logo itself, for example, by raised bosses or lowered channels.

When installed at the speaker housing 11620, the speaker housing stud 11630 has a flange 11632 that, together with the strain relief 11610 and the speaker assembly 11640, substantially seals off the interior of the speaker housing 11620 from the environment. At its rear side, the speaker housing stud 11630 has speaker arms 11633, best shown in FIG. 117, that securely holds the speaker assembly 11640 therebetween. At its front or earbud side, the speaker housing stud 11630 has a core-assembly stud 11634. The speaker housing stud 11630 has various features. First, sound from the speaker assembly 11640 needs to be communicated to the user. In the particular exemplary embodiment of FIGS. 116 to 118, the interior hollow of the core-assembly stud 11634 forms a sound channel that communicates sound from the speaker assembly 11640 to the user's inner ear. A second feature holds an earbud core assembly 11650 to the speaker housing stud 11630 when the earbud core assembly 11650 is connected thereto. In the particular exemplary embodiment of FIGS. 116 to 118, the flange 11632 of the speaker housing stud 11630 has two windows 11638 that removably receive tabs 11652 therein when the earbud core assembly 11650 is installed on the core-assembly stud 11634. These windows 11638 clock the earbud core assembly 11650 to a pre-set installation orientation. In the particular exemplary embodiment of FIGS. 116 to 118, there are two windows 11638 but there can be any number of windows 11638 and tabs 11652, for example, from one to five. This clocking feature will be described in further detail below.

Figure 117:
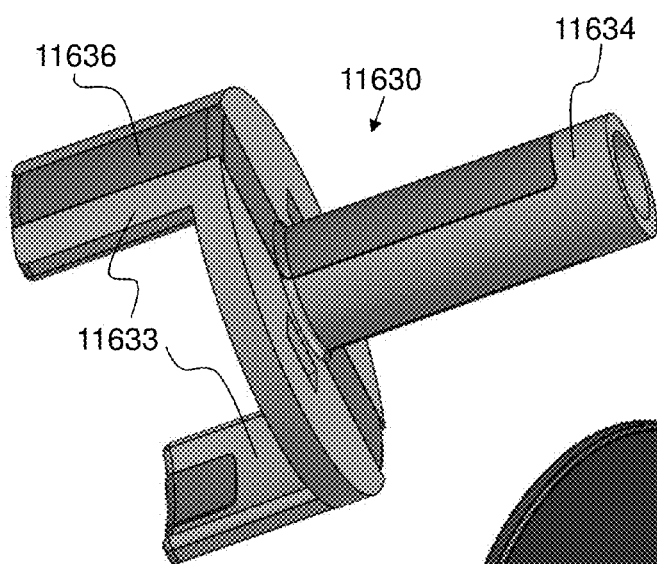
FIG. 117 is a fragmentary, enlarged, perspective view of a speaker housing stud of the earbud-type neurostimulator device of FIG. 116.
Figure 118:
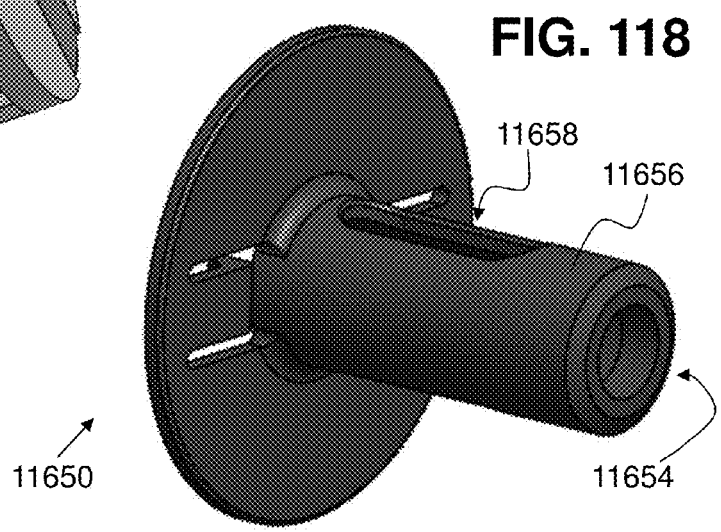
FIG. 118 is an enlarged, perspective view of an earbud core assembly of the earbud-type neurostimulator device of FIG. 116.

The speaker housing stud 11630 has two electrical contacts that provide an electrical conduit for electrostimulation arriving through the electrostimulation leads 8118. As explained in the embodiments herein, this conduit can take various forms. One exemplary configuration for the electrostimulation leads 8118 shown in FIGS. 116 to 118 is a set of electrically conductive strips 11636 each respectively extending from one of the arms 11633 on the speaker housing (or rear) side of the flange 11632. Each lead 8118 is connected to a strip 11636 at the rear side of the flange 11632 in any way, for example, by soldering. Each strip 11636 extends towards the earbud 11660 on the outer surface of the arm 11633, across the flange 11632, inwardly to the core-assembly stud 11634, and then along the outer surface of the core-assembly stud 11634 to a given extent sufficient to oppose a window on the earbud core assembly 11650 that is described in further detail below. The strips 11636 can be attached to the speaker housing stud 11630 in a variety of ways, some of which are described herein. They can be attached using an adhesive. They can be a liquid that is painted on the surface. The strips 11636 can be formed in the same manufacturing process that creates the speaker housing stud 11630 itself. To make contact with conductive surfaces 11662, 11664 of the earbud 11660, the conductive strips 11636 can be made to protrude from the outer surface of the earbud core stud 11634. In this regard, any part or all of the portion of the conductive strips 11636 that extend along the exterior of the earbud core stud 11634 can be bent outward or produced thicker to insure conductive connection to conductive interior surfaces 11662, 11664 of the earbud 11660.

The earbud core assembly 11650 is semi-rigid and can be made of plastic, for example, ABS. The earbud core assembly 11650 can be 3D printed if desired and forms the structural support for the earbud 11660. The earbud core assembly 11650 also possesses various features. First, the earbud core stud 11656 has a central bore 11654 that receives the core-assembly stud 11634 therein. The two studs are sized to not have the distal end of the core-assembly stud 11634 protrude from the distal end of the earbud core assembly 11650; although, if desired, the distal end can protrude therefrom. It is noted that the earbud 11660 is envisioned to be a disposable part and, therefore, must be replaced (although it can be reusable). Thus, it must be able to be removed from either or both of the speaker housing stud 11630 and the earbud core assembly 11650. If desired, the earbud core assembly 11650 can also be disposed with the earbud 11660 or it can be retained for use with a replacement earbud 11660.

The earbud core assembly 11650 does not possess any part of the electrostimulation conductors. Instead, in this exemplary embodiment, the earbud core stud 11656 provides windows that, allow conductive bosses (e.g., 16301, 16501) on the earbud 11660 to pass therethrough and electrically contact the conductive strips 11636. In this exemplary embodiment, the windows 11658 are on opposing sides (only one is visible in FIGS. 116 and 118) but they can be disposed at any two (or more) locations about the exterior surface of the earbud core stud 11634.

The earbud 11660 is the part that provides electro stimulation from the generator to the ear canal. In an exemplary embodiment, a body 11666 of the earbud 11660 is made of silicone and, therefore, it is flexible and soft enough to place in a user's ear canal without discomfort. The earbud 11660 is envisioned to be disposable (although it can be reusable). The earbud 11660 has eight leaves or tines. The number of tines is not significant as long as a first portion of the outer surface of the earbud 11660 can conduct one part (positive/negative/ground) of the electrostimulation and another different second portion of the outer surface of the earbud 11660 insulated from the first portion can conduct the other part (negative/ground/positive) of the electrostimulation. In the embodiment where eight tines are present, an adjacent set of three of the tines conduct the first part of the signal and an adjacent set of three different tines conduct the other part of the signal, the two individual remaining tines separating and insulating the two sets of three. The earbud 11660 has an interior lumen 11668 that is sized to fit snugly but removably on the earbud core stud 11656 of the earbud core assembly 10050 and two opposing earbud bosses (e.g., 16301, 16501) extend radially inwards from the surface of the interior lumen 11668 to project into and through the windows 11658 and directly contact an outer conductive surface of a respective one of the strips 11636. The bosses (e.g., 16301, 16501) can be of substantially the same shape as the windows 11658 or they can be smaller.

Conductivity of the tines is provided by coating one of the bosses (e.g., 16301, 16501) and a portion of the interior lumen 11668 with a conductive material and extending that coating around the end of the lumen (to the right in FIG. 116) and onto, for example, the first set of three tines to form the first conductive surface 11662. Similarly, the other of the bosses (e.g., 16301, 16501) and a portion of the interior lumen 11668 adjacent the other boss (e.g., 16301, 16501) is conductively coated and the coating is extended around the end of the lumen and onto, for example, the second set of three tines to form the second conductive surface 11664. One way to apply this coating is with an adhesive tape manufactured by 3M, the tape having a conductive surface on one side and a silicone adhesive on the other, although other methods and devices, some of which are mentioned herein, are equally applicable as well. A depth of the interstices between tines can be, for example, between approximately 1 and 4 mm.

With such a configuration, the windows 11658 of the earbud core stud 11656 provide both clocking and securing features for the earbud 11660 to insure that the earbud is fixed for use as well as making electrical contact with the strips 11636. In this way, the conductive bosses (e.g., 16301, 16501) on the earbud 11660 automatically and assuredly enter the windows 11658 and make electrical contact with the leads 8118.

Figure 119:
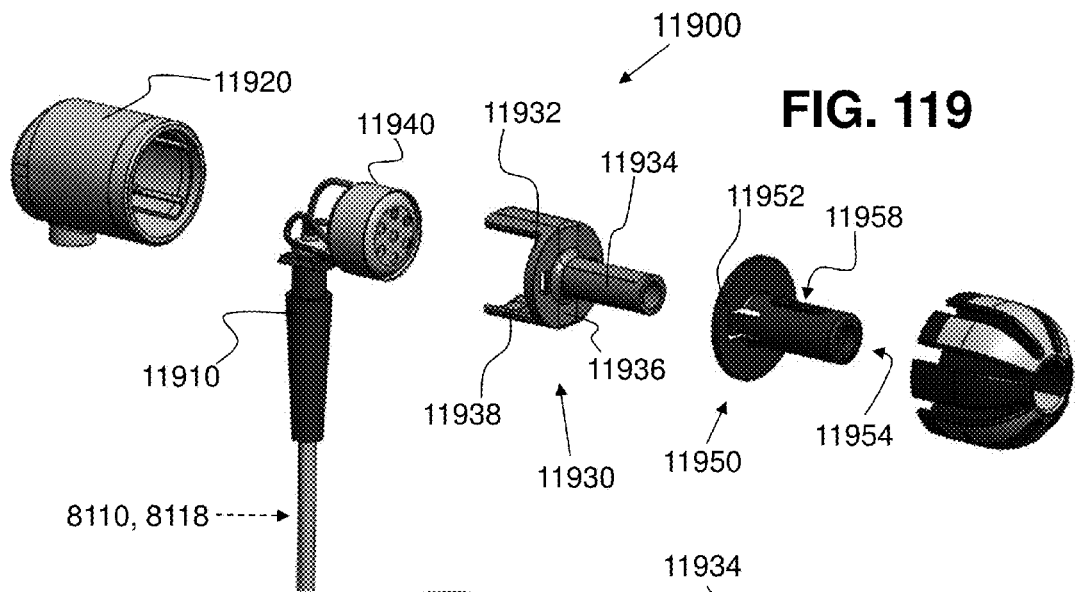
Figure 122:
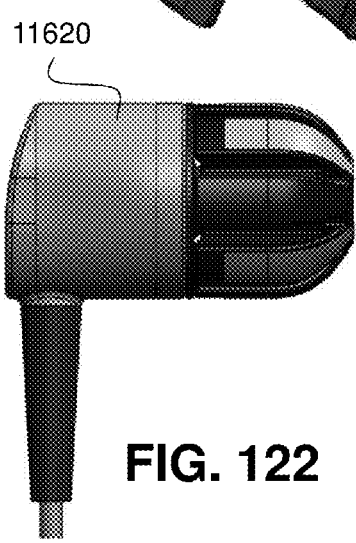
Figure 123:
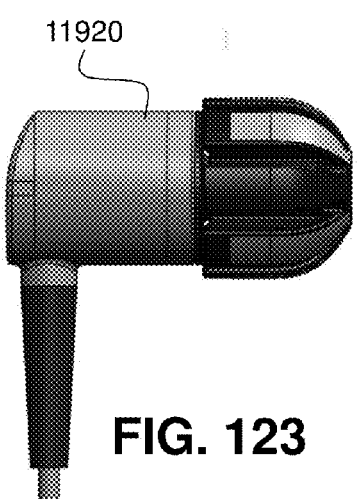

FIG. 119 depicts a second exemplary embodiment of a stand-alone electrostimulation earbud 11900 for a coin-shaped speaker assembly. The strain relief, speaker housing, speaker assembly, and ear bud are all similar to the embodiment of FIG. 116 and, therefore, will not be described in further detail as the descriptions herein are applicable to the instant embodiment. What is different is the speaker housing stud 11930 and the earbud core assembly 11950 (and the speaker housing 11920 is slightly smaller). In the particular exemplary embodiment of FIGS. 119 to 121, the speaker housing stud 11930 is sized for an 8 mm coin-shaped speaker assembly 11940. The speaker housing stud 11930 can be made of ABS, for example, and has an overall length of approximately 15 mm and an outer maximum diameter of about 11.5 mm, thus, as compared to the embodiment of FIG. 116, the speaker housing 11920 can be made smaller, as shown in the comparison of FIGS. 122 and 123, where the embodiment of FIG. 116 is shown in FIG. 122 and the embodiment of FIG. 119 is shown in FIG. 123. With these differences, other attributes of the speaker housing stud 11930 are similar to at least the speaker housing stud 11630 and other attributes of the earbud core assembly 11950 are similar to at least the earbud core assembly 11650 and, therefore, they are not repeated here.

Figures 120, 121:
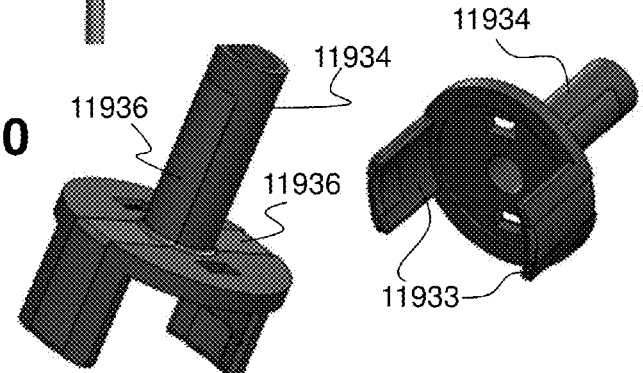

When installed at the speaker housing 11920, the speaker housing stud 11930 has a flange 11932 that, together with the strain relief 11910 and the speaker assembly 11940, substantially seals off the interior of the speaker housing 11920 from the environment. At its rear side, the speaker housing stud 11930 has speaker arms 11933 (see also FIGS. 120 and 121) that securely hold the speaker assembly 11940 therebetween. At its front or earbud side, the speaker housing stud 11930 has a core-assembly stud 11934 with an interior hollow forming the sound channel that communicates sound from the speaker assembly 11940 to the user's inner ear. The speaker housing stud 11930 has two electrical contacts that provide an electrical conduit for electrostimulation arriving through the electrostimulation leads 8118. One exemplary configuration for the electrostimulation leads 8118 shown in FIGS. 119 to 121 is a set of electrically conductive strips 11936 each respectively extending from one of the arms 11933 on the speaker housing (or rear) side of the flange 11932. Each lead 8118 is connected to a strip 11936 at the rear side of the flange 11932. Each strip 11936 extends towards the earbud 11960 on the outer surface of the arm 11933, across the flange 11932, inwardly to the core-assembly stud 11934, and then along the outer surface of the core-assembly stud 11934 to a given extent sufficient to oppose the window 11958 on the earbud core assembly 11950. The earbud core assembly 11950 has an earbud core stud 11956 with a central bore 11954 that receives the core-assembly stud 11934 therein.

FIG. 124 depicts a third exemplary embodiment of a stand-alone electrostimulation earbud 12400 for a coin-shaped speaker assembly. As compared to other exemplary embodiments, here, the earbud core assembly has been eliminated. In particular, starting from the bundle of electrical leads, including two 8110 for the speaker and two 8118 for the electrostimulation signal, a strain relief 12410 guides the leads into a speaker housing 12420 and is fixed within an entry port 12422. The speaker housing 12420 is semi-rigid and can be made of plastic, for example, ABS. The speaker housing 12420 can be 3D printed if desired and forms an encasement for a device that holds a speaker therein. In particular, an internal hollow of the speaker housing 12420 receives a portion of a speaker housing stud 12430, in which is held a speaker assembly 12440. An overall length of the speaker housing stud 11630 is approximately 15 mm. The exemplary embodiment of the speaker housing stud 12430 shown in FIG. 124 is shaped to hold a coin-shaped speaker assembly 12440 that is approximately 8 mm in diameter. Thus, the outer diameter of the speaker housing 12420 can be as little as about 11.5 mm. The speaker leads 8110 pass through the interior of the speaker housing 12420 and are electrically connected to the speaker assembly 12440. Connection of the electrostimulation leads 8118 will be explained below. Finally, the rear of the speaker housing 12420 can be shaped to provide a space for a decal or sticker printed with a trademark thereon or the space can form the logo itself, for example, by raised bosses or lowered channels.

When installed at the speaker housing 12420, the speaker housing stud 12430 has a flange 12432 that, together with the strain relief 1410 and the speaker assembly 12440, substantially seals off the interior of the speaker housing 12420 from the environment, which is shown in FIG. 125. At its rear side, the speaker housing stud 12430 has speaker arms 12433, best shown in FIG. 126, that securely hold the speaker assembly 12440 therebetween, while also providing a surface for the conductive material that passes the electrostimulation signal from the wire to the earbuds, as will be described below. At its front or earbud side, the speaker housing stud 12430 has a earbud stud 12434. The speaker housing stud 12430 has various features. First, sound from the speaker assembly 12440 needs to be communicated to the user. In the particular exemplary embodiment of FIGS. 124 to 129, the interior hollow of the earbud stud 12434 forms a sound channel 12435 that communicates sound from the speaker assembly 12440 to the user's inner ear. A second feature holds an earbud 12460 to the speaker housing stud 12430 when the earbud 12460 is connected thereto. In the particular exemplary embodiment of FIGS. 124 to 129, the earbud stud 12434 has two windows 12438 that removably receive bosses (e.g., 16301, 16501) therein when the earbud 12460 is installed on the earbud stud 12434. These windows 12438, therefore, clock the earbud 12460 to a pre-set installation orientation and, at the same time, provide electrical contact between the leads 8118 and the external conductive surfaces 12462, 12464 of the earbud 12460. In the particular exemplary embodiment of FIGS. 124 to 129, there are two windows 12438 but there can be any number of windows 12438. This clocking feature will be described in further detail below.

The speaker housing stud 12430 has two electrical contacts that provide an electrical conduit for electrostimulation arriving through the electrostimulation leads 8118. As will be explained in the embodiments herein, this conduit can take various forms. One exemplary configuration for the electrostimulation leads 8118 shown in FIGS. 124 to 129 is a set of electrically conductive strips 12436 each respectively extending from one of the arms 12433 on the speaker housing (or rear) side of the flange 12432. These strips are shown separated from the speaker housing stud 12430 in FIG. 129. Each lead 8118 is connected to a strip 12436 at the rear side of the flange 12432 in any way, for example, by soldering. Each strip 12436 starts extending in a direction orthogonal to the arms 12433 at the speaker housing side thereof and then bends 90 degrees to travel along the longitudinal length of the arm 12433 on the exterior surface thereof. At the earbud side of the flange 12432, the strip 12436 bends radially inwards and travels along the side of the flange 12432 until another 90 degree bend has the strip 12436 travel along the exterior surface of the earbud stud 12434. To assist in securing the strip 12436 at the speaker housing stud 12430, the earbud stud 12434 is provided with ports 12437 extending from the interior channel 12435 through to the environment into which distal tips of the strip 12436 extend to rest against the interior surface of the channel 12435 (see FIGS. 127 and 128). In this regard, the distal tip of the strip 12436 forms an S-bend as shown in FIG. 129. The channel 12435 of the earbud stud is formed with cavities in which rest respective distal tips of the strips 12436 when the strips 12436 are installed, these cavities being shown best in the right side of FIG. 126.

These strips 12436 extend along the outer surface of the earbud stud 12434 to a given extent sufficient to connect conductive surfaces on the inner lumen of the earbud 12460. The strips can be attached to the speaker housing stud 12430 in a variety of ways. They can be attached using an adhesive and/or the form of the strips 12436 can provide all of the retaining force. To make contact with conductive surfaces 12462, 12464 of the earbud 12460, the conductive strips 12436 can be made to protrude from the outer surface of the earbud stud 12434. In this regard, any part or all of the portion of the conductive strips 12436 that extend along the exterior of the earbud stud 12434 can be bent outward or produced thicker to insure conductive connection to conductive interior surfaces 12462, 12464 of the earbud 12460.

Significant in this exemplary embodiment is that there is no earbud core assembly, thereby eliminating an entire part; the earbud 12460 directly connects to the earbud stud 12434.

The earbud 12460 is the part that provides electrostimulation from the generator to the ear canal. In an exemplary embodiment, the main body of the earbud 12460 is made of silicone or similar pressure-deformable plastics, rubbers, or polymers, and, therefore, it is flexible and soft enough to place in a user's ear canal without discomfort. The earbud 12460 may be disposable or reusable. In this exemplary embodiment, the earbud 12460 has no tines or any elements of the outer surface that are mechanically isolated or independent from each other, but have a contiguous outer surface and formed as a portion of a prolate spheroid with a central bore 12668. As such, two portions 12462, 12464 of the outer surface of the earbud 12460 are electrically conductive and intervening portions 12466 electrically insulate the two portions 12462, 12464 from one another. The number of electrically independent conductive portions is not significant as long as a first portion of the outer surface of the earbud 12460 can conduct one part (positive/negative/ground) of the electrostimulation and another different second portion of the outer surface of the earbud 12460 insulated from the first portion can conduct the other part (negative/ground/positive) of the electrostimulation. As such any form or shape of the portions 12462, 12464 is possible, such as FIGS. 83 to 90. For example, each tine can have its own electrostimulation signal that is independent from other signals going to other tines, each of which is its own independent electrostimulation circuit and one tine can be a common ground or ground can be placed on another portion of the user's skin that has sufficient conductivity. Alternatively, each of these independent electrostimulation circuits can have their own unique ground to form separate electrostimulation sets on a single earbud.

In yet other embodiments, the earbud has only one conductive element, with the other (negative/ground)

located anywhere else on the body as long at the contact area has sufficiently low resistance for conduction to occur. The earbud 12460 has an interior lumen 12468 that is sized to fit snugly but removably on the earbud stud 12434 and possesses two opposing earbud bosses (e.g., 16301, 16501) extending radially inwards from the surface of the interior lumen 12468 to project into and through the windows 12438 and directly contact an outer surface of a respective one of the strips 12436. The bosses (e.g., 16301, 16501) can be of substantially the same shape as the windows 12438 or they can be smaller. Such a connection retains the earbud 12460 on the earbud stud 12434 until replacement is required.

As consistent, predictable, reliable, comfortable, and secure electrode contact to the skin is important for reliable and reproducible results across varying ear anatomies, exemplary embodiments of the earbud herein contain independent, substantially mechanically isolated or partially mechanically isolated projections or "tines" with sufficiently broad surfaces that extend outward circumferentially to form an outer contact surface that is substantially parallel to the body surface targeted for electrode contact. In these embodiments, the targeted surface is the ear, and more specifically, the ear canal. Having separate tines with electrode surfaces along the outer contact surface allows for independent contact of small portions of the full ear canal-earbud contact area to accommodate to a smaller, less variable portions of the ear canal. Furthermore, each tine is substantially mechanically isolated from the others so that an ear canal that is not circular (or an ear canal with surface irregularities or inconsistencies in certain areas) will not affect the other tines and will maximize the chance of proper, individual tine contact to smaller, more discreet segments of the ear canal. Although each individual tine contacts less surface area of the ear canal, having multiple tines allows for a desired surface area to be contacted by the electrode surfaces. Tines that are in contact with ear canal surface irregularities have a greater chance of making contact to that area because that tine, or tines, can independently adjust to best accommodate contact at that discreet and focal location. In summary, dividing up the outer, radially dispersed contact areas of the earbud into individual, substantially mechanically independent segments, allows the outer perimeter of the earbud to accommodate and replicate the non-circular and variable nature of ear canal anatomy and, thus, have better and more complete contact with the inner surfaces of the ear canal. Furthermore, tines that do not contain electrodes will allow for better retention forces to best resist movement of the earbud and or dislodgement. Conductivity of the tine portions is provided by coating one of the bosses (e.g., 16301, 16501) and a portion of the interior lumen 12468 distally with a conductive material and extending that coating around the end of the lumen (to the right in FIG. 124) and onto a first electrode area to form the first conductive surface 12462. Similarly, the other of the bosses (e.g., 16301, 16501) and a portion of the interior lumen 12468 adjacent the other boss (e.g., 16301, 16501) is coated and extended around the end of the lumen and onto the second electrode area to form the second conductive surface 12464. One way to apply this coating is with an adhesive tape manufactured by 3M, the tape having a conductive surface on one side and a silicone adhesive on the other, although other methods, conductive materials, and devices are equally applicable as well, some of which have been described herein.

With such configuration, the windows 12438 of the earbud stud 12434 provide both clocking and securing features for the earbud 12460 to insure that the earbud is fixed for use as well as making electrical contact with the strips 12436. In this way, the conductive bosses on the earbud 12460 automatically and assuredly enter the windows 12438 and make electrical contact with the leads 8118 and do not have any chance of damaging the conductive connection between the earbud 12460 and the strips 12436.

FIGS. 130 and 131 diagrammatically illustrate a fourth exemplary embodiment of a stand-alone electrostimulation earbud 13000 for a coin-shaped speaker assembly. Depicted is the speaker assembly 13040, the speaker housing stud 13030 with arms 13033, the earbud core assembly 13050, and the conductive strips 13036. In this embodiment, the two conductive strips 13036 connecting to the leads 8118 for the electrostimulation extend out from windows 13058 of the earbud core stud 13056 of the earbud core assembly 13050 instead of just residing at the bottom of the windows 11658, as depicted in FIG. 116, for example. In all other respects, this configuration is similar to at least the configuration of FIGS. 116 to 118 and, therefore, explanation of the other items is not repeated here.

FIGS. 132 to 135 diagrammatically illustrate a fifth exemplary embodiment of a stand-alone electrostimulation earbud 13200 for a coin-shaped speaker assembly 13240. Depicted is the speaker assembly 13240, the speaker housing stud 13230 with arms 13233, and the conductive wires 13236. In this embodiment, the two conductive wires 13236 connecting to the leads 8118 for the electrostimulation extend to a conductive coating of the earbud 13260 instead of to the speaker housing stud 13230. Significantly, this embodiment does not require an earbud core assembly and, in contrast to other embodiments, the conducting path of the strips 13236 do not contact the earbud stud 13234. Instead, a conducting wire simply passes around the flange 13232 and connects to a conductive part 12361 within the earbud 13260 (e.g., within one of the tines), which, in turn, is conductively connected to a conductive area 13262 on the outside of the earbud 13260. This configuration helps retain the earbud 13260 in place and avoids having to make any part of the inner lumen of the earbud 13260 conductive, which could be difficult, complicated, and/or time-consuming. In all other respects, this configuration is similar to other described configurations herein and, therefore, explanation of other features is not repeated here.

The signal generation and transmission architecture for the electrostimulation is not limited to one possible configuration. A first exemplary architecture 13600 is described with regard to FIG. 136. In this first configuration, signal generation and electrode control resides in a first location/device and electrostimulation signal delivery and optional sensing resides in a separate location/device. The two locations being electrically connected by at least one transmission conduit 13610. The generator 13601 contains a power supply 13620, a power switch 13630, user inputs 13640, a controller or control logic 13650, user I/O devices 13660, and an electrostimulation drive circuit 13670. The controller/control logic 13650 is supplied with power through the power supply 13620 and is controlled through the power switch 13630. The power supply 13620 contains any combination of a non-rechargeable battery (such as a 9V), a rechargeable battery, a charging circuit, and/or a parasitic power input system. The power switch 13630 contains any combination of a physical switch, a biometric switch, and a sequence of use action (i.e., connecting a device coupler to an external power source turns on the generator 13601).

User input 13640 or I/O devices 13660 provide the interface between the user and the controller 13650 and are connected to the controller 13650, provide the controller 13650 with user input, and provide the user with feedback in the form of various types of information. The I/O devices 13660 give the user the ability to set parameters such as, but not limited to, amplitude of electrostimulation. The I/O devices 13660 include, for example, a scroll wheel, a collection of buttons, lights (e.g., LED), a speaker(s), and/or a display (e.g., LCD, LED). Sensors 13680, which are optional, can include a heart rate monitor, a physiologic feedback device, or any other system that gives information to a user. The I/O devices 13660 can display to the user a status of the generator 13601, settings of the device, and other information.

The controller 13650 controls the drive circuit 13670, which, in turn, provides the electrodes 13690 with neurostimulation through the at least one transmission conduit 13610. The controller 13650 receives input from the user and the sensor(s) 13680 in the device coupler 13602 and outputs stimulation parameters to the drive circuit 13670. The drive circuit 13670 converts signals from the controller 13650 into electrostimulation at a desired/required power/frequency/amplitude level. The drive circuit 13670 can include a pulse circuit and provide a voltage step-up, for example.

The sensor(s) 13680 of the device coupler 13602 allows for closed loop stimulation control and provides control for a user feedback system. The sensors 13680 or sensor system(s) communicate information to control logic 13650 to maintain a closed loop control on a desired stimulation signal. The sensors 13680 can be isolated sensors or part of the electrodes 13690. Impedance, temperature, electrode separation, tissue $O_2$ concentration, physiologic sensing, capacitance, EEG, heart rate, and perspiration level are among the possible exemplary sensor inputs.

The transmission conduit 13610 in an exemplary embodiment is a wired connection between the generator 13601 and the device coupler 13602. As used in the exemplary architectures described herein, however, electrical connection by the transmission conduit(s) 13610 can be wired, wireless, or both. The transmission conduit 13610 is able to handle a higher potential difference than only a logic voltage. It is either integrated or is detachable.

The device coupler 13602 contains the electrodes 13690, the sensors 13680, or both. The electrodes 13690 provide the conductive points that contact an electrostimulation area for use of the device.

A second exemplary architecture 13700 is described with regard to FIG. 137. In this second configuration, the system is fully integrated with signal generation, electrode control, and signal delivery and sensing residing in a single location/device. For example, the system can be akin to an over-the-ear hearing aid. All of the features of FIG. 136 are equally applicable to this configuration and, therefore, they are not repeated. In this exemplary architecture, the generator/controller/coupler 13700 contains each of the power supply 13620, the controller/control logic 13650, the drive circuit 13670, provides the options for user input 13640, provides user feedback 13660, and has the power switch 13630, the sensors 13680 (if any), and the electrodes 13690.

A third exemplary architecture 13800 is described with regard to FIG. 138. In this third configuration, the system integrates the generator and device coupler into a personal smart device (PSD) application to be implemented by a PSD (e.g., a smart phone, a smart watch, a tablet, a laptop computer, a desktop computer). The generator and controller, therefore, can mostly be formed from software. The PSD application can, in an exemplary embodiment, integrate the neuromodulation device stimulation with onboard audio of the PSD (which can include music, white noise, an audio book, auditory pre-set patterns, or any other desired sounds). All of the features of FIGS. 136 and 137 that are equally applicable to this configuration are not repeated.

The PSD provides all of the user input 13640, the processing 13650, the user feedback 13660, and other capabilities and allows all of the PSD's features to be used as well and in conjunction with the PSD. The Generator-and-Device Coupler (GDC) converts signals from the controller 13650 (e.g., PSD) to stimulation at a desired/required power level. In this configuration, therefore, the communications conduit 13610 is a logic level connection between the PSD and the GDC. The conduit 13610 can be wired (fixed or detachable) or wireless (TX/RX needed on PSD and GDC) using proprietary systems or standards such as Bluetooth, Wi-Fi, and RF, for example. The user input 13640 can be input methods provided by the PSD or input methods otherwise integrated into the system, and the user feedback 13660 can be provided by the PSD or otherwise integrated into the system. As the power requirements for electrostimulation are higher than most hand-held PSDs can provide reasonably, it can be beneficial to provide, at the device coupler, all of the electrostimulation circuitry, including the power supply 13620, the power switch 13630, and the drive circuit 13670, in addition to the electrodes 13690 and sensors 13680 (if any). In other embodiments, the device is made up of a power supply or a connection to accommodate a power supply (if the device uses power from another device or source), a wireless receiver enabling the device to receive and transmit data from a PSD, a generator that can be directed by the PSD through an app to generate a custom signal that has a specific therapeutic benefit, and a patient coupler to deliver the electrical signal to the user. The generator has the ability to interpret the signal instructions from the PSD and the app to direct the generator to deliver a specific wavelength, pulse width, wave shape, amplitude, and amplitude modulation pattern as specifically directed. As research continues and the understanding of neuromodulation progresses, new and unique electrical signals may be discovered to expand uses and effects on the brain and body of the user of this technology. This embodiment, therefore, allows the user to have a device with its own power supply (that has or does not have embedded neuromodulation signal algorithms in its memory) and can be used to generate a customized therapeutic signal that is directed from an app contained within a PSD. Because such apps are ubiquitous when it comes to signal output, the app is able to be updated with new and unique instructions that direct the generator to deliver signals exactly as proscribed by the app and the PSD. In the simplest form of this embodiment, the device is made up of two wireless, self-contained earbuds, each individually containing its own power source. One or both of the earbuds contains a patient coupler with associated electrodes, as well as a pulse generator and a wireless receiver that receives information from a PSD to deliver a custom signal or the signal can be synchronized to a sound source that can originate from the same PSD, from another PSD, or from ambient sound or music. The PSD contains an app that serves as the user interface as well as a source of various electromodulation algorithms that direct the generator to produce the form of the electrical signal desired.

A fourth exemplary architecture 13900 is described with regard to FIG. 139. In this fourth configuration, the system is similar to the first exemplary architecture 13600 in FIG. 136, but adds an integrated audio synchronization capability. Included in this architecture 13900 is an audio source 13902 and a communications conduit 13904 that supplies audio signals to audio logic 13906 within the generator and controller. The audio logic 13906 controls signals conveyed through the conduit 13904 to a speaker 13908 within the device coupler (e.g., speaker assembly 10040, 11640, 11940, 12440, 13040). Any audio source is possible, including such devices as a PSD, a cellphone, an MP3 player, a car stereo, a microphone, and/or an audio input from a person on a stage or in a sound booth. The audio conduit 13904 can be a wired or wireless connection (e.g., Wi-Fi, Bluetooth, or other methods). No conduit is needed if the audio source is directly received by the device, for example, where a built-in microphone is present (e.g., as part of the audio logic 13906). The audio logic 13906 receives an audio input signal and processes the signal into a form the control logic 13650 can utilize. The audio logic 13906 and/or the control logic 13650 also provide output to an optional speaker 13908, which translates the signal from the audio logic 13906 into audible sound that is provided in conjunction with electrostimulation. An exemplary embodiment of interfaceable electrostimulation device (I-Estim) may have its own user interface 13640/13660 and/or can be overridden or augmented by interfacing it with a smartphone or the like. As above, the electrostimulation circuitry includes the power supply 13620, the power switch 13630, and the drive circuit 13670. In addition to the speaker 13908, the device coupler also includes electrodes 13690 and sensors 13680 (if any).

Other embodiments of interfaceable electrostimulation devices may not have a user interface and, instead, may require interfacing with a smartphone, a computer, or the like. A basic example of an I-Estim is one that includes at least one device coupler (e.g., the patient electrode coupling device) that serves as the terminal interface between the device and the user, a conduit, and a connector device that links the conduit to a computer or a smartphone. In this basic example, the coupler is connected to a computer output port (i.e., a USB port). The computer runs software that serves as the user interface 13640, 13660 and directs the user through prompts to determine the user-specific settings. The computer then generates the signal that is output through the USB port into the connector device, travels through the conduit, exits the assembly through the device coupler, and enters the user in a location that the targeting structure (e.g., earbud) resides. In other exemplary embodiments, the I-Estim includes its own power source. The I-Estim may include its own user interface, electronic generator devices, and embedded software, but is overridden by an external computer device, once connected. Sensing inputs, sensed data processing, algorithms, and measures to respond to algorithms may be solely contributed by the external computer and are not necessarily required to be contained in the I-Estim device itself.

As set forth above, the neurostimulation devices can be integrated into an existing computer or they can be stand-alone devices, or they can be some combination. In some embodiments, the generator can interface with a "smartphone" or computer device or the generator can be a program on a smartphone. In the former example, the generator contains an interface device, such as a plug/jack that is reversibly stowable into the generator to protect it while not using the generator or while using the generator with a smartphone. This jack, when released from its stowed position, directly connects with an output interface on the smartphone (e.g., a headphone socket). Alternatively, the plug may include a combined electrostimulation coupler with integrated earbud(s) that interface with the generator. This combined configuration allows for consolidation of the electrostimulation device with the smartphone to allow the user to combine music and electrostimulation simultaneously, even where the electrostimulation signal is not synchronized to the music. It also consolidates the two devices to be more physically manageable for the user. This generator embodiment may be physically mated to the phone by the electronic interface plug and/or by magnetic measures, adhesives, clips, hook-and-loop fasteners, or the like to ensure that the two devices are reversibly, but durably mated and handled/carried as a single composite device. Alternatively, the generator and controller can be permanently (or temporarily) integrated into a personal electric device case, such as in the form of a smartphone case. Additionally, or in an alternative to the previously mentioned smart device integration, the generator, controller, and power source can be integrated within a battery/charging backup to the smart device, which devices can take the form of a piggy-back protective case with an external battery.

Some of these exemplary configurations of the generator/controller/device coupler embodiments are set forth in the embodiments of FIGS. 140 to 143.

A first exemplary configuration for a handheld generator is provided in FIGS. 140 and 141. The generator 14000 contains therein each of the power supply 13620, the controller/control logic 13650, the drive circuit 13670, and the audio logic 13906. On the front face of the case is a power button 13630, a set of user inputs 13640 (including, for example, a select button 13641, decrease 13642 and increase 13643 buttons, and a selection wheel 13644), and at least one user feedback device 13660 in the form of an LED/LCD screen. An audio speaker can be provided as well. To display information to a user, the screen can be, for example, a 3-line, 16-character LCD screen, but any other display screen is also applicable and envisioned. The display indicates to the user certain aspects of the generator 14000 depending upon the mode that is in use, and can provide instructions to the user as well.

The device coupler can be any of the exemplary embodiments described herein. The transmission conduit 13610 (not illustrated) is to be connected to the generator 14000 through signal ports shown in FIG. 141 and includes, for example, an electrode output port 14101, an audio input port 14102, and an audio output port 14103. The electrode output port 14101 supplies the electrostimulation signal to an appropriate connector of the transmission conduit 13610. The audio input port 14102 is an electrical connection that receives an external audio signal (e.g., music) from an external source (e.g., iPhone, iPod, Android, laptop, tablet, computer, or any other digital music player) to be used along with or supplemented to the electrostimulation signal transmitted through the transmission conduit 13610 to the electrodes 13690 on the device coupler (e.g., at the earbuds 8130, 9130, 9430, 9510, 10060, 11660, 12460, 13260, 14242, 16100, 16500). The audio output port 14103 is the electrical connector that supplies the external audio signal actually received at the audio input port 14102 to the speaker assembly within the device coupler. As an alternative to an external source, an integrated microphone 14104 can receive ambient sound (e.g., music or nature sounds) and supply that ambient sound through the transmission conduit 13610 to the speaker assembly (e.g., at the earbuds) or to the controller 13650 for modulation of the electrostimulation in synchronization with that ambient sound, for example, to pulse the electrostimulation in sync with a back beat or rhythm of a song that is being played in the environment of the user.

Another exemplary embodiment of a stand-alone electrostimulation device is shown in FIG. 142. A neurostimulation assembly 14200 in this embodiment is sized to be used with a mobile device 14210, such as a cell phone. The neurostimulation assembly 14200 includes two parts, a complete electro stimulation subassembly 14220 that has all of the functionality of the generator 14000 in FIG. 140, for example, but made in a miniature version and a device coupler 14240. In this embodiment, the electrostimulation subassembly 14220 is shaped to fit inside a pocket or holding belt 14232 of an accompanying arm or wristband 14230 (the band can be eliminated if desired to just provide a piggy-back holder for the mobile device 14210). The band 14230 also has a pocket or channel 14234 sized to fit the user's mobile device 14210 therein. If the arm/wristband is removed, the holder 14230 can be a protective cellphone case that houses the electrostimulation subassembly 14220 in a docking port or pocket.

The device coupler 14240 is, in this exemplary embodiment, a neuromodulation earbud embodiment. A first electrical connector 14244 is the conduit that provides the neuromodulation signal to the electrodes 13690 on the earbuds 14242 by a two-channel electrical connection. If, for example, electrostimulation is to be provided to one of the two earbuds, then two wires connect the first electrical connector 14244 to the electrodes on that one earbud. A second electrical connector 14246 separate from the first electrical connector 14244 connects the audio speakers within the earbuds 14242 to supply audio signals thereto received directly from the mobile device 14210. This second electrical connector 14246 can, therefore, be comprised of a standard stereo audio jack. In this embodiment, with the device coupler 14240 directly connecting to both the mobile device 14210 and the electrostimulation subassembly 14220 separately, the generator 14220 is physically independent from the audio signals received from the mobile device 14210. Thus, if it is desired to have the mobile device 14210 provide control or some other function with the electrostimulation subassembly 14220, this is done through a wireless connection, such as Bluetooth or Wi-Fi.

In the exemplary embodiment of a neurostimulation assembly 14300 in FIG. 143, in contrast, the device coupler 14340 directly connects only to the electrostimulation subassembly 14320. This means that the mobile device 14310 is directly connected only to the electrostimulation subassembly 14320. As such, all signals originating from the mobile device 14310 must pass through the electrostimulation subassembly 14320. In this embodiment, therefore, the electrostimulation subassembly 14320 can supply signals directly to the mobile device 14310 for processing, display, diagnostics, etc., which would allow the mobile device 14310 to act as the I/O display of the electrostimulation subassembly 14320. The electrostimulation subassembly 14320 is shown on the front face of the mobile device 14310 but it is not limited to this configuration and can be on the rear face.

It is noted that any of the alternative exemplary embodiments related to the systems and methods disclosed and envisioned include an electrostimulation device having its own internal power source, an external dedicated power source, or one that derives power parasitically from another device, which can be directly interfaced with a smartphone, a computer tablet, a laptop, or any other form of device with computing/programming such that the computing device can serve as the user interface, a signal processor, a signal timing device, and to carry out the process as well as modulating the user output signal based upon feedback from one or more sensor, and or have embedded algorithms driving the output signal or signals.

In another exemplary embodiment, the systems and methods herein (e.g., software and/or hardware) can be configured similar to standard digital audio workstations that allow a composer to create music but, at the same time, they allow the composer to create therapeutic triggers/cues (such as electrostimulation control) during or after song or video composition. In other words, the composer can create or "mix" a specific neuromodulation signal in synchronization with the track that is being created. In this way, the composer is able to use the systems and methods herein to produce an audio file formatted with embedded electrostimulation cues/triggers. The analogy of this is like a soundboard engineer mixing another instrument into a composition. Alternately, the systems and methods can produce an independent electrostimulation cue/trigger file that is to be used along with a particular composition or just by itself. The systems and methods herein then process either the embedded audio file or a combination of the audio file and the electrostimulation file to allow for manual, semiautomatic, and fully automatic composition of a therapeutic electrostimulation. In this way, all electrostimulation generators described herein can be configured to accept industry standard MIDI files that trigger electrostimulation, such as industry standard audio/visual effects devices.

As set forth herein, electrostimulation can occur dynamically or according to a particular pre-set pattern. In the former, acoustic signals from music or the environment, for example, provide the changes to modulate the electrostimulation and, in the latter, a pre-defined program or routine provides the changing electrostimulation. FIGS. 144 and 145 illustrate an electrostimulation signal graph with a horizontal time scale and a vertical amplitude scale that can be voltage or current. Shown in the two graphs are pulses having a pulse duration, a pulse period, a pulse frequency, a pulse group duration, a dwell off time, and a constant amplitude. In the exemplary embodiments of FIGS. 144 and 145, the amplitude of each pulse is +1, the duration of each pulse is approximately one eighth of a time unit, the pulse group duration is approximately one time unit, and the dwell off time is approximately one time unit. These pulses are shown to be square, but can also be asymmetric, sinusoidal, sawtooth, or any other analog profile or combination of the aforementioned patterns. FIG. 145 is similar to FIG. 144 but the pulses are in an alternate polarity sequence within the pulse group duration. In an exemplary embodiment, the time between alternation of the pulse polarity can be approximately zero and form a uninterrupted transition between polarities (not illustrated).

FIGS. 146 and 147 illustrate other exemplary embodiments of electrostimulation. Here, the signal graph of FIG. 146 has an amplitude modulation as a sine wave with no pulse group duration or dwell off time. The modulation reference can be of either a digital or an analog profile. FIG. 147, in comparison, has a pulse group duration of approximately two time units and a dwell off time of approximately two time units.

FIGS. 148 and 149 illustrate additional exemplary embodiments. FIG. 148 is an electrostimulation signal graph with a continuous square wave pulse that has an amplitude governed by a sine wave modulation reference. Pulse polarity is modulated by a modulation reference polarity. Additionally, the pulse frequency is modulated by the amplitude of the modulation reference profile. When the modulation profile is at its lowest amplitude, the frequency of corresponding pulses is low and, when the amplitude of the modulation profile is highest, the frequency of the corresponding pulses is also highest. In comparison, the electrostimulation signal graph shown in FIG. 149 has a constant frequency and no polarity group. Here, the pulse length is modulated by the modulation reference profile. When the modulation profile is at its lowest amplitude, the length of the corresponding pulses is low and, when the amplitude of the modulation profile is highest, the length of the corresponding pulses is also highest.

The inventors have discovered that users of the electrostimulation devices and methods described herein experience various levels of comfort and discomfort when receiving the electrostimulation. When the polarity of the signal does not change and the stimulation is constant, such as the signal shown in FIG. 144, users feel discomfort with lower current amplitudes. On the other hand, when the polarity changes, and especially when the polarity changes quickly, then, not only can the users tolerate a significantly higher electrostimulation signal current, they find it pleasant and relaxing, thereby providing the benefits that such electrostimulation devices and methods intend. It has been found that the increasing portion of the electrostimulation signal provides the most pleasurable feeling, such as the period between time units 3 and 5 in FIGS. 146 and 149. With regard to FIGS. 144 to 149, time units are used because the time scale can be of any length (e.g., μs, ms, s).

Significantly, the systems and methods of electrostimulation described herein can be customized or even run in real time with audio, such as music. Such an exemplary embodiment is depicted in FIGS. 150 and 151, where the audio band amplitude pulse output is modulated. In the example of FIG. 150, the pulses are generated as a square wave according to the process of the signal graph of FIG. 144, i.e., with a constant polarity square wave but, here, with no pulse group duration or dwell off time. The amplitude of the pulses of electrostimulation are modulated by a profile that is analogous to the amplitude of an audio band. The modulation can be targeted to a particular portion of the audio spectrum. For example, the modulation can track frequencies between approximately 40 and 100 Hz, in particular, between approximately 60 and 80 Hz, thereby providing electrostimulation in synchronization with the beat of very low bass notes. Alternatively, the modulation can function as a VU meter to track the audio signal being provided into the system. This tracking will be described in further detail below. In comparison to FIG. 150, FIG. 151 alternates the polarity of the pulses of electrostimulation while synchronizing the pulses to the provided music audio file. As indicated above, users of the devices and methods prefer receiving stimulation that alternates polarity and, for the reasons described below, prefer receiving stimulation that is modulated to music that the users like instead of utilizing pre-set modulation programs.

A method for performing electrostimulation with a device according to FIGS. 140 and 141 is now described. With an appropriate power source such as a 9V battery in place, the power button 13630 is pressed to turn the generator 14000 on. There are three ports on the top of the device: an electrode port 14101, an audio in port 14102, and an audio out port 14103. The device coupler in this exemplary embodiment is the coupler shown in FIG. 142. Therefore, the dual electrical connector 14244 (which can be a 2.5 mm jack) for the positive and negative leads of the electrostimulation signal is plugged into the electrode port 14101. The three-lead electrical connector 14246 for audio input (which can be a standard 3.5 mm audio jack having separate positive leads and a shared negative lead) is plugged into the audio out port 14103. In this way, the user has the option of listening to music during therapy, in which case, an audio source is plugged into the audio in port 14102 and, like the audio out port 14013, a standard 3.5 mm audio jack having separate positive leads and a shared negative lead can be used.

After the generator 14000 turns on, the LCD screen displays a welcome message or animation before prompting the user to select a desired operating mode. Selection of a mode can be accomplished using the decrease 13642 and increase 13643 buttons. When the desired mode appears on the display 13660, the select button 13641 can be pressed, or the generator 14000 can accept a delay of, e.g., ten seconds to automatically enter the mode that is presently being displayed. One of the modes is an audio mode, of which there are two sub-modes, ambient mode and music mode. Alternating between these two modes can be accomplished, for example, by plug control, i.e., when an audio source is plugged into the audio in port 14102, the device defaults to music mode. In contrast, when the audio in port 14102 is empty, the device automatically enters ambient mode. Additionally, the user can choose to enter a formula mode. Each of these modes is described in further detail below.

Within the audio mode, ambient mode turns on by default when there is no jack within the audio in port 14102. Instead of a direct audio source plugged into the device from a music player, the audio on which the therapy will be based is derived from the user's environment. Ambient mode is ideal for when there is music in the background, as at a music festival, a concert, or a day at the park, where the environment's sounds will be reflected in the user's stimulation. When a jack is within the audio in port 15102, music mode turns on by default if audio mode is selected. In music mode, the generator 14000 receives audio input from a source (e.g., the user's hand-held music player), and then modulates the electrostimulation to compliment the audio that is being input to the generator 14000 in real time. This mode revolutionizes the way one listens to music and is ideal for when the user wants to listen to music and relax at the same time. By matching the electrostimulation current with the user's favorite songs and artists, the generator 14000 provides a state of relaxation personal to each individual user's preferences.

In the formula mode, the user will experience electrostimulation with a preprogrammed algorithm. The user selects a single formula from a set of different electrostimulation formulas. The screen indicates to the user to select a particular formula, which can be done with the decrease 13642 and increase 13643 buttons. This algorithm is stored in a non-illustrated memory of one of the chips of the generator 14000. Any algorithm can be programmed to achieve a particular result or effect, for example, relaxation, pain control, euphoria. In an exemplary embodiment, a first pre-set algorithm will deliver a polarity-alternating signal following a modified square wave pattern. The lowest current output from the generator 14000 is constrained at 0.2 mA, determined by the inventors as being a minimum therapeutic current dose. As described below in further detail, a maximum or ceiling for electrostimulation intensity is selected during setup prior to the electrostimulation session and, regardless of the different pre-set algorithms that can be selected, the user is able to set the maximum intensity of the electrostimulation at any time during the session. As set forth herein, continued research will generate a better understanding of neuromodulation progresses. If new and unique electrical signals are discovered to expand uses and effects on the brain and body of the user of this technology, then users will desire to implement such signals with the generator. Accordingly, an algorithm delivery circuit can be associated with the generator 14000 and have a receiver (e.g., an antenna and transceiver) allowing an external device to communicate with the generator 14000, for example, via Bluetooth or Wi-Fi. The algorithm delivery circuit stores any customized algorithm supplied by the user and includes such stored algorithms in the list of the algorithms for the formula mode and is describe in further detail below.

Calibrating the generator 14000 is an integral part of ensuring that electrostimulation is experienced at its fullest potential. To understand the process of calibration, it is noted that a calibration level chosen is independent of the volume at which the audio is playing.

In music mode, by calibrating the generator 14000 during setup, the user can adjust how the intensity of the electrostimulation will respond to a variance in the music the user has selected to experience. To start calibration, a "ceiling" for the intensity level is set and then signal sensitivity is set. The step of selecting the maximum power level or intensity actually sets the maximum current of the electrostimulation. Here, the screen prompts the user to choose a maximum power level or intensity. Based on the discovered therapeutic minimum level for current of approximately 0.2 mA and the maximum threshold for causing discomfort of approximately 8 mA, the inventors set a range of power level according to Table 1 below and, using increments of 0.2 mA, created a set of forty power levels. These ranges may vary in other embodiments.

TABLE 1

Power Level to Current (mA) Conversion Table

| Level | mA |
|---|---|
| 1 | 0.2 |
| 2 | 0.4 |
| 3 | 0.6 |
| 4 | 0.8 |
| 5 | 1.0 |
| 6 | 1.2 |
| 7 | 1.4 |
| 8 | 1.6 |
| 9 | 1.8 |
| 10 | 2.0 |
| 11 | 2.2 |
| 12 | 2.4 |
| 13 | 2.6 |
| 14 | 2.8 |
| 15 | 3.0 |
| 16 | 3.2 |
| 17 | 3.4 |
| 18 | 3.6 |
| 19 | 3.8 |
| 20 | 4.0 |
| 21 | 4.2 |
| 22 | 4.4 |
| 23 | 4.6 |
| 24 | 4.8 |
| 25 | 5.0 |
| 26 | 5.2 |
| 27 | 5.4 |
| 28 | 5.6 |
| 29 | 5.8 |
| 30 | 6.0 |
| 31 | 6.2 |
| 32 | 6.4 |
| 33 | 6.6 |
| 34 | 6.8 |
| 35 | 7.0 |
| 36 | 7.2 |
| 37 | 7.4 |
| 38 | 7.6 |
| 39 | 7.8 |
| 40 | 8.0 |

By using the decrease 13642 and increase 13643 buttons (or the selection wheel 13644), the desired power level can be selected. As before, holding down either button will lead to a rapid change. Again, this value can be changed during electrostimulation as well. An exemplary default intensity can be set at level 10 (corresponding to 2 mA), but the user can increase or decrease this number based upon experience. The power level desired can be implemented, for example, by pressing the select button 13641. The desired power level can be selected without having any feedback from the generator 14000. However, in an exemplary embodiment, the user can be required to place an electrode at the treatment area (e.g., ear canal) while setting the first maximum power level. In this way, the user can experience what will be felt at the treatment area during application of the electrostimulation.

Then a sensitivity of the electrostimulation signal is set. The display provides a graphic that allows a user to see how sensitivity decreases/increases based upon the audio signal that is present. Exemplary graphics for adjusting the sensitivity include FIGS. 152 and 153. If music mode is selected (there is a jack plugged into the audio in port 14102), then the screen prompts the user to calibrate the generator 14000 with the audio source that is currently being played by the external audio player. First, the user selects a preferred/ideal volume level on the external device being used in conjunction with the generator 14000. Then, the user sets the maximum intensity. Then, the user sets the sensitivity level for that type of music being played using the selection wheel 13644 (or the decrease 13642 and increase 13643 buttons). It is noted that the sensitivity calibration level can be changed once electrostimulation has begun. An exemplary default level for starting sensitivity calibration with regard to FIG. 153 begins with a sensitivity level equal to the number 0, allowing the user to adjust either positively (right) or negatively (left). While calibration occurs, a needle at which the sensitivity level is currently set can, for example, blink. To set the sensitivity level, the select button 13641 can be pressed.

Ambient mode is used when there is ambient sound or music as is the case in a concert or dance club. If ambient mode is selected, the screen prompts the user to calibrate the generator 14000 with the background noise/music in the environment. Calibration is basically the same as in music mode. By calibrating the device during therapy setup, the user can adjust how the therapy's intensity responds to the variance in the environment's sounds. Based on the volume level of the ambient sound as well as the degree of amplitude variation of the sound, the user first adjusts the maximum current level using the selection wheel 13644 (or even the decrease 13642 and increase 13643 buttons). The maximum level calibration can be changed once electrostimulation has begun. Sensitivity of that maximum intensity is then calibrated. If the graph of FIG. 152 is used, then the bar graph consistently moves with respect to ambient sound intensity, and all the user needs to do is simply adjust the calibration dial so that the last bar to the right is reached only at the most intense portions of the ambient sounds. One exemplary default level for starting sensitivity calibration with regard to FIG. 152 begins with a sensitivity level equal to at a middle bar (e.g., the $8^{th}$ vertical bar), allowing the user to adjust to the left or right. While calibration occurs, the bars up to which the level is currently set can, for example, blink. Alternatively, just the one bar indicating the sensitivity level can blink. To set the sensitivity level, the select button 13641 can be pressed.

Sensitivity calibration establishes a relationship between the intensity of electrostimulation and an intensity of the music or the ambient sounds. A higher level of calibration leads to a higher change in electrostimulation intensity with regards to music intensity. In other words, a higher calibration level means that it takes less of a change in the variance of the music intensity to get the same change in variance of electrostimulation intensity. Simply put, a higher calibration is equivalent to a higher sensitivity level. As such, a lower calibration is used if the song being played has higher variability or intensity. An example of this includes songs that shift from a soft pitch to a high rhythmic intensities (deep basses) and do so relatively quickly (e.g., a drop in base). Exemplary music genres with this characteristic include heavy metal and EDM. A higher calibration level is selected if the song being played has lower variability or intensity. An example of this includes songs that stay relatively stable in rhythmic intensity, such as the genre of New Age music. The maximum current amplitude set in the first calibration step constrains the current to a user-selected preset maximum amplitude. If the maximum amplitude is reached too frequently, sensitivity may be adjusted to a "less sensitive" setting. This ensures that the user can "feel" the signal change throughout the full range of the particular piece of music input and avoid signal clipping. In contrast, if the user cannot perceive or "feel" the signal variation, then the sensitivity may be increased. This condition would be more likely in music pieces that have very little variation in intensity. In the exemplary embodiment, this sensitivity adjustment is performed manually using an analog potentiometer. However, in other exemplary embodiments, a digital potentiometer, or "digipot", may be used and the sensitivity adjustment can be software or firmware controlled to automatically adjust and maximize the user's ability to "feel" the full range of signal variation regardless of the type of music or sounds being input into the device and, therefore, into the user's ear.

After the sensitivity level is set, a bar graph akin to a VU meter will move dynamically and track the variations of the music or other ambient sound. The user can further adjust the sensitivity to ensure that the full spectrum of the sound can be "felt" without signal clipping on the high end of the intensity spectrum of the sounds. If the level on the sensitivity graph is constantly reaching the maximum value, then signal clipping is most likely occurring, thus requiring a reduction in sensitivity. If the level on the sensitivity graph is barely moving, the user may increase sensitivity to vary the signal to a greater degree and better "feel" the signal vary in synchronization with the music or sounds.

Setting maximum current and sensitivity and the reasons behind these requirements will be discussed in further detail below with regard to an exemplary circuit diagram.

It is noted that power level and calibration do not affect one another. Intensity is solely a maximum power level that is output to the electrodes. In contrast, calibration determines how often the higher/highest power levels will occur during a treatment sessions. For instance, if the intensity is set at level 10 (2 mA), and the calibration is set at its maximum level, there will be more instances of level 10 power than if the calibration was set at an intermediate or lowest value.

After selecting the desired mode (ambient, music, or formula), the screen prompts the user to choose a duration of the electrostimulation. The inventors have discovered that a therapeutic range for electrostimulation duration is between 5 to 45 minutes. Thus, the user can elect a shortest duration starting at five minutes and a longest duration up to forty-five minutes. For example, a default starting duration can be set to fifteen minutes, with the user adjusting the time (e.g., with five-minute increments) with the decrease 13642 and increase 13643 buttons (or the selection wheel 13644), where holding down either button can lead to a rapid change.

The generator 14000 is now ready to begin electrostimulation treatment. Before starting, the screen can display a countdown to treatment commencement. This countdown can occur automatically after the power level is set or it can require actuation of the select button 13641. Electrostimulation then begins. In an exemplary embodiment, the first fifteen to sixty seconds can be a ramp up period. During the session, the screen can provide a dynamic display of a graphic that tracks the instantaneous (or almost instantaneous) power level being applied to the electrodes. At the same time, a countdown clock can be decrementing to provide a visual cue for the treatment session along with the maximum power level selected. In this way, if the user decides to change the power level or duration settings or calibration during treatment, the display can show the new value after that change is made. For example, to change the intensity, the user simply presses the decrease 13642 and increase 13643 buttons, to adjust the sensitivity, the user can spin the wheel 13644 to a desired location corresponding to the new desired calibration setting. It is noted that, during the session, neither the music nor the electrostimulation treatment session stops while adjusting these parameters. In an exemplary configuration, however, the session can be paused by pressing the power button 13630 (or even the wheel 13644), at which time the screen can indicate a paused status as well as provide instructions on how to resume (press power button 13630). Alternatively, if the user desires to turn the generator 14000 off, holding down the power button 13630 for a given time (e.g., five seconds) can effect this result.

It is noted that the generator 14000 can be turned off at any time with use of the power button 13630 (e.g., by pressing for five seconds).

Based on the above exemplary configuration, a set of specifications for the generator 14000 arise. The current can range from approximately 0.05 mA to approximately 14 mA with use of a power scale from 1 to 40, for example. As discussed in more detail below, the voltage of the electrostimulation treatment ranges from approximately 5 to approximately 120 Volts because the value is determined by the driven load.

Unlike a standard resistor, the impedance or resistance of human tissue is highly variable. Not only is it variable from person to person, but tissue resistance can change during any given electrostimulation session. There are many scenarios when this variability can occur. If the subject sweats and that liquid finds its way into the ear canal, impedance will drop. The electrostimulation itself may cause changes in blood flow to the local tissue surface and, therefore, change impedance. If resistance changes, and voltage remains the same, then the current imparted to the target structure will vary to an unknown degree and, as a result, can either give too much current or too little, rendering the therapy ineffective or less effective. In an exemplary embodiment, the generator 14000 provides current control by varying the voltage delivered to the subject within a range that can maintain constant current at a range of known resistances. As the processor senses a decreasing current draw, voltage is increased to maintain the set current. On the other hand, if the processor senses an increasing current draw, then voltage is decreased. This adjustment occurs many times a second for constant current control. In one exemplary embodiment, the processer makes checks on the current and, therefore, opportunities to adjust the current fifty times per second. For therapies where even more current variability is required, the current checks and opportunities to adjust could be set to 100 times per second or greater (and vice versa). Other exemplary embodiments maintain a pre-set current by intermittently stopping therapy for a user-imperceptible duration of time, while resistance between electrodes is measured and voltage is adjusted. The frequency of these resistance "checks" depends on what the therapy is being performed. Waveform shapes, polarities, pulse durations, time between opposite polarities, and frequencies are either completely or partially preset at fixed values or may vary during certain therapies for specific indications, may vary only from one therapy indication to another, or may be dictated by an app on a PSA. Exemplary ranges of values are shown in Table 2 below.

TABLE 2

| Pulse Variables | Values | Control Method |
|---|---|---|
| Current | 0.05-14 mA | User setting |
| Voltage | 0.01-16 V | Load driven |
| Waveform | Modified square wave, saw tooth, square wave, analog waveforms, or combinations thereof | Preset |
| Polarity | Positive, Negative, Alternating | Preset |
| Pulse Duration | 1-1000 μs | Preset |
| Time Duration Between Opposite Polarities | 0 second minimum to 5 seconds | Preset |
| Frequency | 5-2500 Hz | Preset |

One exemplary set of factory default settings retained in the permanent memory of the generator 14000 can be seen in Table 3 below.

TABLE 3

Factory Default Settings (Retained in Permanent Memory)

| | |
|---|---|
| Minimum current in Formula Mode | Level 1 (.2 mA) |
| Calibration level | $8^{th}$ bar out of 16 |
| Therapy duration | 15 minutes |
| Intensity | Level 10 (2 mA) |
| Ramp up period of therapy | 15 seconds |
| Therapy duration options | 5 to 45 minutes (5 minute increments) |
| Countdown to therapy beginning | 3 seconds |
| Notification of completion of therapy | 5 seconds |
| Time to hold down ON-OFF for powering | 5 seconds |

With the preceding explanation of the functionality and methods of use of the various systems and processes for delivering electrostimulation, FIGS. 154 through 156 illustrate one exemplary circuit configuration for an electrostimulation delivery device such as the generator 14000. The circuit is comprised of various subsets including a power control circuit 15410, a voltage regulation circuit 15420, an electrostimulation pulse generation circuit 15510, a microphone circuit 15610, an audio transceiver circuit 15620, a sensitivity adjustment circuit 15630, and a display circuit 15640. Each will be explained in turn along with the relevant connectivity.

In the exemplary embodiment, power is supplied to the entire circuit at the power control circuit 15410 through a power supply 15412, for example, a 9V battery. The power button 13630 can be part of the power control circuit 15410, which, when powered on, provides power for operation of the entire generator 14000. As set forth above, when the circuit is powered on for the first time, the user needs to set a maximum current to be delivered. This is done with the electrostimulation pulse generation circuit 15510 in a process also referred to as setting a power threshold. The user can set this threshold without knowing what the first-set power would feel like or, as an alternative, the user can place an electrostimulation electrode in the user's ear canal to experience the level that is being set as the power threshold. As a baseline, the electrostimulation pulse generation circuit 15510 sets a level of 2 mA to start this step, which corresponds to level 1 in Table 1. If the user is going to be using music mode, then a headphone jack will have been inserted in the audio in port 14102 of the audio transceiver circuit 15620. The audio out port 14103 is connected to the audio in port 14102 to provide the received audio signal to speaker assemblies in earbuds of the device coupler. If the user is going to use ambient mode, then a headphone jack will not be present in the audio in port 14102 of the audio transceiver circuit 15620 and the received audio signal provided to the speaker assemblies in earbuds of the device coupler will be provided through the microphone circuit 15610. In either mode, maximum electrostimulation power now needs to be adjusted, which entails setting a maximum current amplitude. Setting a maximum current amplitude make sure that the highest level of audio input (e.g., loudest notes in music) produce at the electrodes the highest level of current. Simply put, this level is a ceiling for a highest dose of electrostimulation and corresponds to a power level in Table 1. The user enters the corresponding level of the maximum current amplitude into the electrode processor 15512 of the pulse generation circuit 15510 to confine the electrode processor 15512 during audio mode to not deliver current above this set maximum level. As the user might be able to tolerate or want a higher level, this can be increased dynamically during an electrostimulation session; the user can also lower the level. For example, if the user selects Level 10 as the maximum current amplitude, then the electrode processor 15512 locks the floor of the current to Level 1 (corresponding to 0.2 mA) and locks the ceiling of the current to Level 10 (corresponding to 2.0 mA).

Now that the maximum current amplitude is set, the user needs to set how often that maximum current amplitude will arise during a session and that procedure is accomplished by setting a sensitivity adjustment with the sensitivity adjustment circuit 15630. If, for example, the user wants the maximum current amplitude to be present very often, the sensitivity will be set higher and, if the user wants the maximum current amplitude to be present infrequently, the sensitivity will be set lower. There exists a problem when listening to a mellow song where a user can feel particular lows and highs but, if the next song is a metal or EDM song, then the lows and highs will be much different and second song with much more frequent highs will clip both medium and high tones to the maximum current amplitude.

There are a few ways to set the sensitivity. As explained above, frequency filters can be used to find peaks at various frequency ranges, e.g., the bass line of a song. However, with music being different in every song and with ambient sound not necessarily having frequencies within such ranges, the inventors discovered that it would be beneficial to set sensitivity using a VU processor to meter the input audio. A VU processor produces an average of an overall volume without regard to wavelength (e.g., it is wavelength agnostic) and then the output level of the VU processor is used to modulate the electrostimulation. The VU-type output is provided with the sensitivity adjustment circuit 15630, having its sensitivity circuit 15631 and its audio envelope follower circuit 15632. A potentiometer of the sensitivity adjustment circuit 15630 is set to vary a current provided to the audio envelope follower circuit 15632. With the sensitivity adjustment circuit 15630, the VU output can be displayed to a user to have the bar graph/needle (FIG. 152/153) bounce/move between the preset low and high levels. In the bar graph embodiment, an ideal setting for sensitivity will have the user sets the level so that the highest bar is rarely activated at the strongest beat of the song and, in the needle embodiment, an ideal setting for sensitivity will have the user sets the level so that the needle remains close to the "0" and goes into the red zone rarely and only at the strongest beat of the song. This manual (analog) setting of the sensitivity allows the user to customize the delivered electrostimulation throughout the song and to change it for each different song if desired. It is noted that sensitivity is also dependent upon the input volume of the signal that enters the audio in port 14102. If the user raises the volume, then the sensitivity can be correspondingly changed by the user to account for that increase. The sensitivity can also be done digitally and automatically. In a first exemplary embodiment, a digital potentiometer can be associated with the processor 15512 and be programmed to prevent the bar/needle from going above a pre-set or user-set level during any given song and, thereby, adjust the sensitivity on the fly that is also dependent upon the volume of the audio selected by the user. In a second exemplary embodiment, the digital potentiometer can be controlled by the processor 15512 to back off the current level if the maximum current amplitude is being hit too often within a set amount of time. In another more sophisticated embodiment, there can be a database of songs with corresponding VU level profiles and the processor 15512 can look at the profile of the to-be-played or currently-played song and back off or increase the sensitivity dependent upon both the profile and on the user's selected volume. Finally, in a completely dynamic embodiment, the generator 14000 can communicate with a song identification application (such as SoundHound® and Shazam®) to identify the next song to be played or the one current playing and, by knowing the song, automatically set the sensitivity based upon a known profile of that song or based upon an on-the-fly analysis of the audio file while, at the same time, take into account the user's volume setting.

Each of the audio signals, either at the microphone 14104 or the audio in port 14102, is amplified and powered 15422 from the output 15422 of a voltage regulator circuit 15420. The resulting output signal is applied to line 15634, which is an input line to the display processor 15640. This signal is then output from the display processor 15642 as the input signal 15514 to the pulse generation circuit 15510, which is the signal that is pulse modulated by the processor 15512 and output to the electrode(s) 14101.

The decrease 13642 and increase 13643 buttons and the select button 13641 are other input variables to the display processor 15642, thereby enabling control through the display processor 15642. The maximum current amplitude of the electrostimulation signal is controlled through increment 15516 and decrement 15517 inputs of the electrode processor 15512 from the display processor 15642. With 0.2 mA set as a default minimum, therefore, the range of current to be supplied to the electrodes 14101 from the generator 14000 is set between the user-selected maximum current and the pre-set minimum current.

As indicated herein, it is important for the generator 14000 to keep the electrostimulation current where it should be at any given time, i.e., between the default minimum and the user-selected maximum current, and to not exit out of this range. This is done through the voltage regulation circuit 15420. What could cause an improper amount of current to be applied to the electrode(s) 14101 is a variability in the resistance of the tissue that is disposed between the two poles of the electrode 14101. It is known that biological tissue does not have a constant resistance. Thus, the problem of variable resistivity must be addressed. There are two aspects to this. First, each person's target tissue does not have the same resistivity and placement of the electrodes circumferentially within an ear canal, for example, will have different resistance values. Further, the inventors have discovered that tissue changes in resistance when a constant initial current is applied. In most cases the resistance tends to drop as the current is maintained, but resistance can increase, for example when the environment (e.g., weather) is cold. Simply put, human tissue is a biological resistor, it is not a fixed resistor. So the circuit needs to know how to maintain the current with an ever-changing resistance. This problem is solved with the voltage regulation circuit 15420. During the electrostimulation session, the voltage regulation circuit 15420 either can sample the resistance at the electrodes or it can measure a current drawn from the output of the electrodes and, based upon either (or both) of these values, the voltage regulation circuit 15420 will dynamically constrain the current and prevent it from going above the user-selected maximum current and the pre-set minimum current to maintain the therapeutic range and not provide user discomfort. From this it can be said that the electrostimulation signal (i.e., a neuromodulation electric signal (NES)) is the character of the current that is being delivered to an area of the body that is in proximity or adjacent to a targeted nerve or other biologic structure (e.g., blood vessel).

With regard to a maximum power level or intensity, the inventors discovered various considerations and one significant one is that a user can become tolerant of the electrostimulation signal. The problem facing advancing electronic nerve stimulator devices and methods is whether or not an individual user can tolerate the discomfort associated with the delivery of a signal delivered at the power necessary to maximize therapeutic benefit. The systems and methods herein improve the art by including algorithms and processes that prevent a user from becoming tolerant to the electronic signals delivered.

In a first exemplary embodiment, electrostimulation provided by the hereindescribed devices and methods are supplemented by including auditory stimulation in the form of prerecorded audio, not only by combining the theory of neurologic distraction, but also by the physical release of endogenous endorphins. Users are provided with the ability to listen to such prerecorded audio or any other auditory stimulation (e.g., white noise, an audio book, pre-set patterns, and the like) during the electrostimulation therapy. This is enabled because the device coupling the electrostimulation electrodes to the user can be configured within earbuds or headphones.

In another exemplary embodiment, the generator is provided with a microphone or similar input device that is able to sense an ambient audio signal and modulate the electrostimulation signal dependent upon that ambient audio signal. Of course, this modulation is performed within a proscribed therapeutic range as the power varies the electrostimulation signal in accordance with the ambient audio signal.

With regard to ease of use of the inventive systems and methods, the generator is hard-wired, wirelessly connected, or optically connected to the audio source that is to deliver the audio signal forming the modulation of the electrostimulation.

As set forth herein, continued research will generate a better understanding of neuromodulation progresses. If new and unique electrical signals are discovered to expand uses and effects on the brain and body of the user of this technology, then users will desire to implement such signals with the generator. Accordingly, the embodiment of FIG. 156 is supplied with an algorithm delivery circuit 15612 having a transceiver 15614 allowing an external device to communicate with the generator 14000 through the algorithm delivery circuit 15614, for example, via Bluetooth or Wi-Fi. The algorithm delivery circuit 15612 contains all of the circuitry necessary for such communication as well as a memory to store customized algorithms supplied by the user. Control of the algorithm delivery circuit 15612 can occur with any of the on-board processors or it can be done through other processors of the generator 14000. The algorithms for the formula mode above can also be stored in the memory of the algorithm delivery circuit 15612, for example. In an exemplary embodiment, to utilize the generator 14000 with either a pre-set formula or one of the stored algorithms, the algorithm delivery circuit 15612 can deliver the output signal to be modulated through a switch 15616 that, when set to either the formula mode or an algorithm mode, bypasses the input of the microphone and uses the preamp portion of the microphone circuit 15610 to supply the signal to the sensitivity circuit 15620.

In another exemplary embodiment, the audio signal desired by the user (e.g., a particular song) can be pre-converted into an electrostimulation signal so that the signal is modulated/synchronized to that song. This signal can then be administered to a user in the absence of music. This kind of "shadow" synchronization gives the user a "feeling" of the song as an electrical sensation and the ability to mentally "hear" the song even though the user is not actually hearing it. The effect produced is akin to mentally singing or humming a song. This shadow synchronization confers a beneficial signal tolerance by allowing the user to "anticipate" higher doses of electrostimulation (assuming that the user knows the song) because he/she can predict the signal. This process also confers an audio endorphin release as if the subject was actually listening to the audio recording. This particular process utilizes the theories of ramp-up and pattern following. It is known that the longer a subject is exposed to a noxious stimulation at a constant delivery, the tolerance to that noxious stimulation increases. In the inventive "ramp-up" stimulation feature, if the noxious stimulation increases from a low-level (low power/intensity/current) of stimulation that is initially tolerated up to an increased level, and is done so incrementally, then the user can tolerate the higher level and tolerance is increased. This is analogous to the situation of a cold pool getting more comfortable after the initial shock of jumping in. The systems and methods herein, therefore, provide a signal delivering process that modulates the power of the signal to have the signal strength rise progressively and linearly from a well-tolerated, low power signal to a progressively increasing power over time, until an asymptote is reached, such that the power stays just below and is restricted from going above that asymptote.

Delivery of the signal needs not be a constant ramp. It could also be provided as a sinusoidal increase of the power, with power progressively increasing over time until an asymptote is reached and then decreases to a lower-but-therapeutic level asymptote. The signal can remain sinusoidal or it can rise in amplitude or simply flatten out to a linear therapeutic level. Any desirable ramping up pattern of increasing to and subsequently maintaining the ideal target power is also envisioned.

With the theory of "pattern following," a subject can increase his/her tolerance by experiencing stimulation varying between tolerable and noxious if it is done in a pattern that is, or ultimately is, predictable by the subject. In other words, if the power of the nerve stimulation varies between tolerable and initially noxious within a therapeutic range, but follows a pattern, the subject will tolerate the peaks in power delivered better, once the subject can anticipate when the power will again decrease to lower levels. Over time, the "duration" principle takes effect and the subject becomes able to tolerate the signal at a constant, high power/high efficacy signal. An example of this can be illustrated with waterboarding. If a user was told beforehand that his/her head would be forced under water for only five seconds, the event would be well tolerated. However, if the same act was performed by a stranger who did not indicate what the duration would be, the five-second dunk would be quite poorly tolerated. Putting the discomfort in an acceptable context allows the brain to anticipate a shorter duration and block out the discomfort when it occurs.

The inventive systems and methods can also be used to counteract seizures caused by epilepsy. It is known that epilepsy can be triggered, such as by a fluorescent light. The systems and methods can be configured to detect fluorescent, flashing lights, and/or other lights known to cause seizures and, when detected, to administer an electrostimulation treatment in advance of a seizure.

The inventive systems and methods can also be used to induce a physiologically beneficial wake up from sleep. It is known to be beneficial to have elevated cortisol levels when waking in order to have a more pleasant and physically positive waking from sleep. The systems and methods can be configured to include a wake-facilitation feature. In particular, when worn during sleep, the generator can be programmed to deliver electrostimulation at therapeutic levels sufficient to induce cortisol and wake the user up at a particular time. A short time before waking (e.g., thirty minutes), the systems and methods slowly develop an electrostimulation signal to raise the user's cortisol levels and, at waking time, the cortisol levels will be at a physiologically beneficial level. This feature is available particularly with the systems and methods described and illustrated herein because they are so comfortable. As such, sleeping with the device couplers installed will not cause or will not impose any measurable defect in a person's sleep.

As set forth above, each of the various neurostimulation devices 1610, 2700, 2900, 3200, 3600, 4410, 5200, 5800, 6000, 6200, 6600, 6700, 6900, 7100, 7300, 8100, 9500, 9800, 10000, 10400, 11300, 11600, 11900, 12400 described herein can be used to treat a number of conditions and ailments through stimulation of the vagus nerve. Some of these include depression, multiple sclerosis, weight loss, motion disorders, insomnia, obesity, and Alzheimer's disease. Importantly, stimulation of the vagus nerve aids in management of pain, in particular, for headaches and migraines. It is known, however, that, for headaches and migraines, better treatment with neuromodulation occurs at one or more of the facial artery and the trigeminal nerve.

With knowledge of the above neurostimulation devices, the inventors discovered that securement within the ear canals can be used to exploit the proximity to both the trigeminal nerve and the facial artery. Accordingly, the above-mentioned headband configuration can be changed to the neurostimulation device 15700 shown in FIGS. 157 to 159. In this variation, a C-shaped headband 15702 has distal ends at which an earbud/neurostimulator device can be placed at one or both of the distal ends but, in this exemplary embodiment, as will be described in further detail, the focus points for electrical stimulation are the facial artery and the trigeminal nerve and not the vagus nerve (although it is equally possible to include the earbud/neurostimulator device at one or more of the distal ends in a desirable configuration). At the distal ends are ear canal centering devices 15704. When worn, each of the centering devices 15704 fits into a respective ear canal of a user. If the centering devices 15704 are to double as audio headphones, then acoustic speakers are present within the centering devices 15704 and are supplied with signals through a non-illustrated cable. However, most therapies for curing headache and migraine pain are associated with quiet and, therefore, the centering device 15704 in this exemplary embodiment serves to minimize sound, acting as ear plugs but they may combine the vagus nerve stimulation described herein and combine music and/or other sounds. The exemplary neurostimulation device 15700 is to be worn about the back of a user's head, as the embodiment shown in FIG. 160. While the neurostimulation device 15700 can be rotated about the axis between the user's ears to place the headband 15702 under the user's chin, as will be seen below, that orientation is not as desirable. As used with the headband embodiment, "rear" is referred to as a position that will be closer to the rear of a user's head when in use and "front" is referred to as a position that will be closer to the face of a user when in use.

As above, this embodiment of the neurostimulation device 15700 is that the headband 15702 is of a material with spring-back properties such that, when the C-shape of the headband 15702 is opened to fit on the user's head, the spring-back of the C-shape provides an inwardly directed force on the centering devices 15704 to press each into its respective ear canal. As above, this headband 15702 is also adjustable to allow a user to increase or decrease the force that the distal ends can place on the user's head. The mechanism for adjusting this force is, however, somewhat different. To adjust this force, a main body 15705 defines two cavities that form a spindle holder 15706 and in which a spindle 15708 is disposed. Each of the two ends of the spindle 15708 has an internally threaded bore into which is threaded a rear end of one of two tension cords 15720. The opposing front end of each tension cord 15720 is fixed in a respective cord holder 15710 disposed away from the spindle 15706 around the main body 15705 (to approximately the 3 and 9 o'clock positions of the C-shaped headband 15702 when viewed from above a user's head). The threads of the two bores that receive the rear ends of the tension cords 15720 (and the corresponding threads of the rear ends of the tension cords 15720) are reversed so that rotation of the spindle 15708 in one direction will pull the two rear ends of the tension cords 15720 together and rotation of the spindle 15708 in the opposite direction will push the two rear ends of the tension cords 15720 apart. In this way, as the distal ends of the tension cords 15720 are pulled towards one another, a rearwardly directed force is imparted on each of the cord holders 15710 to, thereby, move the two centering devices 15704 away from one another and as the distal ends of the tension cords 15720 are pushed away from one another, a forwardly directed force is imparted on each of the cord holders 15710 to, thereby, move the two centering devices 15704 towards one another.

With such an inward and outward force adjustability of the headband 15702, the centering devices 15704 are replaced with centering and force-imparting booms 15910 that, when placed about a user's head and within the ear canals, make possible easy access to either or both of the facial artery and the trigeminal nerve. In particular, each boom 15910 has a rearward end at which is disposed a centering device 15904 that is pointed inwards (i.e., towards a center of the C-shape). The centering devices 15904 are shaped to fit within a user's ear canal (as in any of the exemplary embodiments described or shown herein) and act to center the booms 15910 about the user's temples, which is a consistent location that facilitates placement of electrodes at targeted locations at or near the trigeminal and/or vagus nerves. This also allows the headband embodiments to target the occipital nerves with electrodes that extend from the inside circumference of a rear portion of the headband 15702 toward the back of the user's head.

The centering device 15904 can be gimbaled (as is illustrated in FIGS. 95 to 97) at the rearward end of the boom 15910 to permit the centering device 15904 to accommodate different user's ear canal shapes and angular orientations. Each boom 15910 has a concave extension 15912 that runs forward from the centering device 15904 to a pivot 15904 that connects the boom 15910 to the forward end of the headband 15902 and allows the boom 15910 to pivot at least in the plane of the headband 15902 (i.e., the view of FIG. 159). The pivot 15904 can be a gimbal so that the boom 15910 can pivot in any way at the connection to the forward end of the headband 15902. Forward of the pivot 15904 on the concave extension 15912 are two structures: a facial artery compressor 15914 and a trigeminal nerve stimulator 15916. In the exemplary embodiment, the facial artery compressor 15914 is the first structure forward of the pivot 15904 and the trigeminal nerve stimulator 15916 is the second structure even further forward than the facial artery compressor 15914. The facial artery compressor 15914 is used to place pressure on the facial artery. Accordingly, the inward-most surface that contacts the user's skin is hammer shaped, although it can be any equivalent shape that can compress the facial artery when placed thereagainst. Mechanical compression can be enhanced by adding electrostimulated compression, which can occur by adding electrodes at the facial artery compressor 15914 that apply electrical signals having characteristics that impart vasoconstriction. The trigeminal nerve stimulator 15916 is used to place an electrical contact at the trigeminal nerve just forward of the facial artery. Accordingly, the inward-most surface that contacts the user's skin is shaped to be sufficiently long enough to contact the user's skin adjacent the trigeminal nerve when the facial artery compressor 15914 is compressing the facial artery. Installation of the system is easy, as centering occurs on the user's ear canals just as with conventional earphones.

A length of the concave extension 15912 that is rear of the pivot 15904 is longer than a length of the concave extension 15912 forward of the pivot 15904. In this way, the pivot 15904 acts as a fulcrum to multiply the force that the facial artery compressor 15914 will place against the facial artery. This insures that the trigeminal nerve stimulator 15916 contacts the skin and positions the trigeminal nerve stimulating electrode 15918 adjacent the trigeminal nerve when the centering device 15904 is within the user's ear canals and the headband 15902 is also placing an inwardly directed force on the pivot. In such a state, which is shown in FIG. 160, there are two forward contact points, one on the facial artery for either or both of vasoconstriction and neurostimulation and one adjacent the trigeminal nerve for neurostimulation. In particular, the facial artery is mechanically compressed bilaterally. With such mechanical processes, the headband 15902 can be adjusted to compress the facial artery at a level greater than blood pressure. When this occurs, the facial artery occludes and provides the desired relief. The facial artery compressor 15914 can also be fitted with sensing devices to sense characteristics of the temporary artery. For example, ultrasound, Doppler, and/or impedance sensors can assist with determining efficacy of occlusion and give the user feedback of such occlusion. With feedback, the user is provided with information to permit dynamic adjustment of the headband 15902. If electrodes are present on the facial artery compressor 15914, then electrical signals can be applied to the facial artery to electronically collapse the artery.

If the adjustment device of the headband 15902 are motorized (e.g., the spindle 15908), then such sensors can be used to automatically adjust the compression of the facial artery compressor 15914 as well as the level of stimulation being provided by the facial artery compressor 15914.

At the same time, stimulation of the trigeminal nerve, which supplies sensation to the head, can take place. It is known that stimulation of the trigeminal nerve makes the head numb, thereby, stopping headaches and migraines. One cause of pain for treating headaches and migraines with prior art devices is due to the discomfort that is associated with muscular contraction of the forehead. Because the device of FIGS. 157 to 160 places pressure at the anterior auricular location, instead of forehead, there is no musculature to contract and, therefore, no resulting discomfort. In this way, the device is able to impart more stimulation with less pain than prior art devices.

Sizing the concave extension 15912 properly places both the facial artery compressor 15914 and the trigeminal nerve stimulator 15916 in a desired position when the centering devices 15904 are within the user's ear canals. Significantly, in such a state, the system can take advantage of the location of the centering devices to, for example, also deliver audio sound into the ears if speakers are present and/or also deliver vagus nerve stimulation into the ear canal or concha if vagus nerve electrodes are present.

The booms of FIGS. 159 and 160 can also be replaced with a goggles embodiment. Such a configuration can provide both compression and neuromodulation, but in different areas of the head and face. In contrast to the boom, goggles do not contact the forehead and, instead, are located at orbits of the eye. In such an orientation, the goggles can be provided with electrodes positioned to stimulate the trochlear nerve.

Electrostimulation with the systems and methods described herein are not limited to the vagus and trigeminal nerves, even though exemplary embodiment for these nerves have been provided. Other exemplary areas for treatment are mentioned herein and can also include transcutaneous stimulation of peripheral, cranial, or central nervous system target locations. An example of the latter is the spinal cord. In such a case, novel aspects of the systems and methods herein are applicable and, for example, transcutaneous stimulation of a certain area of the spinal cord will be different for persons that have more fat than others. This would present a higher impedance than someone who is thin and, therefore, the automatic current control circuit with voltage adjustment resolves any issue with a person receiving current to the target structure that different from another.

The embodiments herein are described as treating pain, such as headaches and migraines. However, the devices and methods can also be used to treat shingles, trigeminal neuralgia, TMJ dysfunction, and atypical facial pain (e.g., after dental procedures).

Described herein are various earbud embodiments for the electrostimulation device coupler. These configurations are not intended to be limited to such embodiments and include additional exemplary embodiments for the earbuds in FIGS. 161 through 168. In the embodiment of FIGS. 161 to 164, the outer surface between the audio output end and the distal end of the channels between adjacent petals is enlarged, thereby providing a distal surface extent 16110. In comparison, the embodiment of FIGS. 165 to 168, there is an intermediate radial wall 16510 within the channels that are defined by adjacent petals. Also shown in these and the previous embodiments of the earbuds are exemplary prolate spheroid shapes. The inventors have discovered that a shape of the outer surface of the prolate spheroid earbuds can improve connectivity between the conductive outer surfaces of the earbuds and the target tissue of the ear canal. It is noted that users have different ear canal shapes and sizes. Accordingly, the following formulas were derived to dictate a curvature of the outer surface of the earbud form for various sizes of the patient coupler. These formulas vary based upon the maximum or "terminal diameter" of the various sized earbuds. These formulas plot a longitudinal curvature of the outer surface of the terminal diameters as listed below. Therefore, major diameters not listed would use the formula listed below that is closest to the major diameters listed. The earbud outer surface longitudinal curvature derived from the following formulas provide the best contact of electrodes to the skin surface and provide proper fit to varying ear canal anatomies and diameters. In the formulas below, the earbud profile polynomials are for a controlled 8.0 mm length with an 11.00 mm overall length.

Size: Small $$-(0.0031x^3)+(0.0024x^2)-(0.0178x)+4.1852 \quad \text{Equation:}$$

Domain: x0=0 & xf=8.00
Major Diameter=8.37 mm/8.3704 mm

Size: Intermediate 1

$$-(0.0034x^3)-(0.0066x^2)-(0.0016x)+4.7888 \quad \text{Equation:}$$

Domain: x0=0 & xf=8.00
Major Diameter=9.58 mm/9.5776 mm

Size: Medium $$-(0.0004x^4)+(0.0008x^3)-(0.0191x^2)-(0.0621x)+5.3912 \quad \text{Equation:}$$

Domain: x0=0.50 & xf=8.00
Major Diameter=10.72 mm/10.7824 mm

Size: Intermediate 2

$$-(0.001x^4)+(0.0118x^3)-(0.0787x^2)-(0.0037x)+5.9404 \quad \text{Equation:}$$

Domain: x0=0.00 & xf=8.00
Major Diameter=11.88 mm/11.8808 mm

Size: Large $$-(0.0071x^3)+(0.00009x^2)-(0.0295x)+6.4818 \quad \text{Equation:}$$

Domain: x0=0 & xf=8.00
Major Diameter=12.96 mm/12.9636 mm

In the above, the Y-intercept (where x=0) represents (in millimeters) the radius of the major diameter of the earbud. These exemplary earbuds have a 3.0 mm taper section for domain x=−3.0 to 0.

Various different features can be added to the embodiments of the device couplers (e.g., helix cuffs and ear buds) described herein. For example, the device couplers at the user's ears can be partially or completely illuminated. Illumination can backlight a product logo, can be pulsed with respect to therapeutic pulses, can be pulsed with respect to audio emanating from a coupled audio device such as an earbud, can be pulsed with respect to audio emanating from the environment in which the user is using the device, and/or can be pulsed with respect to control from an external source, such as from a DJ in a night club.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

The electrical combinations of ground/positive and positive/negative are used in various places herein. These various alternatives are not to be considered as limiting the described embodiment to one or the other in each case and are to be taken as equally interchangeable wherever used herein.

For the purposes of the description, a phrase in the form "A/B" or in the form "A and/or B" or in the form "at least one of A and B" means (A), (B), or (A and B), where A and B are variables indicating a particular object or attribute. When used, this phrase is intended to and is hereby defined as a choice of A or B or both A and B, which is similar to the phrase "and/or". Where more than two variables are present in such a phrase, this phrase is hereby defined as including only one of the variables, any one of the variables, any combination of any of the variables, and all of the variables, for example, a phrase in the form "at least one of A, B, and C" means (A), (B), (C), (A and B), (A and C), (B and C), or (A, B and C).

The foregoing description and accompanying drawings illustrate the principles, exemplary embodiments, and modes of operation of the invention. However, the invention should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. An electrostimulation device, comprising:
a transcutaneous electrostimulation generator:
  receiving an input music signal; and
  providing at an output a nerve electrostimulation signal modulated by the input music signal;
an electronic signal conduit having at least two conductive leads conductively connected to the output of the electrostimulation generator; and
an electrode coupler comprising an earbud:
  shaped to form fit inside an ear canal of a human ear; and
  composed of a pliable material that conforms to the ear canal when inserted therein; and
  having at least two electrostimulation electrodes:
    each conductively connected to a respective one of the at least two conductive leads of the electronic signal conduit to receive the nerve electrostimulation signal; and
    conductively connected to at least two different, electrically conductive exterior surface portions of the earbud to contact tissue within the ear canal when disposed therein and to apply the nerve electrostimulation signal from the at least two conductive leads to the tissue transcutaneously.

2. The device according to claim 1, wherein the input music signal is at least one of a recorded music signal, a transmitted music signal, and an ambient signal obtained from the environment surrounding the electrostimulation generator.

3. The device according to claim 1, wherein the electrostimulation generator comprises a modulation drive circuit into which the input music signal is received, the modulation drive circuit creating the output nerve electrostimulation signal modulated dependent upon the input music signal.

4. The device according to claim 1, which further comprises:
a mobile music supply device generating the input music signal; and
a generator coupler removably attaching the electrostimulation generator to the music supply device and shaped to permit a user to carry the electrostimulation generator.

5. The device according to claim 1, wherein:
the earbud has a speaker assembly; and
the electronic signal conduit comprises:
  a speaker conduit conductively connected to the speaker assembly and having a standard audio jack shaped to be inserted into a standard audio output to receive therefrom the input music signal; and
  an electrostimulation conduit comprising the at least two conductive leads to conductively connect the music-modulated, nerve electrostimulation signal to a respective one of the at least two electrostimulation electrodes.

6. The device according to claim 1, wherein:
the earbud has a speaker assembly having at least one speaker;
the electrostimulation generator wirelessly transmits the nerve electrostimulation signal; and
the electrode coupler has a receiver:
  receiving the nerve electrostimulation signal;
  receiving the input music signal;
  conductively connected to the at least two electrostimulation electrodes to thereby provide nerve electrostimulation to the at least two electrostimulation electrodes; and
  conductively connected to the speaker assembly to thereby provide the input music signal to the at least one speaker of the speaker assembly.

7. The device according to claim 1, further comprising an audio source outputting the input music signal, the electrode coupler comprising at least one audio speaker communicatively connected to the audio source through the electronic signal conduit and receiving the input music signal for output into the ear canal when the electrode coupler is worn, the electrostimulation generator sending the nerve electrostimulation signal to the electrode coupler while the input music signal is output by the at least one audio speaker.

8. The device according to claim 7, wherein the audio source is one of:
generating the input music signal from within the electrostimulation generator; and
separate from the electrostimulation generator and generating the input music signal externally from the electrostimulation generator.

9. An electrostimulation device, comprising:
an audio source outputting a music signal;
a transcutaneous electrostimulation generator:
receiving the music signal; and
providing at an output a nerve electrostimulation signal modulated by the music signal;
an electronic signal conduit conductively connected to the output of the electrostimulation generator; and
an electrode coupler comprising an earbud:
shaped to form fit inside an ear canal of a human ear;
composed of a pliable material that conforms to the ear canal when inserted therein;
having at least one audio speaker communicatively connected to the audio source and receiving the audio signals for output into the ear canal when worn;
having at least two electrostimulation electrodes:
each conductively connected to the electronic signal conduit to receive the nerve electrostimulation signal; and
conductively connected to at least two different, electrically conductive exterior surface portions of the earbud to contact tissue within the ear canal when disposed therein and to apply the nerve electrostimulation signal to the tissue transcutaneously; and
supplying the nerve electrostimulation signal while the music signal is output from the at least one audio speaker.

10. The device according to claim 9, wherein:
the electronic signal conduit has at least two conductive leads conductively connected to the output of the electrostimulation generator; and
the at least two electrostimulation electrodes:
are conductively connected to a respective one of the at least two conductive leads of the electronic signal conduit to receive the nerve electrostimulation signal; and
are conductively connected to the at least two surface portions of the earbud to apply the nerve electrostimulation signal from the at least two conductive leads to the tissue transcutaneously.

11. The device according to claim 9, wherein the music signals are at least one of a recorded music signal, a transmitted music signal, and an ambient signal obtained from the environment surrounding the electrostimulation generator.

12. The device according to claim 9, wherein the electrostimulation generator comprises a modulation drive circuit into which the music signal is received, the modulation drive circuit creating the output nerve electrostimulation signal modulated dependent upon the received music signal.

13. The device according to claim 9, wherein the audio source is a mobile music supply device and which further comprises a generator coupler removably attaching the electrostimulation generator to the music supply device and shaped to permit a user to carry the electrostimulation generator.

14. The device according to claim 9, wherein:
the audio source has a standard audio output;
the at least one audio speaker is within the earbud; and
the electronic signal conduit comprises:
a speaker conduit conductively connected to the at least one audio speaker and having a standard audio jack shaped to be inserted into the standard audio output to receive therefrom the music signal; and
an electrostimulation conduit conductively connecting the audio-signal-modulated nerve electrostimulation signal to a respective one of the at least two electrostimulation electrodes.

15. The device according to claim 9, wherein:
the earbud has a speaker assembly having at least one speaker;
the electrostimulation generator wirelessly transmits the nerve electrostimulation signal; and
the electrode coupler has a receiver:
receiving the nerve electrostimulation signal;
receiving the music signal;
conductively connected to the at least two electrostimulation electrodes to thereby provide nerve electrostimulation to the at least two electrostimulation electrodes; and
conductively connected to the at least one audio speaker to thereby provide the music signal to the at least one speaker.

16. An electrostimulation device to be connected to an audio source supplying a music signal, the device comprising:
a transcutaneous electrostimulation generator receiving the music signal and providing at an output a nerve electrostimulation signal modulated by the music signal;
an electronic signal conduit having at least two conductive leads conductively connected to the output of the electrostimulation generator;
an electrode coupler comprising:
an earbud:
shaped to form fit inside an ear canal of a human ear;
having at least two different, electrically conductive exterior surface portions;
having at least two electrostimulation electrodes:
each conductively connected to a respective one of the at least two conductive leads of the electronic signal conduit to receive the nerve electrostimulation signal; and
conductively connected to the at least two exterior surface portions to contact tissue within the ear canal when the earbud is disposed therein and to apply the nerve electrostimulation signal from the at least two conductive leads to the tissue transcutaneously; and
at least one audio speaker within the earbud and receiving the music signal for output into the ear canal when the electrode coupler is worn, the electrostimulation generator supplying the nerve electrostimulation signal while the music signal is output.

17. The device according to claim 16, wherein the electrostimulation generator is one of:
wirelessly connected to the audio source; and
directly connected to the audio source.

18. The device according to claim 16, wherein the at least one audio speaker is one of:

wirelessly connected to the audio source; and
directly connected to the audio source.

19. The device according to claim 17, wherein the at east one audio speaker is one of:
wirelessly connected to the audio source; and
directly connected to the audio source.

20. The device according to claim 16, wherein the earbud is composed of a pliable material that conforms to the ear canal when inserted therein.

\* \* \* \* \*